United States Patent
Bazan et al.

(10) Patent No.: US 11,684,599 B2
(45) Date of Patent: Jun. 27, 2023

(54) VERY-LONG-CHAIN POLYUNSATURATED FATTY ACIDS, ELOVANOID HYDROXYLATED DERIVATIVES, AND METHODS OF USE

(71) Applicants: Board of Supervisors of Louisiana State University and Agricultural and Mechanical College, Baton Rouge, LA (US); University of Southern California, Los Angeles, CA (US)

(72) Inventors: Nicolas G. Bazan, New Orleans, LA (US); Nicos A. Petasis, Los Angeles, CA (US)

(73) Assignees: Board of Supervisors of Lousiana State University and Agricultural and Mechanical College, Baton Rouge, LA (US); University of Southern California, Los Angeles, CA (US)

( * ) Notice: Subject to any disclaimer, the term of this patent is extended or adjusted under 35 U.S.C. 154(b) by 281 days.

(21) Appl. No.: 16/576,456

(22) Filed: Sep. 19, 2019

(65) Prior Publication Data

US 2020/0009100 A1 Jan. 9, 2020

Related U.S. Application Data

(63) Continuation-in-part of application No. PCT/US2018/023082, filed on Mar. 19, 2018.
(Continued)

(51) Int. Cl.
*A61K 31/202* (2006.01)
*A61P 39/06* (2006.01)
(Continued)

(52) U.S. Cl.
CPC .......... *A61K 31/202* (2013.01); *A23L 33/12* (2016.08); *A61K 9/0014* (2013.01);
(Continued)

(58) Field of Classification Search
CPC .. A61K 31/202; A61K 9/0014; A61K 9/0029; A61K 31/685; A61K 9/0019;
(Continued)

(56) References Cited

U.S. PATENT DOCUMENTS

| | | |
|---|---|---|
| 2012/0071558 A1 | 3/2012 | Anderson et al. |
| 2013/0190399 A1 | 7/2013 | Raman et al. |

FOREIGN PATENT DOCUMENTS

| | | | |
|---|---|---|---|
| WO | 2016/130522 | 8/2016 | |
| WO | WO-2016130522 A1 * | 8/2016 | ............ C07C 59/42 |
| WO | 2016182452 | 11/2016 | |

OTHER PUBLICATIONS

Winkler, JeremyW., et al."Stereocontrolledtotalsynthesisofthepotentanti-inflammatoryandpro-resolvinglipidediatorresolvinD3anditsaspirin-triggered17R-epimer."Organicletters15.7(2013):1424-1427. (Year: 2013).*

(Continued)

*Primary Examiner* — Deborah D Carr
(74) *Attorney, Agent, or Firm* — Baker Donelson

(57) ABSTRACT

Provided are compounds, pharmaceutical compositions, cosmetic and dermatological compositions or nutritional supplement compositions, comprising omega-3 very-long-chain polyunsaturated fatty acids (n-3 VLC-PUFAs) and/or their endogenous hydroxylated derivatives thereof, known as elovanoids. This disclosure provides methods for neuroprotection, organ and tissue protection or restoration, prevention or slowing down of aging-related diseases and conditions, and sustainment of function during the aging process.

41 Claims, 70 Drawing Sheets

Related U.S. Application Data

(60) Provisional application No. 62/864,672, filed on Jun. 21, 2019, provisional application No. 62/609,531, filed on Dec. 22, 2017, provisional application No. 62/473,697, filed on Mar. 20, 2017.

(51) Int. Cl.
  *A61P 25/28* (2006.01)
  *A61K 9/00* (2006.01)
  *A61K 31/685* (2006.01)
  *A23L 33/12* (2016.01)

(52) U.S. Cl.
  CPC .......... *A61K 9/0029* (2013.01); *A61K 31/685* (2013.01); *A61P 25/28* (2018.01); *A61P 39/06* (2018.01); *A23V 2002/00* (2013.01)

(58) Field of Classification Search
  CPC .. A61K 9/0024; A61K 9/0031; A61K 9/0034; A61K 9/0043; A61K 9/0048; A61K 9/0053; A61K 9/006; A61K 9/0075; A61K 9/02; A61K 9/06; A61K 9/08; A61K 9/10; A61K 9/107; A61K 9/127; A61K 9/1605; A61K 9/2004; A61K 9/7023; A61K 9/4841; A23L 33/12; A61P 25/28; A61P 39/06; A23V 2002/00
  USPC .......................................................... 514/76
  See application file for complete search history.

(56) References Cited

OTHER PUBLICATIONS

S.H. Shi, Z.F. Qi, Y.M. Luo, X.M. Ji, K.J. Lui, Normobaric oxygen treatment in acute ischemic stroke: a clinical perspective. Med. Gas. Res. 6, 147-153 (2016). Pmid: 27867482; doi: 10.4103/2045-9912.191360.

Saudek et al. (1989). N. Engl. J. Med. 321:574).

Sefton MV. Implantable pumps. Crit Rev Biomed Eng. 1987;14(3):201-40. PMID: 3297487.

Serhan CN, Gotlinger K, Hong S, Lu Y, Siegelman J, Baer T, Yang R, Colgan SP, Petasis NA. Anti-inflammatory actions of neuroprotection D1/protectin D1 and its natural stereoisomers: Assignments of dihydroxy-containing docosatrienes. J Immunol. 176(3): 1848-5 (2006).

Serhan, C. N. & Petasis, N. A. Resolvins and protectins in inflammation resolution. Chem. Rev. 111, 5922-5943, (2011).

Sherry D, et al., Front. Neuroanat. 2017; 11. PMID: 28507511.

Sripathi, S.R. et al. Prohibitin as the molecular binding switch in the retinal pigment epithelium. Protein J. 35, 1-16 (2016).

Sripathi, S.R., et al. Altered cytoskeleton as a mitochondrial decay signature in the retinal pigment epithelium. Protein J. 35, 179-192 (2016).

Winkler, Jeremy W., et al. "Stereocontrolled total synthesis of the potent anti-inflammatory and pro-resolving lipid mediator resolvin D3 and its aspirin-triggered 17 R-epimer." Organic letters 15.7 (2013): 1424-1427.

Written Opinion for PCT/US2018/023082 dated May 31, 2018.

"IUPAC-IUB [International Union of Pure and Applied Chemistry—International Union of Biochemistry] Commission of Biochemical Nomenclature. Abbreviated nomenclature of synthetic polypeptides (polymerized amino acids). Revised recommendations (1971)," Biochemistry 1972, 11, 5, 942-944 https://doi.org/10.1021/bi00755a039.

Agabaga, M.P. et al. Role of Stargardt-3 macular dystrophy protein (ELOVL4) in the biosynthesis of very long chain fatty acids. Proc. Nat. Acad. Sci. USA 105, 12843-12848 (2008).

Agabaga, M.P., et al. Retinal very long-chain PUFAs: new insights from studies on ELOVL4 protein. J. Lipid Rs. 51, 1624-1642 (2010).

Agbaga, M.P. Different mutations in ELOVL4 affect very long chain fatty acid biosynthesis to cause variable neurological disorders in humans. Adv. Exp. Med. Biol. 854, 129-135 (2016).

Aldahmesh, M.A. et al. Recessive mutations in ELOVL4 cause ichthyosis, intellectual disability, and spastic quadriplegia. Am. J. Hum. Genet. 89, 745-750 (2011).

Ansel et al., Pharmaceutical Dosage Forms and Drug Delivery Systems (1999) H.C. eds., 7th ed., Lippincott, Williams & Wilkins. Ansel Introduction to Pharmaceutical Dosage Forms, Fourth Edition 1985, 126.

Ansel, et al., "Pharmaceutical dosage forms and drug delivery systems", 6th Edition, (Media, PA: Williams and Wilkins, 1995) (We also have both the 7th edition and 10th edition downloaded as well).

Aursnes, M., et al. "Stereoselective synthesis of protectin D1: a potent anti-inflammatory and proresolving lipid mediator." Organic & biomolecular chemistry 12.3 (2014): 432-437.

Aveldano MI. Phospholipid species containing long and very long polyenoic fatty acids remain with rhodopsin after hexane extraction of photoreceptor membranes. Biochemistry. 27, 1229-1239 (1988).

Back, J.W., et al. A structure for the yeast prohibitin complex: structure prediction and evidence from chemical crosslinking and mass spectrometry. Protein Sc. 11, 2471-2478 (2002).

Balaban, R.S., Nemoto, S. & Finkel, T. Mitochondria, oxidants, and aging. Cell. 120, 483-495 (2005).

Bazan NG, Eady TN, Khoutorova L, Atkins KD, Hong S, Lu Y, Zhang C, Jun B, Obenaus A, Fredman G, Zhu M, Winkler JW, Petasis NA, Serhan CN, Belayev L. Novel aspirin-triggered neuroprotection D1 attenuates cerebral ischemic injury after experimental stroke. Exp Neurol. 2012;236(1):122-30.

Bazan NG. Docosanoids and elovanoids from omega-3 fatty acids are pro-homeostatic modulators of inflammatory responses, cell damage and neuroprotection. Mol Aspects Med. Dec. 2018;64:18-33. doi: 10.1016/j.mam.2018.09.003. Epub Oct. 1, 2018. PMID: 30244005; PMCID: PMC6204315.

Bazan, N.G. The docosanoid neuroprotection D1 induces homeostatic regulation of neuroinflammation. Prostaglandins Leukot. Essent. Fatty Acids, 88, 127-129 (2013).

Bazan, N.G. (2009). Cellular and molecular events mediated by docosahexaenoic acid-derived neuroprotection D1 signaling in photoreceptor cell survival and brain protection. Prostaglandins Leukot. Essent. Fatty Acids. 81, 205-211.

Bazan, N.G. Homeostatic regulation of photoreceptor cell integrity: significance of the potent mediator neuroprotection D1 biosynthesized from docosahexaenoic acid: The Proctor Lecture. Invest. Opthalmol. Vis. Sci. 48, 4866-4881 (2007).

Bazan, N.G. Neuroprotectin D1-mediated anti-inflammatory and survival signaling in stroke, retinal degenerations, and Alzheimer's disease. J. Lipid Res. 50 Suppl., S400-S405 (2009).

Bazan, N.G., Calandria, J.M. & Serhan, C.N. Rescue and repair during photoreceptor cell renewal mediated by docosahexaenoic acid-derived neuroprotection D1. J. Lipid Res. 51, 2018-2031 (2010).

Bazan, Nicolas G. "Cell survival matters: docosahexaenoic acid signaling, neuroprotection and photoreceptors." Trends in neurosciences 29.5 (2006): 263-271.

Begum G, Yan HQ, Li L, Singh A, Dixon CE, Sun D. Docosahexaenoic acid reduces ER stress and abnormal protein accumulation and improves neuronal function following traumatic brain injury. J Neurosci. Mar. 5, 2014;34(10):3743-55. doi: 10.1523/JNEUROSCI.2872-13.2014. PMID: 24599472; PMCID: PMC6608987.

Belayev, L., O.F. Alonso, R. Busto, W. Zhao, M.D. Goinsberg, Middle cerebral artery occlusion in the rat by intraluminal suture. Neurological and pathologicxal evaluation of an improved model. Stroke. 27, 1616-1622 (1996). Pmid: 8784138.

Bhattacharjee S, Jun B, Belayev L, Heap J, Kautzmann M-A, Obenaus A, Menghani H, Marvell SJ, Khoutorova L, Yang R, Petasis NA, Bazan NG. Elovanoids are a novel class of homeostatic lipid mediators that protect neural cell integrity upon injury. Science Advances. 2017;3(9):1-13.

Bligh, E.G. & Dyer, W.J. A rapid method of total lipid extraction and purification. Can. J. Biocjem. Physiol 37, 911-917 (1959).

Buchwald et al. (1980). Surgery 88:507.

(56) References Cited

OTHER PUBLICATIONS

Calandria, J.M. et al. Selective survival rescue in 15-lipoxygenase-1-deficient retinal pigment epithelial cells by the novel docosahexaenoic acide-derived mediator, neuroprotection D1. J. Biol. Chem. 284, 17877-17882 (2009).

Cameron, D.J. et al. Essential role of ELOVL4 in very long chain fatty acid synthesis, skin permeability barrier function, and neonatal survival. Int. J. Biol. Sci. 3, 111-119 (2007).

Corey, E. J., and Natarajan Raju. "A new general synthetic route to bridged carboxylic ortho esters." Tetrahedron letters 24.50 (1983): 5571-5574.

D.T. Stark, N.G. Bazan. Synaptic and extrasynaptic NMDA receptors differentially modulate neuronal cyclooxygenase-2 function, lipid peroxidation, and neuroprotection. J. Neurosci. 31, 13710-13721 (2011).

Durand, Sandrine, Jean-Luc Parrain, and Maurice Santelli. "Construction of (Z, Z) skipped 1,4-dienes. Application to the synthesis of polyunsaturated fatty acids and derivatives." Journal of the Chemical Society, Perkin Transactions 1 3 (2000): 253-273.

E. H. Lo, T. Dalkara, M. A. Moskowitz, Mechanisms, challenges and opportunities in stroke. Nat. Rev. Neurosci. 4, 399-415 (2003) Pmid: 12728267; doi: 10.1038/nm1106.

Gennaro, A. R. Remington's Pharmaceutical Sciences, Mack Publishing Company, Easton, Pennsylvania, 17th edition, 1985.

Harkewicz R, Du H, Tong Z, Alkuraya H, Bedell M, Sun W, Wang X, Hsu Y-H, Esteve-Rudd J, Hughes G, Su Z, Zhang M, Lopes VS, Molday RS, Williams DS, Dennis EA, Zhang K. Essential Role of ELOVL4 Protein n Very Long Chain Fatty Acid Synnthesis and Retinal Function. J Biol Chem. 2012;287(14): 11469-80.

International search report for PCT/US2018/023082 dated May 31, 2018.

Jiang, H., Xu, Z., Zhong, P. et al. Cell cycle and p53 gate the direct conversion of human fibroblasts to dopaminergic neurons. Nat Commun 6, 10100 (2015). https://doi.org/10.1038/ncomms10100.

Jun B, Mukherjee PK, Asatryan A, Kautzmann M-A, Heap J, Gordon WC, Bhattacharjee S, Yang R, Petasis NA, Bazan NG. Elovanoids are novel cell-specific lipid mediators necessary for neuroprotective signaling for photoreceptor cell integrity. Scientific Reports. 2017;7(5279):1-14.

K. Eltzschig, T. Eckle, Ischemia and reperfusion—from mechanism to translation. Nat Med. 17, 1391-1401 (2011). Pmid: 22064429; doi: 10.1038/nm.2507.

Kibbe, Arthur H., ed. Handbook of Pharmaceutical Excipients. Amer Pharmacists Assn, 2000.

Lagali, et Al. Evolutionarily conserved ELOVL4gene expression in the vertebrate retina. Invest. Opthalmol. Vis. Sci. 44, 2841-50 (2003).

Langer (1990). Science 249:1527-1533.

Li, L., et al. "Prohibitin 1 gene delivery promotes functional recovery in rats with spinal cord injury." Neuroscience 286 (2015): 27-36.

Lieberman, et. Al. Pharmaceutical dosage form tablets, eds. (New York, Marcel Dekker, Inc., 1989).

Monroig O, Rotllant J, Cerdá-Reverter JM, Dick JR, Figueras A, Tocher DR. Expression and role of Elovl4 elongases in biosynthesis of very long-chain fatty acids during zebrafish Danio rerio early embryonic development. Biochim Biophys Acta. Oct. 2010;1801(10):1145-54. doi: 10.1016/j.bbalip.2010.06.005. Epub Jul. 1, 2010. PMID: 20601113.

Mukherjee, P.K., Chawla, A., Loayza, M.S., Bazan, N.G. Docosanoids are multifunctional regulators of neural cell integrity and fate: significance in aging and disewase. Prostaglandins Lewukot. Essent. Fatty Acids. 77, 233-238 (2007).

Mukherjee, P.K., Marcheselli, V.L., Serhan, C.N. & Bazan, N.G. Neuroprotectin D1: a docosahexaenoic acid-derived docosatriene protects human retinal pigment epithelial cells from oxidative stress. Proc. Natl. Acad. Sci. U.S.A. 101, 8491-8496 (2004).

Nijtmans, L. G. et al. Prohibitins act as a membrane-bound chaperone for the stabilization of mitochondrial proteins. EMBO J. 19, 2444-2451 (2000).

Petasis, Nicos A., et al. "Stereocontrolled total synthesis of neuroprotectin D1/protectin D1 and its aspirin-triggered stereoisomer." Tetrahedron letters 53.14 (2012): 1695-1698.

Petrus E, et al. PNAS. 2019, pii; 201810132. PMID: 30846552.

Rice, D. et al., Adiponectin receptor 1 conserves docosahexaenoic acid and promotes photoreceptor cell survival. Nat. Commun. 6, 6228 (2015).

Roberts, S.B. & Rosenberg, I. Nutrition and aging: changes in the regulation of energy metabolism with aging. Physiol. Rev. 86, 651-667 (2006).

Third Party Observation in Japanese Patent Application No. 2019-552198 Mailed on Apr. 27, 2021.

\* cited by examiner

UV spectrum from
ELV-N32

UV spectrum from
ELV-N34

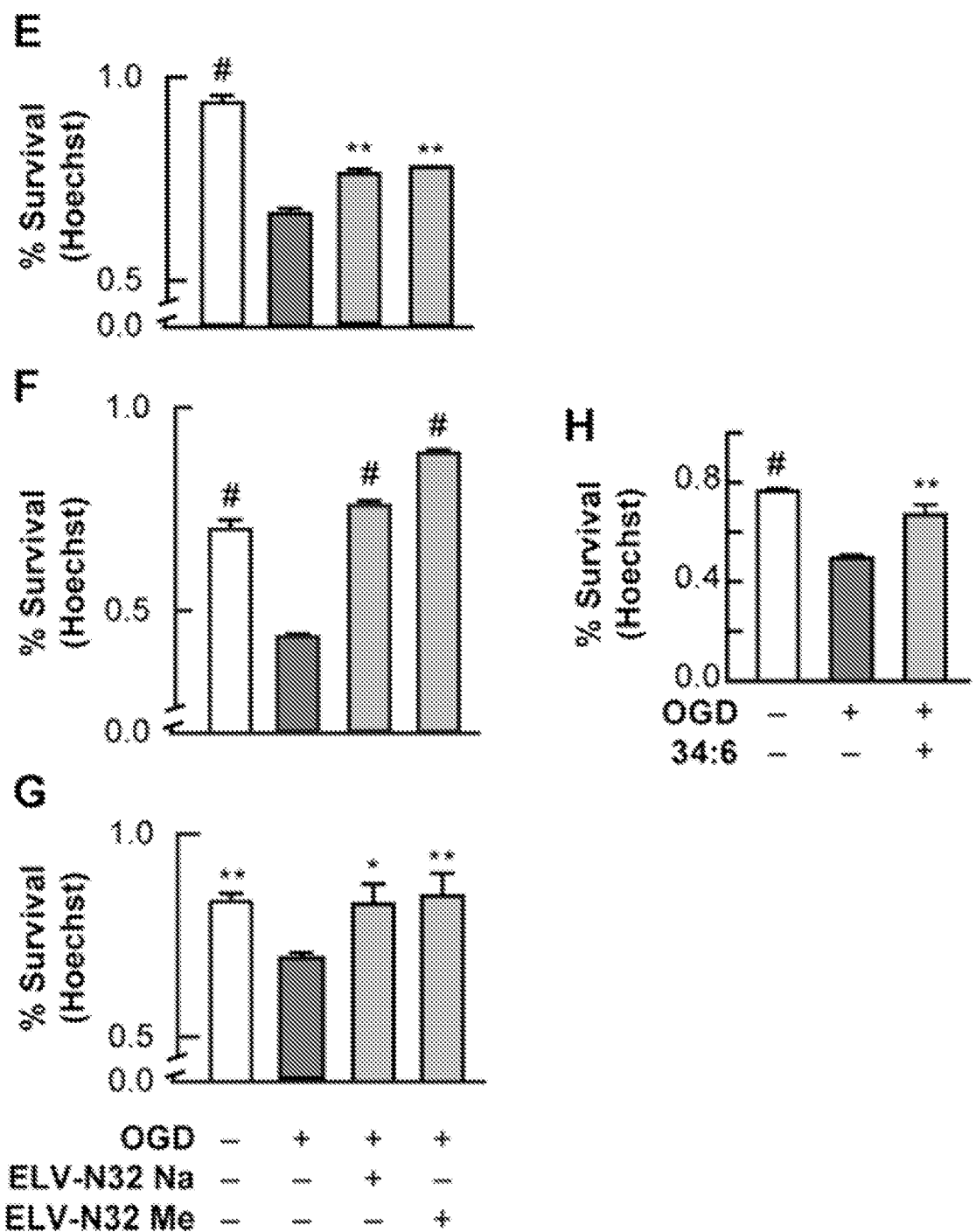
*Fig. 17-cont'd*

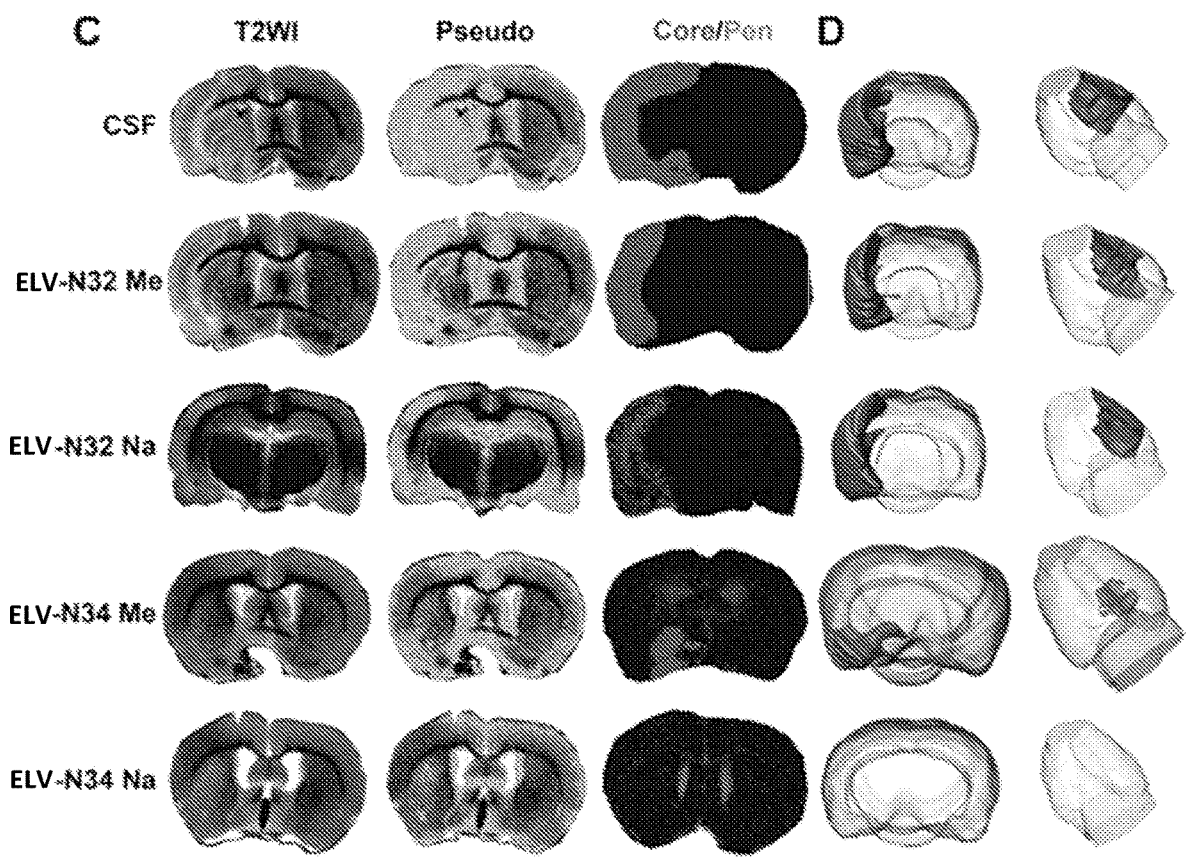
*Fig. 20C*  *Fig. 20D*

VERY-LONG-CHAIN POLYUNSATURATED FATTY ACIDS, ELOVANOID HYDROXYLATED DERIVATIVES, AND METHODS OF USE

CROSS REFERENCE TO RELATED APPLICATIONS

This application is a non-provisional application of U.S. 62/864,672, filed on Jun. 21, 2019; and is a Continuation in Part of International Application PCT/US2018/023082, filed on Mar. 19, 2018, which claims priority from U.S. Provisional Application No. 62/473,697 filed Mar. 20, 2017, and U.S. Provisional Application No. 62/609,531, filed Dec. 22, 2017, the entire contents of each which are incorporated herein by reference in their entireties.

STATEMENT REGARDING FEDERALLY SPONSORED RESEARCH OR DEVELOPMENT

This invention was made with government support under contracts EY005121 and GM103340 awarded by the National Institutes of Health. The Government has certain rights in the invention.

FIELD OF THE DISCLOSURE

This disclosure relates to organ-protective, disease-preventive, health-restorative, and anti-aging compounds, compositions and methods of use related to omega-3 very-long-chain polyunsaturated fatty acids (n-3 VLC-PUFA) and their hydroxylated derivatives known as elovanoids.

BACKGROUND

While the human aging process is inevitable, recent discoveries have led to the identification of factors that disrupt homeostasis and/or accelerate cell and tissue damage, and promote the onset of age-related diseases and conditions. For example, prolonged exposure to uncompensated oxidative stress, the accumulation of damaged cells and cellular debris, and the delay of tissue repair and clearance, is associated with the onset of aging-related conditions and diseases, such as chronic inflammation, cancer, neurodegenerative diseases, cardiovascular diseases, and cerebrovascular diseases. By reducing key factors that disrupt homeostasis, accelerate cell damage and cell death (cellular senescence), it is possible to prevent or delay age-related diseases and conditions, to improve quality of life, and to increase human life-span.

Age-related and non-age related inflammatory, degenerative, neurodegenerative, traumatic, dermatological, and cardiovascular diseases include a large number of diseases that affect a very large number of people worldwide. In most cases, these diseases and related conditions and disorders are difficult to treat, lead to impaired quality of life and/or reduced life span, and remain a major unmet medical need.

Inflammatory, degenerative or neurodegenerative diseases and conditions in the scope of this disclosure include acute and chronic disorders were homeostasis is disrupted by abnormal or dysregulated inflammatory response. These conditions are initiated and mediated by a number of inflammatory factors, including uncompensated oxidative stress, chemokines, cytokines, breakage of blood/tissue barriers, autoimmune diseases, calcium dysregulation including calcium overload in cells, mitochondria dysfunctions, genetic factors being gene susceptibility, polymorphisms or inherited conditions, epigenomic modifications, or other conditions that engage leukocytes, monocytes/macrophages, microglia, astrocytes or parenchymal cells that induce excessive amounts of pro-cell injury, pro-inflammatory/disruptors of cellular and/or organ homeostasis. These diseases occur in a wide range of tissues and organs, including skin, muscles, stomach, intestines, liver, kidneys, lungs, eyes, ears, and brain. These diseases are currently treated, by anti-inflammatory agents such as corticosteroids, non-steroidal anti-inflammatory drugs, TNF modulators, COX-2 inhibitors, etc.

Systemic inflammatory or degenerative diseases and conditions can affect vital organs such as the heart, muscles, stomach, intestines, liver, kidneys and lungs, and can lead to age-related chronic inflammatory diseases such as rheumatoid arthritis, atherosclerosis, and lupus.

Ophthalmic inflammatory or degenerative diseases and conditions typically affect the cornea, optic nerve, trabecular mesh work, and the retina. Without an effective prevention or treatment, they can lead to blinding eye diseases, such as glaucoma, cataracts, diabetic retinopathy, and age-related macular degeneration (AMD).

Brain-related inflammatory, degenerative or neurodegenerative diseases and conditions, such as Alzheimer's disease, Parkinson's disease, multiple sclerosis, ischemic stroke, traumatic brain injury, epilepsy, amyotrophic lateral sclerosis, often cause premature aging, cognitive dysfunctions and death.

Skin inflammatory or degenerative diseases and conditions often result from skin damage from sun exposure or other factors, including skin inflammation (dermatitis or eczema), atopic dermatitis (atopic eczema), skin dehydration, or from abnormal cell proliferation of the skin that results in excess flaking. Skin damage from sun exposure or other factors is associated with numerous diseases and conditions, such as eczema, psoriasis, atopic dermatitis or neurodermatitis, and can result by exposure to ultraviolet light and other types of contact dermatitis. Additionally, pruritus resulting from certain systemic diseases and conditions, provokes skin itching from various inflammatory and other types of stimuli, and causes the need to scratch, which can lead to further skin damage or altered skin appearance.

Despite much progress, our understanding related to the pathophysiology of inflammatory, neuroinflammatory, degenerative or neurodegenerative diseases and conditions that often lead to organ damage, chronic diseases, and accelerated aging, remains poorly understood. Therefore, organ protection, prevention of aging-related diseases and conditions, and overall health restoration remain a major unmet medical need. There is also a major void for the effective protection of skin tissues from inflammatory, neuroinflammatory, hyper-proliferative, or dehydrative skin conditions. In particular, our understanding related to the pathophysiology of skin damage, skin altered appearance, and skin aging, remain unclear. Being the body's largest organ, the skin provides protection and support and plays a key role in the human overall appearance and sense of well-being.

Considering the overall importance of skin health, skin function, and skin appearance, numerous efforts have been dedicated to the development of methods for skin protection and overall skin health. Most current treatments involve the dermal delivery of corticosteroids, or the use of oils and lotions containing vitamins, minerals, or herbal ingredients, which often are not able to effectively prevent or treat many types of skin damage, and also have side-effects such as skin thinning and muscle loss. While such preparations can offer some protection, there is an unmet need to develop compounds, compositions and methods that effectively protect damaged skin, prevent skin damage, restore skin health, improve skin appearance, and delay skin aging.

The disclosure also relates to previously unknown organ-protective, disease-preventive, health-restorative, nutrition enhancing, and anti-aging compounds, compositions and methods. In particular, the disclosure relates to the protection of cell and organ functions when confronted with disease onset, to the restoration of healthy tissues and organs, and to the delay of aging and the prevention of aging-related diseases and conditions. The disclosure also relates to the treatment or prevention of a wide range of diseases and conditions, including inflammatory, degenerative, neurodegenerative, traumatic, cardiovascular, aging-related diseases and conditions, and for the prevention and treatment of damaged or distorted skin, as a result of sunlight exposure, aging, or other causes.

With the discovery of the anti-inflammatory and pro-resolving effects of omega-3 long-chain polyunsaturated fatty acids 20 or 22 carbon omega-3 polyunsaturated fatty acids (n-3 or n3 PUFA), i.e. eicosapentaenoic acid (EPA), docosahexaenoic acid (DHA) or docosapentaenoic acid (DPA), these beneficial lipid molecules and certain types of their enzymatically hydroxylated derivatives, are increasingly used for therapeutic purposes, and as nutritional or dietary supplements for the prevention and management of excessive inflammation.

The present disclosure relates to previously unknown beneficial effects of omega-3 very long chain polyunsaturated fatty acid compounds (n3 VLC-PUFA), which contain carbon chains of at least 23 carbons.

The disclosure also relates to previously unknown findings that n3 VLC-PUFA are endogenously converted to therapeutically beneficial hydroxylated derivatives, known as elovanoids, which exhibit previously unknown bioactivities, function as beneficial modulators of inflammatory responses, and promote the restoration of disrupted function.

In summary, the disclosure relates to compounds, compositions and methods involving omega-3 very long chain polyunsaturated fatty acids (n3 VLC-PUFA or n-3 VLC-PUFA) and their hydroxylated derivatives (elovanoids), for use in preventive, protective, restorative, therapeutic, or nutritional applications.

SUMMARY OF THE DISCLOSURE

Provided are compounds, pharmaceutical compositions, cosmetic and dermatological compositions or nutritional supplement compositions, comprising omega-3 very-long-chain polyunsaturated fatty acids (n3 VLC-PUFA) and/or their endogenous hydroxylated derivatives thereof, known as elovanoids. This disclosure provides methods for neuroprotection, organ and tissue protection or restoration, prevention or slowing down of aging-related diseases and conditions, and sustainment of function during the aging process.

n3 VLC-PUFAs are converted in vivo to several previously unknown types of VLC-PUFA hydroxylated derivatives named elovanoids (ELVs) that are able to protect and prevent the progressive damage to tissues and organs, whose functional integrity has been disrupted.

n3 VLC-PUFA in neuronal cells and tissues in the brain and retina are released locally in response to neuronal stress conditions and are enzymatically converted into elovanoids which provide localized neuroprotection to ensure neuronal survival.

Aging-related cellular senescence can be effectively suppressed by providing certain compounds related to n3 VLC-PUFA and their corresponding elovanoids (ELVs). Accordingly, the disclosure is related to the prevention and treatment of health-perturbing conditions and aging-related diseases and conditions. In particular, the disclosure provides compounds, compositions and methods that protect and prevent from insults that threaten the function and integrity of vital tissues and organs, prevent accelerated aging, and delay cellular senescence.

The present disclosure provides compounds, compositions and methods that can promote the protection, prevention, and treatment of disturbances in many organs triggered by persistent inflammation, injury or trauma.

Accordingly, one aspect of the disclosure encompasses embodiments of a composition comprising at least one omega-3 very long chain polyunsaturated fatty acid having at least 23 carbon atoms in its carbon chain.

In some embodiments of this aspect of the disclosure, the composition comprises at least one n3 VLC-PUFA having at least 23 carbon atoms in its carbon chain, wherein the n3 VLC-PUFA can be in the form of a carboxylic acid, carboxylic ester, carboxylate salt, or phospholipid derivative.

In some embodiments of this aspect of the disclosure, the n3 VLC-PUFA compound can be selected from the group consisting of the formulas A or B:

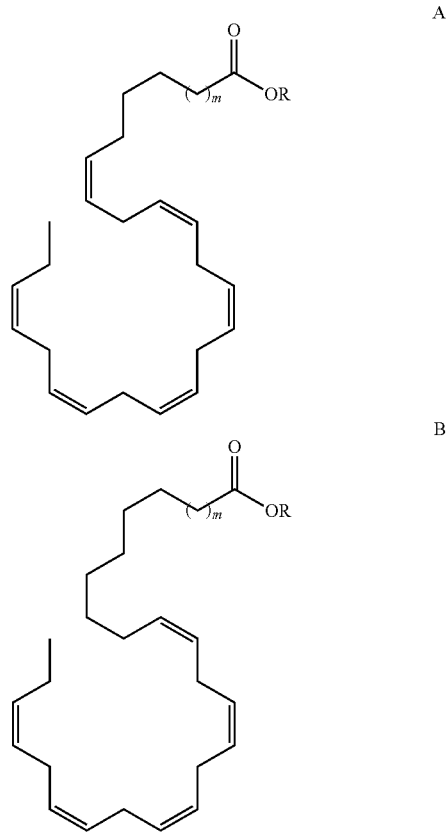

wherein: m can be 0 to 19 and —CO—OR can be a carboxylic acid group, or a salt or an ester thereof, and wherein: if —CO—OR can be a carboxylic acid group and the compound A or B can be a salt thereof, the cation of the salt can be a pharmaceutically acceptable cation, and if —CO—OR can be an ester, then R can be an alkyl group.

In some other embodiments, the disclosure, the n3 VLC-PUFA compound can be in the form of a phospholipid selected from the group consisting of the formulas C, D, E or F, wherein m can be 0 to 19:

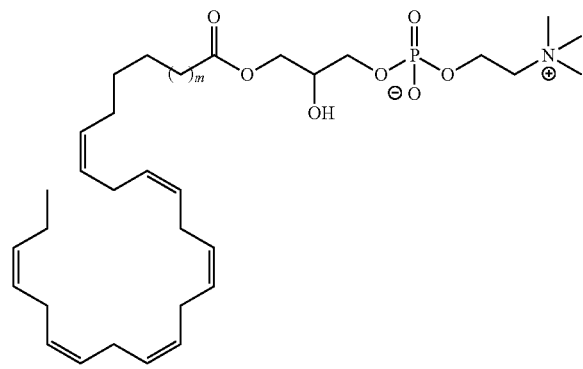

C

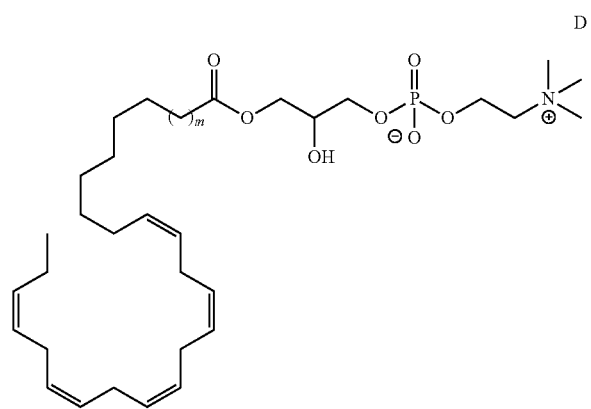

D

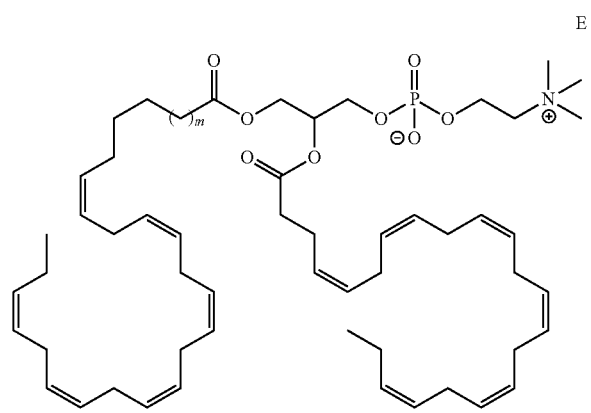

E

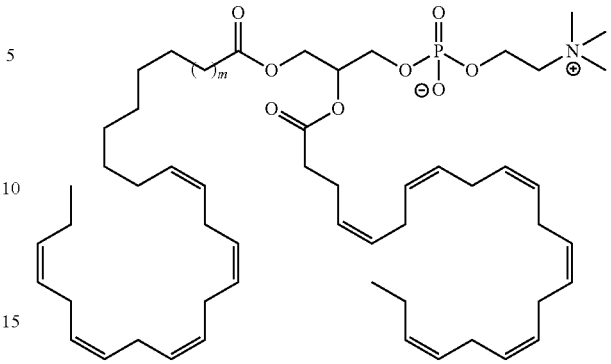

F

In some embodiments of this aspect of the disclosure, the composition can further comprise a pharmaceutically-acceptable carrier and formulated for delivery of an amount of the at least one omega-3 very long chain polyunsaturated fatty acid effective in reducing a pathological condition of a tissue of a recipient subject or the onset of a pathological condition of a tissue of a recipient subject.

In some embodiments of this aspect of the disclosure, the pathological condition can be aging or inflammation of a tissue of the recipient subject.

In some embodiments of this aspect of the disclosure, the composition can be formulated for topical delivery of the at least one very long chain polyunsaturated fatty acid tissue to the skin of a recipient subject.

In some embodiments of this aspect of the disclosure, the pathological condition can be of a neurological tissue of the recipient subject.

In some embodiments of this aspect of the disclosure, the composition can further comprise at least one nutritional component, and the composition can be formulated for the oral or parenteral delivery of the at least one very long chain polyunsaturated fatty acid to a recipient subject.

In some embodiments, the composition can be formulated for the nasal delivery of at least one very long chain polyunsaturated fatty acid to a recipient subject.

In some embodiments of this aspect of the disclosure, the at least one omega-3 very long chain polyunsaturated fatty acid can have from about 26 to about 42 carbon atoms in its carbon chain.

In some embodiments of this aspect of the disclosure, the at least one omega-3 very long chain polyunsaturated fatty acid can have 32 or 34 carbon atoms in its carbon chain.

In some embodiments of this aspect of the disclosure, the omega-3 very long chain polyunsaturated fatty acid can have in its carbon chain five or six alternating double bonds with cis geometry.

In some embodiments of this aspect of the disclosure, the omega-3 very long chain polyunsaturated fatty acid is 14Z,17Z,20Z,23Z,26Z,29Z)-dotriaconta-14,17,20,23,26,29-hexaenoic acid or (16Z,19Z,22Z,25Z,28Z,31Z)-tetratriaconta-16,19,22,25,28,31-hexaenoic acid.

In some embodiments of this aspect of the disclosure, the at least one omega-3 very long chain polyunsaturated fatty acid can be 14Z,17Z,20Z,23Z,26Z,29Z)-dotriaconta-14,17,20,23,26,29-hexaenoic acid or (16Z,19Z,22Z,25Z,28Z,31Z)-tetratriaconta-16,19,22,25,28,31-hexaenoic acid.

Another aspect of the disclosure encompasses embodiments of a composition comprising at least one elovanoid having at least 23 carbon atoms in its carbon chain.

In some embodiments of this aspect of the disclosure, the composition can further comprise a pharmaceutically-acceptable carrier and can be formulated for delivery of an amount of the at least one elovanoid effective in reducing a pathological condition of a tissue of a recipient subject or delaying at least one effect of aging in a tissue of a recipient subject.

In some embodiments of this aspect of the disclosure, the pathological condition can be aging or inflammation of a tissue of the recipient subject.

In some embodiments of this aspect of the disclosure, the composition can be formulated for topical delivery of the at least one elovanoid to the skin of a recipient subject.

In some embodiments of this aspect of the disclosure, the pathological condition can be of a neurological tissue of the recipient subject.

In some embodiments of this aspect of the disclosure, the composition can further comprise at least one nutritional component, and the composition can be formulated for the oral or parenteral delivery of the at least one elovanoid to a recipient subject.

In some embodiments of this aspect of the disclosure, the at least one elovanoid can be selected from the group consisting of: a mono-hydroxylated elovanoid, a di-hydroxylated elovanoid, an alkynyl mono-hydroxylated elovanoid, and an alkynyl di-hydroxylated elovanoid, or any combination thereof.

In some embodiments of this aspect of the disclosure, the at least one elovanoid can be a combination of elovanoids, wherein the combination is selected from the group consisting of: a mono-hydroxylated elovanoid and a di-hydroxylated elovanoid; a mono-hydroxylated elovanoid and an alkynyl mono-hydroxylated elovanoid; a mono-hydroxylated elovanoid and an alkynyl di-hydroxylated elovanoid; a di-hydroxylated elovanoid and an alkynyl mono-hydroxylated elovanoid; a di-hydroxylated elovanoid and an alkynyl di-hydroxylated elovanoid; a mono-hydroxylated elovanoid, a di-hydroxylated elovanoid, and an alkynyl mono-hydroxylated elovanoid; a mono-hydroxylated elovanoid, a di-hydroxylated elovanoid, and an alkynyl di-hydroxylated elovanoid; and a mono-hydroxylated elovanoid, a di-hydroxylated elovanoid, and an alkynyl mono-hydroxylated elovanoid an alkynyl di-hydroxylated elovanoid, wherein each elovanoid is independently a racemic mixture, an isolated enantiomer, or a combination of enantiomers wherein the amount of one enantiomer greater than the amount of another enantiomer; and wherein each elovanoid is independently a diastereomeric mixture, an isolated diastereomer, or a combination of diastereomers wherein the amount of one diastereomer is greater than the amount of another diastereomer.

In some embodiments of this aspect of the disclosure, the mono-hydroxylated elovanoid can be selected from the group consisting of the formulas G, H, I or J:

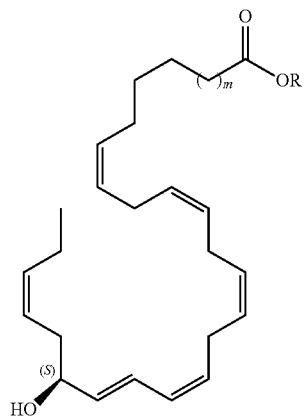

G

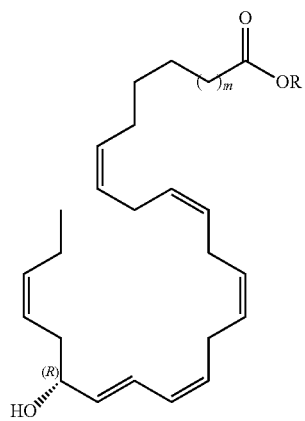

H

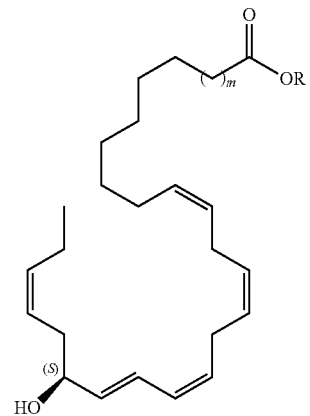

I

J

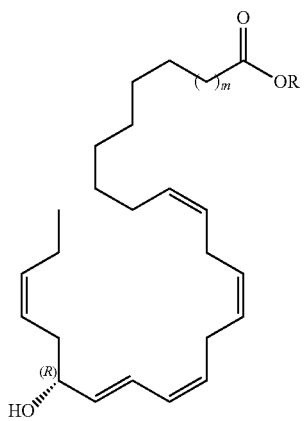

wherein: m can be 0 to 19 and —CO—OR can be a carboxylic acid group, or a salt or an ester thereof, and wherein: if —CO—OR can be a carboxylic acid group and the compound G, H, I or J can be a salt thereof, the cation of the salt can be a pharmaceutically acceptable cation, and if —CO—OR can be an ester, then R can be an alkyl group.

In some embodiments of this aspect of the disclosure, the composition can comprise equimolar amounts of the enantiomers G and H wherein the enantiomers have (S) or (R) chirality at the n-6 carbon bearing the hydroxyl group.

In some embodiments of this aspect of the disclosure, the composition can comprise amounts of the enantiomers I and J wherein the enantiomers have (S) or (R) chirality at the n-6 carbon bearing the hydroxyl group.

In some embodiments of this aspect of the disclosure, the composition can comprise one of the enantiomers of G or H in an amount exceeding the amount of the other enantiomer of G or H.

In some embodiments of this aspect of the disclosure, the composition can comprise one of the enantiomers of I or J in an amount exceeding the amount of the other enantiomer of I or J.

In some embodiments of this aspect of the disclosure, the di-hydroxylated elovanoid can be selected from the group consisting of the formulas K, L, M, and N:

K

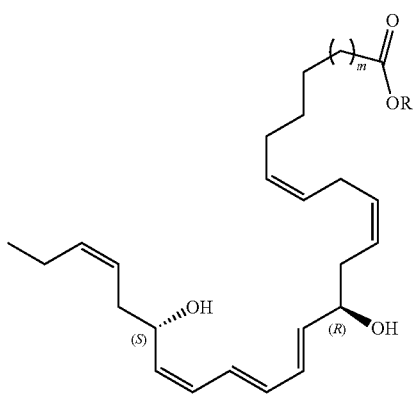

L

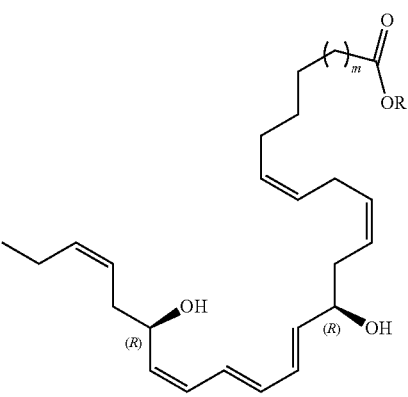

M

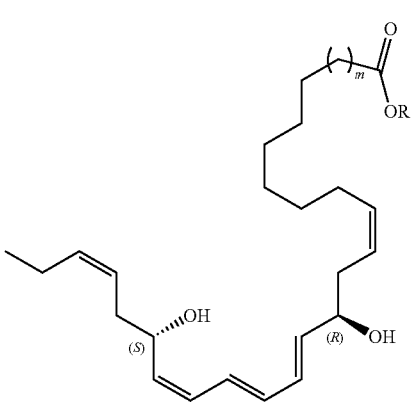

N

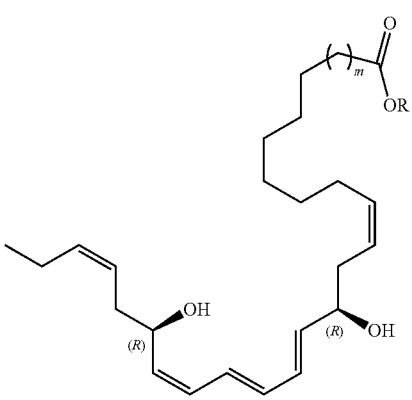

wherein: m can be 0 to 19 and —CO—OR can be a carboxylic acid group, or a salt or an ester thereof, and wherein: if —CO—OR can be a carboxylic acid group and the compound K, L, M, or N can be a salt thereof, the cation of the salt can be a pharmaceutically acceptable cation, and if —CO—OR can be an ester, then R can be an alkyl group, and wherein: compounds K and L each have a total from 23 to 42 carbon atoms in the carbon chain, with 4 cis carbon-carbon double bonds starting at positions n-3, n-7, n-15 and n-18, and 2 trans carbon-carbon double bonds starting at positions n-9 and n-11; and compounds M and N each have a total from 23 to 42 carbon atoms in the carbon chain, with 3 cis carbon-carbon double bond starting at positions n-3, n-7 and n-15; and 2 trans carbon-carbon double bonds starting at positions n-9 and n-11.

In some embodiments of this aspect of the disclosure, the composition can comprise equimolar amounts of diastereomers K and L wherein the diastereomers have either (S) or (R) chirality at position n-6, and (R) chirality at position n-13.

In some embodiments of this aspect of the disclosure, the composition can comprise equimolar amounts of one or more diastereomers K and L wherein the diastereomers have either (S) or (R) chirality at position n-6, and either (S) or (R) chirality at position n-13.

In some embodiments of this aspect of the disclosure, the composition can comprise one of the diastereomers of K or L in an amount exceeding the amount of the other diastereomers of K or L.

In some embodiments of this aspect of the disclosure, the composition can comprise equimolar amounts of diastereomers M and N wherein the diastereomers have either (S) or (R) chirality at position n-6, and (R) chirality at position n-13.

In some embodiments of this aspect of the disclosure, the composition can comprise equimolar amounts of one or more diastereomers M and N wherein the diastereomers have either (S) or (R) chirality at position n-6, and either (S) or (R) chirality at position n-13.

In some embodiments of this aspect of the disclosure, the composition can comprise one of the diastereomers of M or N in an amount exceeding the amount of the other diastereomers of M or N.

In some embodiments of this aspect of the disclosure, the alkynyl mono-hydroxylated elovanoid can be selected from the group consisting of the formulas O, P, Q or R:

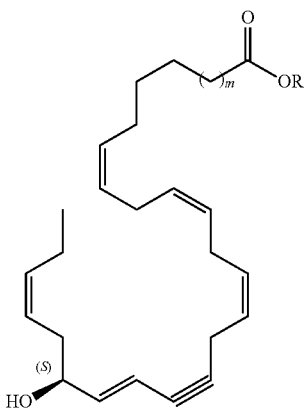

O

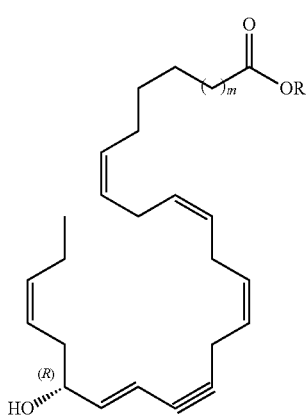

P

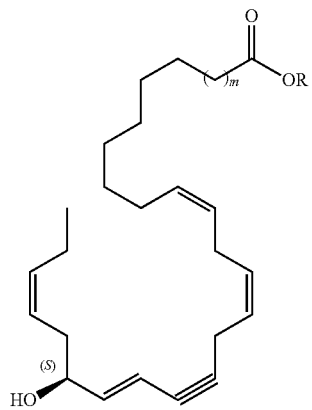

Q

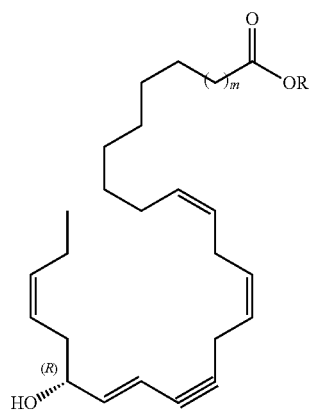

R wherein: m can be 0 to 19 and —CO—OR can be a carboxylic acid group, or a salt or an ester thereof, and wherein: if —CO—OR can be a carboxylic acid group and the compound O, P, Q or R can be a salt thereof, the cation of the salt can be a pharmaceutically acceptable cation, and if —CO—OR can be an ester, then R can be an alkyl group, and wherein: compounds O and P each have a total from 23 to 42 carbon atoms in the carbon chain, with 4 cis carbon-carbon double bonds located at positions starting at n-3, n-12, n-15 and n-18; with a trans carbon-carbon double bond at position starting at n-7, and a carbon-carbon triple bond starting at position n-9; and compounds Q and R each have a total from 23 to 42 carbon atoms in the carbon chain, with 3 cis carbon-carbon double bond starting at positions n-3, n-12 and n-15, with a trans carbon-carbon double bond at position starting at n-7, and a carbon-carbon triple bond starting at position n-9.

In some embodiments of this aspect of the disclosure, the composition can comprise equimolar amounts of the enantiomers O and P wherein the enantiomers have (S) or (R) chirality at the n-6 carbon bearing the hydroxyl group.

In some embodiments of this aspect of the disclosure, the composition can comprise equimolar amounts of the enantiomers Q and R wherein the enantiomers have (S) or (R) chirality at the n-6 carbon bearing the hydroxyl group.

In some embodiments of this aspect of the disclosure, the composition can comprise one of the enantiomers of O or P in an amount exceeding the amount of the other enantiomer of O or P.

In some embodiments of this aspect of the disclosure, the composition can comprise one of the enantiomers of Q or R in an amount exceeding the amount of the other enantiomer of Q or R.

In some embodiments of this aspect of the disclosure, the elovanoid can be an alkynyl di-hydroxylated elovanoid selected from the group consisting of the formulas S, T, U or V:

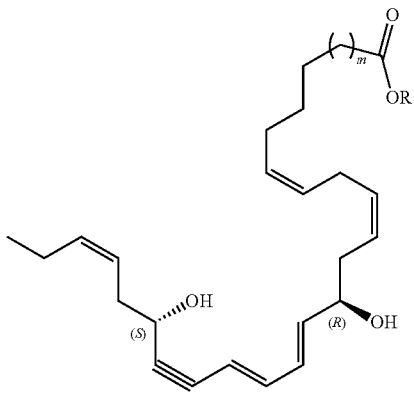

S

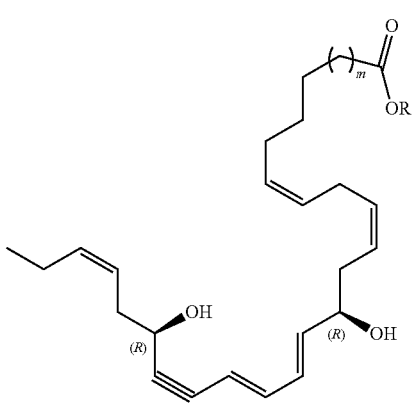

T

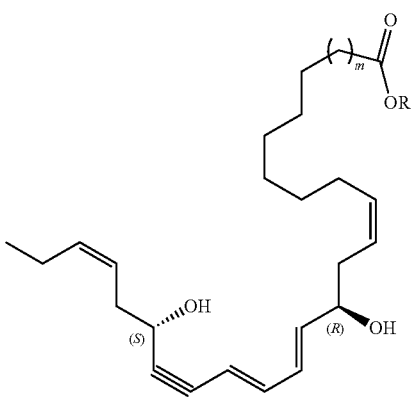

U

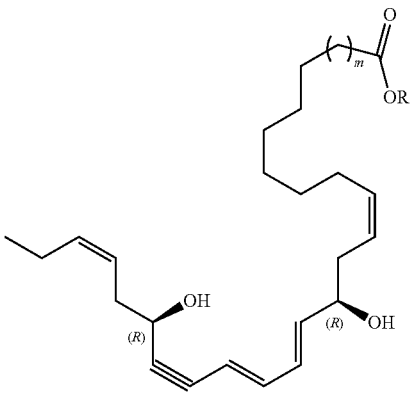

V wherein: m can be 0 to 19 and —CO—OR can be a carboxylic acid group, or a salt or an ester thereof, and wherein: if —CO—OR can be a carboxylic acid group and the compound S, T, U or V can be a salt thereof, the cation of the salt can be a pharmaceutically acceptable cation, and if —CO—OR can be an ester, then R can be an alkyl group, and wherein: compounds S and T each have a total from 23 to 42 carbon atoms in the carbon chain, with 3 cis carbon-carbon double bonds located at positions starting at n-3, n-15 and n-18, with 2 trans carbon-carbon double bonds located at positions starting at n-9 and n-11, and a carbon-carbon triple bond starting at position n-7; and compounds U and V each have a total from 23 to 42 carbon atoms in the carbon chain, with 2 cis carbon-carbon double bond starting at positions n-3 and n-15, with 2 trans carbon-carbon double bonds located at positions starting at n-9, n-11, and a carbon-carbon triple bond starting at position n-7.

In some embodiments of this aspect of the disclosure, the composition can comprise equimolar amounts of diastereomers S and T wherein the diastereomers have either (S) or (R) chirality at position n-6, and (R) chirality at position n-13.

In some embodiments of this aspect of the disclosure, the composition can comprise equimolar amounts of one or more diastereomers S and T wherein the diastereomers have either (S) or (R) chirality at position n-6, and either (S) or (R) chirality at position n-13.

In some embodiments of this aspect of the disclosure, the composition can comprise one of the diastereomers of S or T in an amount exceeding the amount of the other diastereomers of S or T.

In some embodiments of this aspect of the disclosure, the composition can comprise equimolar amounts of diastereomers U and V wherein the diastereomers have either (S) or (R) chirality at position n-6, and (R) chirality at position n-13.

In some embodiments of this aspect of the disclosure, the composition can comprise equimolar amounts of one or more diastereomers U and V wherein the diastereomers have either (S) or (R) chirality at position n-6, and either (S) or (R) chirality at position n-13.

In some embodiments of this aspect of the disclosure, the composition can comprise one of the diastereomers of U or V in an amount exceeding the amount of the other diastereomers of U or V.

In certain advantageous embodiments, the disclosure provides effective amounts of at least one provided compound and/or provided composition for the purpose of exerting potent neuroprotective, tissue-protective, and neuro-restorative actions, that are suitable for neuroprotection, organ protection, and tissue protection.

In other embodiments, the disclosure provides compounds and dermatological or cosmetic compositions for the effective protection, prevention or treatment of skin that has been damaged by sunlight or other causes or has been affected by skin aging. The provided compounds, compositions, and methods induce the survival and normal function of skin cells, protect the skin, improve skin health and skin appearance, and delay skin aging.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure is focused on compounds, compositions and methods for applications in skin diseases, retinal diseases, cardiovascular diseases, gastrointestinal/hepatic diseases, and brain diseases. The unique structures, biosynthesis, and functions of the provided compounds and compositions were initially studied in the brain and retina, as summarized in the following figures. Further aspects of the present disclosure will be readily appreciated upon review of the detailed description of its various embodiments, described below, when taken in conjunction with the accompanying drawings.

FIG. 3A is a scheme illustrating ELV-N32 and ELV-N34 synthesis from the intermediates (1, 2, and 3), each of which was prepared in stereochemically-pure form. The stereochemistry of intermediates 2 and 3 was pre-defined by using enantiomerically-pure epoxide starting materials. The final ELVs (4) were assembled via iterative couplings of intermediates 1, 2, and 3, and were isolated as the methyl esters (Me) or sodium salts (Na).

FIG. 3B illustrates the elution profile of C32:6n3, endogenous mono-hydroxy-C32:6n3, and ELV-N32 shown with ELV-N32 standard. MRM of ELV-N32 shows two large peaks eluted earlier than the peak when standard ELV-N32 is eluted, displaying the same fragmentation patterns (shown in the insert spectra), suggesting that they are isomers.

FIG. 3C illustrates the chromatogram for full daughter scans for ELV-N32 and ELV-N34.

FIG. 3D illustrates the fragmentation pattern of ELV-N32.

FIG. 3E illustrates the elution profile of C34:6n3 and ELV-N34.

FIG. 3F illustrates the UV spectrum of endogenous ELV-N34 showing triene features analogous to NPD1, with $\lambda_{max}$ at 275 nm and shoulders at 268 and 285 nm.

FIG. 3G illustrates the fragmentation pattern of ELV-N32.

FIG. 3H illustrates the full fragmentation spectra of endogenous ELV-N32.

FIG. 3I illustrates the ELV-N32 standard shows that all major peaks from standard match to the endogenous peaks. However, endogenous ELV-N32 has more fragments that don't show up in the standard, suggesting that it includes different isomers.

FIG. 3J illustrates the full fragmentation spectra of endogenous ELV-N34 peaks match to standard ELV-N34.

FIG. 3K illustrates the existence of ELV-N34 isomers.

FIG. 4A is a scheme illustrating ELV-N32 and ELV-N34 synthesis from the intermediates (a, b, and c), each of which was prepared in stereochemically-pure form. The stereochemistry of intermediates b and c was pre-defined by using enantiomerically-pure epoxide starting materials. The final ELVs (d) were assembled via iterative couplings of intermediates a, b, and c, and were isolated as the methyl esters (Me) or sodium salts (Na).

FIG. 4B illustrates the 32:6n3, endogenous mono-hydroxy-32:6, ELV-N32, and ELV-N32 standard in the insert. MRM of ELV-N32 shows two large peaks eluted earlier than the peak when standard ELV-N32 is eluted, but they show the same fragmentation patterns, suggesting that they are isomers.

FIG. 4C illustrates the same features as in FIG. 4A, were shown in 34:6n3 and ELV-N34.

FIG. 4D illustrates the UV spectrum of endogenous ELV-N32 shows triene features, but these are not definite at this concentration.

FIG. 4E illustrates the full fragmentation spectra of endogenous ELV-N32.

FIG. 4F illustrates the UV spectrum of endogenous ELV-N34 showing triene features analogous to NPD1, with 2 at 275 nm and shoulders at 268 and 285 nm.

FIG. 4G illustrates the fragmentation pattern of endogenous ELV-N34.

FIG. 4H illustrates the full fragmentation pattern of endogenous ELV-N32.

FIG. 4I illustrates the ELV-N34 standard shows that all major peaks from the standard match to the endogenous peaks, but not perfectly matched; endogenous ELV-N34 has more fragments that do not show up in the standard, suggesting that it may contain isomers.

FIG. 4J illustrates the ELV-N34 full fragmentation spectra; the endogenous ELV-N34 peaks match to the standard ELV-N34 FIG. 4K illustrates the suggested existence of ELV-N34 isomers.

FIG. 5A illustrates the VLC-PUFA C32:6n3, endogenous 27-hydroxy-32:6n3, endogenous 27,33-dihydroxy-32:6n3 (ELV-N32), and synthetic ELV-N32 prepared in stereochemical pure form via stereocontrolled total organic synthesis. MRM of endogenous ELV-N32 matches well with the MRM of the synthetic ELV-N32 standard.

FIG. 5B illustrates the same features as in FIG. 5A were shown in C34:6n3 and ELV-N34, with more peaks in ELV-N34 MRMs, which implies isomers.

FIG. 7A illustrates the concentration-dependent anti-apoptotic activity of C32:6n3 and C34:6n3 in human RPE cells (ARPE-19 cells). Confluent (80%) ARPE-19 cells in 12-well plates were serum starved for 8 h, UOS was induced and then challenged with 50-500 nM C32:6n3 or 34:6n3 free acids for 16 h. Treated cells were harvested, and Hoechst-positive pyknotic cells detected. Data are averages of the counts of 15 wells of Hoechst-positive pyknotic cells of three independent experiments.

FIG. 7B illustrates the comparison of cytoprotection of DHA (100 nM) with 32:6n3 and 34:6n3 (250 nM each) for 16 h. UOS was introduced in serum-starved ARPE-19 cells and apoptotic cell death detected as described in FIG. 7A. Results are averages of the three independent experiments.

FIG. 7C illustrates the SIRT1 upregulation by C32:6n3 and C34:6n3 in RPE under UOS. Effect of PD146176, a 15-LOX-1 inhibitor on C32:6n3 and C34:6n3 induced upregulation of SIRT1 in RPE under the influence of UOS. The results are the averages of three independent experiments (9 wells for each experiment) unless otherwise indicated.

FIG. 7D illustrates the 15-LOX-1 inhibitor PD146176 attenuates C32:6n3- or C34:6n3-induced Iduna upregulation in RPE cells under UOS.

FIG. 7E-7I illustrate the effect of C32:6n3 or C34:6n3 on anti- and pro-apoptotic proteins in ARPE-19 cells under UOS. Western blot detection of the effect of C32:6n3 and C34:6n3 on the up and down regulation of the above proteins in ARPE-19 cells under UOS.

FIG. 7E illustrates the effect of C32:6n3 or C34:6n3 on anti-apoptotic protein Bcl-2.

FIG. 7F illustrates the effect of C32:6n3 or C34:6n3 on anti-apoptotic protein Bc-xL.

FIG. 7G illustrates the effect of C32:6n3 or C34:6n3 on pro-apoptotic protein Bax.

FIG. 7H illustrates the effect of C32:6n3 or C34:6n3 on pro-apoptotic protein Bim.

FIG. 7I illustrates the effect of C32:6n3 or C34:6n3 on pro-apoptotic protein Bid.

FIG. 7J illustrates the concentration-dependent (100 and 250 nM) upregulation of Prohibitin (type-1) by C32:6n3 and C34:6n3 in RPE cells under UOS.

FIG. 7K illustrates the effects of NPD1 (200 nM), C32:6n3 or C34:6n3 (3 µM) on primary human RPE cell survival.

FIG. 7L illustrates the cytoprotection by C32:6n3 or C34:6n3 on primary human RPE cells in the presence of 10 µM PD146176. Error bars, SEM; * p<0.05.

Figure 9A:
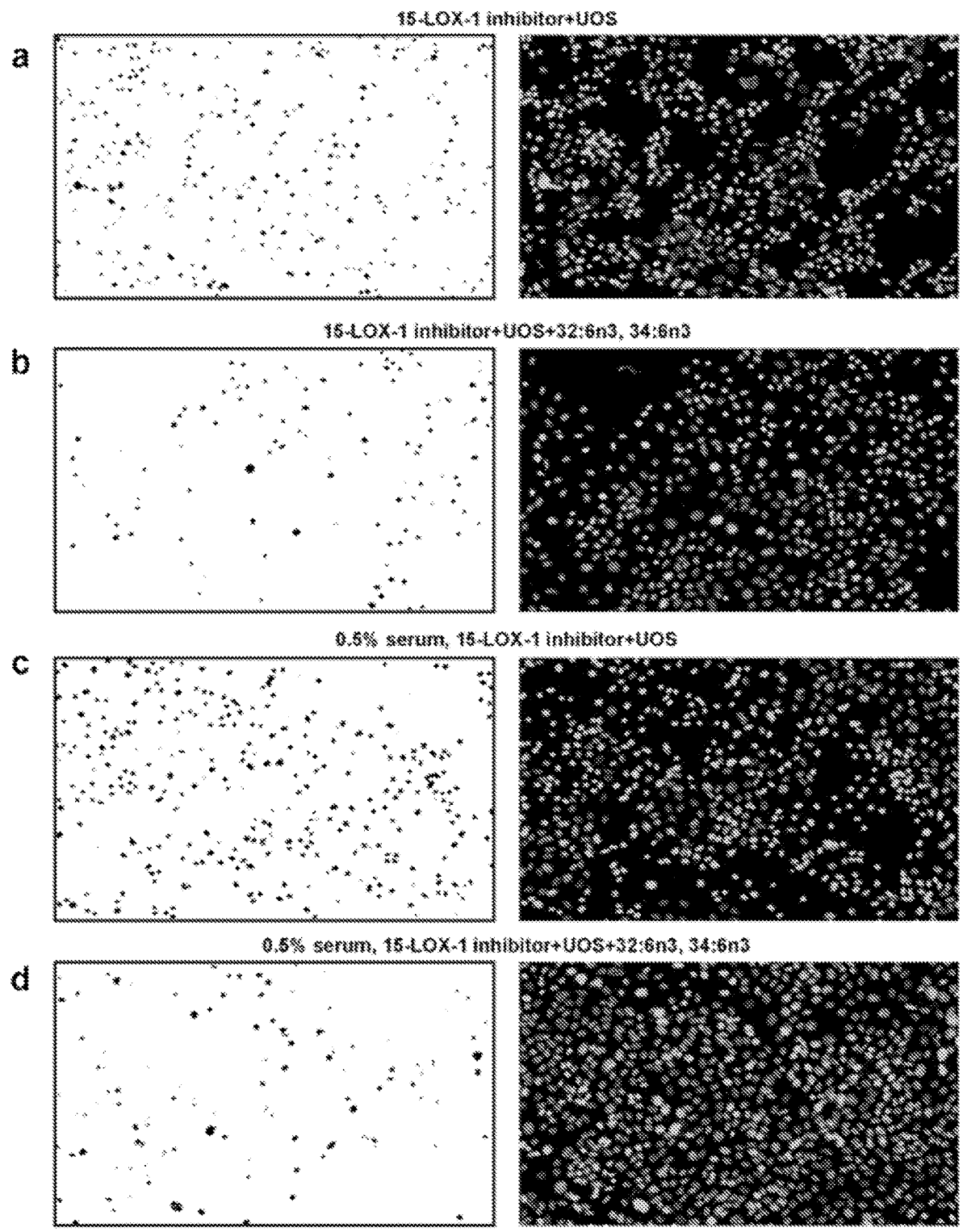
FIGS. 9A-9C illustrate that a 15-LOX-1 inhibitor does not modify cytoprotection against UOS mediated by 32:6n3 and 34:6n3 on primary human RPE cells. Serum-deprived (FIG. 9A, Panels a and b) and low serum (FIG. 9A, Panels c and d) primary human RPE cells were incubated with the 15-lipoxygenase-1 (15-LOX-1) inhibitor (10 micromolar, PD146176) for 1 h, then subjected to oxidative stress ($H_2O_2$/TNFα) for 16 h to induce apoptosis (FIG. 9A, Panels a-d, FIG. 9C).

The addition of 32:6n3 and 34:6n3 protected human RPE cells (FIG. 9A, Panels b and d, FIG. 9C) from cell death. Typical fields of cell cultures are represented in FIG. 9A, Panels a-d, right column. Nuclei are labeled with Hoechst staining, and the dead cells are highlighted. These were separated using an intensity threshold algorithm and counted using an Image J macro (FIG. 9A, Panels a-d, left column).

Figure 9B:
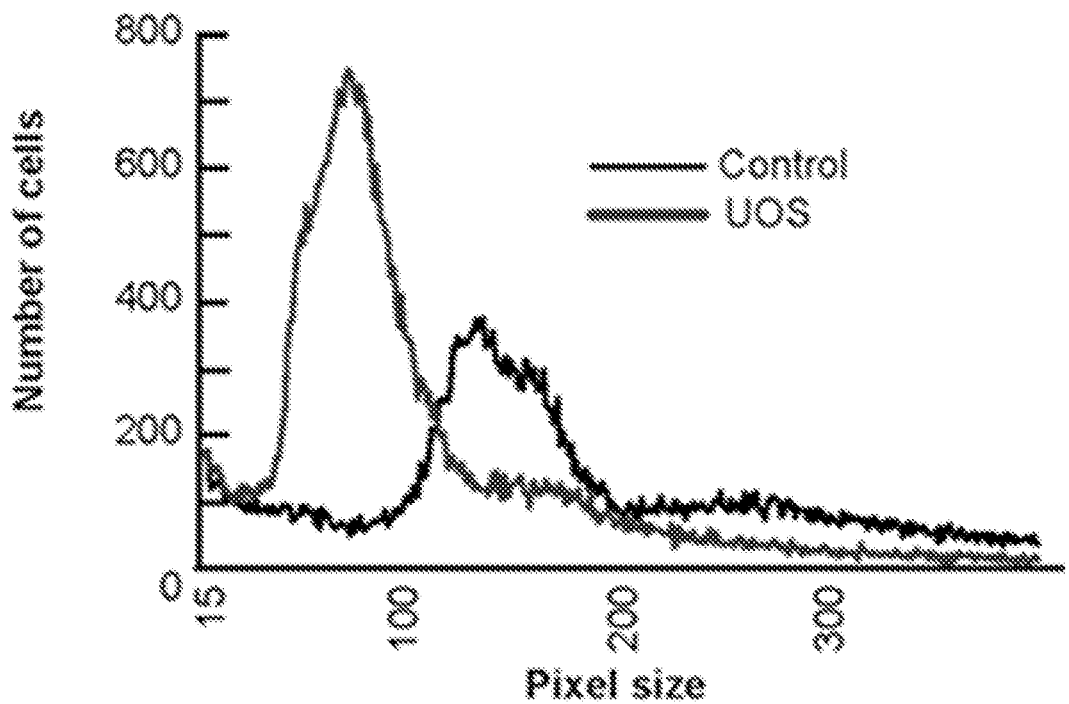

FIG. 9B illustrates the quantification of live (control cells) and dead (UOS cells) cells was based on nuclear size. Error bars, SEM; *p<0.05.

FIGS. 10A-10H illustrate ELV-N32 and ELV-N34 enhance abundance of pro-homeostatic proteins and decrease abundance of cell damaging proteins in RPE cells under UOS.

Figure 10A:
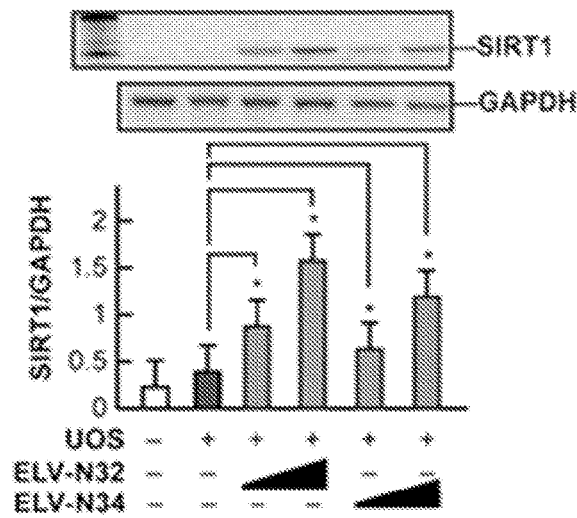

FIG. 10A illustrates the concentration-dependent (100 and 250 nM) upregulation of SIRT1 in ARPE-19 cells under UOS. The results are the averages of three independent experiments.

Figure 10B:
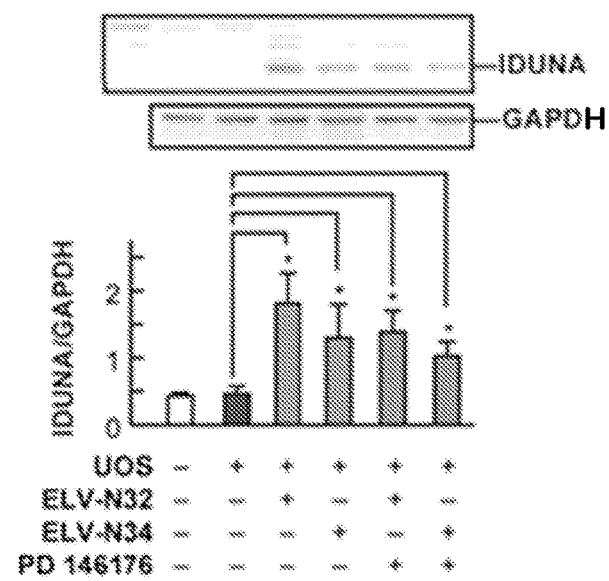

FIG. 10B illustrates the effect of PD146176 on ELV-N32- and ELV-N34-induced upregulation of Iduna in RPE cells under UOS.

Figure 10C:
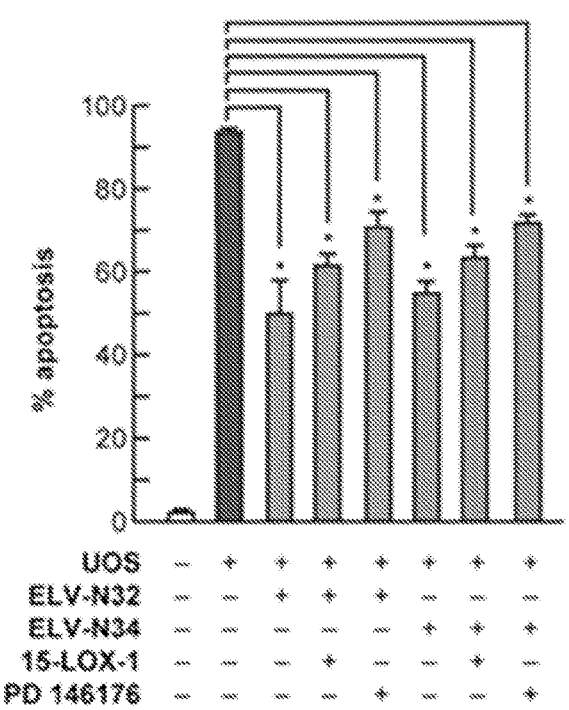

FIG. 10C illustrates the cytoprotective capacities of ELV-N32 and ELV-N34 in RPE cells under UOS. Effect of lipoxygenase inhibitors on apoptosis inhibition.

Figure 10D:
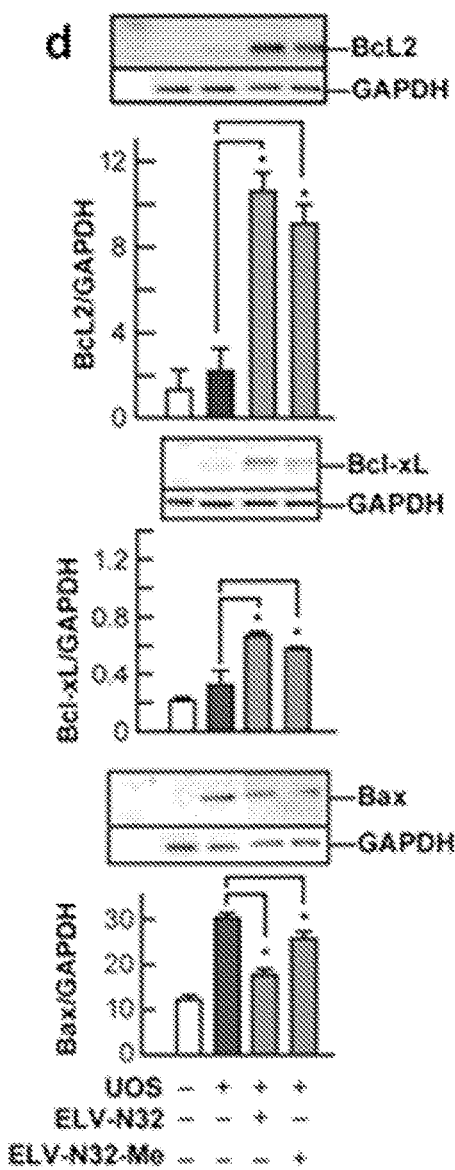

FIG. 10D illustrates the effect of ELV-N32 Na or ELV-N32 Me on anti-apoptotic proteins Bcl-2, Bcl-xL, and pro-apoptotic protein Bax in ARPE-19 cells under UOS.

Figure 10E:
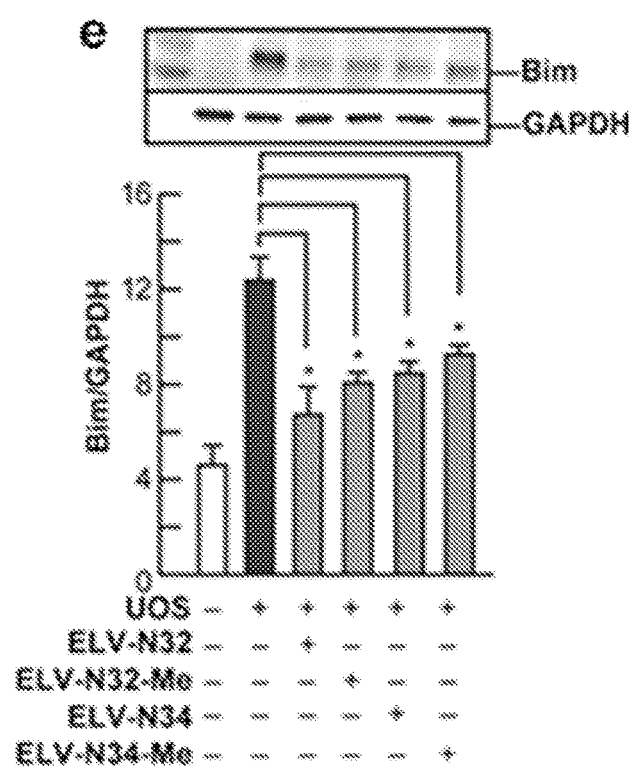

FIG. 10E illustrates a comparison of the effect of ELV-N32 Na or ELV-N32 Me and ELV-N34 Na or ELV-N34 Me on induction of pro-apoptotic protein Bim (e) in RPE under-UOS.

Figure 10F:
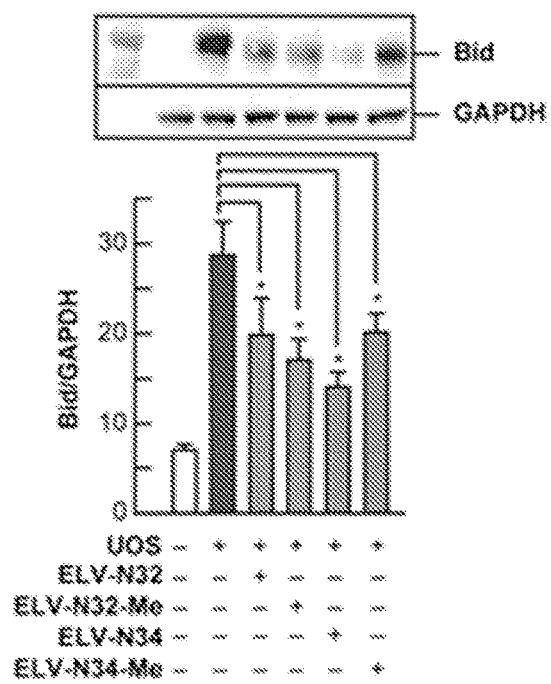

FIG. 10F illustrates a comparison of the effect of ELV-N32 Na or ELV-N32 Me and ELV-N34 Na or ELV-N34 Me on induction of pro-apoptotic protein Bid (f) in RPE under-UOS.

Figure 10G:
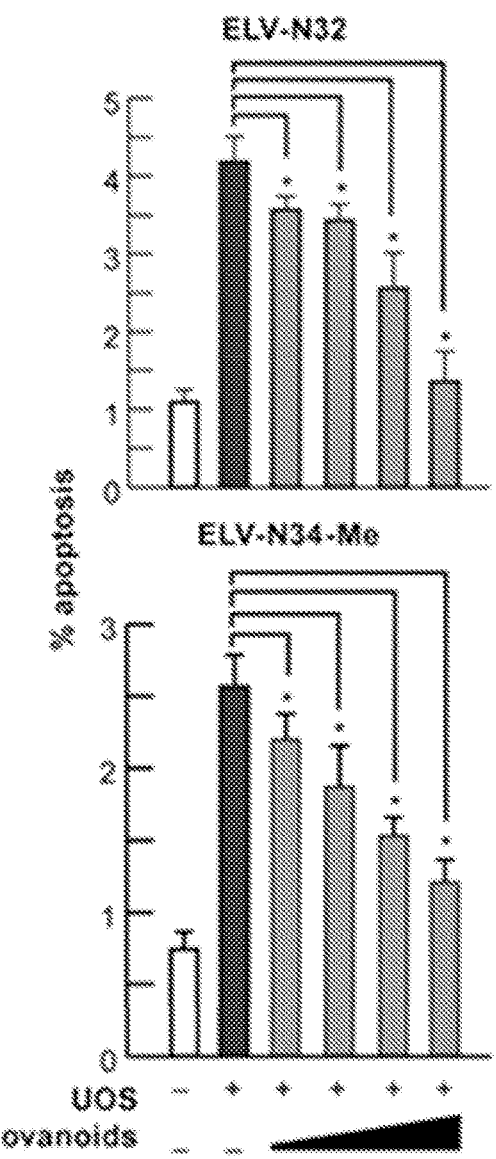

FIG. 10G illustrates the concentration-dependent (50, 100, 250, and 500 nM) reduction of UOS-induced apoptosis by ELV-N32 Na or ELV-N34 Me in ARPE-19 cells.

Figure 10H:
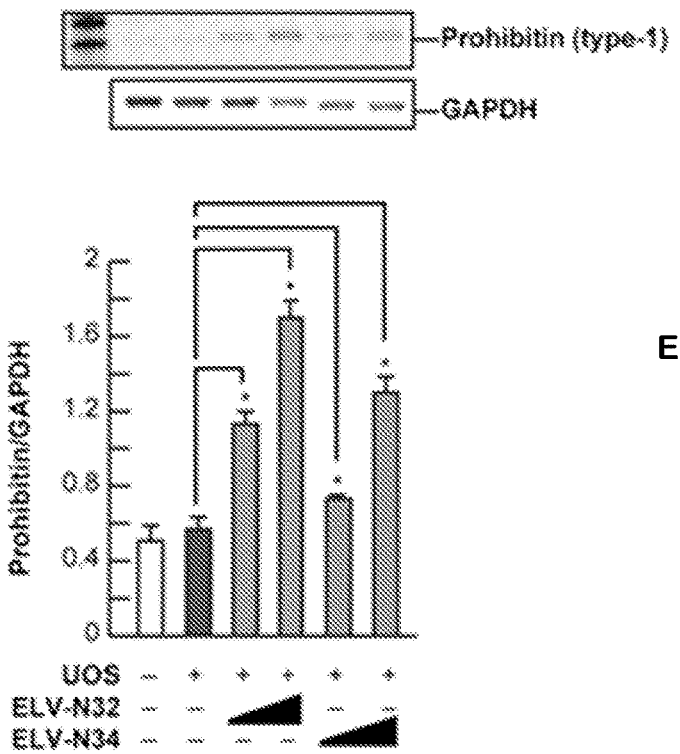

FIG. 10H illustrates the prohibitin (type-1) upregulation by ELV-N32 or ELV-N34 in ARPE-19 cells under UOS depends on concentration (100 and 250 nM). Error bars, SEM; * p<0.05.

FIGS. 11A-11D illustrate the genetic ablation of Adiponectin receptor 1 leads to depletion of VLC-PUFAs and of its derivatives in retina.

Figure 11A:
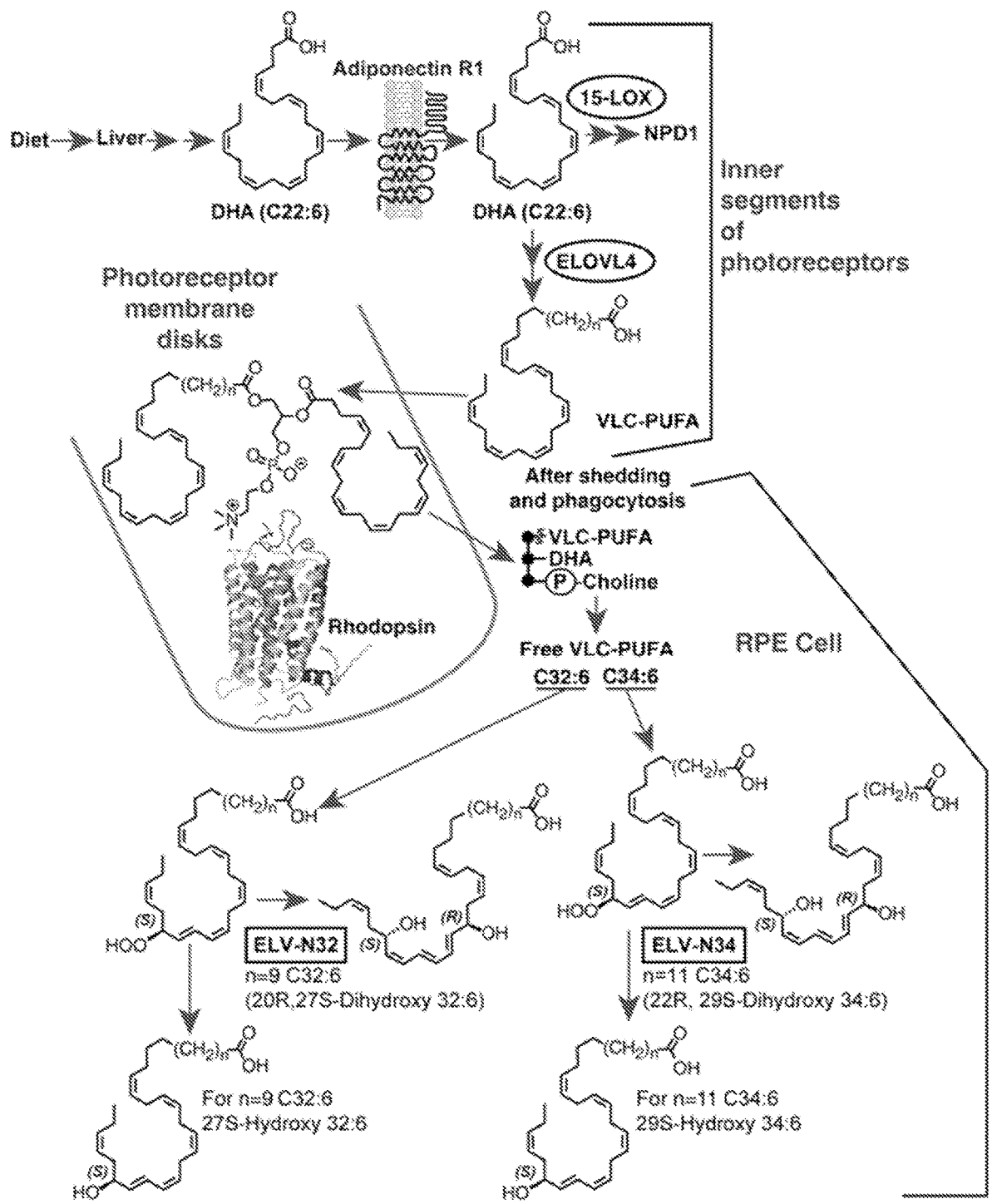

FIG. 11A illustrates the dietary DHA, or that derived from dietary 18:3n3, is supplied by the liver and captured by AdipoR1, followed by elongation in the inner segment of PRC by ELOVL4 to VLC-PUFA and incorporation into phosphatidylcholine molecular species, which also contains DHA. During daily PRC outer segment renewal these phosphatidylcholine molecular species interact with rhodopsin and, after shedding and phagocytosis, become part of RPE cells. UOS or other disruptors of homeostasis trigger the release of VLC-PUFAs. C32:6n3 and C34:6n3 are depicted generating hydroperoxy forms, and then ELV-N32 or ELV-N34, respectively.

Figure 11B:
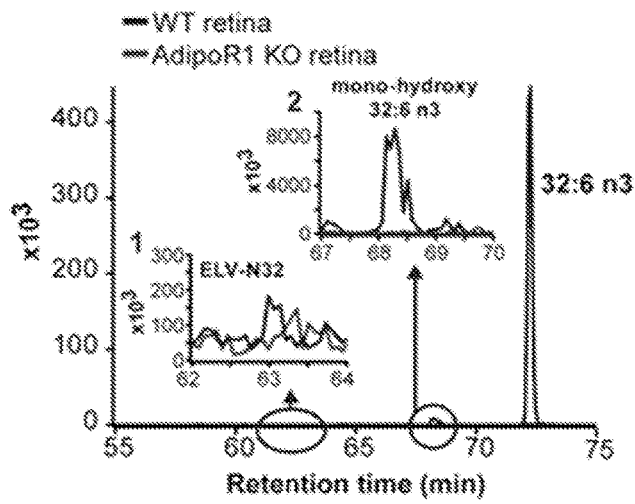

FIG. 11B illustrates the pool size of free C32:6n3 in retinas of AdipoR1 knockout (KO) mice is decreased as compared with that in WT. Insert 1 shows ELV-N32 in KO and wild type (WT); insert 2 shows mono-hydroxy 32:6n3, the stable derivative of the hydroperoxy precursor of ELV-N32, in WT and lack of detectable signal in the KO.

Figure 11C:
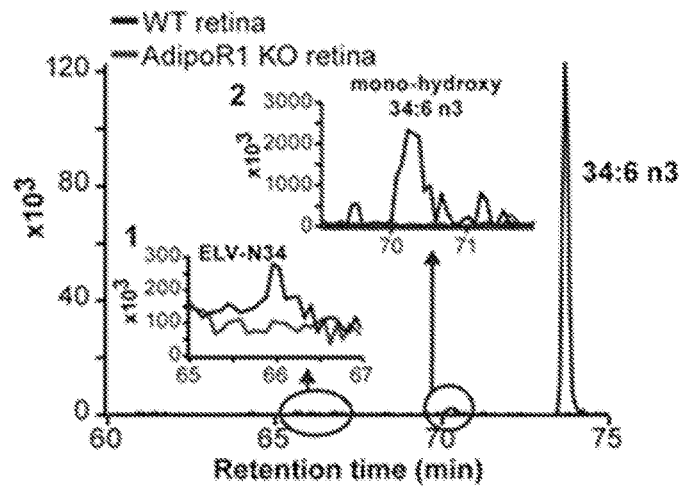

FIG. 11C illustrates the similar pool size of free 34:6n3 in retinas of AdipoR1 KO mice is decreased as compared with that in WT. Insert 1 shows ELV-N32 in KO and WT; insert 2 shows mono-hydroxy C34:6n3, the stable derivative of the hydroperoxy precursor of ELV-N34, in WT and lack of detectable signal in the KO.

Figure 11D:
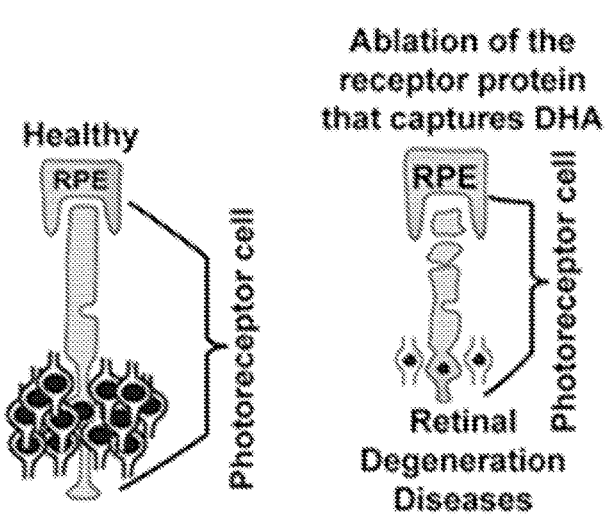

FIG. 11D illustrates that the RPE cells sustain PRC functional integrity (left); right, the ablation of Adiponectin receptor 1 (AdipoR1) switches off DHA availability, and PRC degeneration ensues.

Figure 12A:
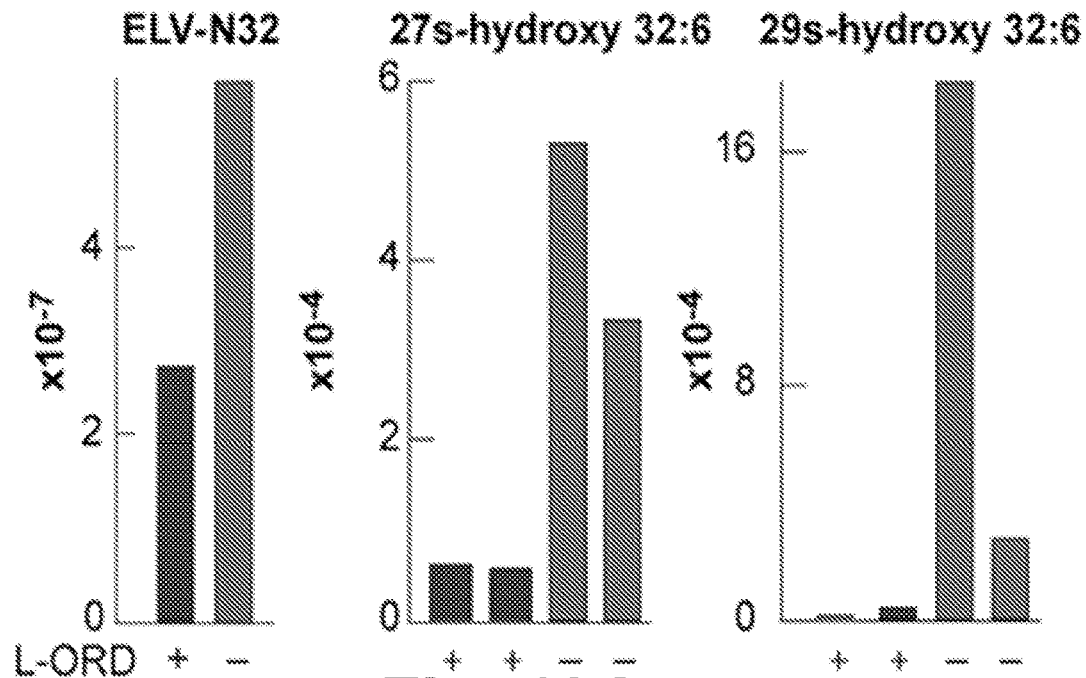
Figure 12B:
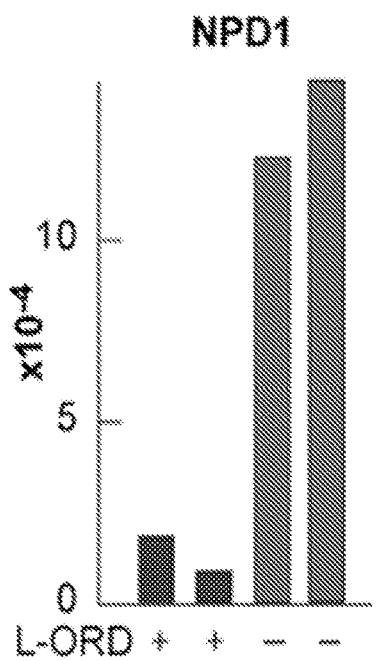

FIGS. 12A and 12B illustrate that the elovanoids of the disclosure play a role in neuroprotection and in sustaining photoreceptor cell integrity in retinal degenerations.

FIG. 12A illustrates that the elovanoid pathway is decreased in pluripotent stem cells iPSC-RPE derived from a family affected by Late-Onset Retinal Degeneration (L-ORD). This disease is due to a mutation (S163R) in CTRP5. pluripotent stem cells (iPSCs) differentiated into retinal pigment epithelial cell (RPE) from L-ORD patients and unaffected siblings were used. Cells were incubated in serum free media and fed approximately 5 photoreceptors outer segments (POS)/cell for 4 h to recapitulate shedding and disc phagocytosis or incubated with 1 μM 32:6 and 34:6 free fatty acids (VLC-PUFAs) for 24 h in 0.5% serum containing media. Media and cell lysate were collected for LC-MS/MS-based metabolipidomic analysis. Metabolipidomic analysis showed that iPSC-RPE fed POS or VLC-PUFAs secrete stable elovanoid biosynthetic intermediates (27s-hydroxy 32:6 n-3 and 29s-hydroxy 34:6 n-3) in a polarized manner, predominantly on the apical side of the cells. Control iPSC-RPE secrete significantly more of the elovanoids ELV-N32 and ELV-N34, compared to patients.

FIG. 12B illustrates that in the absence of POS or VLC-PUFAs 27s-hydroxy 32:6 n-3 was still detected in controls, but not patient iPSC-RPE. Also, DHA-derived lipid mediator, neuroprotectin D1 (NPD1) was found to be secreted significantly higher in controls (p<0.05). Because NPD1 and elovanoids are derived from the same phospholipid precursor, a deficit in both lipid mediators may take place in L-ORD.

FIGS. 13A-13D illustrate an in vitro model of Oxygen-Glucose Deprivation (OGD) in primary cortical neurons. Omega-3 VLC-PUFA and elovanoids are locally released in response to neuronal stress and provide protection of cortical neurons exposed to oxygen-glucose deprivation.

Figure 13A:
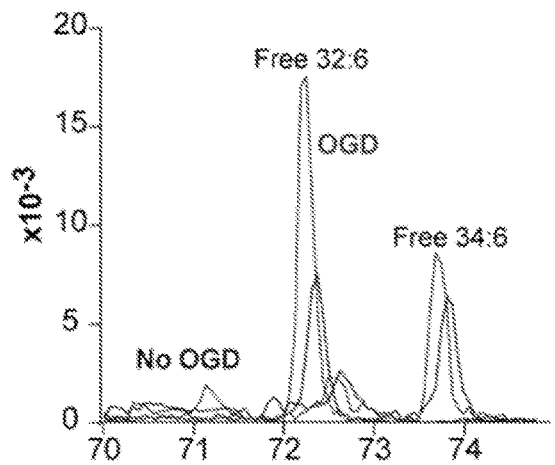

FIG. 13A illustrates that OGD medium has more free fatty acids (FA32:6 and FA34:6) released than the control (No OGD) medium.

Figure 13B:
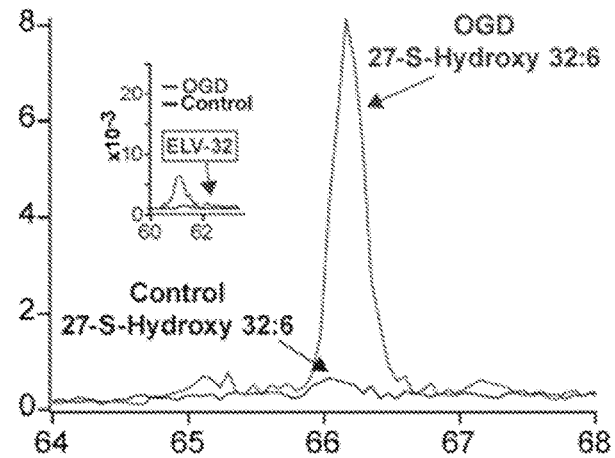

FIG. 13B illustrates that 27-S-hydroxy 32:6 is detected in OGD medium (red), but control medium has negligible amounts of 27-S-hydroxy 32:6 (blue). Daughter scans for ELV-N32 are shown (in the inset) representing ELV-N32 peak.

Figure 13C:
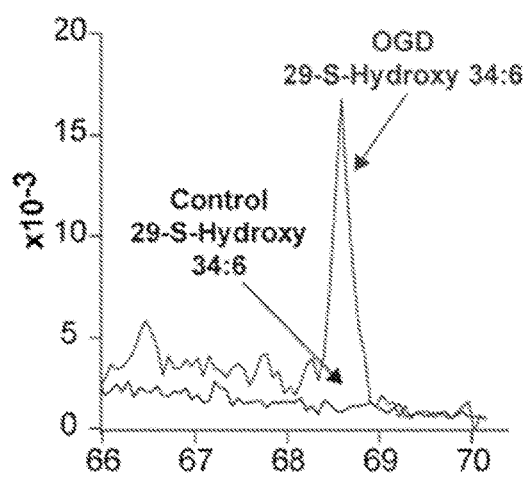

FIG. 13C illustrates that 29-S-hydroxy 34:6 is detected in OGD medium, but control medium has negligible amounts of 29-S-hydroxy 34:6.

Figure 13D:
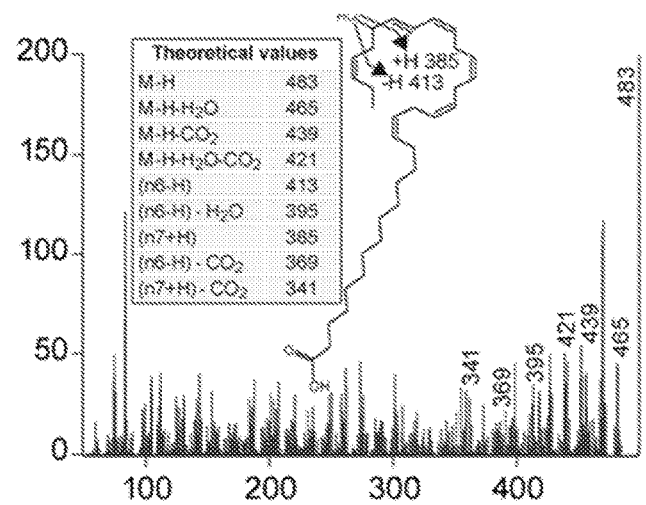

FIG. 13D illustrates the Full fragmentation pattern of 27-S-hydroxy 32:6 with theoretical values of daughter molecules which match very well.

Figure 14A:
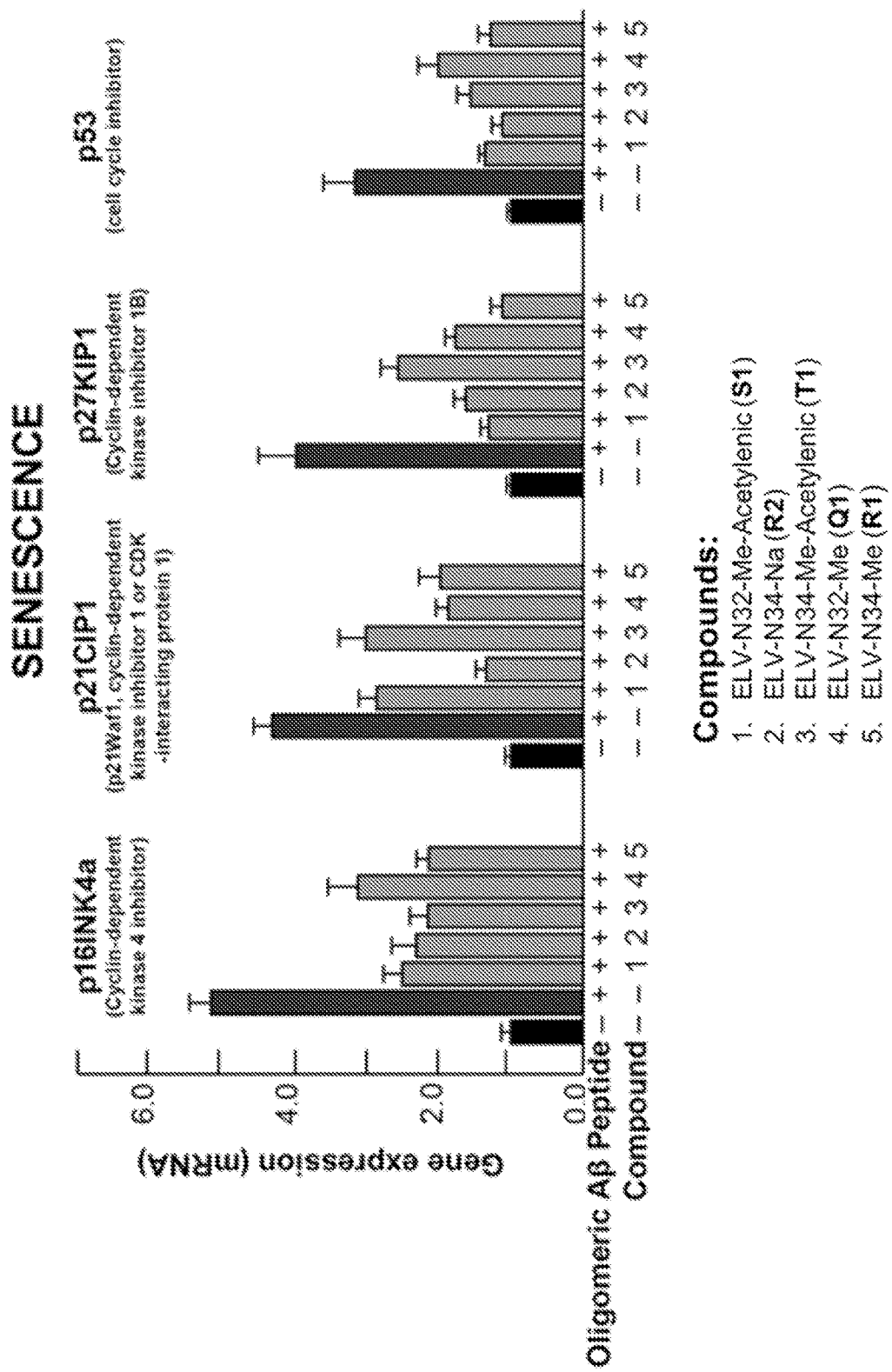
Figure 14B:
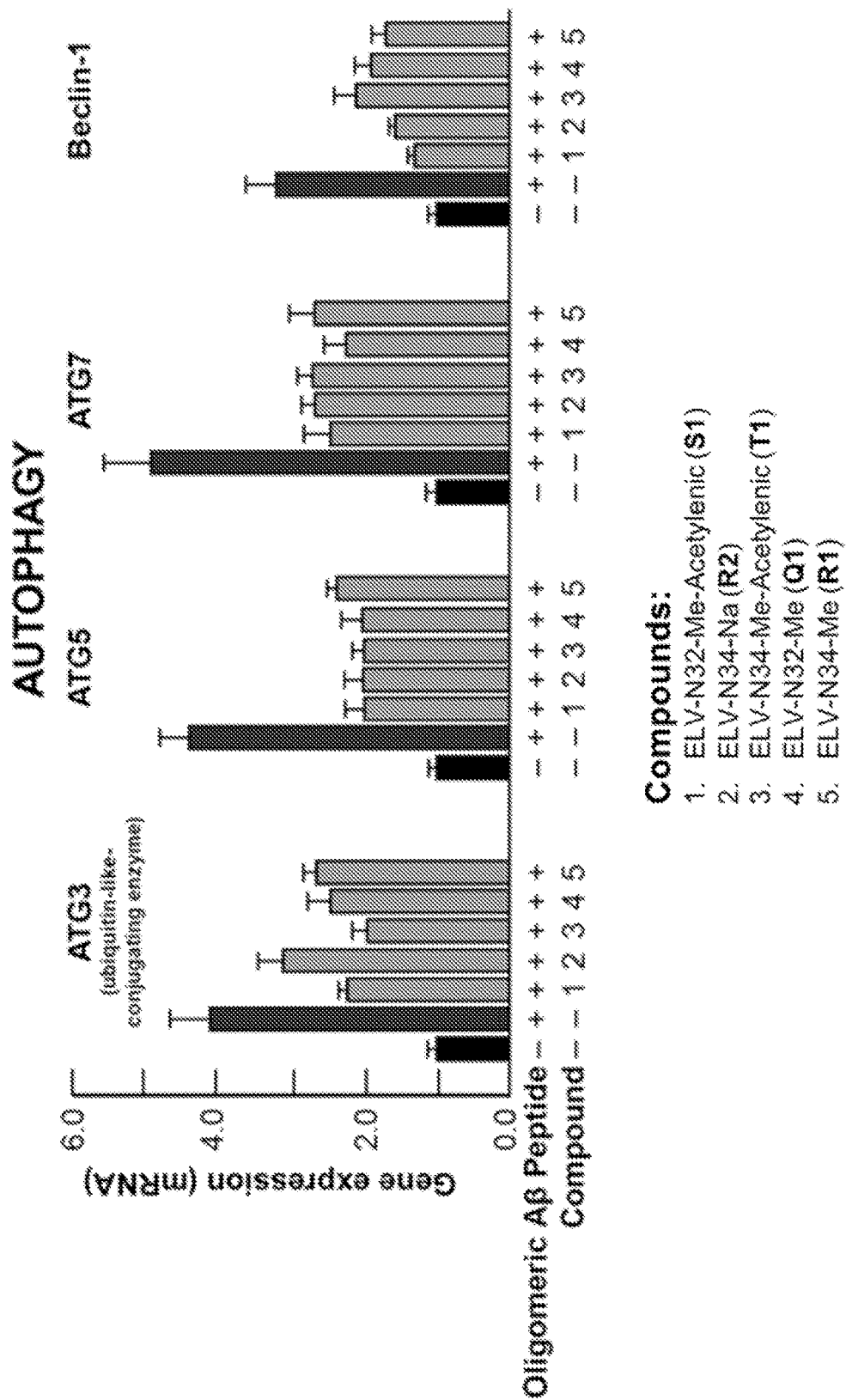
Figure 14C:
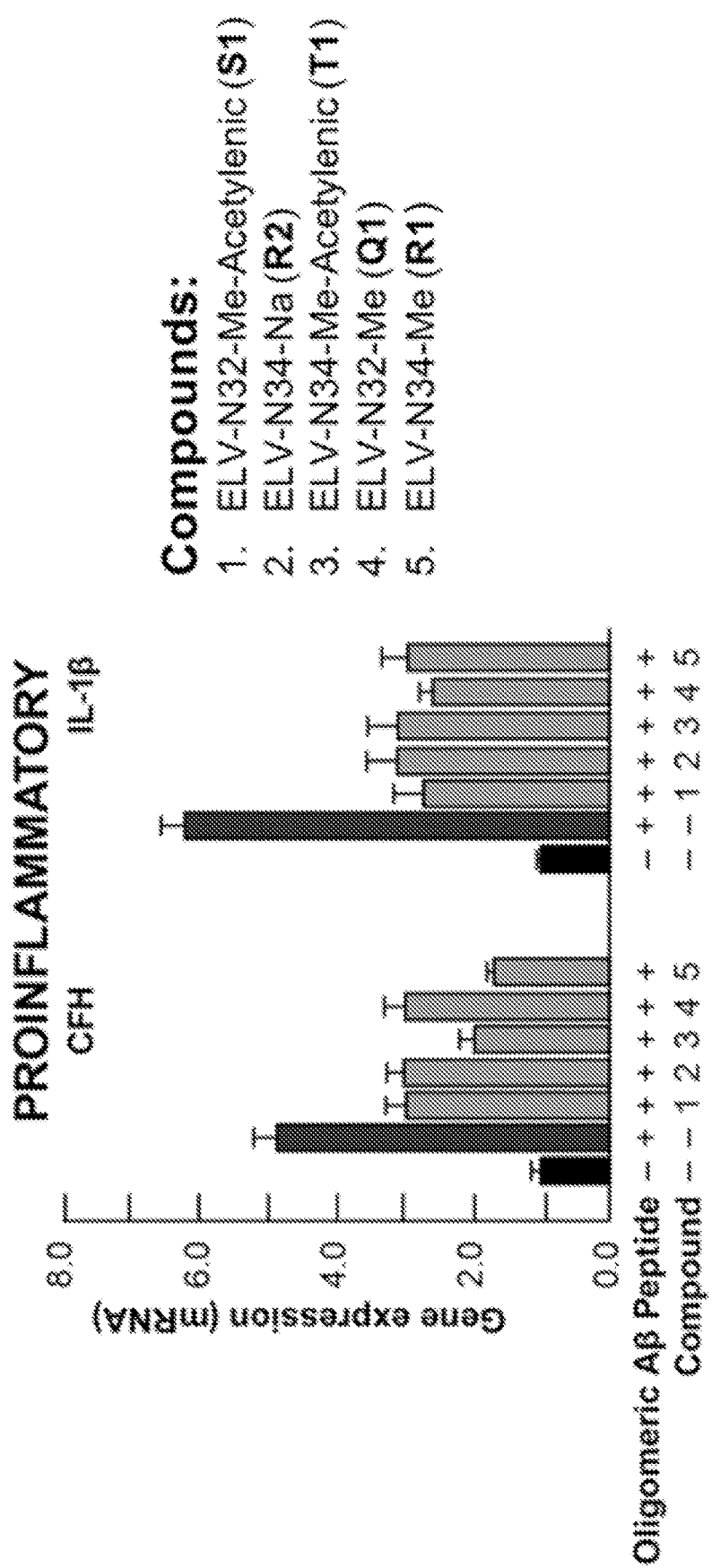

FIGS. 14A-14C illustrate that elovanoids suppress key factors that accelerate cell damage and cell death (cellular senescence), leading to the delay of age-related cell death and related diseases and conditions, resulting in the increase human life-span.

FIG. 14A illustrates that elovanoids suppress the activation of the senescence signaling pathways.

FIG. 14B illustrates that elovanoids activate autophagy by inducing the expression of autophagy factors (ATG3, ATG5, ATG7, Beclin-1), leading to autophagic clearance and removal of oligomeric Aβ peptide, thereby suppressing cell senescence progression. There are more than 100 genes involved in the autophagic process. The following genes are elevated in AMD disease:

FIG. 14C illustrates that elovanoids reduce the gene expression of pro-inflammatory factors (CHF, IL-1β) induced by oligomeric Aβ peptide.

FIGS. 15A-15L illustrate ELV-N32 and ELV-N34 elicit protection of cerebral cortical mixed neuronal culture exposed to oxygen glucose deprivation (OGD) or NMDA excitotoxicity.

Figure 15A:
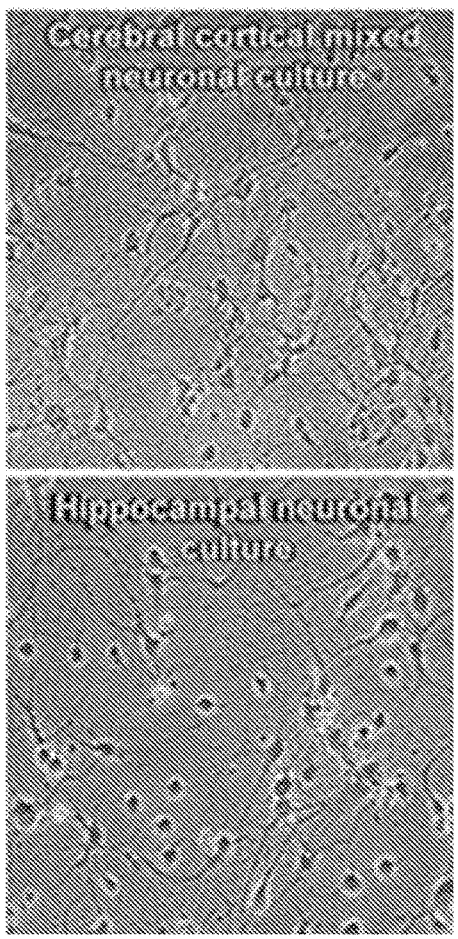

FIG. 15A illustrates bright field images (10×) of cerebral cortical and hippocampal neurons in culture showing morphology.

Figure 15B:
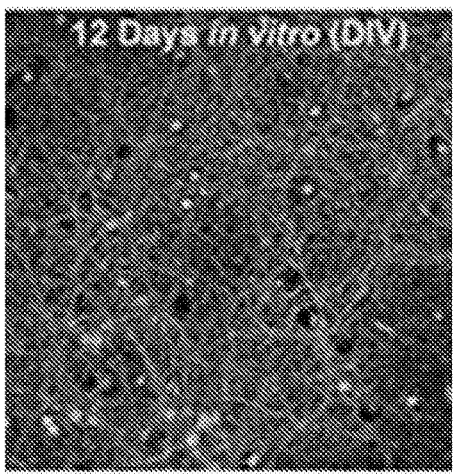

FIG. 15B illustrates representative immunofluorescent image of cerebral cortical neurons in culture 12 days in vitro (DIV12) stained for βIII tubulin, GFAP and Hoechst.

Figure 15C:
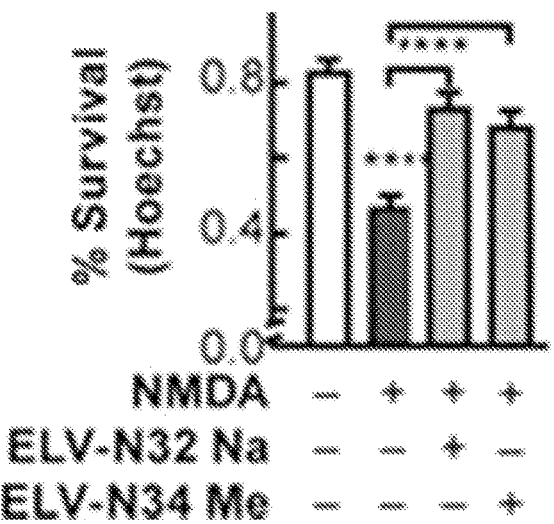
Figure 15D:
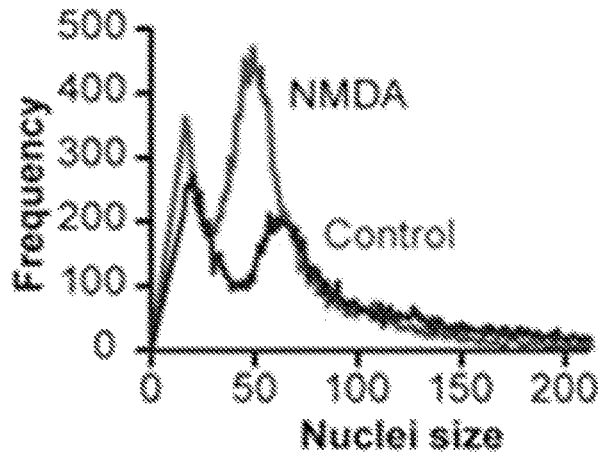
Figure 15E:
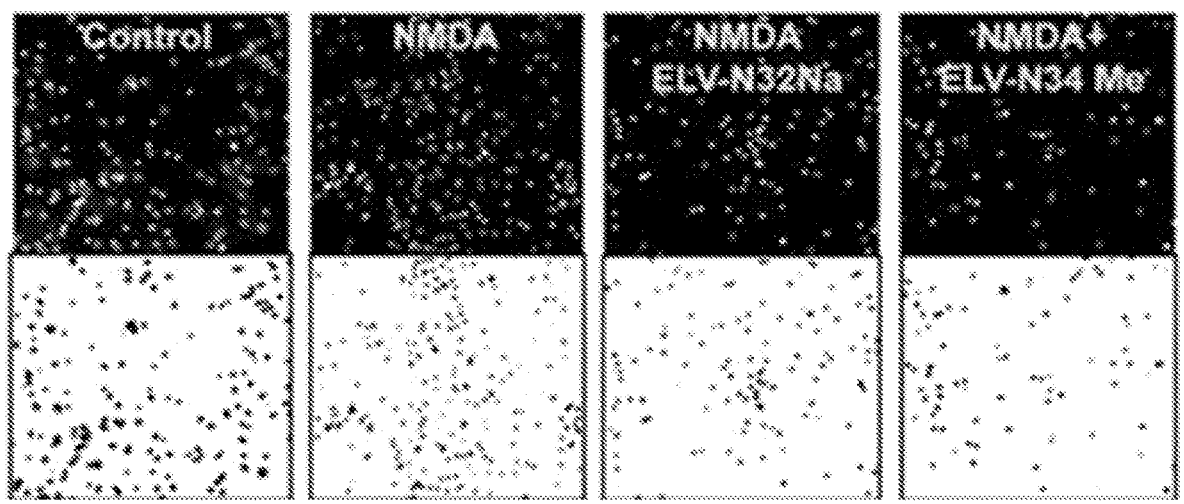
Figure 15F:
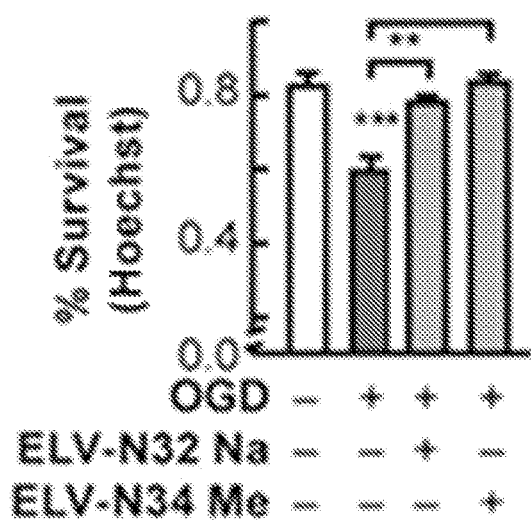

FIGS. 15C and 15F illustrate cerebral cortical neurons exposed to either NMDA (50 μM) excitotoxicity (FIG. 15C) or OGD (FIG. 15F) and neuroprotection elicited by ELV-N32-Na or ELV-N34-Me at (500 nM) concentration as assessed by fixing and staining the cells with Hoechst 33258. (**$p<0.0001$, *$p<0.001$ and **$p<0.05$, n=9, one-way ANOVA, followed by Holm-Sidak's multiple comparisons test).

Figure 15G:
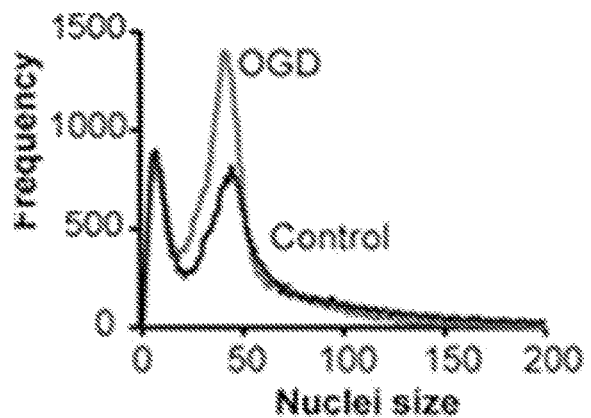

FIGS. 15D and 15G illustrate an unbiased image analysis method applied to count Hoechst positive nuclei and frequency distribution of pyknotic vs non-pyknotic nuclei in the presence of NMDA (FIG. 15D) or OGD (FIG. 15G) respectively.

Figure 15H:
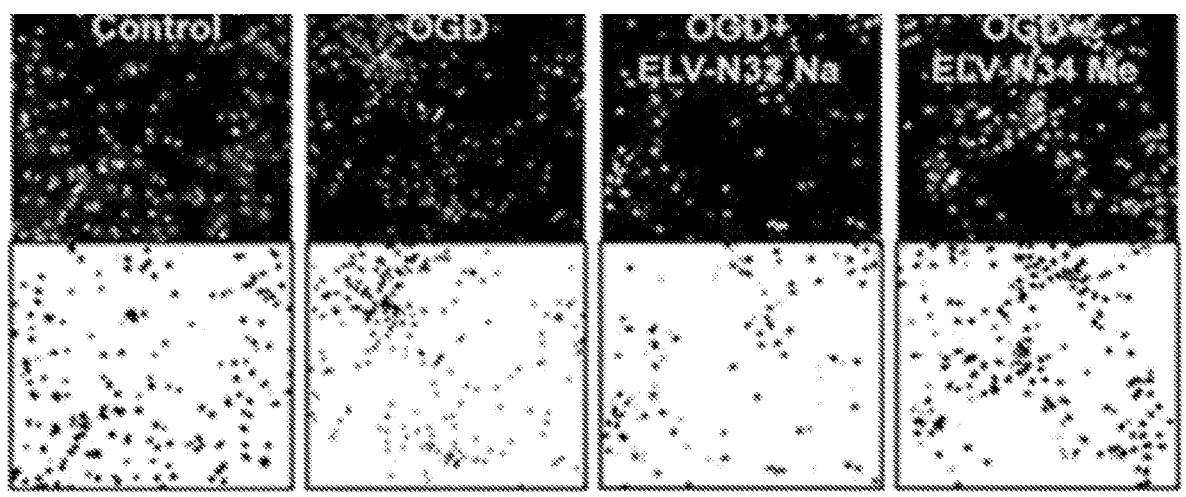
Figure 15I:
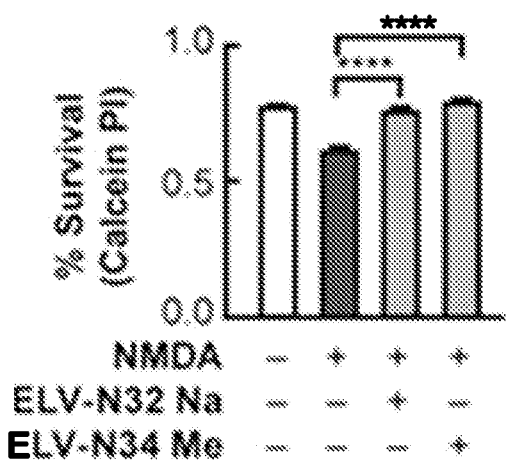

FIGS. 15E and 15H illustrate representative images showing thresholding and size exclusion of Hoechst positive nuclei being challenged by NMDA (FIG. 15E) or OGD stress (FIG. 15H) respectively.

Figure 15K:
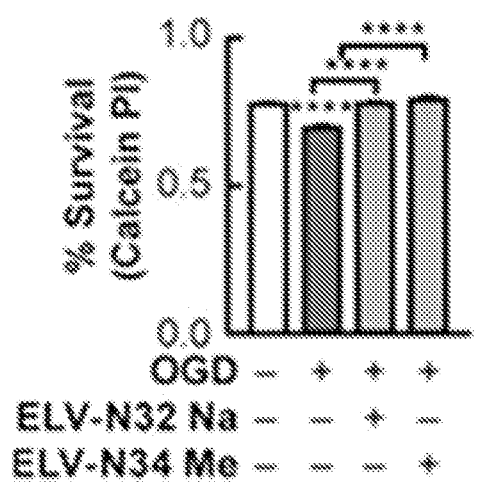
Figure 15J:
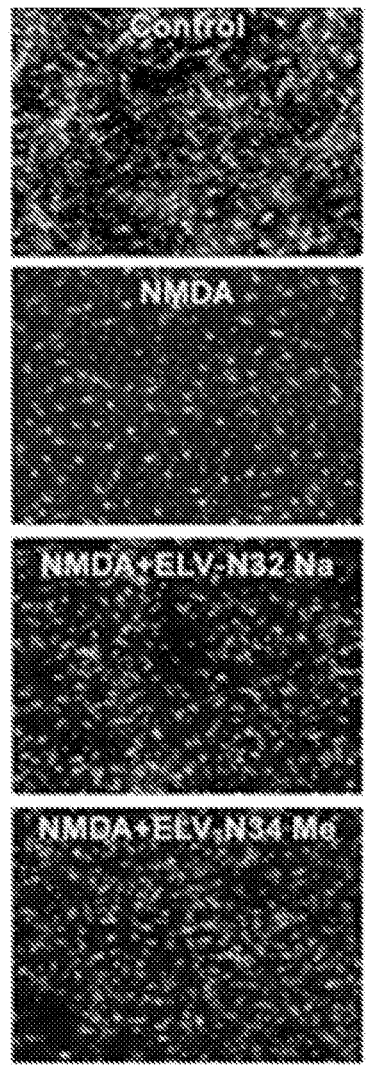
Figure 15L:
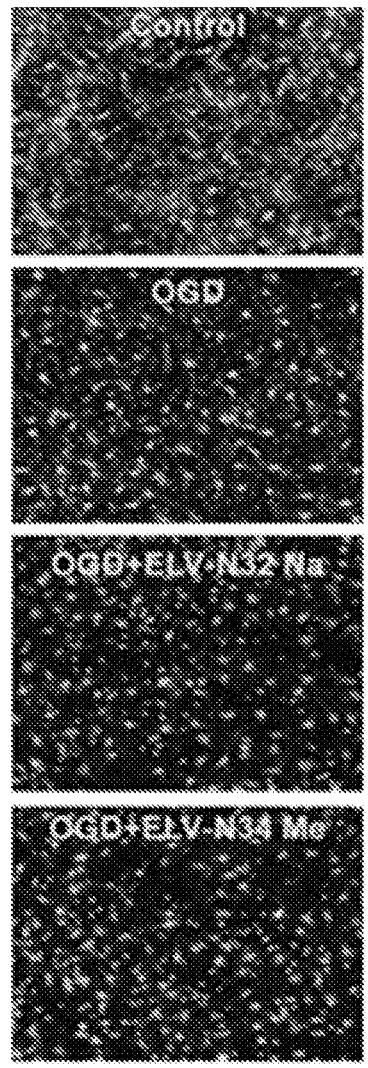

FIGS. 15I-15L illustrate neuroprotection elicited by ELV-N32-Na or ELV-N34-Me as assessed by Calcein-positive cell counting after exposure to NMDA (FIGS. 15I and 15J) or OGD (FIGS. 15K-15L).

FIGS. 16A-16I illustrate that ELV-N32 and ELV-N34 induce protection of cerebral cortical mixed and hippocampal neuronal cultures exposed to uncompensated oxidative stress, oxygen glucose deprivation (OGD) or NMDA excitotoxicity.

Figure 16A:
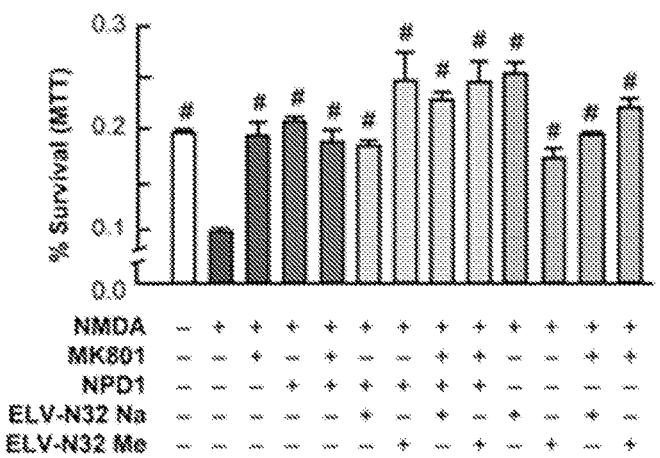

FIG. 16A illustrates cell survival as assessed by MTT assay after exposing cerebral cortical mixed neurons in culture to NMDA (100 μM) excitotoxicity in the presence of non-competitive NMDA receptor antagonist MK801 maleate (dizocilpine) (10 μM) or Neuroprotectin D1 (NPD1) (100 nM) or ELV-N32-Na (200 nM) or ELV-N32-Me (200 nM). (#$p<0.001$ n=6, one-way ANOVA, followed by Holm-Sidak's multiple comparisons test).

Figure 16B:
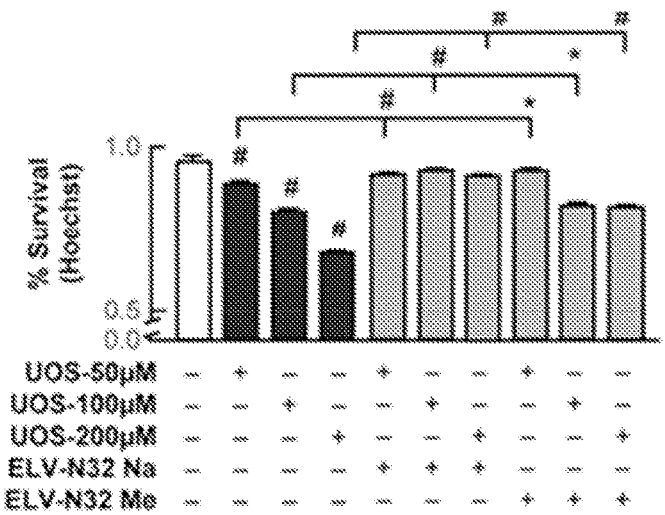
Figure 16C:
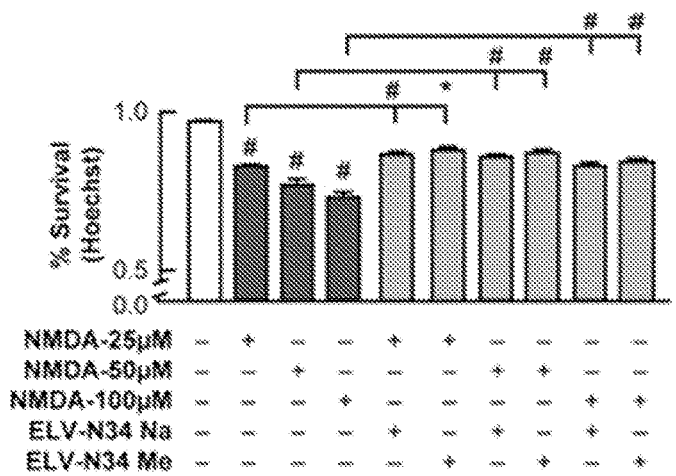

FIGS. 16B and 16C illustrate the neuroprotective effects of ELV-N32-Na or ELV-N32-Me at 200 nM concentration after exposure of cortical neurons to either uncompensated oxidative stress by TNFα (10 ng/mL) plus $H_2O_2$ (50 μM, 100 μM or 200 μM) (FIG. 16B) or NMDA excitotoxicity (25 μM, 50 μM or 100 μM) (FIG. 16C) respectively. Cell survival was assessed by unbiased image analysis and counting of Hoechst positive nuclei. (#$p<0.0001$, and *$p<0.05$, n=9, one-way ANOVA, followed by Holm-Sidak's multiple comparisons test).

Figure 16D:
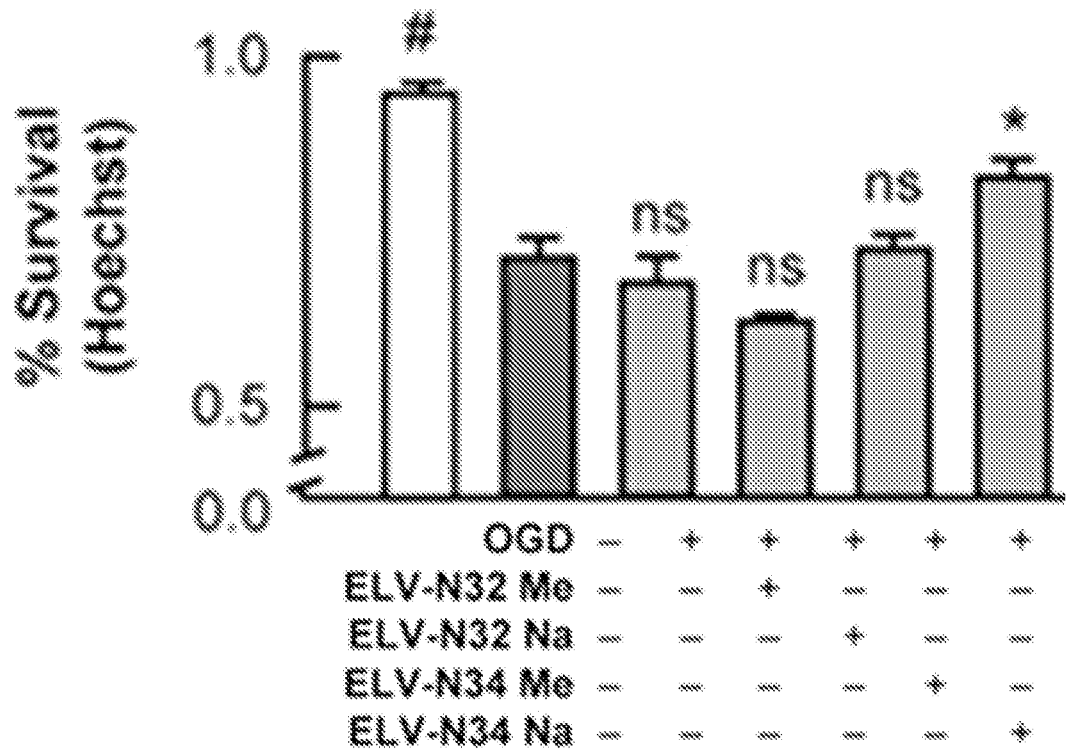
Figure 16E:
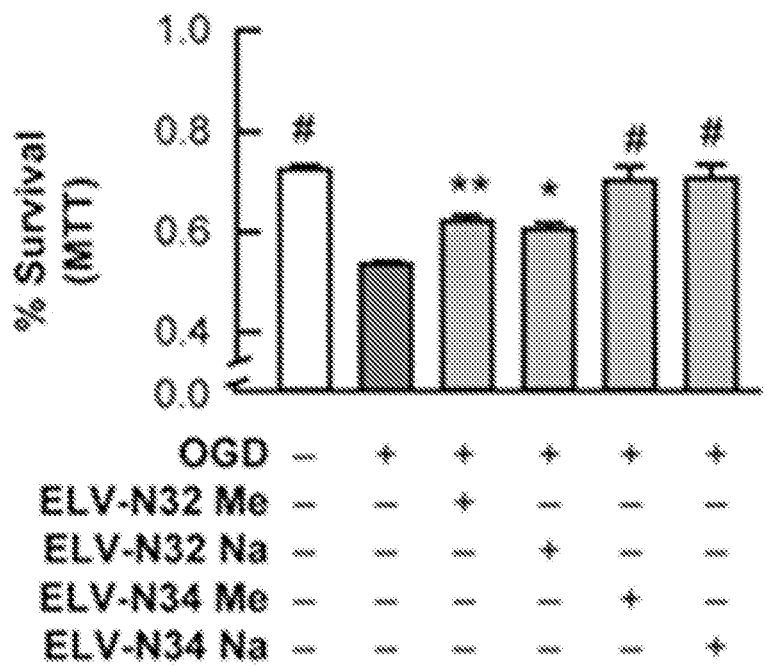

FIGS. 16D and 16E illustrate cell survival assessed by Hoechst staining (FIG. 16D) and MTT assay (FIG. 16E) after OGD exposure in the presence of ELV-N32-Na, ELV-N32-Me, ELV-N34-Na or ELV-N34-Me at 1 µM concentration. (#p<0.0001, **p<0.001, and *p<0.05, n=9, one-way ANOVA, followed by Holm-Sidak's multiple comparisons test).

Figure 16F:
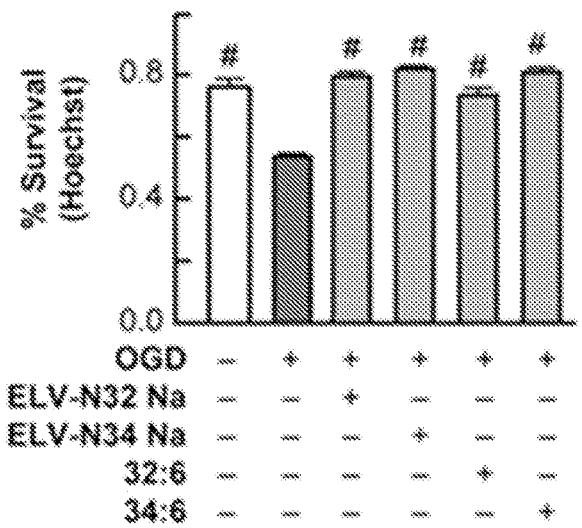
Figure 16G:
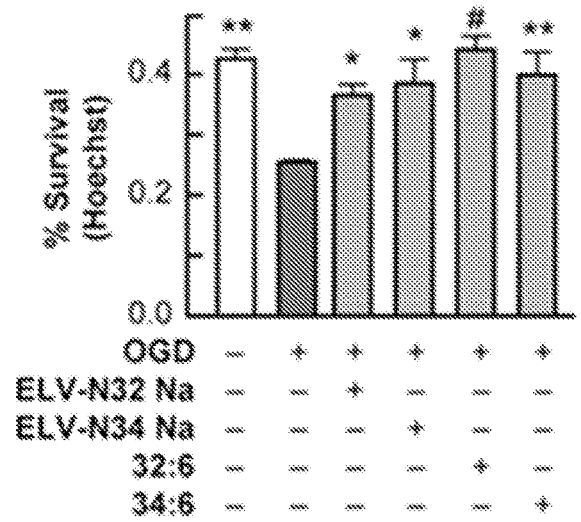

FIGS. 16F and 16G illustrate neuroprotection assessed in hippocampal neurons (DIV 12) (FIG. 16F) or cortical neurons in culture (DIV12) (FIG. 16G) after OGD stress in the presence or absence of ELV-N32-Na or ELV-N34-Me at (500 nM) concentration by Hoechst-positive cell counting. 32:6 or 34:6 when added at (500 nM) concentration also showed neuroprotection.

Figure 16H:
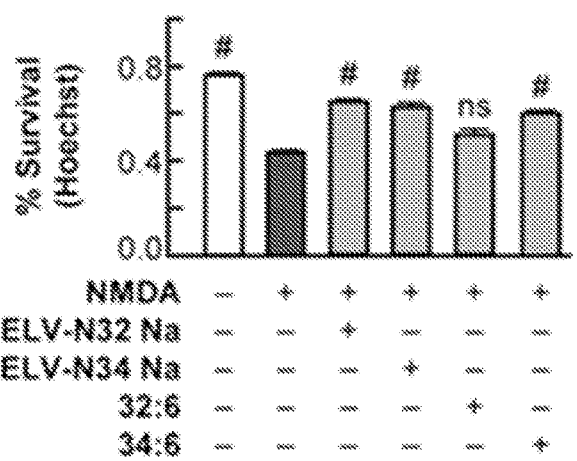
Figure 16I:
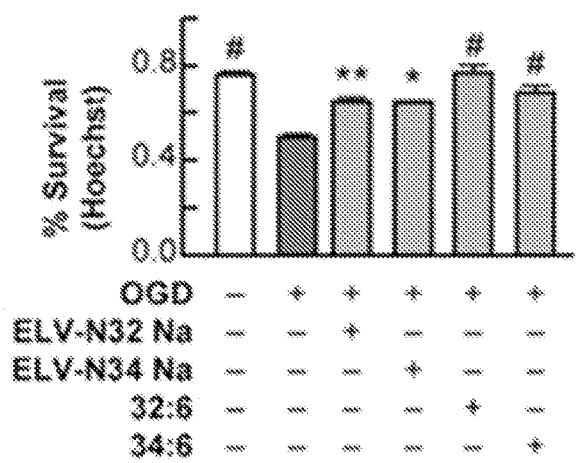

FIGS. 16H and 16I illustrate cerebral cortical mixed neurons in culture (DIV 28) exposed to either NMDA (50 µM) (FIG. 16H) or OGD (FIG. 16I) in the presence or absence of ELV-N32-Na or ELV-N34-Na or 32:6 or 34:6 (500 nM) assessed by Hoechst staining and cell counting.

Figure 17:
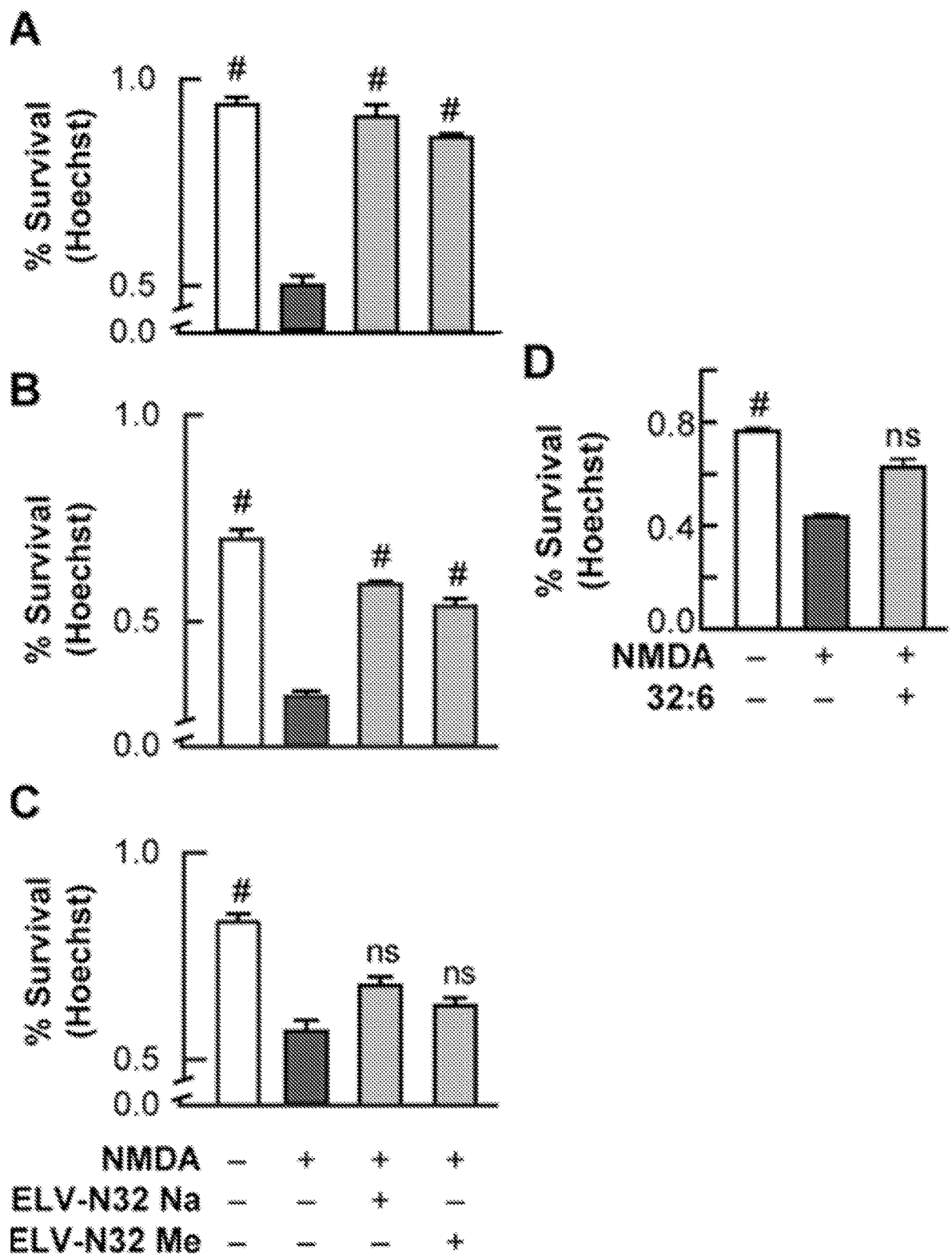

FIG. 17 illustrates cell survival assessed by Hoechst positive nuclei counting and unbiased image analysis after cortical neurons in culture (DIV 12) were exposed to NMDA (50 µM) (graphs A-C) or OGD (graphs E-G), respectively, in the presence of either ELV-N32-Na or ELV-N32-Me (500 nM). Results from three separate experiments. (#p<0.0001, **p<0.001 and *p<0.05, n=9, one-way ANOVA, followed by Holm-Sidak's multiple comparisons test).

32:6 (250 nM) could attenuate NMDA excitotoxicity (graph D) and 34:6 (250 nM) elicits neuroprotection to cortical neurons in culture (DIV 28) exposed to OGD (#p<0.0001, and **p<0.001) (graph H).

FIGS. 18A-18G and FIG. 18I illustrate that ELV-N32 and ELV-N34 elicit protection of cerebral cortical mixed neuronal or hippocampal mixed neuronal cultures exposed to oxygen glucose deprivation (OGD) or uncompensated oxidative stress (UOS).

Figure 18A:
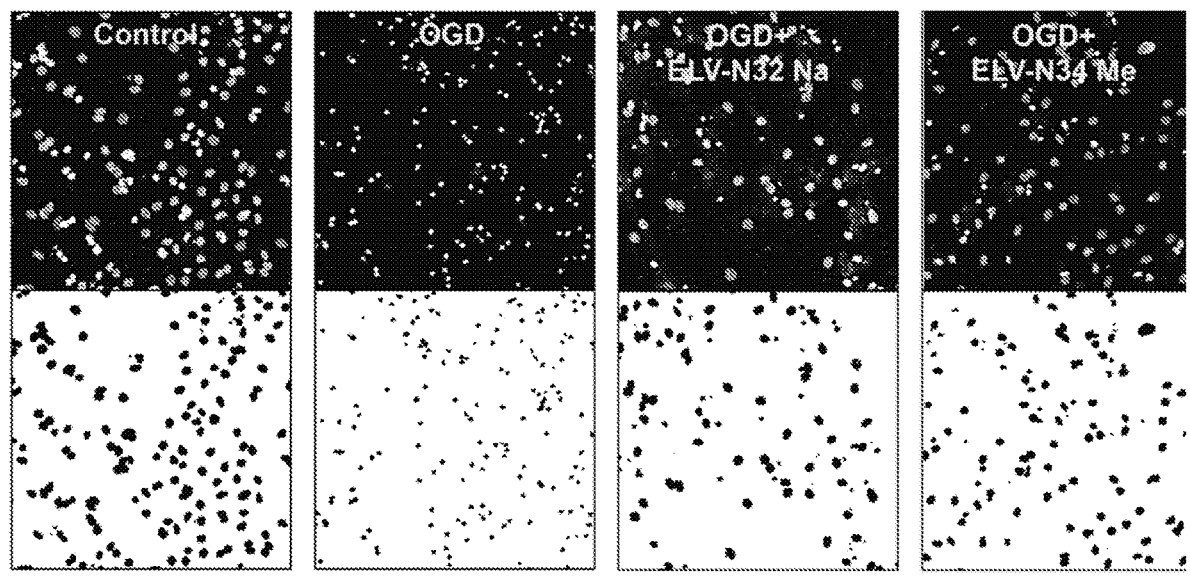

FIG. 18A illustrates representative images of cerebral cortical mixed neuronal cultures (DIV 12) challenged with 90 min OGD. The cells were fixed and stained with Hoechst 33258 after 12 h treatment with ELV-N32 Na or ELV-N34 Me at (500 nM) concentration, showing pyknosis as a result of OGD and neuroprotection elicited by ELV-N32 Na or ELV-N34 Me.

Figure 18B:
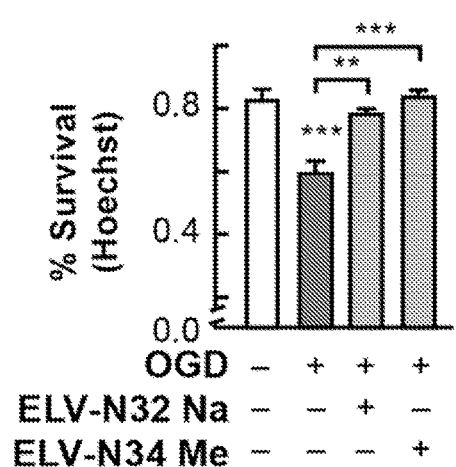

FIG. 18B illustrates a summary of data from FIG. 18A (*p<0.0001 and p<0.001, n=9, one-way ANOVA, followed by Holm-Sidak's multiple comparisons test).

Figure 18C:
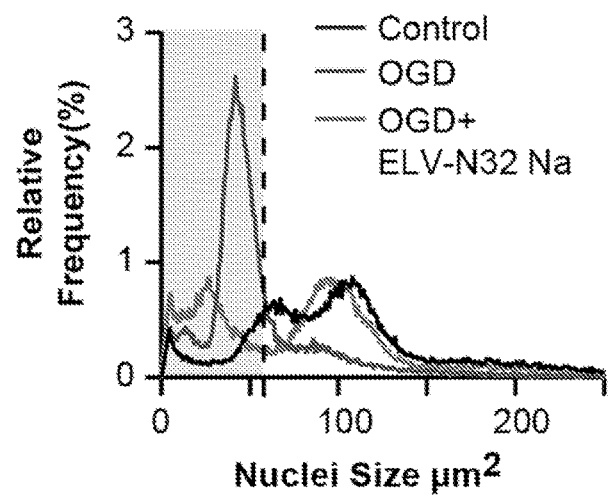
Figure 18D:
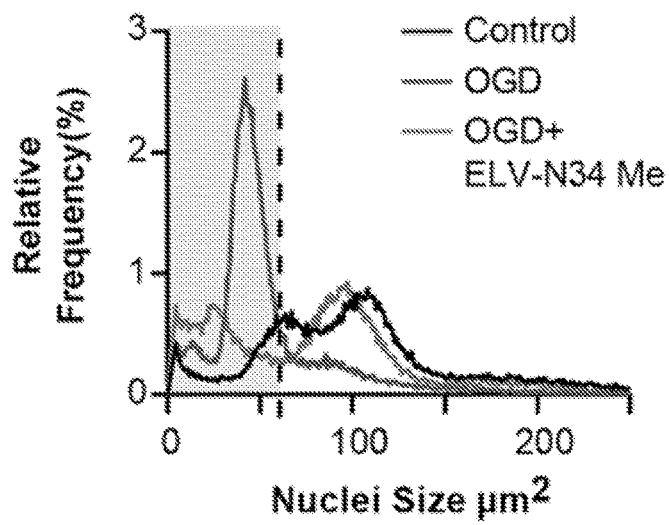

FIGS. 18C and 18D illustrate an unbiased image analysis method applied to count Hoechst-positive nuclei and % relative frequency distribution of pyknotic vs. non-pyknotic nuclei is shown in the presence of OGD+ELV-N32 Na (FIG. 18C) or OGD+ELV-N34 Me (FIG. 18D) respectively. When subjected to OGD stress, the cells underwent pyknosis, as shown by the leftward shift of the nuclear peak. Upon treatment with either ELV-N32 Na or ELV-N34 Me, there was a positive rightward shift towards the control nuclear population peak, indicating that cellular survival was elicited by these novel lipid mediators. The nuclear size cutoff for defining pyknotic vs non-pyknotic nuclei is represented by black dashed lines and highlighted by a rectangle.

Figure 18E:
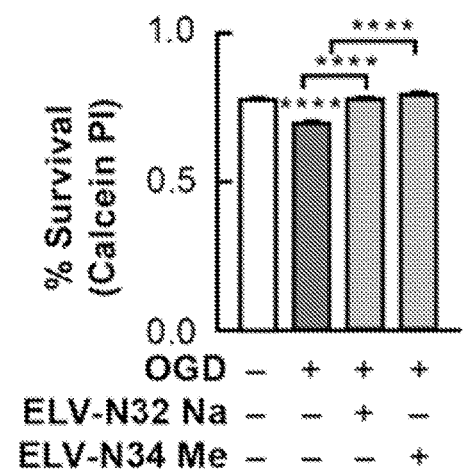

FIG. 18E illustrates neuroprotection elicited by ELV-N32 Na or ELV-N34 Me as assessed by Calcein-positive cell counting after exposure of cerebral cortical mixed neuronal cultures (DIV 12) challenged with 90 min OGD (****p<0.0001, n=3, one-way ANOVA, followed by Holm-Sidak's multiple comparisons test).

Figure 18F:
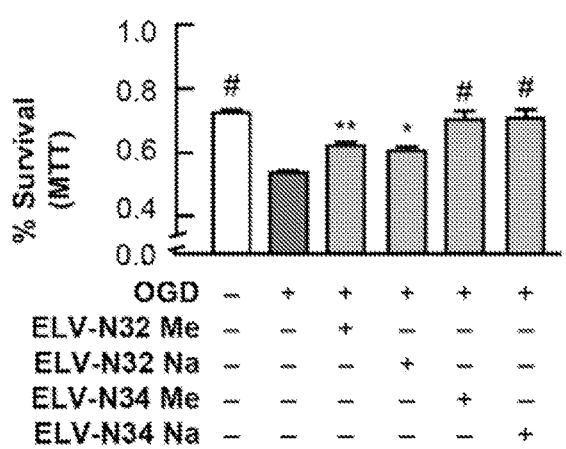

FIG. 18F illustrates cell survival as assessed by MTT assay after exposure of cerebral cortical mixed neuronal cultures (DIV 12) challenged with 90 min OGD followed by treatment with ELV-N32 Me, ELV-N32 Na, ELV-N34 Me or ELV-N34 Na at 1 µM concentration. (#p<0.0001, **p<0.001, and *p<0.05, n=9, one-way ANOVA, followed by Holm-Sidak's multiple comparisons test).

Figure 18G:
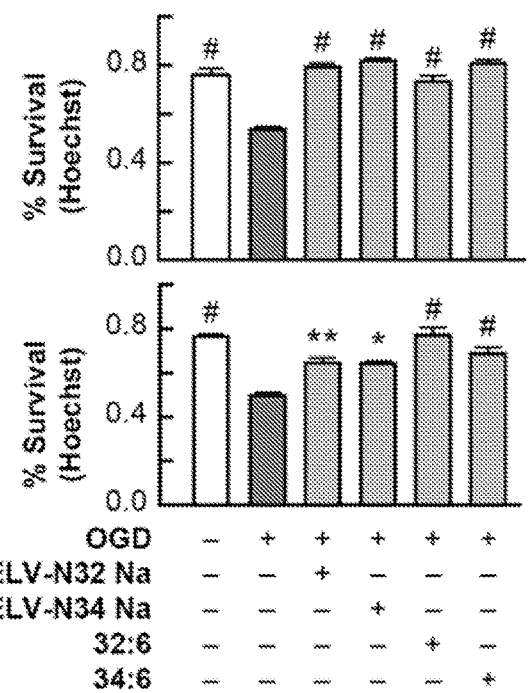

FIG. 18G illustrates neuroprotection elicited by ELV-N32 Na, ELV-N34 Na, 32:6 or 34:6 as assessed by an unbiased image analysis followed by Hoechst positive nuclei counting after a hippocampal mixed neuronal culture (DIV 12) is subjected to OGD stress in the presence or absence of ELV-N32 Na or ELV-N34 Me at (500 nM) concentration.

32:6 or 34:6 when added at (500 nM) concentration also showed neuroprotection (#p<0.0001, n=3 one-way ANOVA, followed by Holm-Sidak's multiple comparisons test) (FIG. 18G) or cortical mixed neuronal culture (DIV 28) (#p<0.0001, **p<0.001 and *p<0.05, n=3, one-way ANOVA, followed by Holm-Sidak's multiple comparisons test) (FIG. 18G) respectively were subjected to 90 min OGD.

Figure 18I:
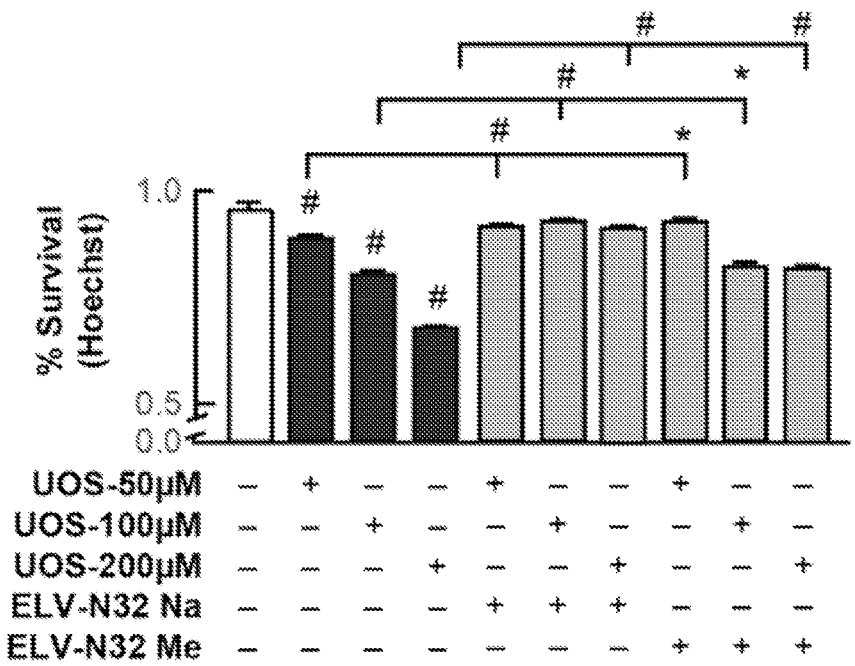

FIG. 18I illustrates neuroprotection elicited by ELV-N32 Na or ELV-N34 Na at 200 nM concentration as assessed by an unbiased image analysis following Hoechst positive nuclei counting after cortical mixed neuronal culture (DIV 12) were subjected to 12 h uncompensated oxidative stress (UOS) induced by the addition of addition of TNFα (10 ng/mL) and $H_2O_2$ (50 µM, 100 µM, or 200 µM) (#p<0.0001 and *p<0.001, n=9 one-way ANOVA, followed by Holm-Sidak's multiple comparisons test).

FIGS. 19A-19H illustrate ELV-N32 and ELV-N34 induced protection of cerebral cortical mixed neuronal cultures exposed to NMDA excitotoxicity.

Figure 19A:
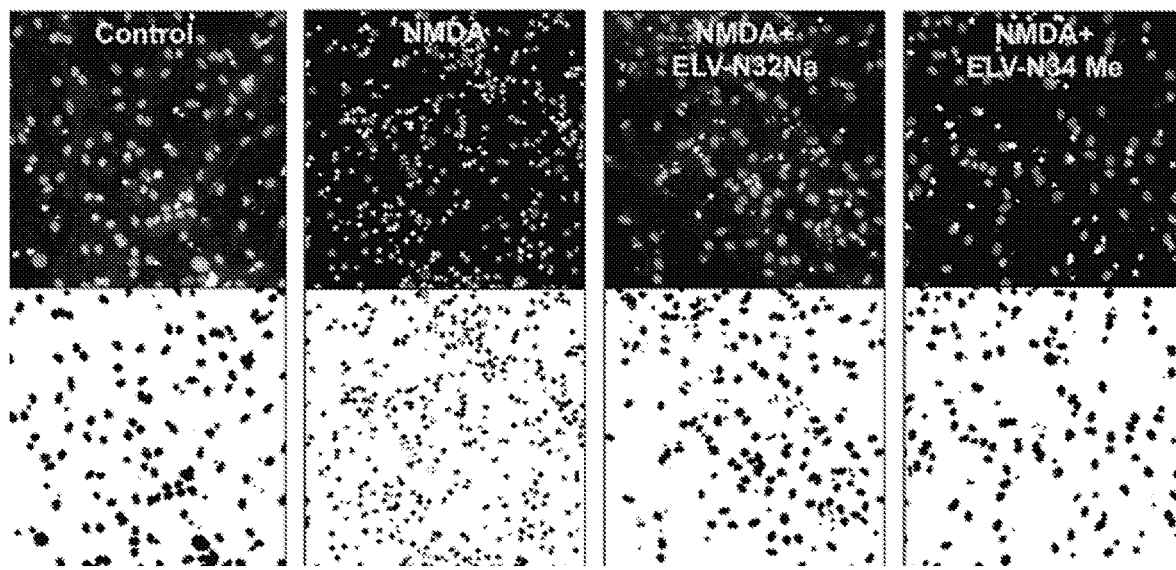

FIG. 19A illustrates representative images of cerebral cortical mixed neuronal cultures (DIV 12) subjected to 12 h NMDA excitotoxicity. The cells were fixed and stained with Hoechst 33258 after 12 h treatment with ELV-N32 Na or ELV-N34 Me at (500 nM) concentration along with NMDA (100 µM) concentration, showing pyknosis as a result of NMDA excitotoxicity and neuroprotection elicited by ELV-N32 Na or ELV-N34 Me.

Figure 19B:
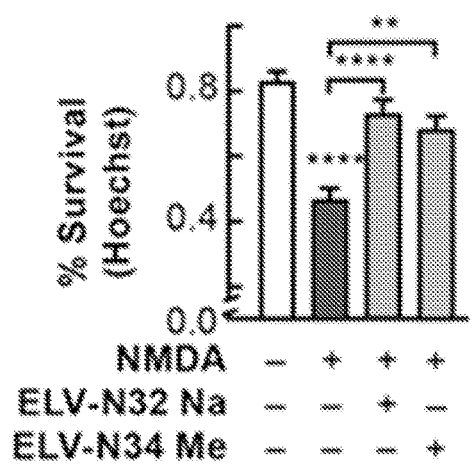

FIG. 19B illustrates summary of data from (FIG. 19A) (**p<0.0001 and p<0.05, n=9, one-way ANOVA, followed by Holm-Sidak's multiple comparisons test).

Figure 19C:
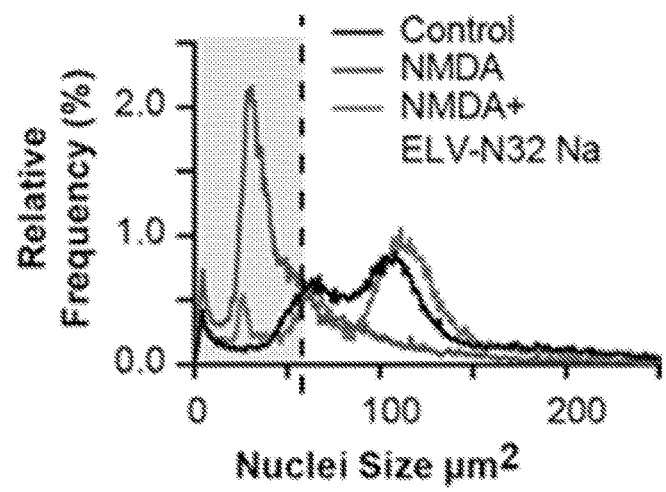
Figure 19D:
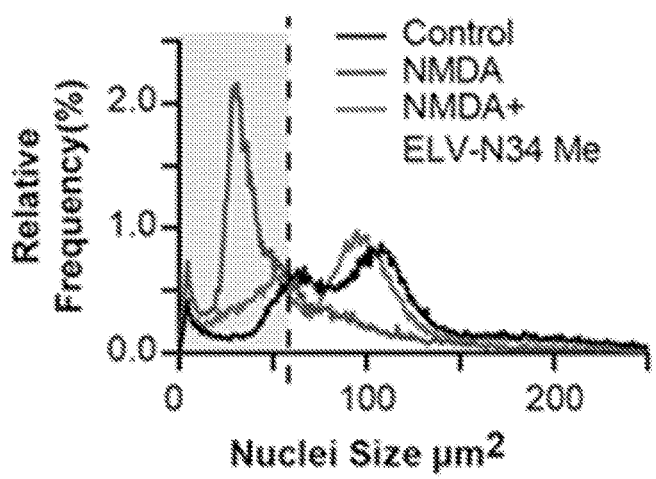

FIGS. 19C and 19D illustrate an unbiased image analysis method applied to count Hoechst-positive nuclei and % relative frequency distribution of pyknotic vs non-pyknotic nuclei in presence of NMDA+ELV-N32 Na (FIG. 19C) or NMDA+ELV-N34 Me (FIG. 19D) respectively. When the cells were subjected to NMDA excitotoxicity, they underwent pyknosis as shown by the leftward shift of the nuclear peak. Upon treatment with either ELV-N32 Na or ELV-N34 Me, there was a positive rightward shift towards the control nuclear population peak, indicating cellular survival elicited by these elovanoids. The nuclear size cutoff for defining pyknotic vs non-pyknotic nuclei is represented by dashed lines and highlighted by a rectangle.

Figure 19E:
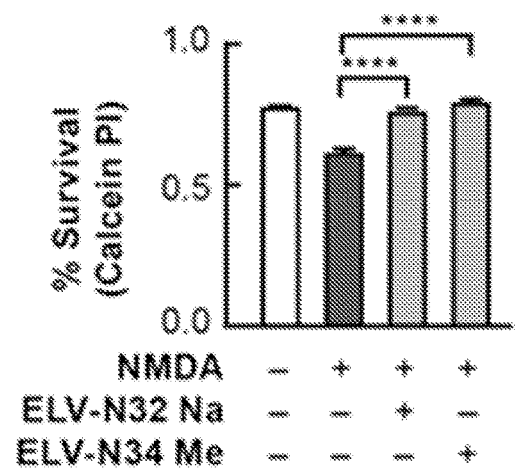

FIG. 19E illustrates neuroprotection elicited by ELV-N32 Na or ELV-N34 Me as assessed by Calcein-positive cell counting after exposure of cerebral cortical mixed neuronal cultures (DIV 12) challenged with 12 h NMDA (100 µM) concentration (****p<0.0001, n=3, one-way ANOVA, followed by Holm-Sidak's multiple comparisons test).

Figure 19F:
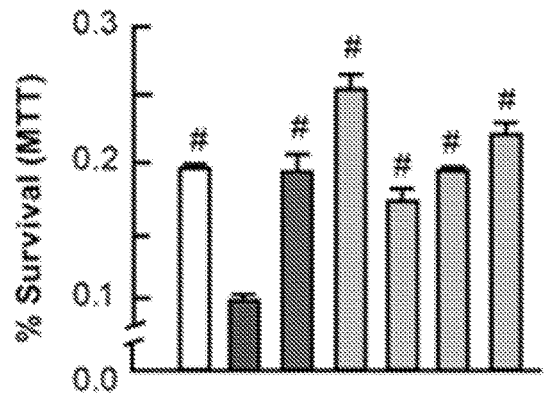

FIG. 19F illustrates cell survival as assessed by MTT assay after exposing cerebral cortical mixed neurons in culture (DIV 12) to NMDA (100 µM) excitotoxicity in the presence of non-competitive NMDA receptor antagonist MK801 maleate (dizocilpine) (10 µM) or ELV-N32 Na (200 nM) or ELV-N32 Me (200 nM). (#p<0.001 n=6, one-way ANOVA, followed by Holm-Sidak's multiple comparisons test).

Figure 19G:
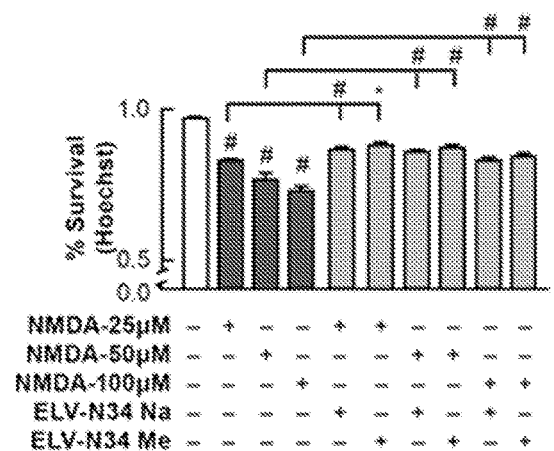

FIG. 19G illustrates neuroprotective effects of ELV-N32 Na or ELV-N32 Me at 200 nM concentration after exposure of cerebral cortical mixed neurons (DIV 12) to NMDA excitotoxicity (25 µM, 50 µM or 100 µM). Cell survival assessed by unbiased image analysis and counting of Hoechst positive nuclei. (#p<0.0001, and *p<0.05, n=9, one-way ANOVA, followed by Holm-Sidak's multiple comparisons test).

Figure 19H:
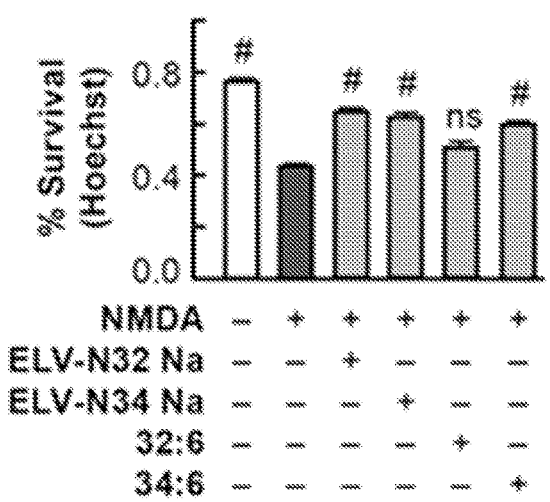

FIG. 19H illustrates cerebral cortical mixed neurons in culture (DIV 28) exposed to NMDA (50 µM) in the presence or absence of ELV-N32 Na or ELV-N34 Na or 32:6 or 34:6 (500 nM) assessed by Hoechst staining and cell counting. (#p<0.0001, n=3, one-way ANOVA, followed by Holm-Sidak's multiple comparisons test).

FIGS. 20A-20D illustrate that. ELV-N32 and ELV-N34 improve neurological/behavioral score, protect the penumbra and reduce MRI lesion volumes after ischemic stroke.

Figure 20A:
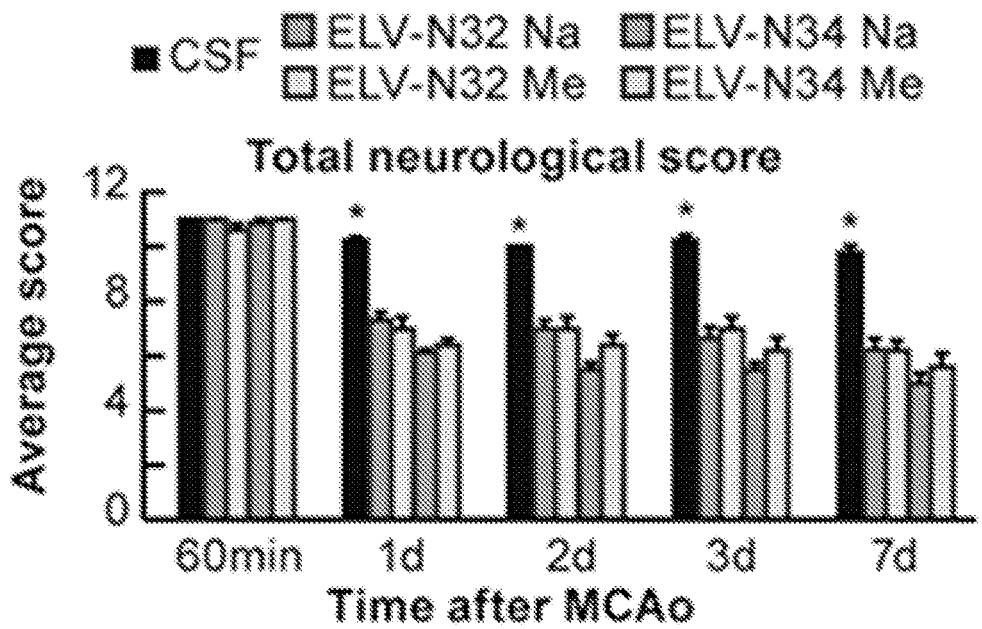

FIG. 20A illustrates the total neurological score (normal score=0, maximal score=12) during MCAo (60 min) and at various times after treatment. At 60 min of MCAo, all animals had a score of 11 (of a possible 12). Elovanoid-treated rats had significantly improved neurological scores on day 1, 3 and 7 compared to the vehicle (cerebral spinal fluid; CSF)-treated group.

Figure 20B:
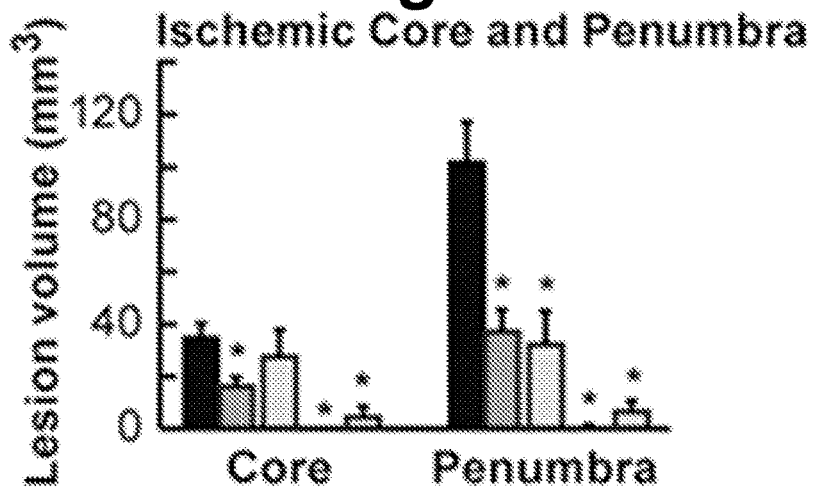
Figure 20B:
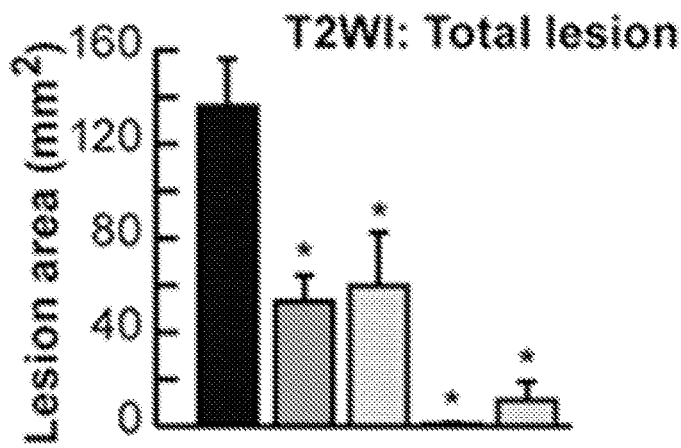

FIG. 20B illustrates the ischemic core, penumbra and total lesion volumes, computed from T2WI on day 7 were significantly reduced by elovanoid treatment compared to the vehicle group.

FIGS. 20C and 20D illustrate the representative T2WI, pseudo images, core/penumbra (FIG. 20C) and (FIG. 20D) 3D infarct volumes computed from T2WI on day 7. Core and penumbra were extracted from the entire brain. Core and penumbral) tissues were automatically identified in vehicle- and elovanoid-treated animals using the computational MRI method Hierarchal Region Splitting for penumbra identification. T2 hyperintensities were observed in the ischemic core and penumbra of vehicle-treated rats, consistent with edema formation. In contrast, elovanoid-treated animals had smaller lesion sizes. 3D-reconstructions are from the same animal in each group on day 7. Values shown are means±SD (n=5-6 per group). *p<0.05, versus CSF group (repeated measures ANOVA followed by Bonferroni tests).

Figure 21A:
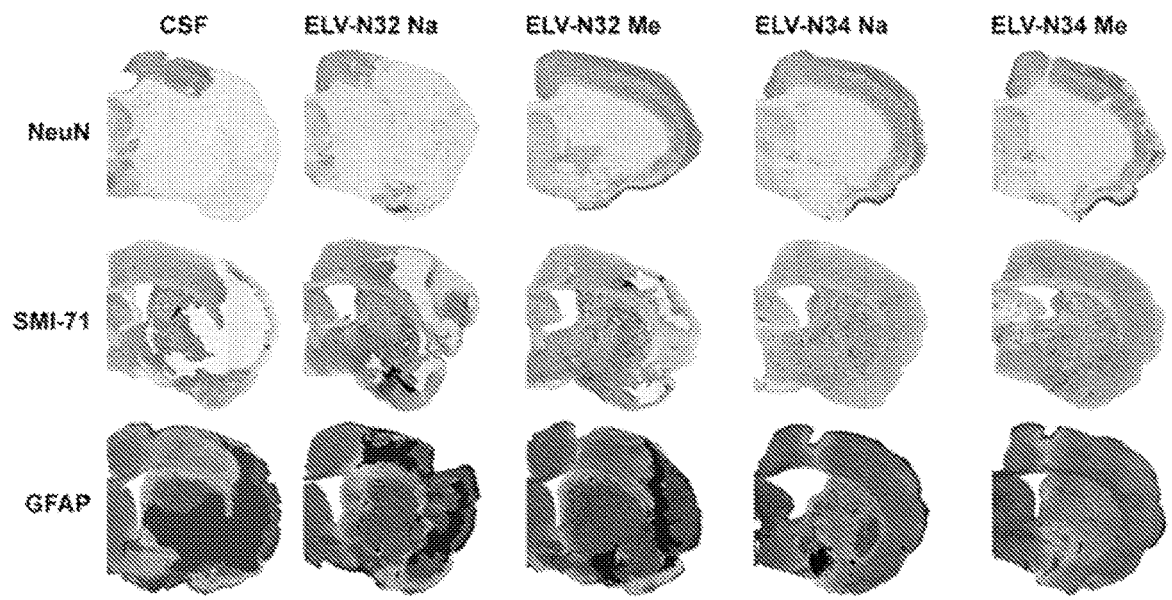

FIGS. 21A 20C illustrate ELV-N32 and ELV-N34 attenuate experimental ischemic stroke-induced neuronal and astrocyte cellular damage.

Figure 21B:
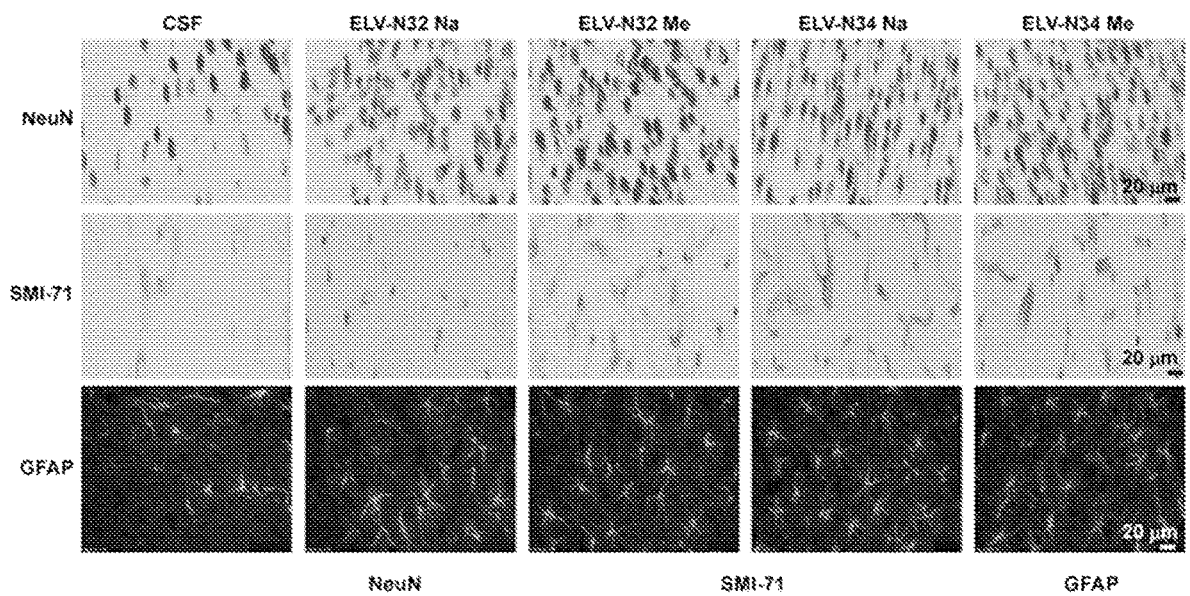

FIGS. 21A and 21B illustrate representative NeuN, SMI-71 and GFAP stained brain sections from all groups. Vehicle (cerebral spinal fluid; CSF)-treated rats showed extensive neuronal loss, reduction of GFAP reactive astrocytes and SMI-71 positive vessels. In contrast, treatment with elovanoids increased NeuN-, SMI-71- and GFAP-positive cells.

Figure 21C:
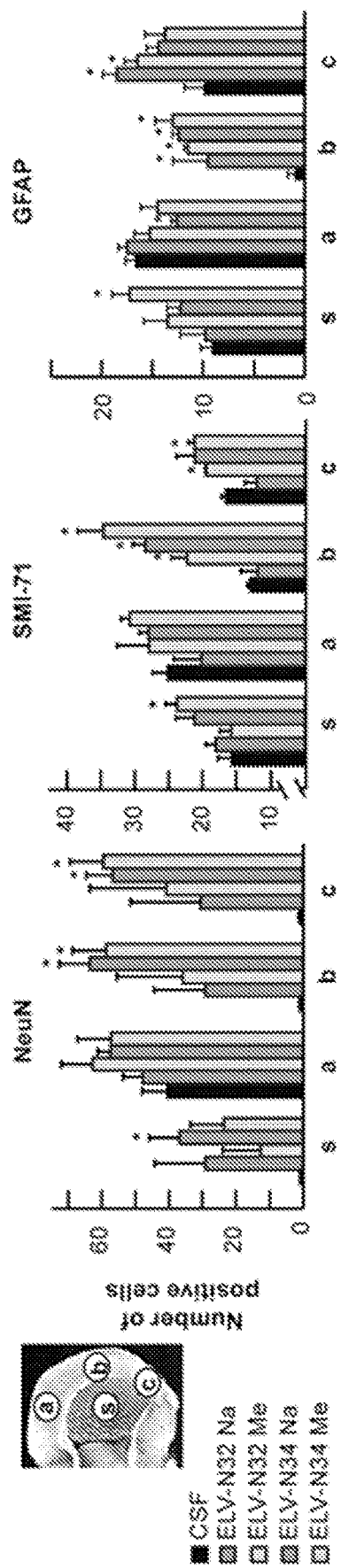

FIG. 21C illustrates coronal brain diagram (bregma+1.2 mm) showing locations of regions for NeuN-, SMI-71- and GFAP-positive cell counts in the cortex (columns a, b and c) and striatum (column s). Numbers of NeuN-positive neurons, SMI-positive vessels and GFAP-positive astrocytes, increased by elovanoid treatment in the ischemic core (S) and different penumbral areas (a, b and c). Values shown are means±SD (n=5-6 per group). *, significantly different from vehicle (p<0.05; repeated-measures ANOVA followed by Bonferroni tests).

FIGS. 22A-22D illustrate ELV-N32 and ELV-N34 diminish NVU disruption and reduces brain infarction after ischemic stroke.

Figure 22A:
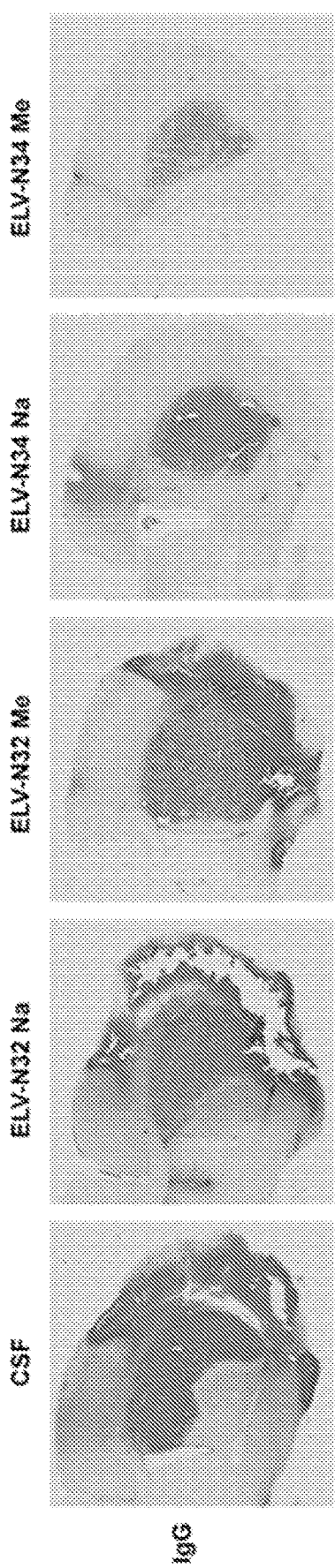

FIG. 22A illustrates NVU breakdown assessed by immunodetection of immunoglobulin G (IgG) within the parenchyma. IgG staining indicated NVU breakdown. Vehicle (cerebral spinal fluid; CSF)-treated rats displayed increased IgG immunoreactivity in the cortex and subcortex. Treatment with ELV-N34-Na or ELV-N34-Me showed less IgG staining in cortex and was mostly localized in the core of infarction (subcortex).

Figure 22B:
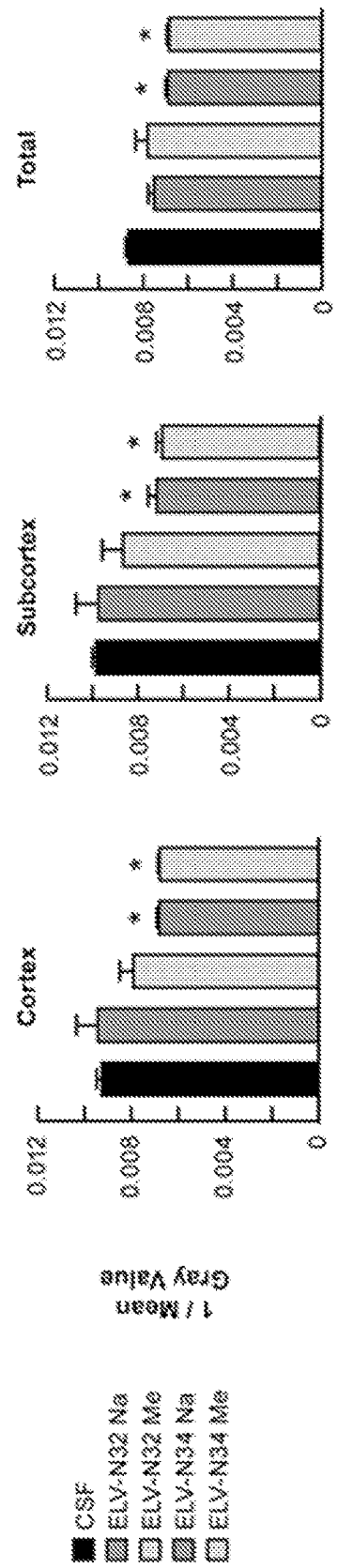

FIG. 22B illustrates bar graphs showing that ELV-N34-Na and ELV-N34-Me significantly reduced IgG immunoreactivity in cortex, subcortex and whole hemisphere (total). Values shown are means±SD (n=5-6 per group). *p<0.05, versus the vehicle group (repeated measures ANOVA followed by Bonferroni tests).

Figure 22C:
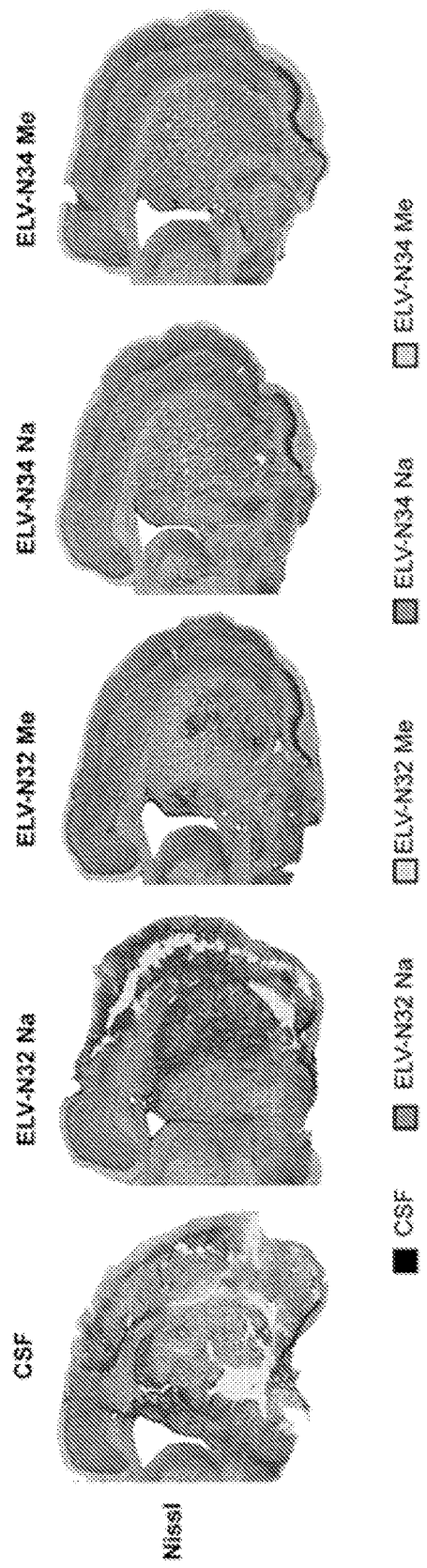

FIG. 22C illustrates Nissl stained brain sections from rats treated with vehicle and elovanoids. Vehicle-treated rat show large cortical and subcortical infarction. In contrast, rats treated with elovanoids show less extensive damage, mostly in the subcortical area.

Figure 22D:
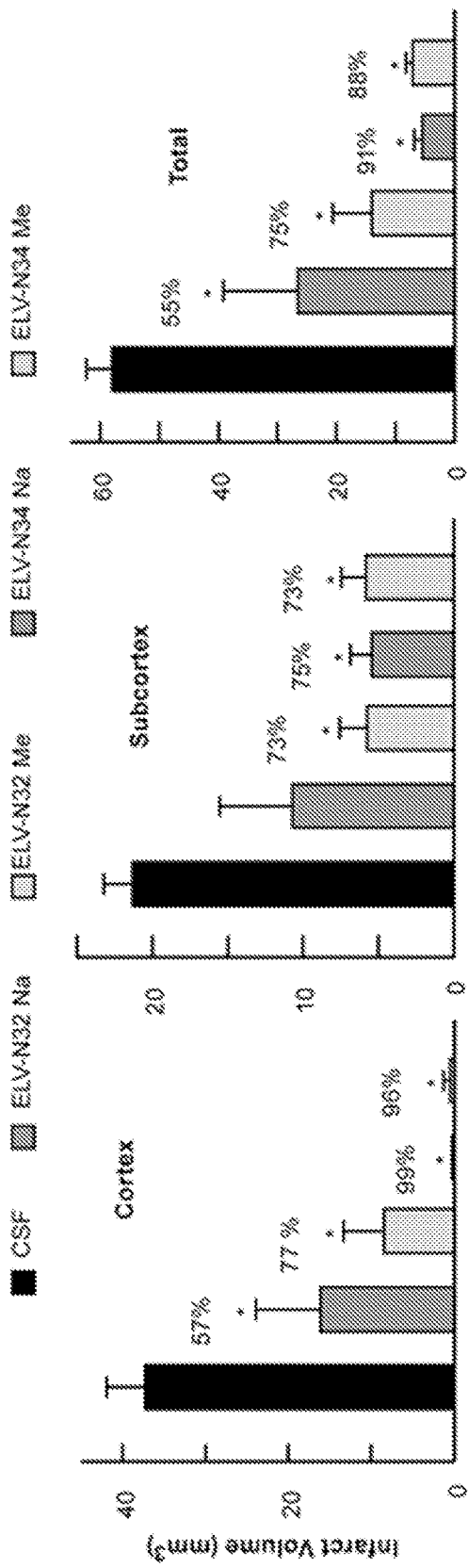

FIG. 22D illustrates cortical, subcortical and total corrected infarct volumes. All ELV treatments dramatically reduced cortical, subcortical and total infarct volumes compared to the vehicle-treated group. Values shown are means±SD (n=5-6 per group). *, significantly different from vehicle (p<0.05; repeated-measures ANOVA followed by Bonferroni tests).

Figure 23A:
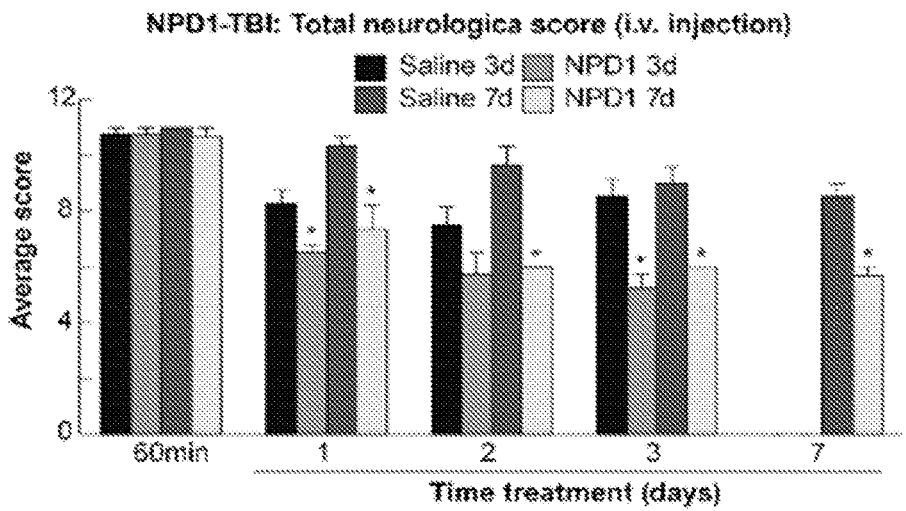
Figure 23B:
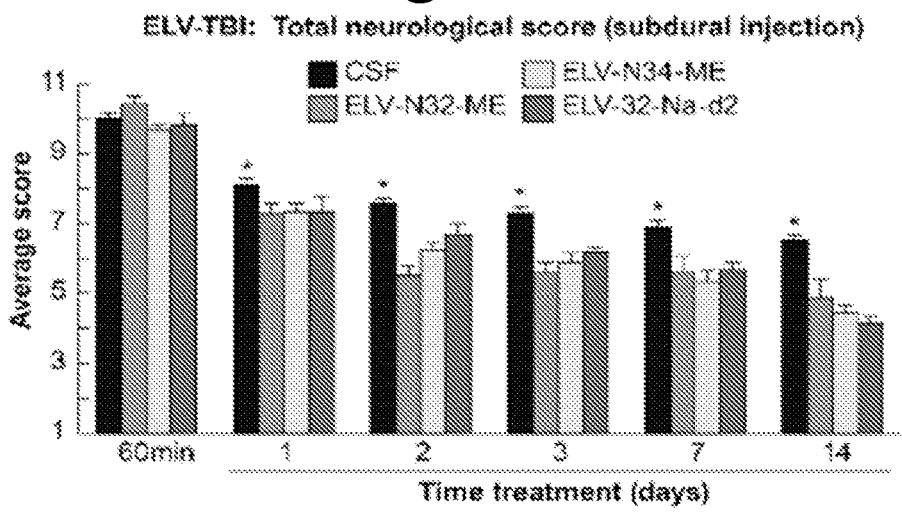
Figure 23C:
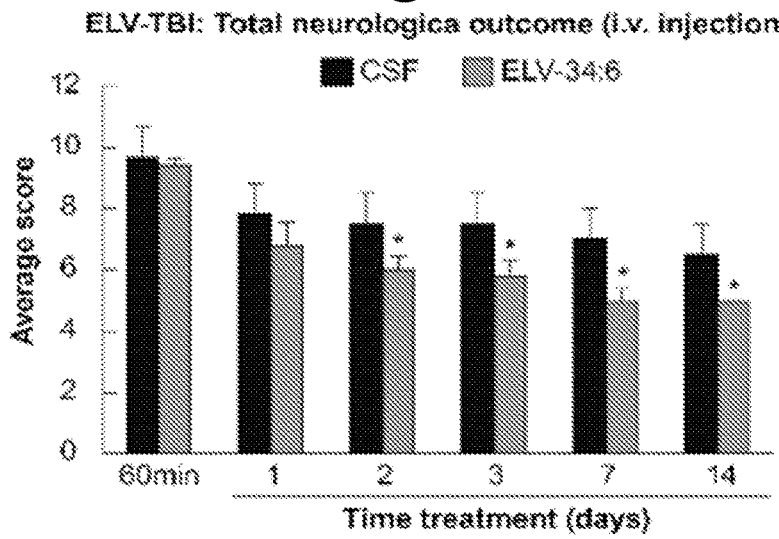

FIGS. 23A-23C illustrate that elovanoids provide neuroprotection and improve neurological deficit following traumatic brain injury (TBI). The total neurological score was significantly reduced following treatment with a 32-carbon or 34-carbon elovanoid methyl ester of sodium salt. FIGS. 23A and 23C: delivery via an intravenous injection; FIG. 23B: delivery via subdural injection. SD rats were subjected to a moderate fluid percussion injury (FPI) model and treated (1 µg/per rat) with 32- and 34 carbon elovanoids as the methyl ester (ME) or sodium salt (Na) (ELV-N32-ME, ELV-N34-ME, ELV-32-Na-d2, ELV-N34-Alkyne) or of vehicle (cerebral spinal fluid; CSF). Treatments were delivered into subdural space at 1 h after TBI. Animals received neurobehavioral examination (normal=0, maximal deficit=12) on days 1, 2, 3, 7 or 14. All ELV treatments improved neurologic score beginning on day 1, which persisted throughout 2 weeks survival period compared to the CSF-treated groups. Values shown are means±SEM (n=6-8 per group) *significantly different from corresponding saline group (P<0.05; repeated measures ANOVA followed by Bonferroni tests). ELV-N34-Alkyne (IV, 300 µg/per animal). All animals received neurobehavioral examination (normal=0, maximal deficit=12) on days 1, 2, 3, 7 or 14.

Figure 24:
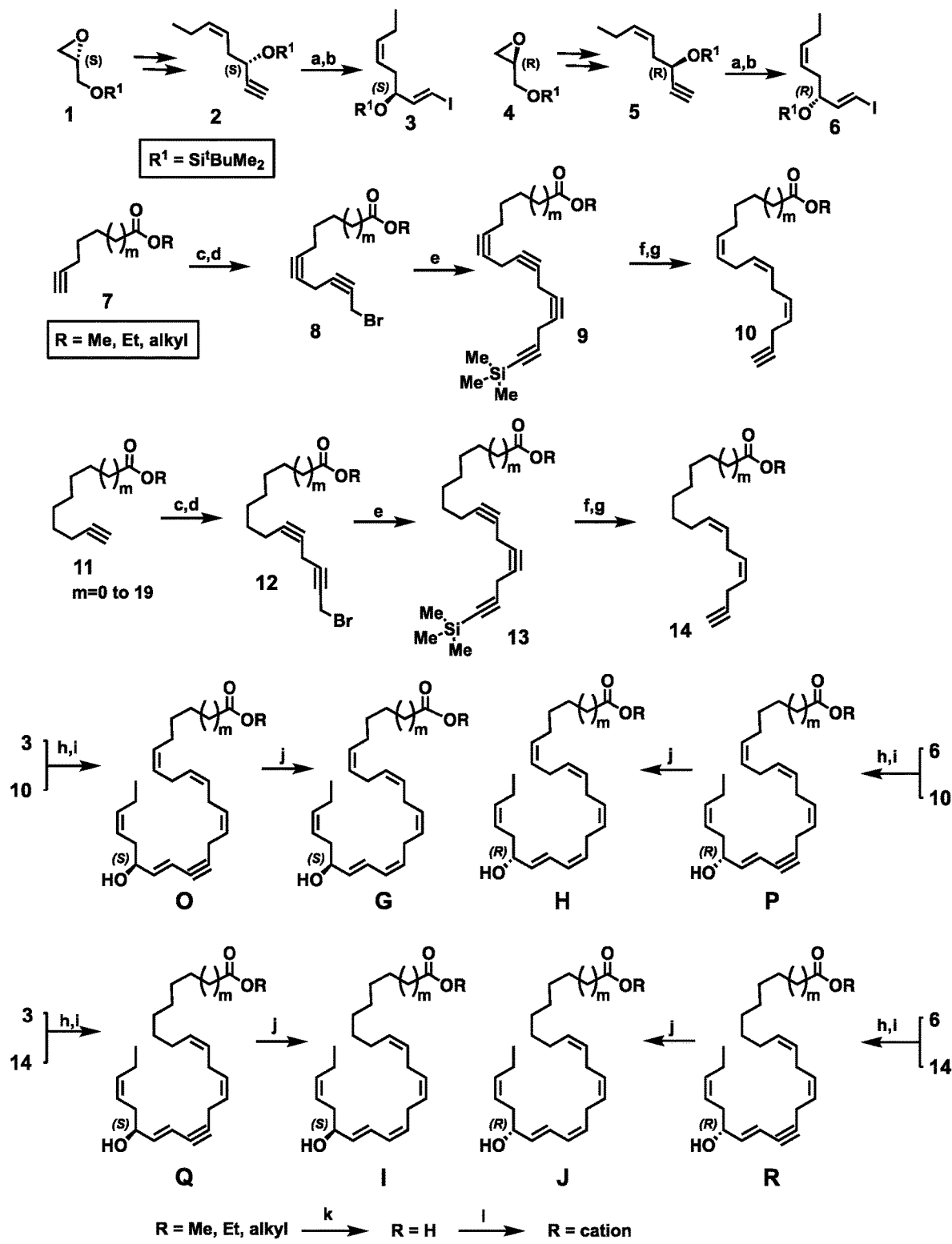

FIG. 24 illustrates Scheme 1 for the total synthesis of mono-hydroxylated elovanoids G, H, I, J, O, P, Q, R.

Reagents & Conditions: (a) Catechol borane, heat; (b) N-iodo-succinimide, MeCN; (c) 4-chlorobut-2-yn-1-ol, $Cs_2CO_3$, NaI, CuI, DMF; (d) $CBr_4$, $PPh_3$, $CH_2Cl_2$, 0° C.; (e) ethynyl-trimethylsilane, CuI, NaI, $K_2CO_3$, DMF; (f) Lindlar cat., $H_2$, EtOAc; (g) $Na_2CO_3$, MeOH; (h) $Pd(PPh_3)_4$, CuI, $Et_3N$: (i) $^tBu_4NF$, THF; (j) Lindlar cat., $H_2$, EtOAc or Zn(Cu/Ag), MeOH; (k) NaOH, THF, $H_2O$, then acidification with $HCl/H_2O$; (l) NaOH, KOH, or the like. or amine, imine, etc.

Figure 25:
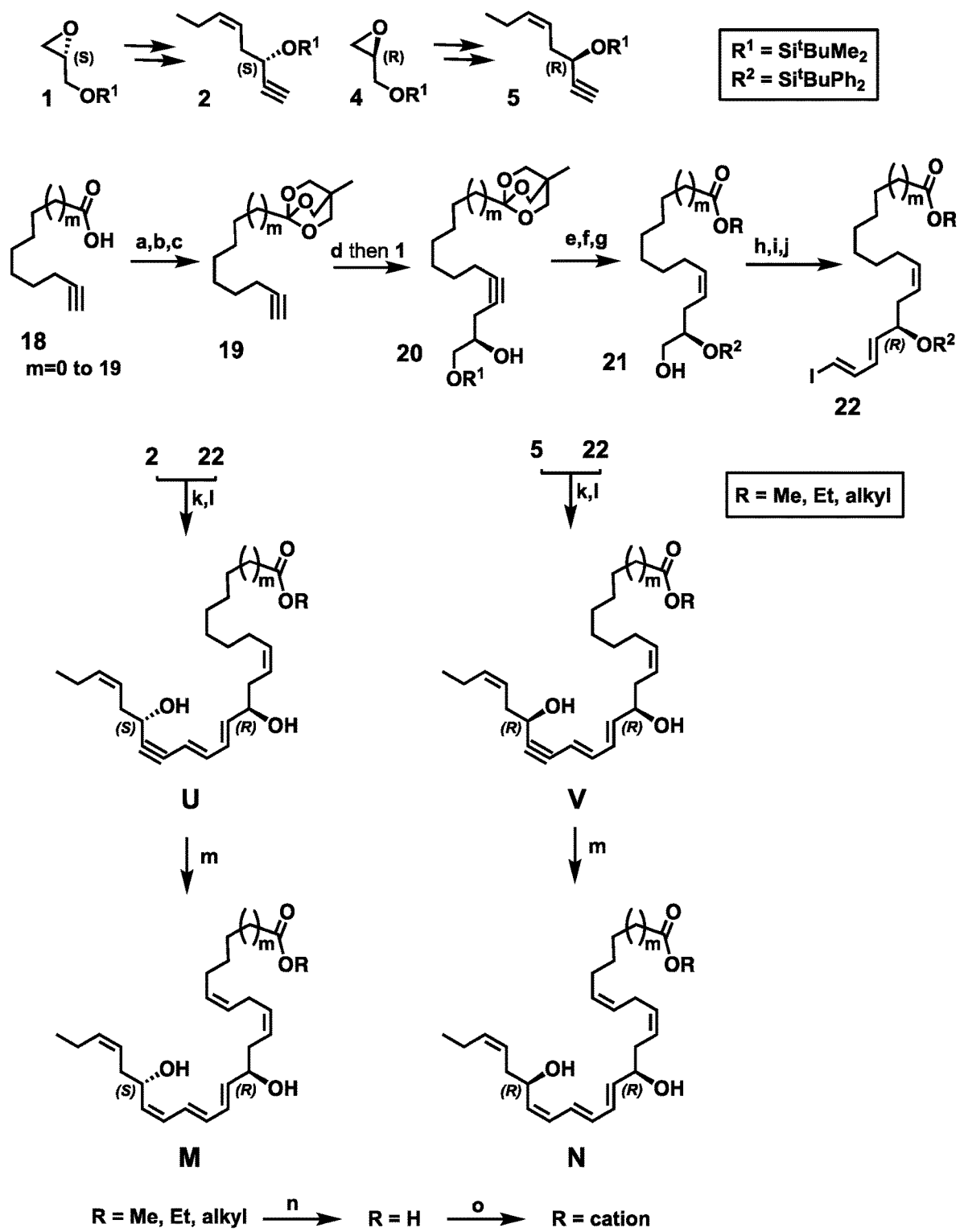

FIG. 25 illustrates Scheme 2 for the total synthesis of di-hydroxylated elovanoids K, L, S, and T.

Reagents & Conditions: (a) CuI, NaI, $K_2CO_3$, DMF; (b) camphorsulfonic acid (CSA), $CH_2Cl_2$, MeOH, rt; (c) Lindlar cat., $H_2$, EtOAc; (d) DMSO, $(COCl)_2$, $Et_3N$, −78° C.; (e) $Ph_3P$=CHCHO, PhMe, reflux; (f) $CHI_3$, $CrCl_2$, THF, 0° C.; (g) cat. $Pd(Ph_3)_4$, CuI, PhH, rt; (h) $^tBu_4NF$, THF, rt; (i) Zn(Cu/Ag), MeOH, 40° C.; (j) NaOH, THF, $H_2O$, then acidification with HCl/$H_2O$; (k) NaOH, KOH, etc. or amine, imine, etc.

Figure 26:
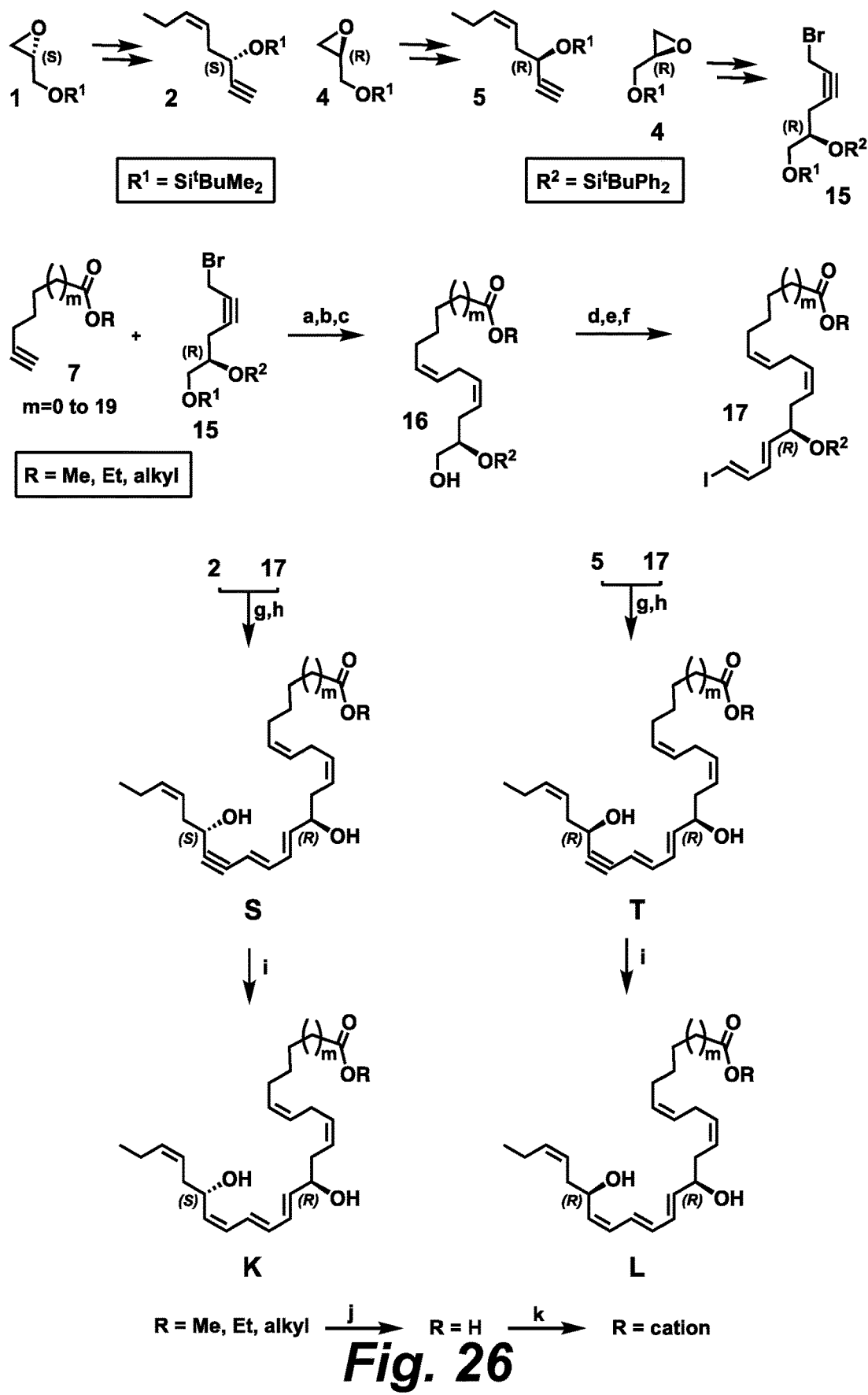

FIG. 26 illustrates Scheme 3 for the total synthesis of di-hydroxylated elovanoids M, N, U, and V.

Reagents & Conditions: (a) cyanuric chloride, $Et_3N$, acetone, rt; (b) (3-methyloxetan-3-yl)methanol, pyridine, $CH_2Cl_2$, 0° C.; (c) $BF_3.OEt_2$, $CH_2Cl_2$; (d) nBuLi, $BF_3.OEt_2$, THF, −78° C., then 1; (e) $^tBuPh_2SiCl$, imidazole, DMAP, $CH_2Cl_2$, rt; (f) camphorsulfonic acid, $CH_2Cl_2$, ROH, rt; (g) Lindlar cat., $H_2$, EtOAc; (h) DMSO, $(COCl)_2$, $Et_3N$, −78° C.; (i) $Ph_3P$=CHCHO, PhMe, reflux; (j) $CHI_3$, $CrCl_2$, THF, 0° C.; (k) cat. $Pd(Ph_3)_4$, CuI, PhH, rt; (l) $^tBu_4NF$, THF, rt; (m) Zn(Cu/Ag), MeOH, 40° C.; (n) NaOH, THF, $H_2O$, then acidification with HCl/$H_2O$; (o) NaOH, KOH, etc. or amine, imine, etc.

Figure 27:
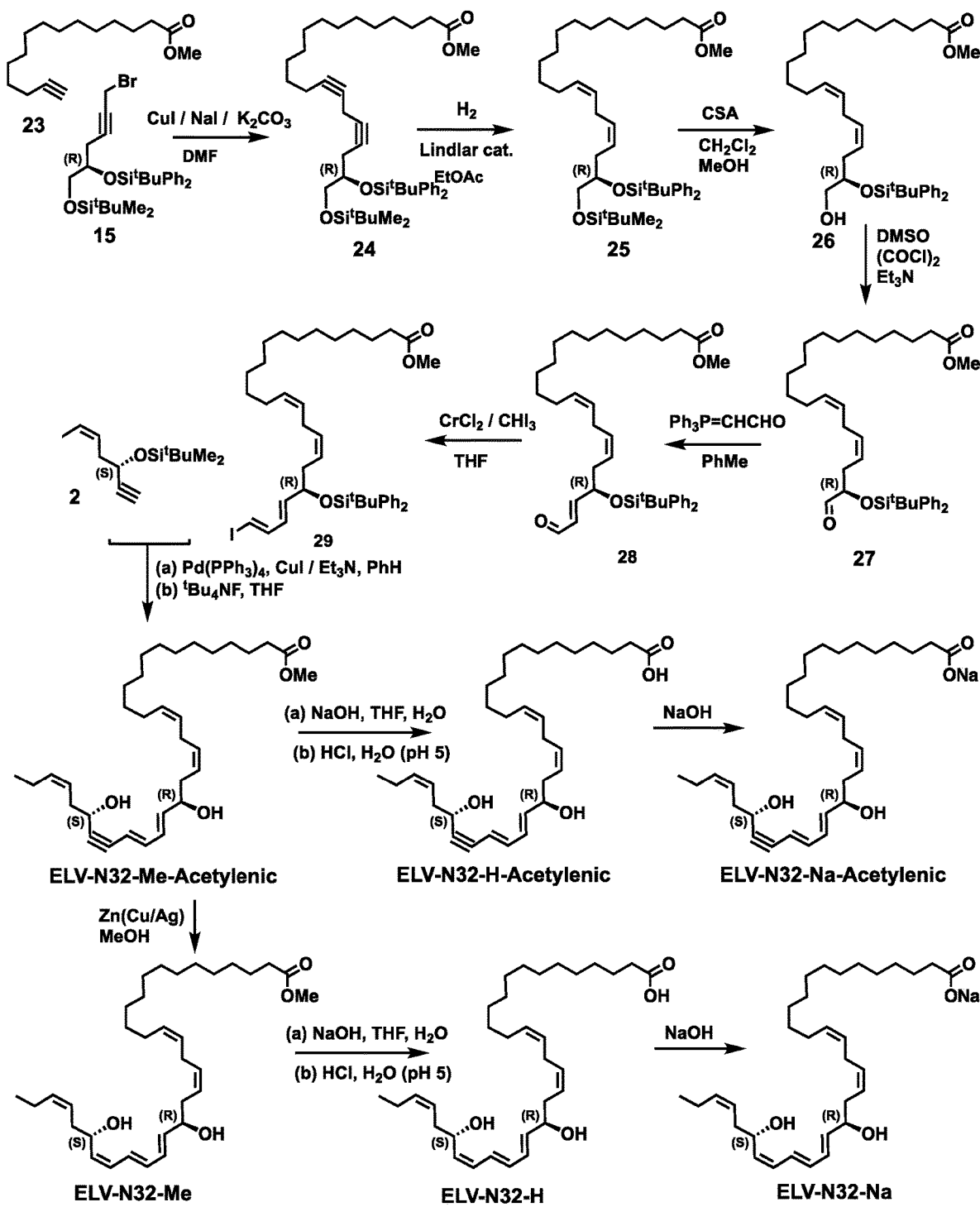

FIG. 27 illustrates Scheme 4 for the total synthesis of 32-carbon di-hydroxylated elovanoids.

Figure 28:
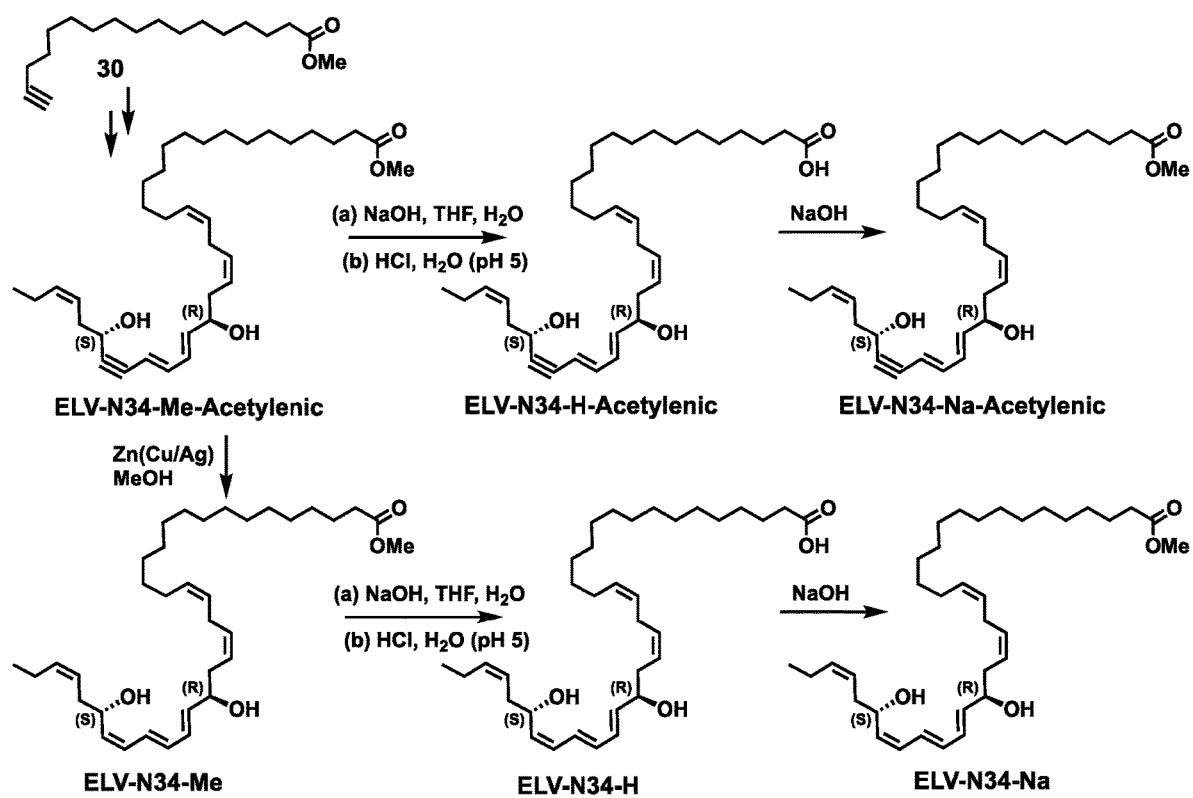

FIG. 28 illustrates Scheme 5 for the total synthesis of 34-carbon di-hydroxylated elovanoids.

Figure 29:
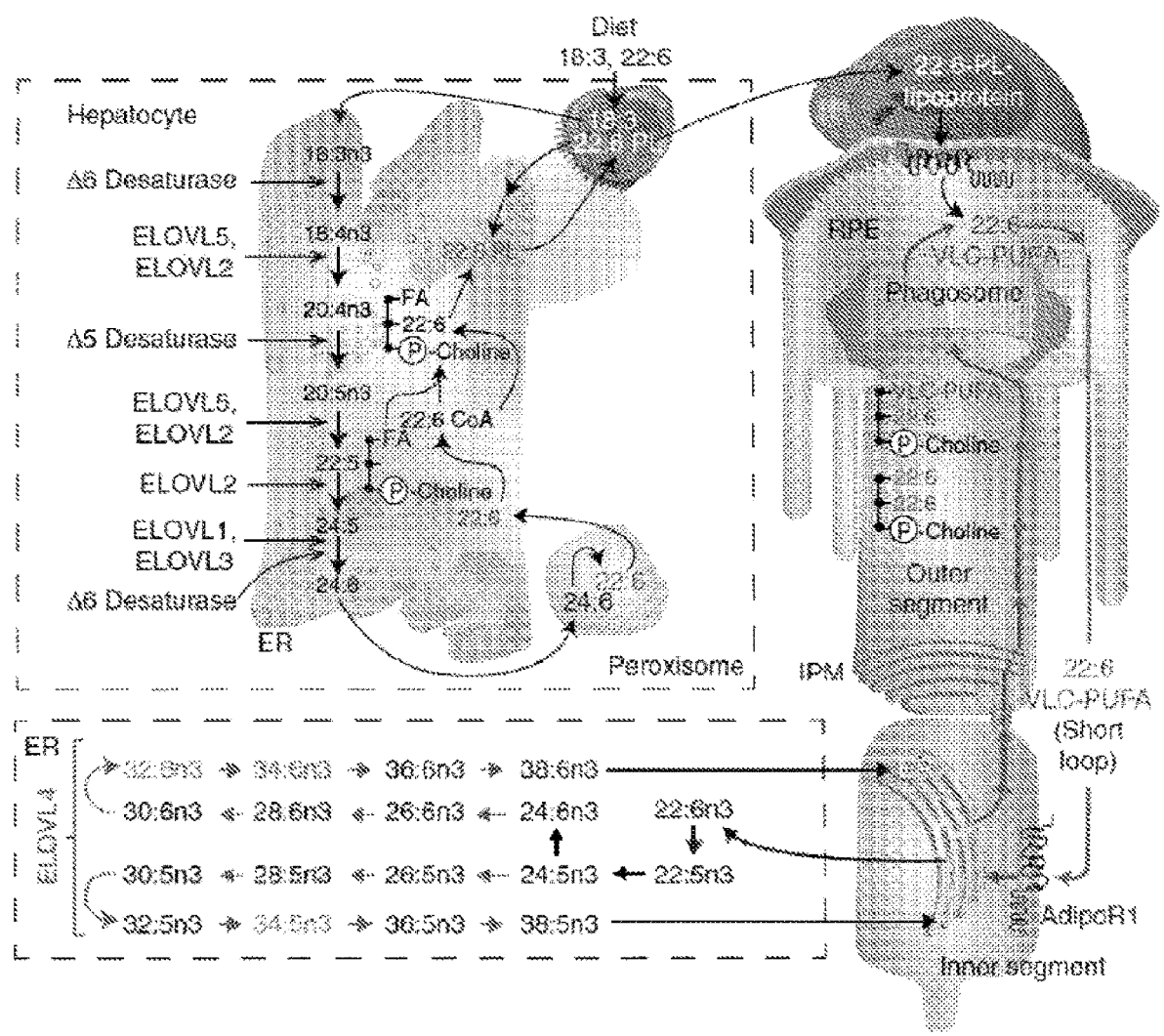

FIG. 29 illustrates the role of omega-3 very long chain-polyunsaturated fatty acids (n3-VLCPUFAs) in the survival of photoreceptor cells, the protection of the retina, and the prevention of sight loss (Nat. Commun. 2015; 6:1-14). Daily photoreceptor outer segment shed their tips that in turn are taken-up and digested in the phago-lysosomal system of the retinal pigment epithelial cell. Omega-3 fatty acids from outer segment membrane phospholipids are shuttled back to the inner segment of the photoreceptor to be incorporated again into phospholipids for membrane biogenesis of the outer segment. So there is recycling of this essential fatty acid and conservation during a process called photoreceptor outer segment renewal. Without being bound by theory, the VLC-PUFAs in the RPE cells directly or upon enzymatic conversion into hydroxylated derivatives, foster integrity of the cell and as result of the photoreceptors. This diagram depicts the desaturation and elongation steps in the generation of VLC-PUFAs as these molecules traffic through the endoplasmic reticulum and the peroxisome of the hepatocyte, the endoplasmic reticulum of the photoreceptor inner segment and into the photoreceptor outer segment. The elongation steps catalyzed by ELOVL4 are highlighted in red. RPE retrieval of DHA (C22:6) and of the VLC-PUFAs from shed photoreceptor apical disk membranes is followed by recycling of DHA and of the VLCPUFAs back to the photoreceptor inner segment.

Figure 30A:
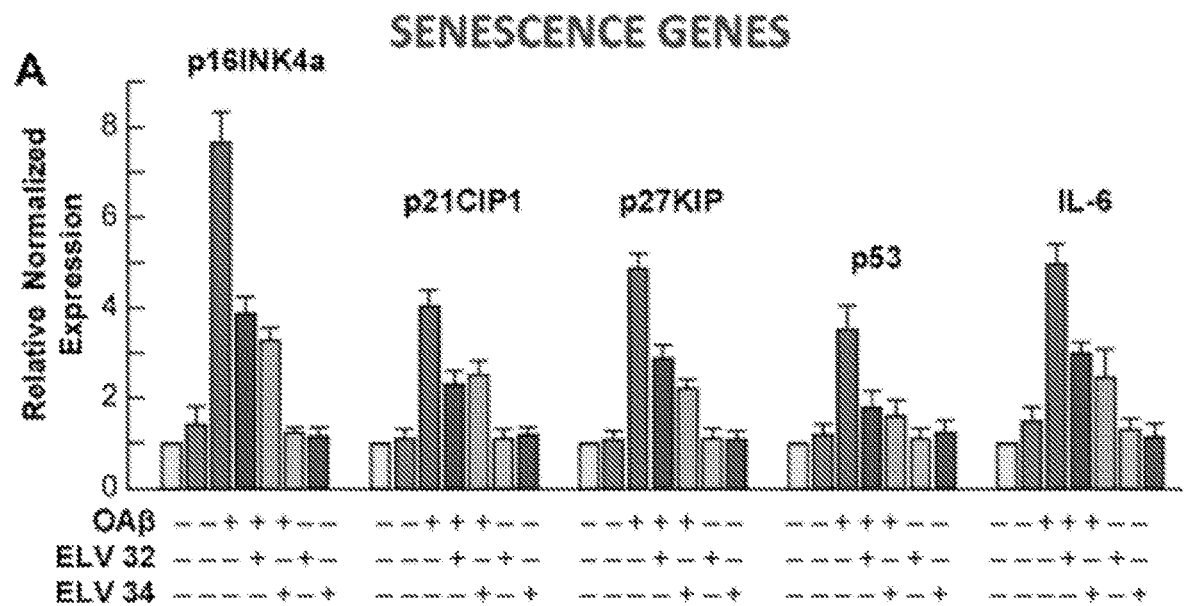

FIG. 30A illustrates that elovanoids suppress the activation of the senescence signaling pathways.

Figure 30B:
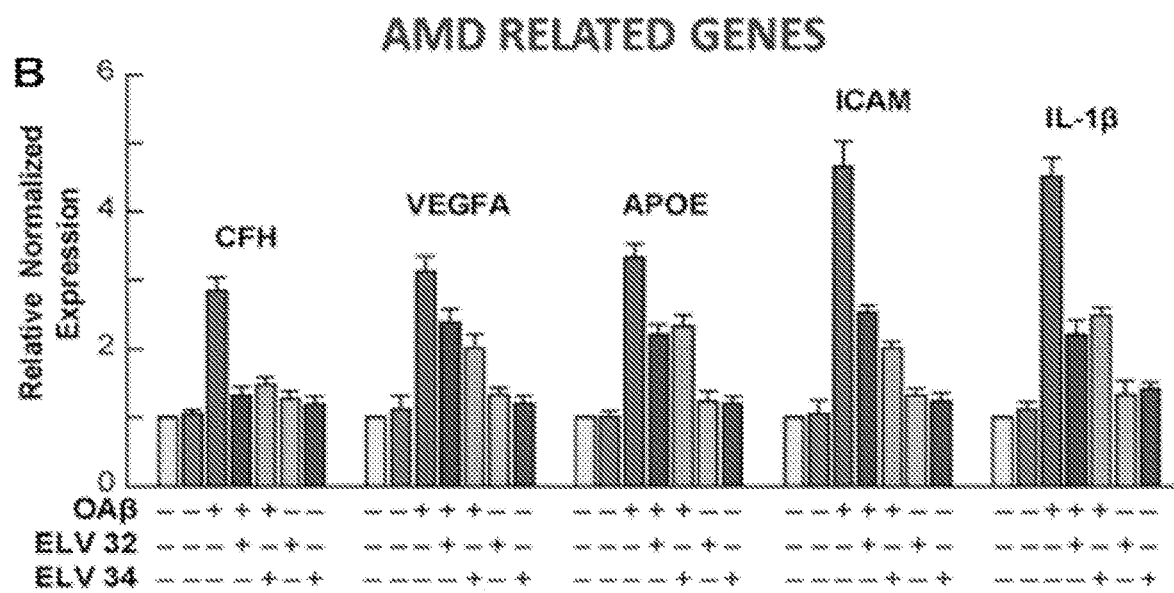

FIG. 30B illustrates that elovanoids reduce the expression of AMD related genes (CHF, VEGFA, APOE, ICAM, and IL-1β) induced by oligomeric Aβ peptide.

Figure 31:
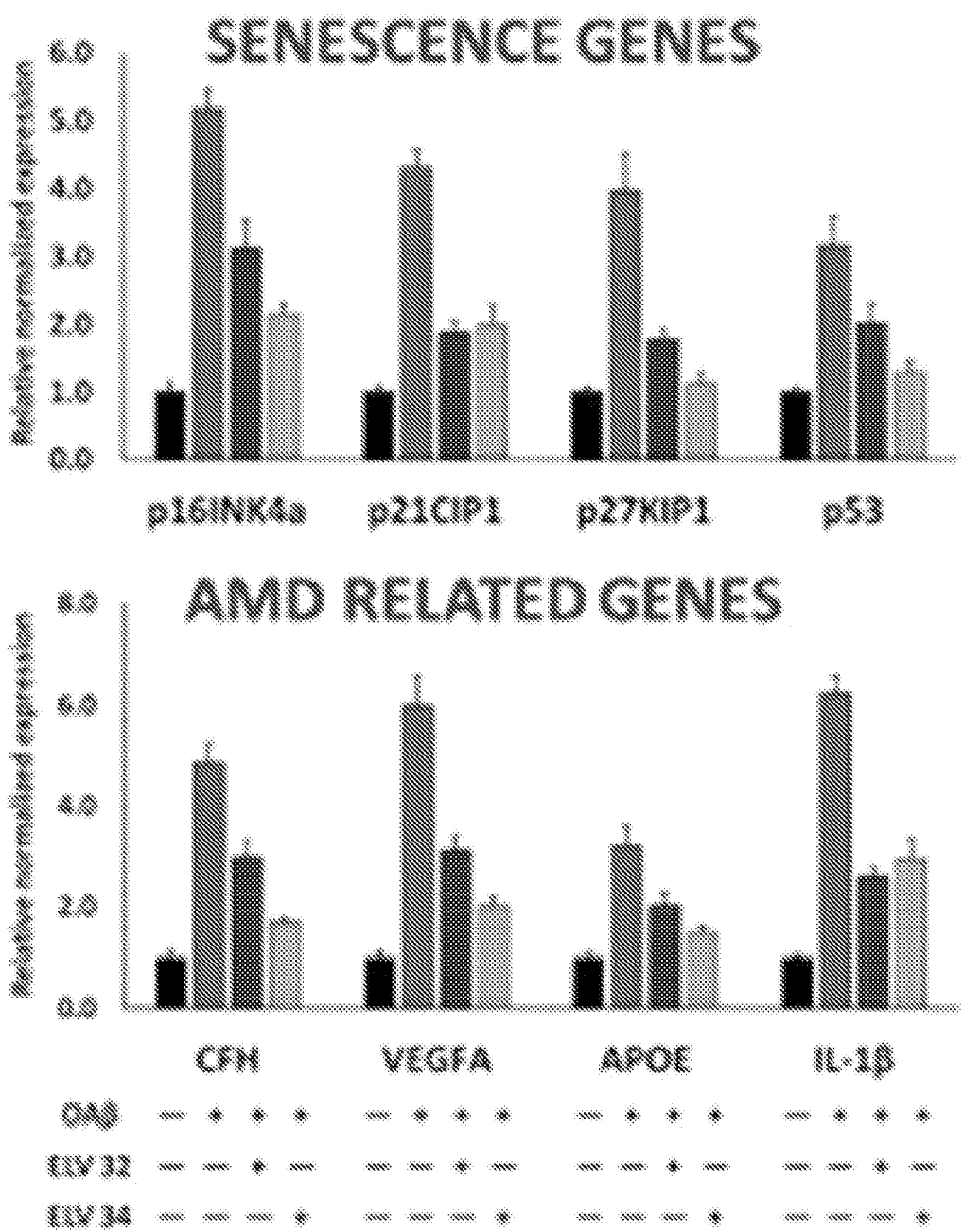

FIG. 31 illustrates that elovanoids rescue the OAβ peptide-induced senescence in primary hRPE culture.

Figure 32:
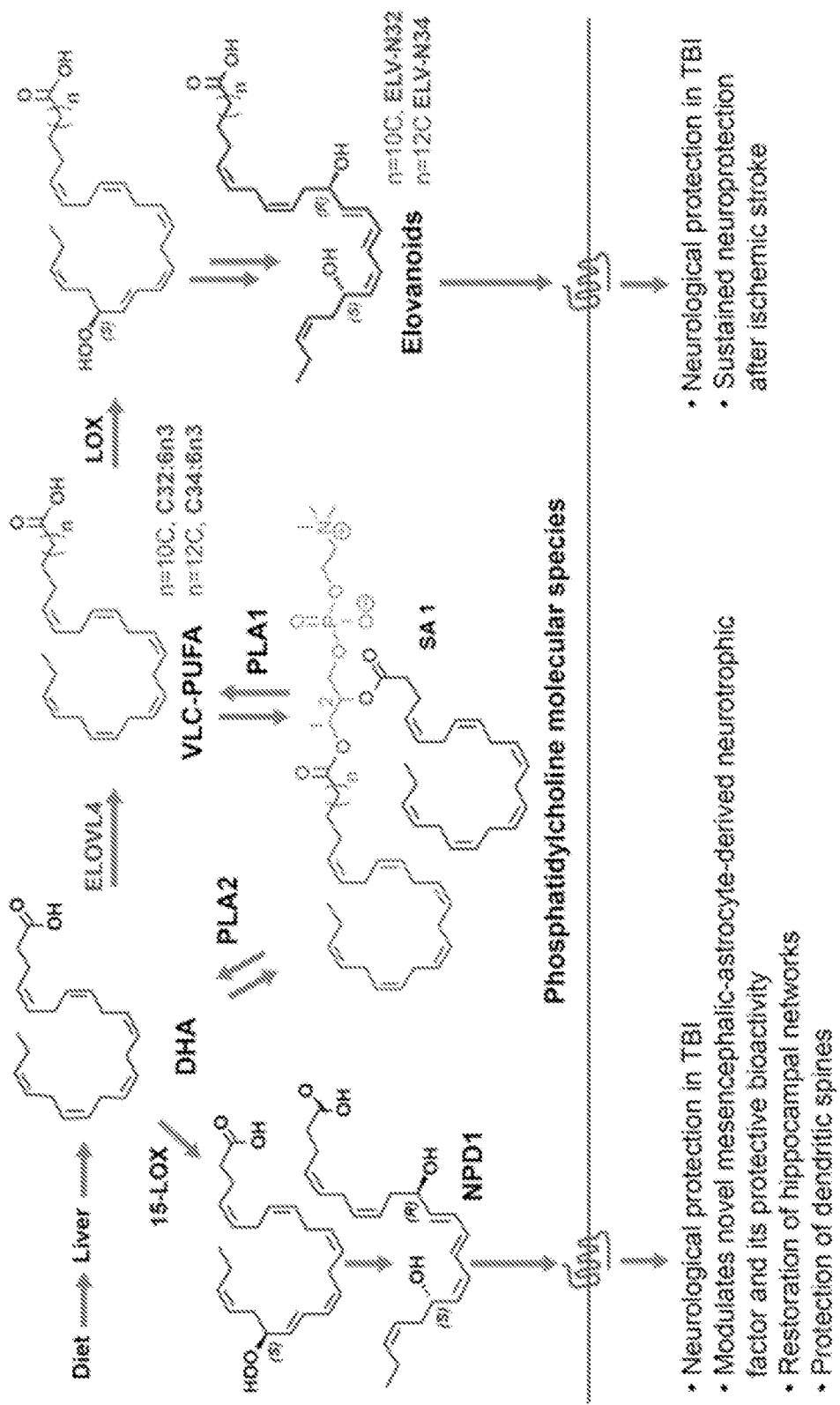

FIG. 32 is a scheme illustrating the postulated relationship between the biosynthesis of elovanoids (ELV), NPD1, and phosphatidylcholine molecular species. from DHA. This figure further illustrates exemplary beneficial physiological effects of NPD1 and elovanoids.

Figure 33:
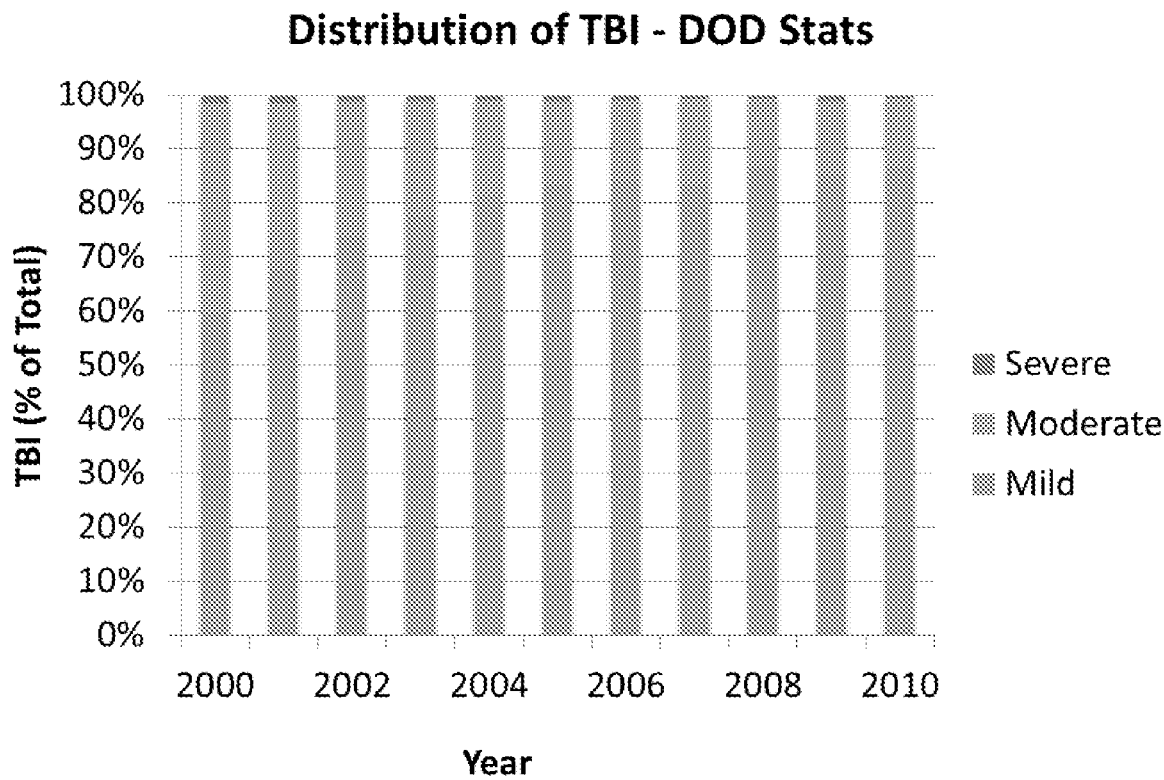

FIG. 33 provides a graphical representation of TBI severity distribution.

Figure 34:
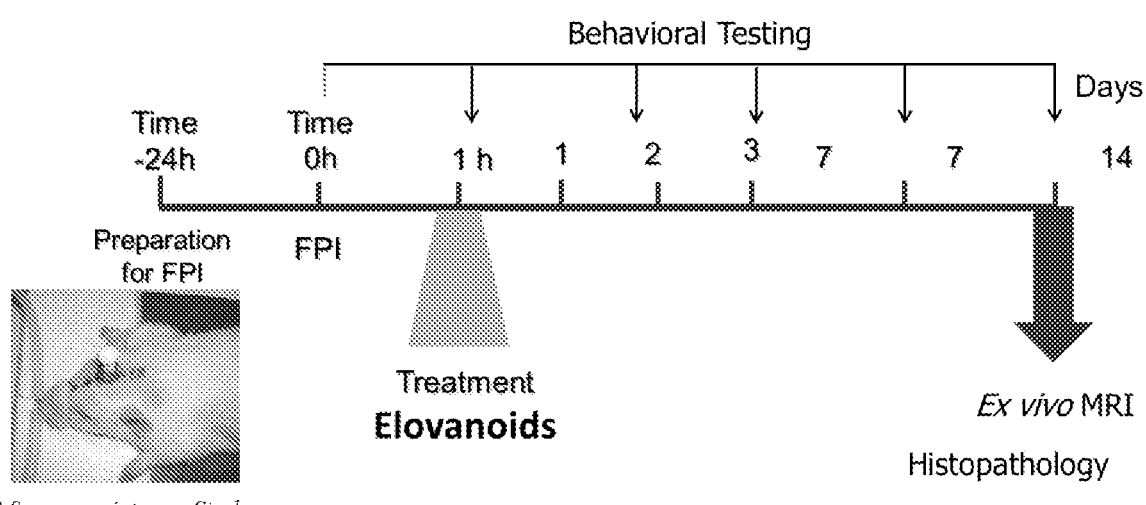

FIG. 34 is a schematic representation of an experimental protocol for to study the effects of traumatic brain injury through one exemplary model. Briefly, moderate TBI was administered via fluid percussion injury (FPI) to the right parieto-occipital area in male Sprague Dawley rats followed by treatment with elovanoids, behavioral testing, and ex vivo MRI histopathology.

Figure 35:
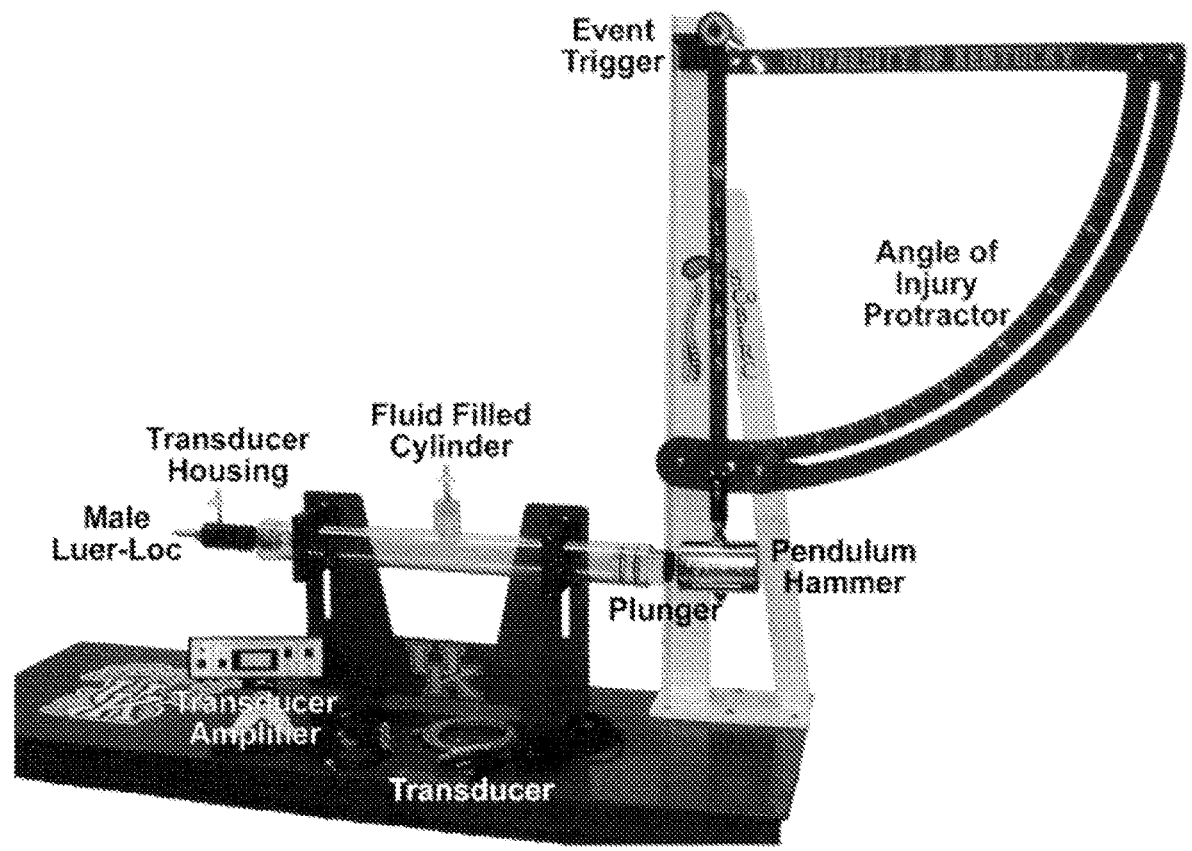

FIG. 35 is a photographic representation of an exemplary instrument used to induce fluid percussion injury in one experimental model.

Figure 36:

FIG. 36 shows a dorsal view of a rat immediately following surgical preparation for FPI under one experimental model. Briefly, Sprague-Dawley rats (280-350 g) were subjected to 4.8 mm craniotomy overlying the right parietal cortex (3.8 mm posterior to bregma and 2.5 mm lateral to midline) was performed 24 hours before fluid percussion injury. A plastic adaptor with a plug was positioned over the craniotomy. The scalp closed with sutures, and the animal returned to its cage and allowed to recover overnight.

Figure 37:

FIG. 37 provides a photographic view of a rat immediately before FPI.

Figure 38:
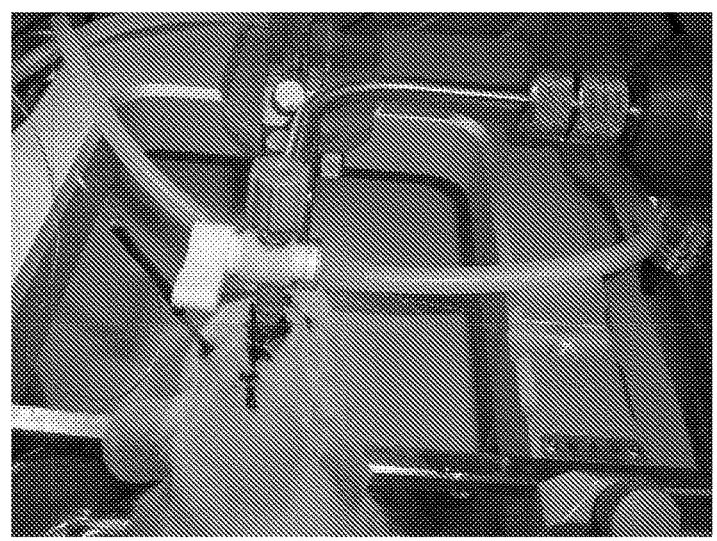

FIG. 38 provides a photographic detailed view showing the manner by which the rat in FIG. 37 is attached to the FPI instrument.

Figure 39:
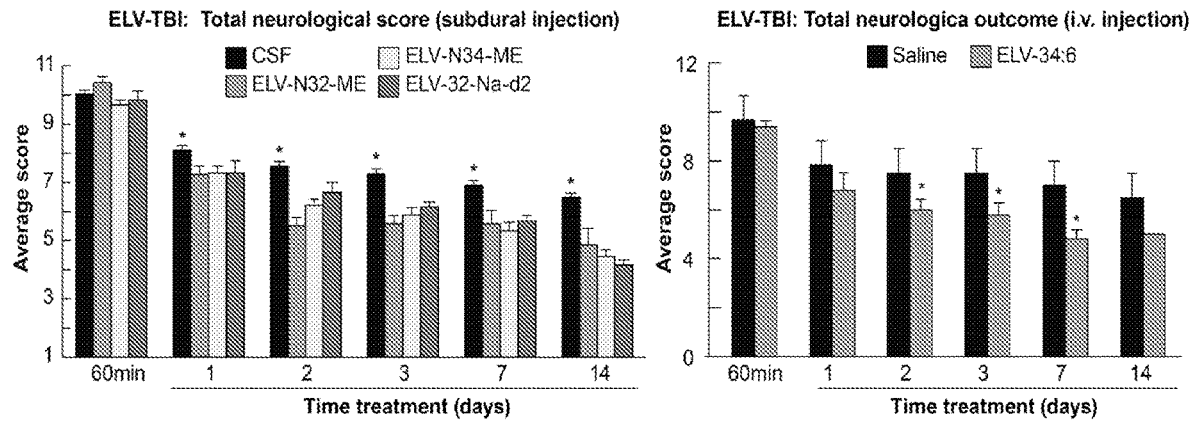

FIG. 39 provides a graphic illustration that elovanoids improve neurological deficit after TBI (2 weeks survival) wherein a normal score is 0 and the maximal deficit is 12. ELVS were given 1 hour after TBI. ELV-TBI: Total neurological score following subdural injection is provided on the left, wherein the ELVs were dosed at 5 μg/per animal. ELV-TBI: Total neurological outcome following i.v. injection is provided on the right, wherein the ELVs were dosed at 300 μg/per animal.

Figure 40:
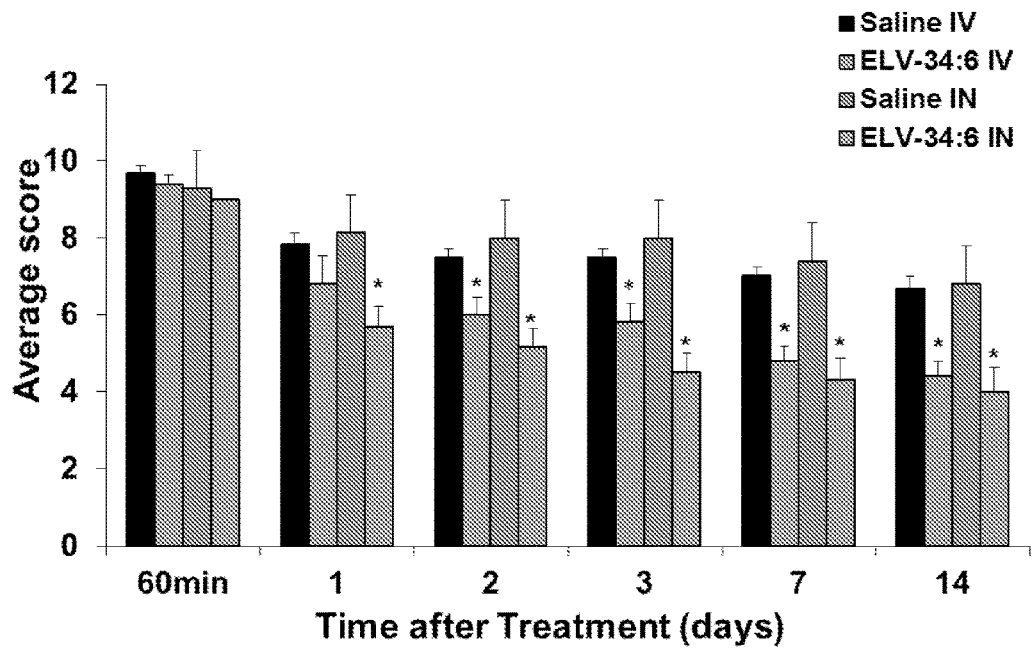
Figure 41:
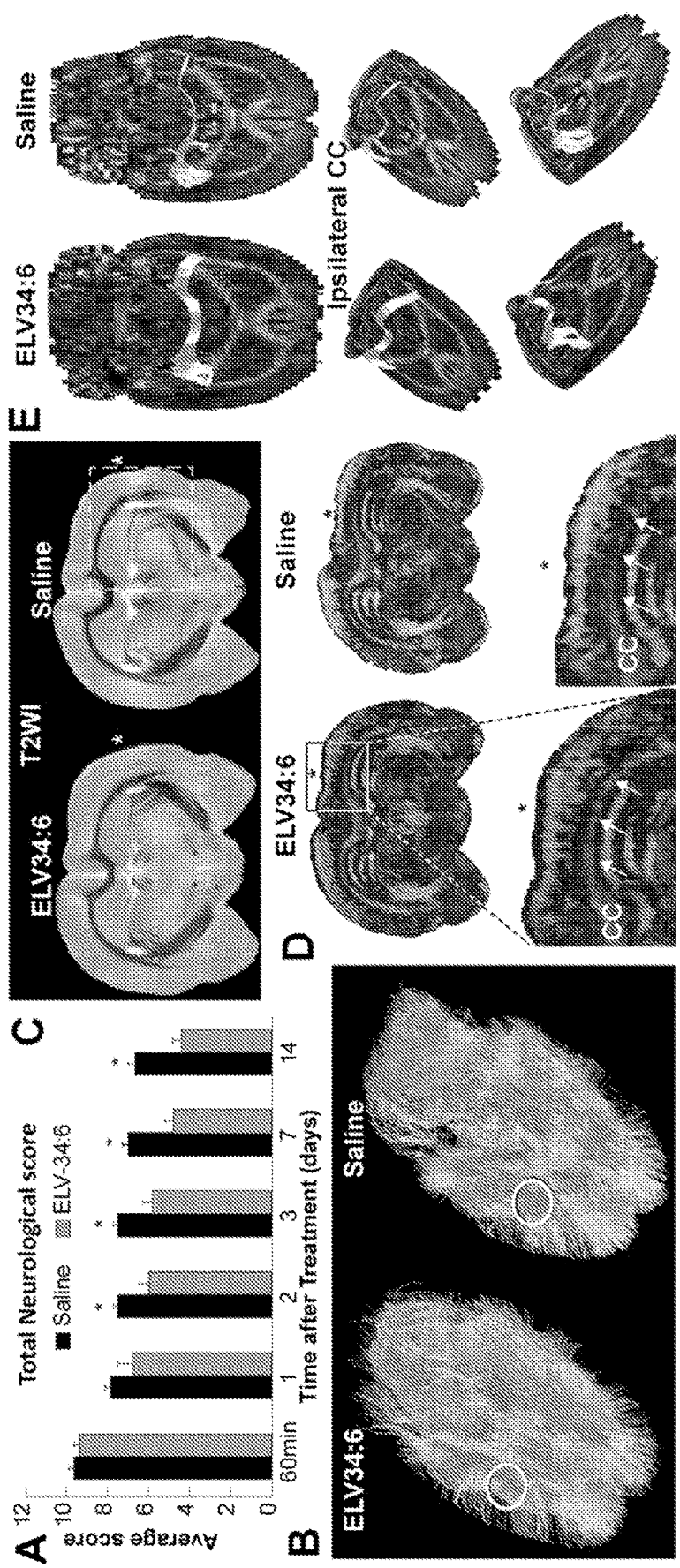

FIG. 40 is a graphical illustration showing the comparison of the intranasal and intravenous delivery of ELVs on total neurological score FIG. 41 illustrates (A) ELV-34:6 i.v. 1 hr after mild TBI improved neurobehavioral score (normal=0, maximal deficit=12) up to 2 weeks. (B) Brain tractography shows that in ELV treated rats there is increased numbers of cortical fibers in the impacted cortex. The area of impact (arrows) has more green fibers in the same region compared to the FPI only rats. (C) Representative T2 weighted imaging (T2WI) shows large lesion in saline vs. very small lesion in ELV rat. (D) Directionally encoded fractional anisotropy maps demonstrate preservation of cortex (green) and improved corpus callosum (CC) integrity (red, arrows). *impact site. (E) Tractography of the CC was examined using a single ROI placed in the ipsilateral CC (injured hemisphere). In the ELV, treated rats compared to the Saline, there was increased numbers of streamlines (tracts) and increased connectivity to the contralateral hemisphere. Thus, ELV appears to protect the integrity of the white matter (WM). Values are means±SD (n=4-6/group) *significantly different from saline group (P<0.05; repeated measures ANOVA followed by Bonferroni tests).

Figure 42:
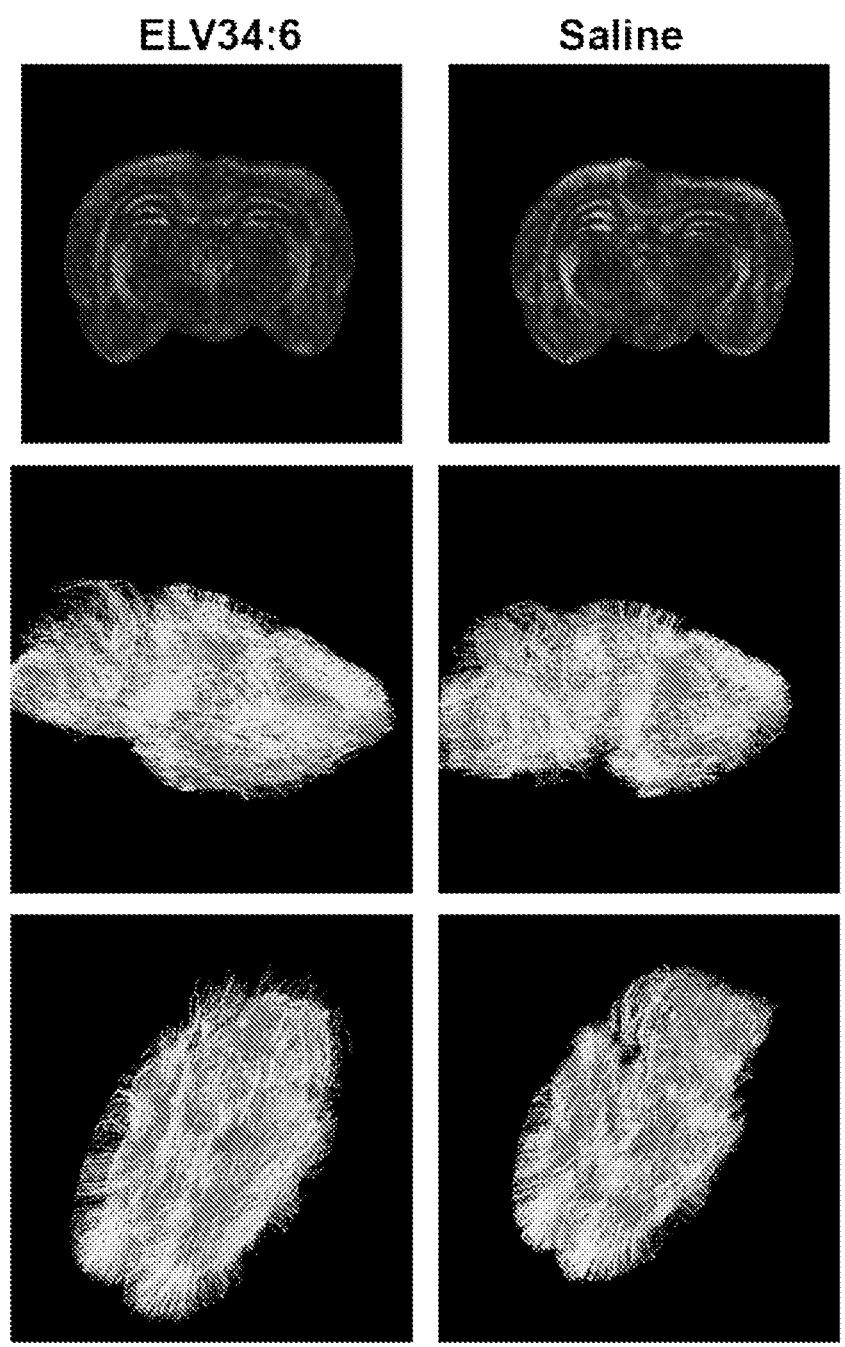

FIG. 42 provides additional representative images of directionally encoded fractional anisotropy maps (see top two images) and brain tractography (see bottom four images).

Figure 43:
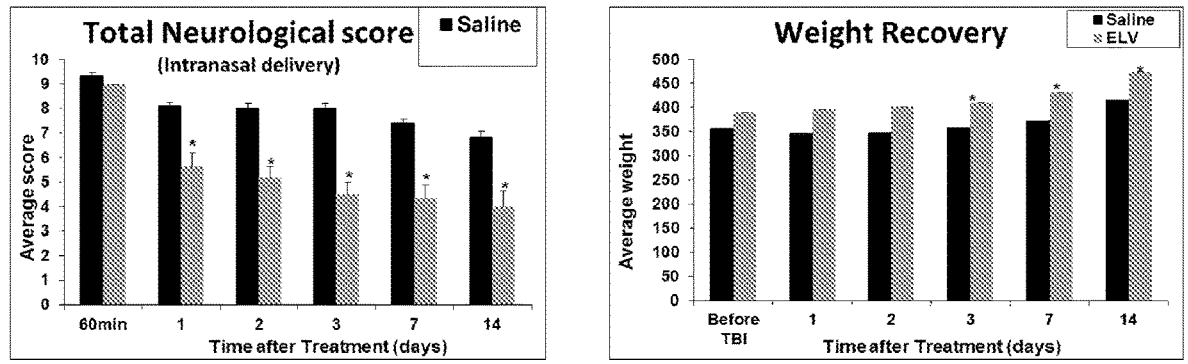

FIG. 43 shows graphical representations of the total neurological score following intranasal delivery of ELV (green) as compared to saline (black) (see left bar graph) and a comparison of weight recovery following intranasal delivery of ELV and saline (see the bar graph on the right).

Figure 44:
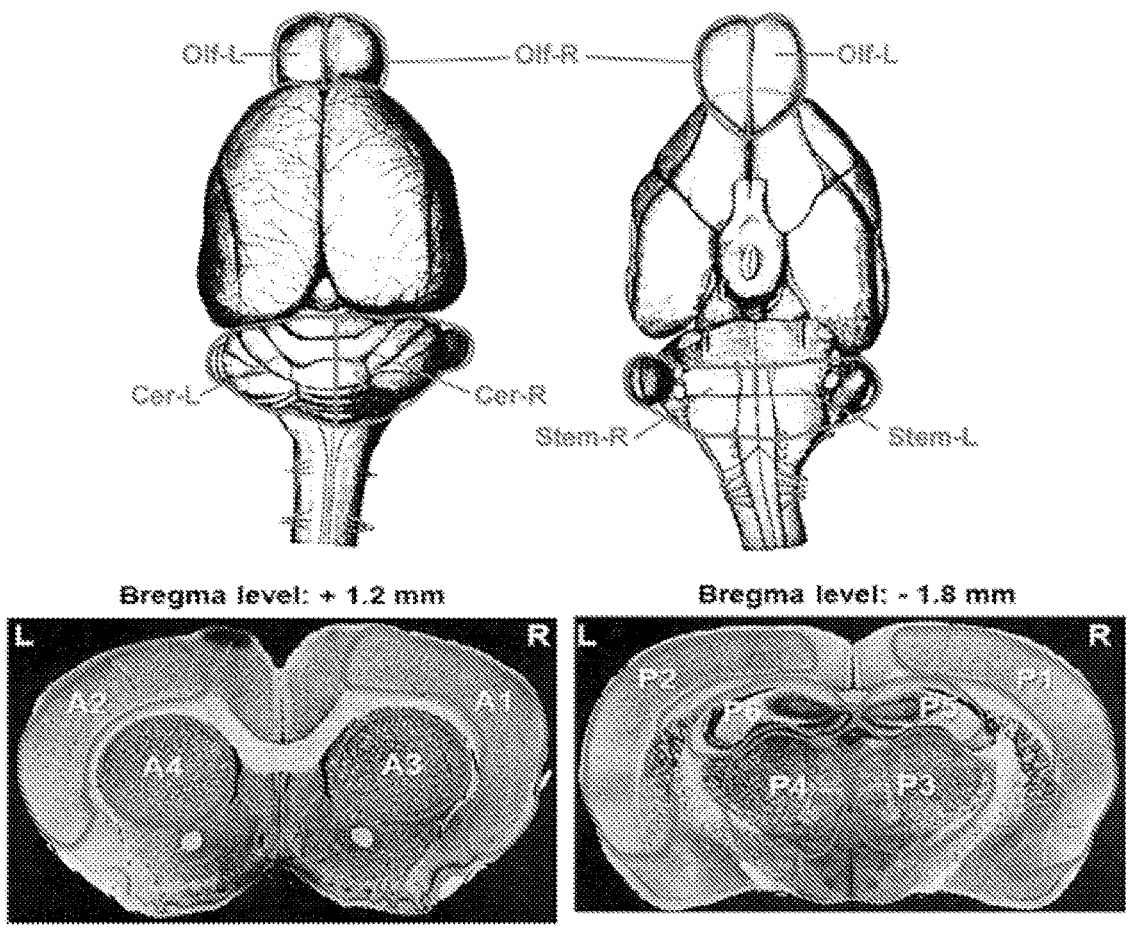

FIG. 44 illustrates anatomical drawings of a rat brain (top) and identifies anterior (bottom left) and posterior (bottom right) regions from coronal rat brain sections that were assayed by liquid chromatography tandem mass spectrometer (LC-MS/MS) to confirm that elovanoids reach the brain after intranasal delivery.

Figure 45:
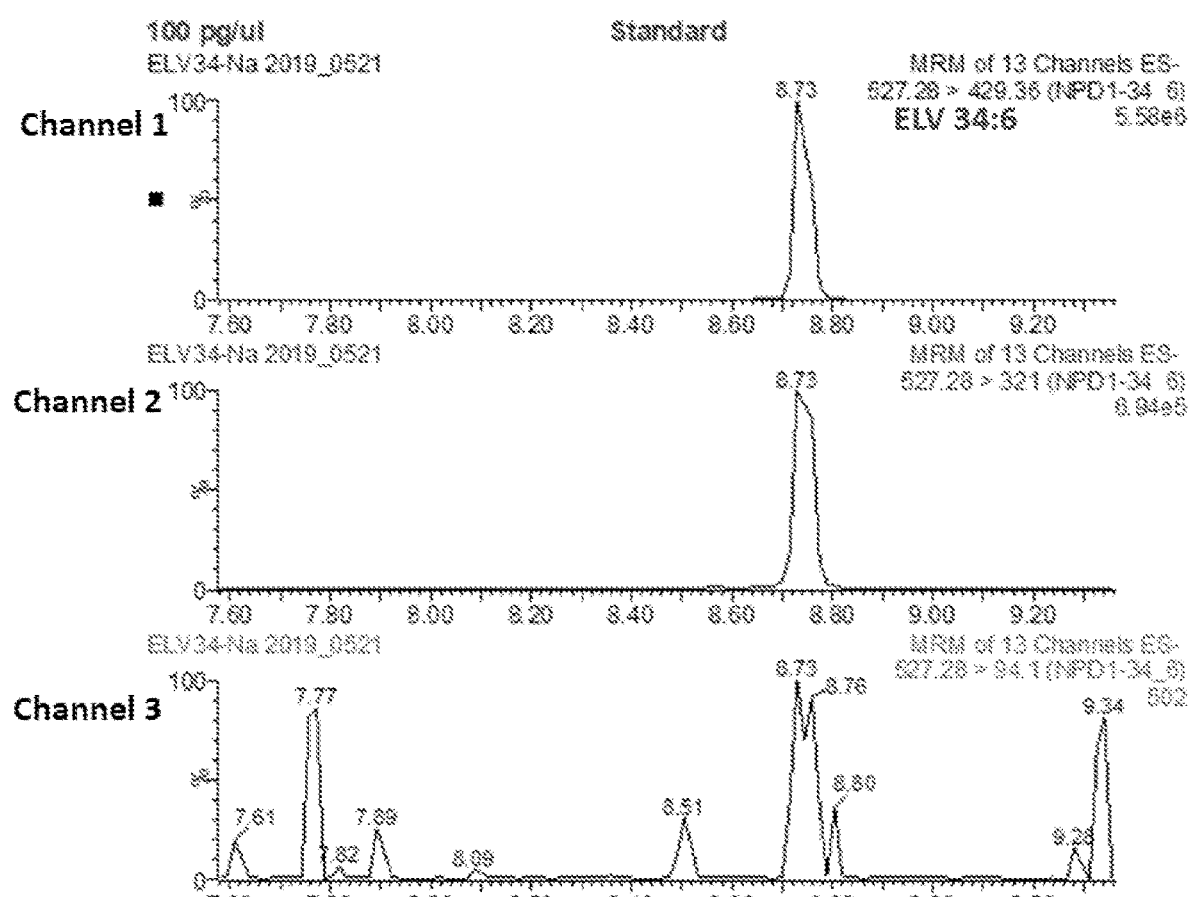

FIG. 45 shows LC-MS/MS of standard ELV-34:6 (Na+).

Figure 46:
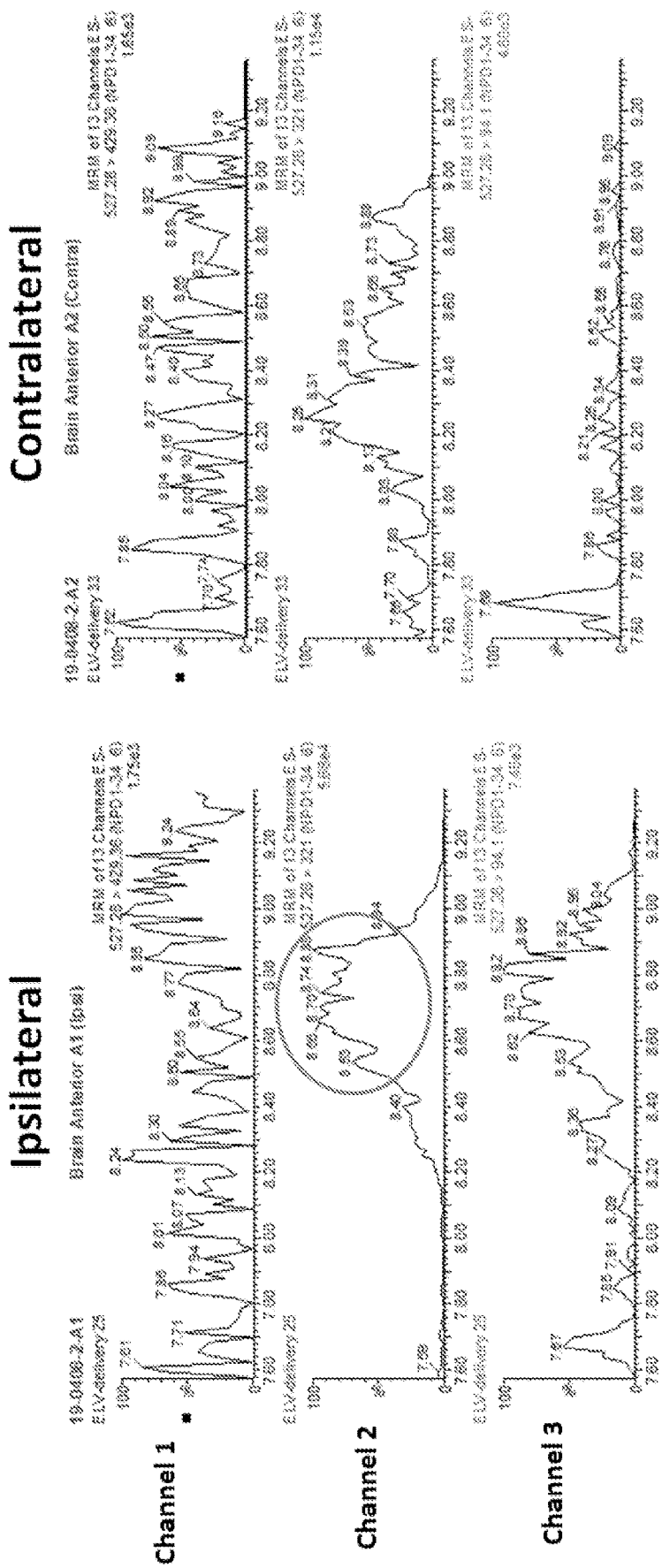

FIG. 46 illustrates ipsilateral and contralateral elovanoids after intranasal delivery, A1 and A2 as in FIG. 44. Red circle depicts elovanoids.

Figure 47:
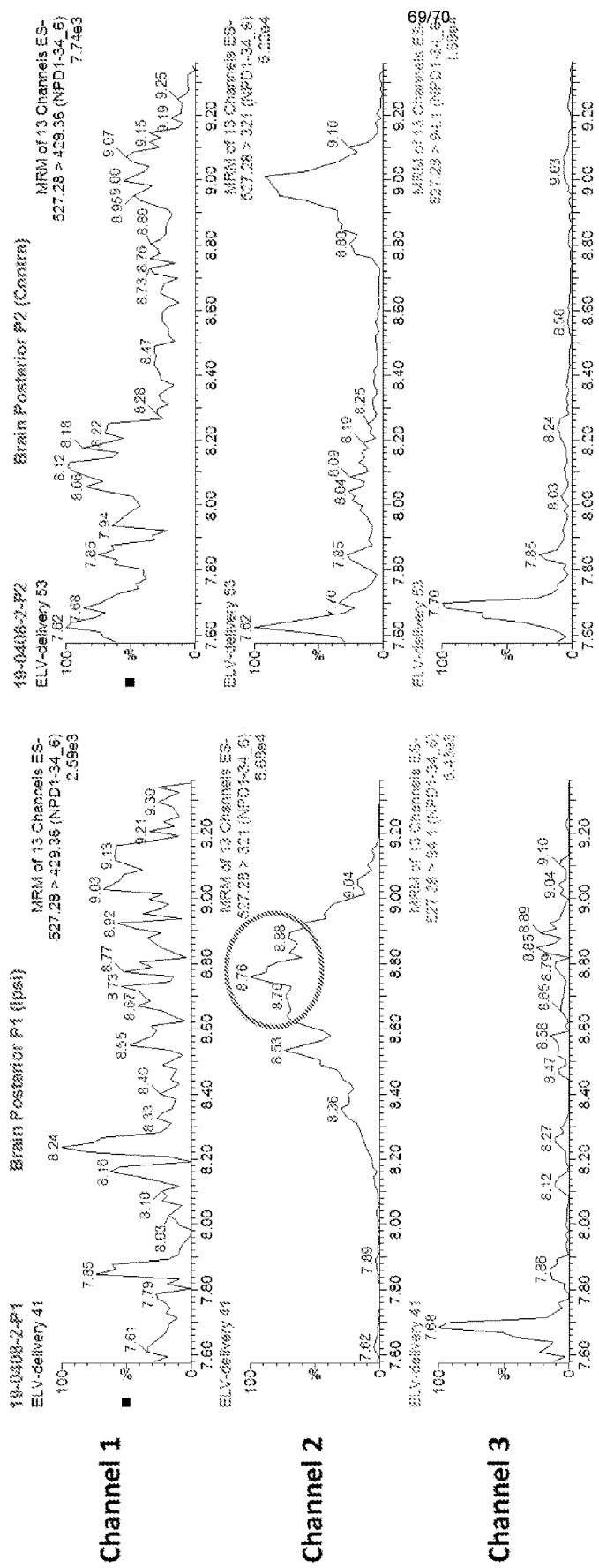

FIG. 47 illustrates ipsilateral and contralateral elovanoids after intranasal delivery, P1 and P2 as in FIG. 44. Red circle depicts elovanoids.

Figure 48:
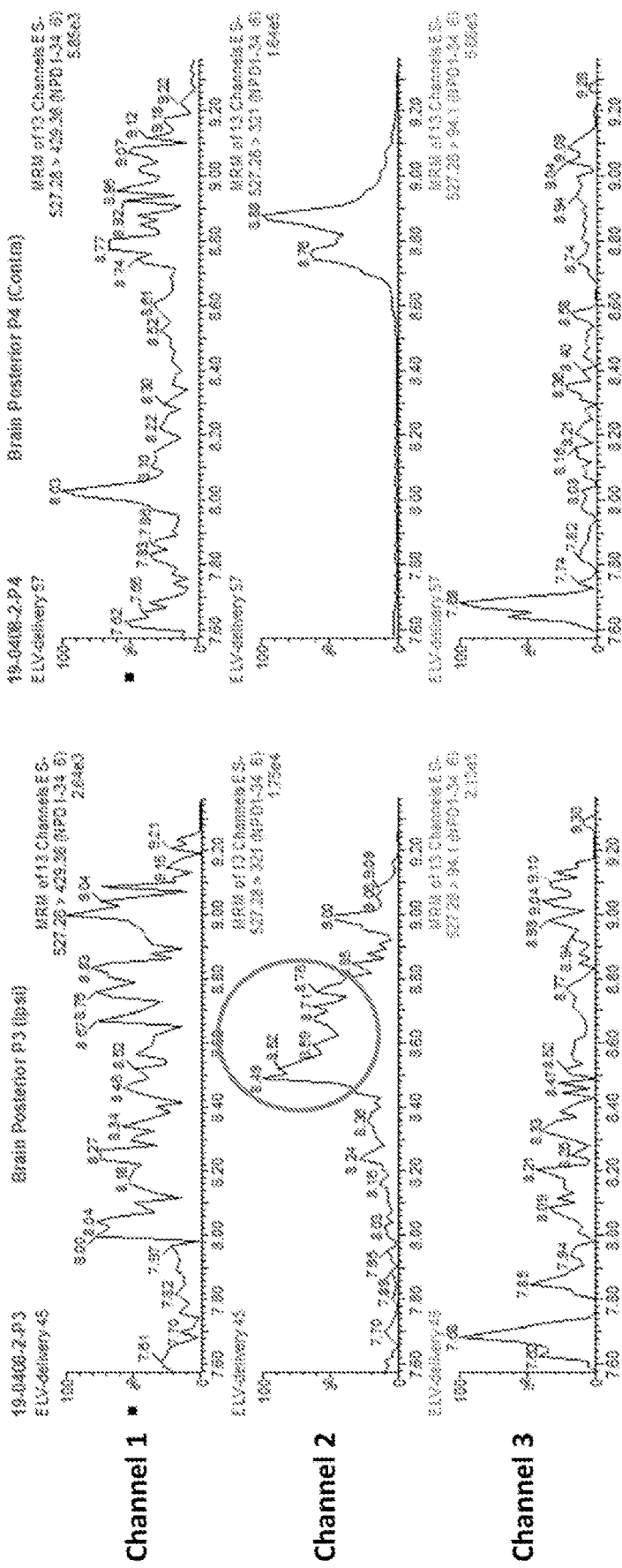

FIG. 48 illustrates ipsilateral and contralateral elovanoids after intranasal delivery, P3 and P4 as in FIG. 44. Red circles depicts elovanoids.

DETAILED DESCRIPTION OF THE DISCLOSURE

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the advantageous methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Alkyl groups herein include, but are not limited to, methyl, ethyl, propyl, isopropyl, isobutyl, n-butyl, sec-butyl, tert-butyl, isopentyl, neopentyl, tert-pentyl and isohexyl.

As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multi-cyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein, "n-3" or "n3", "n-6" or "n6", etc. refers to the customary nomenclature of polyunsaturated fatty acids or their derivatives, wherein the position of a double bond (C=C) is at the carbon atom counted from the end of the carbon chain (methyl end) of the fatty acid or fatty acid derivative. For example, "n-3" means the third carbon atom from the end of the carbon chain of the fatty acid or fatty acid derivative. Similarly, "n-3" or "n3", "n-6" or "n6", etc. also refers to the position of a substituent such as a hydroxyl group (OH) located at a carbon atom of the fatty acid or fatty acid derivative, wherein the number (e.g. 3, 6, etc.) is counted from the end of the carbon chain of the fatty acid or fatty acid derivative.

As used herein, the abbreviations for any protective groups and other compounds, are, unless indicated otherwise, in accord with their common usage, recognized abbreviations, or the IUPAC-IUB Commission on Biochemical Nomenclature (see, (1972) *Biochem.* 11:942-944).

As used herein, wherein in chemical structures of the compounds of the disclosure are shown having a terminal carboxyl group "—COOR" the "R" is intended to designate a group covalently bonded to the carboxyl such as an alkyl group. In the alternative, the carboxyl group is further intended to have a negative charge as "—COO$^-$" and R is a cation including a metal cation, an ammonium cation and the like.

As used herein "subject" is an animal, typically a mammal, including human, such as a patient.

As used herein, "pharmaceutically acceptable derivatives" of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamineand other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl, or heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl ar heterocyclyl.

Pharmaceutically acceptable solvates and hydrates are complexes of a compound with one or more solvent or water molecules, or 1 to about 100, or 1 to about 10, or one to about 2, 3 or 4, solvent or water molecules.

"Formulation" as used herein shall mean and include any collection of components of a compound, mixture, or solution selected to provide optimal properties for a specified end use, including product specifications and/or service conditions. The term formulation shall include liquids, semi-liquids, colloidal solutions, dispersions, emulsions, microemulsions, and nanoemulsions, including oil-in-water emulsions and water-in-oil emulsions, pastes, powders, and suspensions. The formulations of the present invention may also be included, or packaged, with other non-toxic compounds, such as cosmetic carriers, excipients, binders and fillers, and the like. Specifically, the acceptable cosmetic carriers, excipients, binders, and fillers contemplated for use in the practice of the present invention are those which render the compounds amenable to oral delivery and/or provide stability such that the formulations of the present invention exhibit a commercially acceptable storage shelf life.

As used herein, the term "administering" refers to providing a therapeutically effective amount of a formulation or pharmaceutical composition to a subject, using intravitreal, intraocular, ocular, subretinal, intrathecal, intravenous, subcutaneous, transcutaneous, intracutaneous, intracranial, topical and the like administration. The formulation or pharmaceutical compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; other proteins and peptides; synthetic polymers; microspheres; nanoparticles; and the like.

The formulations or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable to intravitreal delivery, intraocular delivery, ocular delivery, subretinal delivery, intrathecal delivery, intravenous delivery, subcutaneous delivery, transcutaneous delivery, intracutaneous delivery, intracranial delivery, topical delivery and the like. Moreover, the packaging material may be biologically inert or lack bioactivity, such as plastic polymers, silicone, etc. And may be processed internally by the subject without affecting the effectiveness of the composition/formulation packaged and/or delivered therewith.

Different forms of the present inventive formulation can be calibrated in order to adapt both to different individuals and to the different needs of a single individual. Implementing this concept is complicated, and the necessary research is challenging. However, the present formulation need not counter every cause in every individual. Rather, by countering the necessary causes, the present formulation will restore the body and brain to their normal function. Then the body and brain themselves will correct the remaining deficiencies. No drug can possibly correct every single cause of AD, but the present formulation will maximize the possibility.

The term "therapeutically effective amount" as used herein refers to that amount of an embodiment of the composition or pharmaceutical composition being administered that will relieve to some extent one or more of the symptoms of the disease or condition being treated, and/or that amount that will prevent, to some extent, one or more of the symptoms of the condition or disease that the subject being treated has or is at risk of developing. As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" or a "pharmaceutical formulation" is meant to encompass a composition or pharmaceutical composition suitable for administration to a subject, such as a mammal, especially a human and that refers to the combination of an active agent(s), or ingredient with a pharmaceutically acceptable carrier or excipient, making the composition suitable for diagnostic, therapeutic, or preventive use in vitro, in vivo, or ex vivo. In a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intratracheal, intramuscular, subcutaneous, by stent-eluting devices, catheters-eluting devices, intravascular balloons, inhalational and the like.

The term "administration" refers to introducing a composition of the present disclosure into a subject. One advantageous route of administration of the composition is topical administration. However, any route of administration, such as oral, intravenous, subcutaneous, peritoneal, intra-arterial, inhalation, vaginal, rectal, nasal, introduction into the cerebrospinal fluid, intravascular either veins or arteries, or instillation into body compartments can be used.

As used herein, "treatment" and "treating" refer to the management and care of a subject for the purpose of combating a condition, disease or disorder, in any manner in which one or more of the symptoms of a disease or disorder are ameliorated or otherwise beneficially altered. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications.

The patient to be treated is preferably a mammal, in particular a human being. Treatment also encompasses any pharmaceutical use of the compositions herein, such as use for treating a disease as provided herein.

The term nutritional component" as used herein refers to such as protein, a carbohydrate, vitamins, minerals and other beneficial nutrients including functional ingredients of the disclosure, that is, ingredients intended to be produce specific benefits to a person consuming the food. The carbohydrate can be, but is not limited to, glucose, sucrose, fructose, dextrose, tagatose, lactose, maltose, galactose, xylose, xylitol, dextrose, polydextrose, cyclodextrins, trehalose, raffinose, stachyose, fructooligosaccharide, maltodextrins, starches, pectins, gums, carrageenan, inulin, cellulose based compounds, sugar alcohols, sorbitol, mannitol, maltitol, xylitol, lactitol, isomalt, erythritol, pectins, gums, carrageenan, inulin, hydrogenated indigestible dextrins, hydrogenated starch hydrolysates, highly branched maltodextrins, starch and cellulose.

Commercially available sources of nutritional proteins, carbohydrates, and the like and their specifications are known, or can be ascertained easily, by those of ordinary skill in the art of processed food formulation.

The compositions of the disclosure that include nutritional components can be food preparations that can be, but are not limited to, "snack sized", or "bite sized" compositions that is, smaller than what might normally be considered to be a food bar. For instance, the food bar can be indented or perforated to allow the consumer to break off smaller portions for eating, or the food "bar" can be small pieces, rather than a long, bar-shaped product. The smaller pieces can be individually coated or enrobed. They can be packaged individually or in groups.

The food can include solid material that is not ground to a homogeneous mass, such as, without limitation. The food can be coated or enrobed, such as, and without limitation, with chocolate, including dark, light, milk or white chocolate, carob, yogurt, other confections, nuts or grains. The coating can be a compounded confectionary coating or a non-confectionary (e.g., sugar free) coating. The coating can be smooth, or can contain solid particles or pieces.

Discussion

Age-related and non-age-related inflammatory, degenerative, neurodegenerative, traumatic, dermatological, and cardiovascular diseases include a large number of diseases that affect a very large number of people worldwide. In most cases, these diseases and related conditions and disorders are difficult to treat, lead to impaired quality of life and/or reduced life span, and remain a major unmet medical need.

Inflammatory, degenerative or neurodegenerative diseases and conditions that may be reduced or eliminated by the compositions of the disclosure include, but are not limited to, acute and chronic disorders where homeostasis is disrupted by abnormal or dysregulated inflammatory response. These conditions are initiated and mediated by a number of inflammatory factors, including uncompensated oxidative stress, chemokines, cytokines, breakage of blood/tissue barriers, autoimmune diseases, calcium dysregulation including calcium overload is cells, mitochondria dysfunctions, genetic factors being gene susceptibility, polymorphisms or inherited conditions, or other conditions that engage leukocytes, monocytes/macrophages, microglia, astrocytes or parenchymal cells that induce excessive amounts of pro-cell injury, pro-inflammatory/disruptors of cellular and/or organ homeostasis. These diseases occur in a wide range of tissues and organs, including skin, muscles, stomach, intestines, liver, kidneys, lungs, eyes, ears, and brain. These diseases are currently treated, by anti-inflammatory agents such as corticosteroids, non-steroidal anti-inflammatory drugs, TNF modulators, COX-2 inhibitors, etc.

Degenerative diseases include conditions that involve progressive loss of vital cells and tissues that result in progressive impairment of function, such as loss of cartilage in knees, hip joints or other joints such as in osteoarthritis. Other degenerative diseases engage cellular and intercellular homeostasis perturbations and includes heart disease, atherosclerosis, cancer, diabetes, intestinal bowel disease, osteoporosis, prostatitis, rheumatoid arthritis, etc.

Neurodegenerative diseases include some of the major diseases of the brain, retina, spinal cord and peripheral nerves, whereby a progressive demise of cellular organization leads to impaired function. These are due to immune or inflammatory disorders and/or to inherited conditions or aging. They include multiple sclerosis, Alzheimer's disease, Parkinson's disease, amyotrophic lateral sclerosis, retina degenerative diseases such as age-related macular degeneration, inherited eye diseases such as retinitis pigmentosa, glaucoma, etc.

Ophthalmic inflammatory or degenerative diseases and conditions typically affect the cornea, optic nerve, trabecular mesh work, and the retina. Without an effective prevention or treatment, they can lead to blinding eye diseases, such as glaucoma, cataracts, diabetic retinopathy, and age-related macular degeneration (AMD).

Retinal degenerative diseases are the leading causes of blindness that affects very large numbers of people. Retinal degeneration is the deterioration of the retina caused by the progressive and eventual death of the photoreceptor cells of the retina. Examples of common retinal degenerative diseases include retinitis pigmentosa, age-related macular degeneration, and Stargardt disease. Retinitis pigmentosa affects between 50,000 and 100,000 people in the United States alone, and macular degeneration is the leading cause of vision loss for those aged 55 and older in the United States, affecting more than 10 million people. There are no effective treatments for these and other retinal degenerative diseases.

For retinal degenerative diseases, the detailed molecular mechanisms involved in the progressive loss of photoreceptor cells remain unknown, and available treatments today are not able to effectively treat these major diseases and prevent loss of sight. What is needed is a method for the prevention and treatment of retinal degenerative diseases that ensures the survival of the retina photoreceptor cells.

Systemic inflammatory or degenerative diseases and conditions can affect vital organs such as the heart, muscles, stomach, intestines, liver, kidneys and lungs, and can lead to age-related chronic inflammatory diseases such as rheumatoid arthritis, atherosclerosis, and lupus.

Brain-related inflammatory, degenerative or neurodegenerative diseases and conditions, such as Alzheimer's disease, Parkinson's disease, multiple sclerosis, ischemic stroke, traumatic brain injury, epilepsy, amyotrophic lateral sclerosis, often cause premature aging, cognitive dysfunctions and death.

Skin inflammatory or degenerative diseases and conditions often result from skin damage from sun exposure or other factors, including skin inflammation (dermatitis or eczema), atopic dermatitis (atopic eczema), skin dehydration, or from abnormal cell proliferation of the skin that results in excess flaking. Skin damage from sun exposure or other factors is associated with numerous diseases and conditions, such as eczema, psoriasis, atopic dermatitis or neurodermatitis, and can result by exposure to ultraviolet light and other types of contact dermatitis. Additionally, pruritus resulting from certain systemic diseases and conditions, provokes skin itching from various inflammatory and other types of stimuli, and causes the need to scratch, which can lead to further skin damage or altered skin appearance.

Despite much progress, understanding of the pathophysiology of inflammatory, neuroinflammatory, degenerative or neurodegenerative diseases and conditions that often lead to organ damage, chronic diseases, and accelerated aging, remains poorly understood.

Therefore, organ protection, prevention of aging-related diseases and conditions, and overall health restoration remain a major unmet medical need. There is also a major void for the effective protection of skin tissues from inflammatory, neuroinflammatory, hyper-proliferative, or dehydrative skin conditions. In particular, understanding of the pathophysiology of skin damage, skin altered appearance, and skin aging, remain unclear.

Available treatments today are not able to effectively treat these major diseases or to slow-down their progressive impairment of vital functions. What is needed is a method that ensures the survival of critical cells undergoing oxidative stress or other homeostatic disruptions. Therefore, there is a major therapeutic void for the management of inflammatory, neuroinflammatory, degenerative and neurodegenerative diseases.

The disclosure encompasses embodiments of compounds, compositions, and methods for the prevention and treatment of inflammatory and degenerative diseases, including neurodegenerative diseases and retinal degenerative diseases. This is based on new findings regarding the key protective role of certain omega-3 or omega-6 very long chain-polyunsaturated fatty acids (n3 or n6 VLC-PUFA) and their related hydroxylated derivatives.

Investigations have shown that certain long chain polyunsaturated fatty acids (LC-PUFAs) play important roles in inflammation and related conditions. These include the omega-3 (n3) and omega-6 (n6) polyunsaturated fatty acids containing 18-22 carbons including: arachidonic acid (ARA, C20:4n6, i.e. 20 carbons, 4 double bonds, omega-6), eicosapentaenoic acid (EPA, C20:5n3, 20 carbons, 5 double bonds, omega-3), docosapentaenoic acid (DPA, C22:5n3, 22 carbons, 5 double bonds, omega-3), and docosahexaenoic acid (DHA, C22:6n3, 22 carbons, 6 double bonds, omega-3).

LC-PUFAs are converted via lipoxygenase-type enzymes to biologically active hydroxylated PUFA derivatives that function as biologically active lipid mediators that play important roles in inflammation and related conditions. Most important among these are hydroxylated derivatives generated in certain inflammation-related cells via the action of a lipoxygenase (LO or LOX) enzyme (e.g. 15-LO, 12-LO), and result in the formation of mono-, di- or tri-hydroxylated PUFA derivatives with potent actions including anti-inflammatory, pro-resolving, neuroprotective or tissue-protective actions, among others. For example, neuroprotectin D1 (NPD1), a dihydroxy derivative from DHA formed in cells via the enzymatic action of 15-lipoxygenase (15-LO) was shown to have a defined R/S and Z/E stereochemical structure (10R,17S-dihydroxy-docosa-4Z,7Z,11E,13E,15Z,19Z-hexaenoic acid) and a unique biological profile that includes stereoselective potent anti-inflammatory, homeostasis-restoring, pro-resolving, bioactivity. NPD1 has been shown to modulate neuroinflammatory signaling and proteostasis, and to promote nerve regeneration, neuroprotection, and cell survival.

Other important types of fatty acids are the n3 and n6 very-long-chain polyunsaturated fatty acids (n3 VLC-PUFA, n6 VLC-PUFA) that are produced in cells containing elongase enzymes that elongate n3 and n6 LC-PUFA to n3 and n6 VLC-PUFA containing from 24 to 42 carbons (C24-C42). The most important among these seem to be VLC-PUFA with 28-38 carbons (C28-C38). Representative types of VLC-PUFA include C32:6n3 (32 carbons, 6 double bonds, omega-3), C34:6n3, C32:5n3, and C34:5n3. These VLC-PUFA are biogenically-derived through the action of elongase enzymes, particularly ELOVL4 (ELOngation of Very Long chain fatty acids 4). VLC-PUFA are also acylated in complex lipids including sphingolipids and phospholipids particularly in certain molecular species of phosphatidyl choline.

The biosynthetic role of ELOVL4 and the biological functions of VLC-PUFA have been the subject of a number of recent investigations that have suggested roles in the retina, brain, testis, and skin. These VLC-PUFA are thought to display functions in membrane organization, and their significance to health is increasingly recognized.

The importance of VLC-PUFA in the retina, an integral part of the central nervous system, as well as in the brain has been shown. For example, the autosomal dominant Stargardt-like macular dystrophy (STGD3), a Juvenile-onset retinal degenerative disease is caused by mutations in exon 6 of the ELOVL4 gene that leads to a truncated ELOVL4 protein (a key elongase enzyme) without an endoplasmic reticulum (ER) retention/retrieval signal, resulting in severe decrease in the biosynthesis of VLC-PUFA. Low retinal levels of VLC-PUFA and abnormally low n3/n6 ratios also occur in age-related macular degeneration (AMD) donor eyes as compared to age-matched control eye donors. Recessive ELOVL4 mutations display clinical features of ichthyosis, seizures, mental retardation, and spastic quadriplegia that resembles Sjogren-Larsson syndrome (SLS) with severe neurologic phenotype implying the significance of VLC-PUFA synthesis for the central nervous system and cutaneous development.

VLC-PUFA were found to be incorporated in phospholipids of the photoreceptor outer membrane and were shown to play important roles in the longevity of photoreceptors, and in their synaptic function and neuronal connectivity. Therefore, bioactive derivatives based on VLC-PUFA, which are able to prevent the apoptosis of photoreceptor cells may provide therapeutic benefits for various types of retinal degenerative diseases, including Stargardt-like macular dystrophy (STGD3), and X-linked juvenile retinoschisis (XLRS) an inherited early onset retinal degenerative disease caused by mutations in the RS1 gene, which is the leading cause of juvenile macular degeneration in males. This condition denotes a significant photoreceptor synaptic impairment for which there is no available treatment.

The compounds, compositions and methods encompassed by the embodiments of the disclosure involve the use of n3 VLC-PUFA for the induction of survival signaling in the brain and the retina, particularly in the retinal pigment epithelial cells and photoreceptors.

Biosynthetic Pathways for n3 VLC-PUFA:

The biosynthesis of n3 VLC-PUFA begins from lower-carbon PUFA that contain only an even number of carbons in their carbon chain, such as docosahexaenoic acid (DHA) that contains 22 carbons and 6 alternating C=C bonds (C22:6n3), and docosapentaenoic acid (DPA) that contains 22 carbons and 5 alternating C=C bonds (C22:5n3). The biosynthesis of n3 VLC-PUFA requires the availability of DHA or other shorter-chain PUFA as substrates, and the presence and actions of certain elongase enzymes, e.g. ELOVL4. As summarized in FIGS. 1 and 2, these 22-carbon omega-3 long-chain fatty acids (n3 LC-PUFA) are substrates to elongase enzymes, such as ELOVL4, which adds a 2-carbon $CH_2CH_2$ group at a time to the carboxylic end, forming n3 VLC-PUFA that contain carbon chains with at least 24 carbons of up to at least 42 carbons.

Docosahexaenoic acid (DHA, C22:6n3, 1 is incorporated at the 2-position of phosphatidyl choline molecular species (3) and is converted by elongase enzymes to longer-chain n3 VLC-PUFA. Elongation by the elongase enzyme ELOVL4 (ELOngation of Very Long chain fatty acids-4) leads to the formation of very long chain omega-3 polyunsaturated fatty acids (n3 VLC-PUFA, 2, including C32:6n3 and C34:6n3 that are then incorporated at the 1-position of phosphatidyl choline molecular species, 3. Without wishing to be bound by theory, the presence of DHA at the 2-position and n3 VLC-PUFA at the 1-position can offer redundant, complementary, and synergistic cytoprotective and neuroprotective actions that amplify the survival of neurons and other key cell types when challenged with pathological conditions.

Lipoxygenation of n3-VLC-PUFA, 3 leads to the formation of enzymatically-hydroxylated derivatives of n3-VLC-PUFA, termed elovanoids, which include monohydroxy compounds (e.g. ELV-275 and ELV-29S, 4, and dihydroxy derivatives, e.g. ELV-N32 and ELV-N34, 5. Elovanoid ELV-N32 is the 20R,27S-dihydroxy 32:6 derivative (32-carbon, 6 double bond elovanoid with a neuroprotectin-like 20(R),27(S)-dihydroxy pattern). Elovanoid ELV-N34 is the 22R,29S-dihydroxy 34:6 derivative (34-carbon, 6 double bond elovanoid with a 22(R),29(S)-dihydroxy pattern).

Figure 1:
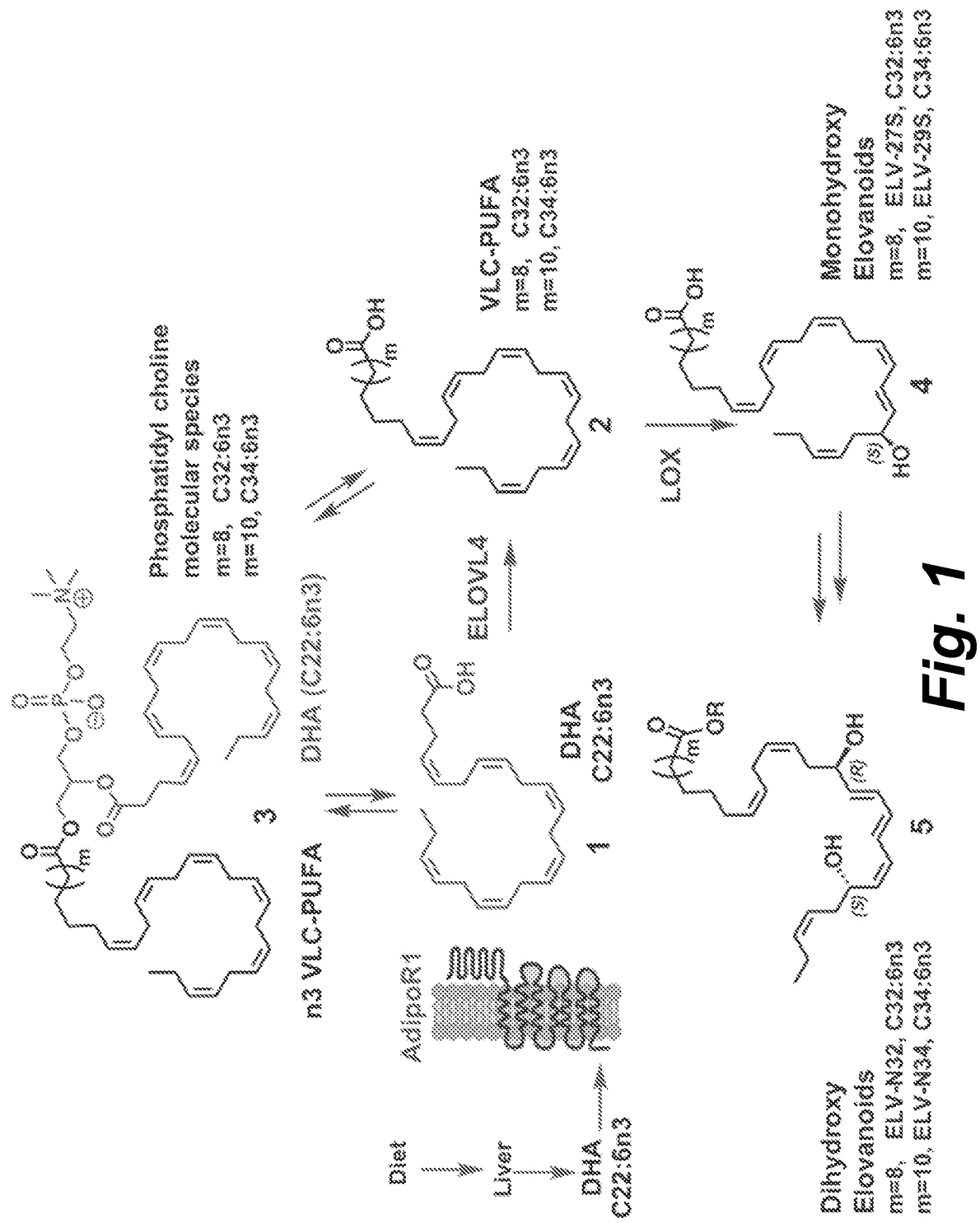
FIG. 1 is a scheme illustrating the postulated biosynthesis of elovanoids (ELV) from omega-3 (n-3 or n3) very long chain polyunsaturated fatty acids (n3 VLC-PUFA).
Figure 2:
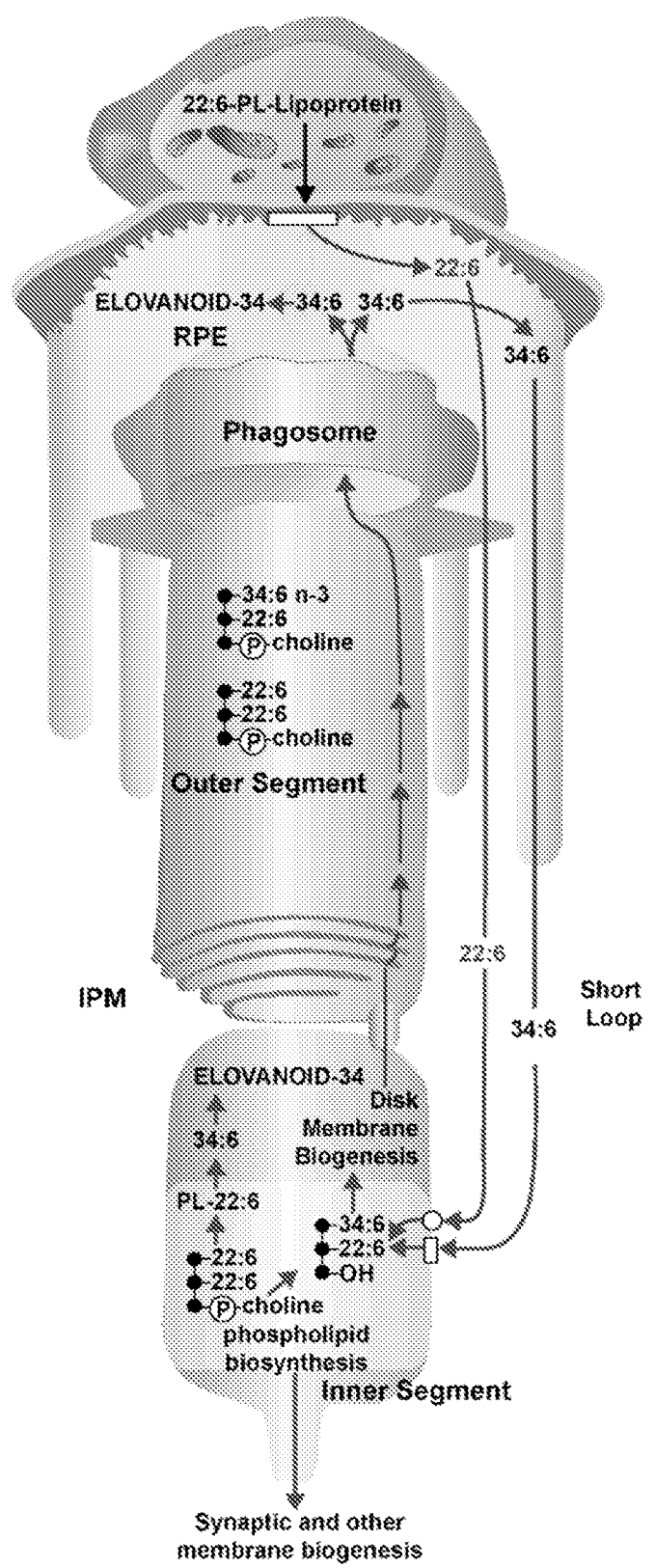
FIG. 2 is a scheme illustrating the postulated biosynthesis of n3 VLC-PUFA.

FIG. 2 illustrates the delivery of docosahexaenoic acid (DHA, C22:6n3) to photoreceptors, photoreceptor outer segment membrane renewal, and the synthesis of elovanoids. DHA or precursor C18:3n3 are obtained by diet, as is DHA itself (FIG. 1). The systemic circulation (mainly the portal system) brings them to the liver. Once within the liver, hepatocytes incorporate DHA into DHA-phospholipid (DHA-PL), which is then transported as lipoproteins to the choriocapillaries, neurovascular unit, and to the capillaries of other tissues.

DHA crosses Bruch's membrane from the choriocapillaries (FIG. 2) and is taken up by the retinal pigment epithelium (RPE) cells lining the back of the retina to be sent to the inner segment of photoreceptors. This targeted delivery route from the liver to the retina is referred to as the DHA long loop.

DHA then passes through the interphotoreceptor matrix (IPM) and to the photoreceptor inner segment, where it is incorporated into phospholipids for the photoreceptor outer segments, cell membrane and organelles. The majority is used in disk membrane biogenesis (outer segments). As new DHA-rich disks are synthesized at the base of the photoreceptor outer segment, older disks are pushed apically toward the RPE cells. Photoreceptor tips are phagocytized by the RPE cells each day, removing the oldest disks. The resulting phagosomes are degraded within the RPE cells, and DHA is recycled back to photoreceptor inner segments for new disk membrane biogenesis. This local recycling is referred to as the 22:6 short loop.

Elovanoids are formed from omega-3 very long chain polyunsaturated fatty acids (n3 VLC-PUFA) biosynthesized by ELOVL4 (ELOngation of Very Long chain fatty acids-4) in the photoreceptor inner segments. Thus, a phosphatidyl-choline molecular species in the inner segment that contains VLC Omega-3 FA at C1 (C34:6n3 is depicted) and DHA (C22:6n3) at C2 is used for photoreceptor membrane biogenesis. This phospholipid has been found tightly associated to rhodopsin. Once the discs are phagocytized in RPE cells as a daily physiological process, upon homeostatic disturbances, a phospholipase A1 (PLA1) cleaves the acyl chain at sn-1, releasing C34:6n3 and leads to the formation of elovanoids (e.g. elovanoid-34, ELV-N34). VLC omega-3 fatty acids that are not used for elovanoid synthesis are recycled through the short loop.

Therefore, for biosynthetic reasons, the naturally occurring and biogenetically derived n3 VLC-PUFA contain only an even number of carbons, ranging from at least 24 carbons to at least 42 carbons (i.e. 24, 26, 28, 30, 32, 34, 36, 38, 40, 42 carbons). Thus, n3 VLC-PUFA that contain only an odd number of carbons ranging from at least 23 of up to at least 41 carbons (i.e. 23, 25, 27, 29, 31, 33, 35, 37, 39, 41 carbons) are not naturally occurring, but they can be synthesized and manufactured using synthetic chemical methods and strategies.

Stereocontrolled Total Synthesis and Structural Characterization of Elovanoids ELV-N32 and ELV-N34 in the Retina and the Brain:

As summarized in FIGS. 3 and 4, ELV-N32 (27S- and ELV-N34 were synthesized from three key intermediates (1, 2, and 3), each of which was prepared in stereochemically-pure form. The stereochemistry of intermediates 2 and 3 was pre-defined by using enantiomerically pure epoxide starting materials. Iterative couplings of intermediates 1, 2, and 3, led to ELV-N32 and ELV-N34 (4) that were isolated as the methyl esters (Me) or sodium salts (Na). The synthetic materials ELV-N32 and ELV-N34 were matched with endogenous elovanoids with the same number of carbons on their carbon chain, obtained from cultured human retinal pigment epithelial cells (RPE) (FIG. 3), and neuronal cell cultures (FIG. 4).

Experimental Detection and Characterization of the Elovanoids:

Experimental evidence documents the biosynthetic formation of the elovanoids, which are mono-hydroxy and di-hydroxy n3 VLC-PUFA derivatives with molecular structures that are analogous to DHA-derived 17-hydroxy-DHA and the di-hydroxy compound NPD1 (10R,17S-dihydroxy-docosa-4Z,7Z,11E,13E,15Z,19Z-hexaenoic acid). The elovanoids are enzymatically generated hydroxylated derivatives of 32-carbon (ELV-N32) and 34-carbon (ELV-N34) n3 VLC-PUFA in that were first identified in cultures of primary human retinal pigment epithelial cells (RPE) (FIGS. 3A-3K) and in neuronal cell cultures (FIGS. 4A-4K).

The disclosure provides compounds having carbon chains related to n3 VLC-PUFA that in addition to having 6 or 5

Figure 5A:
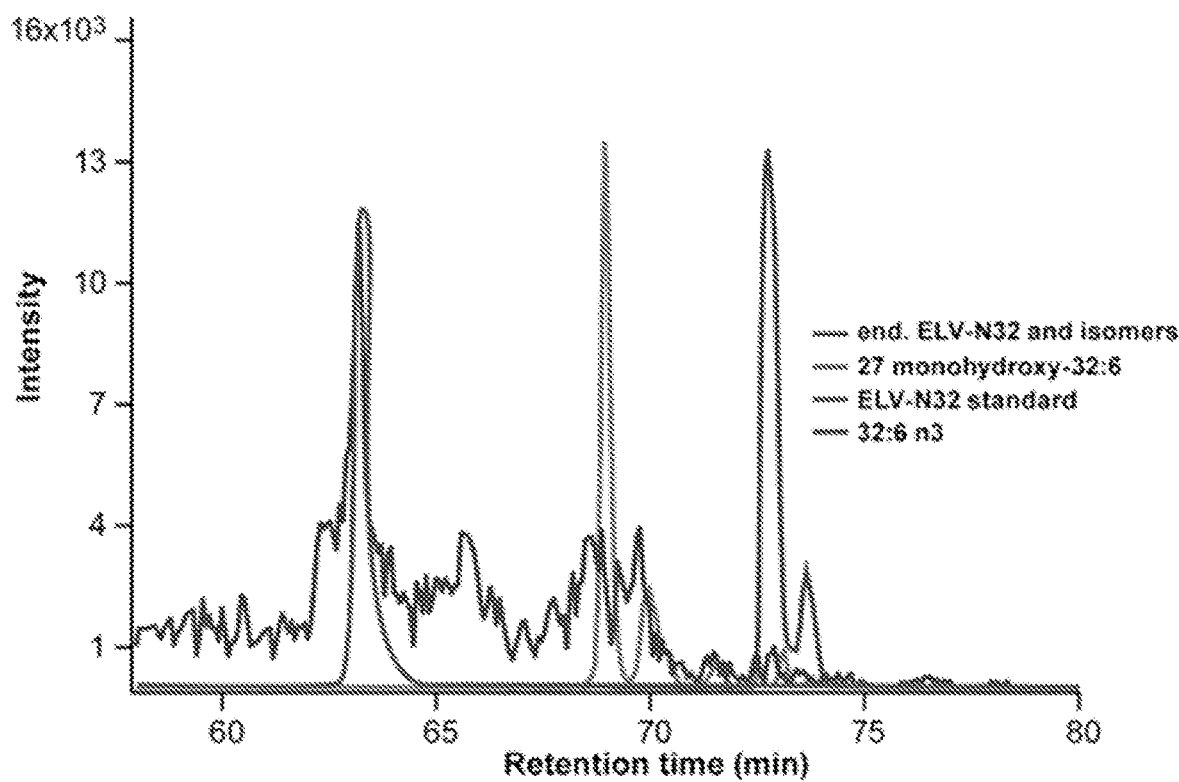
FIGS. 5A and 5B illustrate the detection of ELV-N32 and ELV-N34 in neuronal cell cultures. Cells were incubated with C32:6n3 and C34:6n3 5 μM each, under OGD conditions.
Figure 5B:
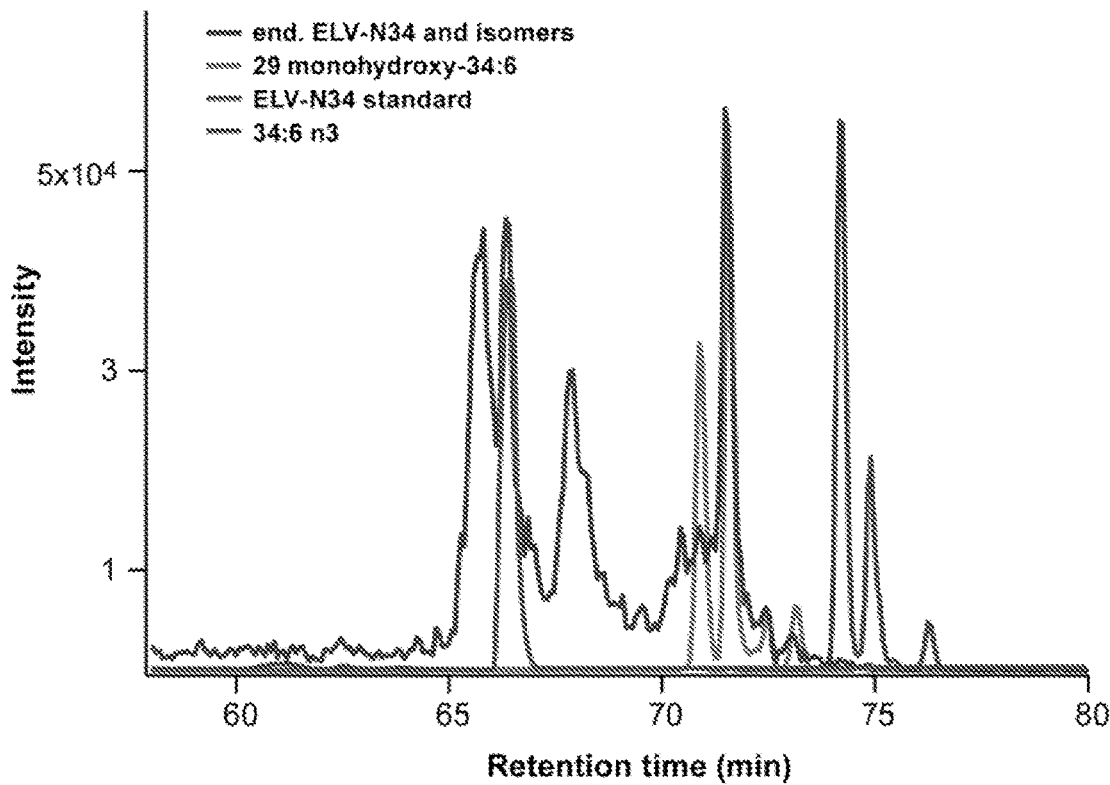

C═C bonds, they also contain one, two or more hydroxyl groups. Because compounds of this type may be responsible for the protective and neuroprotective actions of n3 VLC-PUFA, we sought to identify their existence in human retinal pigment epithelial cells in culture, with added 32:6n3 and 34:6n3 VLC-PUFA fatty acids. Our results indicated monohydroxy- and di-hydroxy elovanoid derivatives from both 32:6n3 and 34:6n3 VLC-PUFA fatty acids. The structures of these elovanoids (ELV-N32, ELV-N34) were compared with standards prepared in stereochemical pure form via stereocontrolled total organic synthesis (FIGS. 5A and 5B).

Beneficial Use of n3 VLC-PUFA and Elovanoids in Ophthalmic Diseases and Conditions:

Ophthalmic inflammatory or degenerative diseases and conditions typically affect the cornea, optic nerve, trabecular mesh work, and the retina. Without an effective prevention or treatment, they can lead to blinding eye diseases, such as glaucoma, cataracts, diabetic retinopathy, and age-related macular degeneration (AMD). There is a growing evidence that ELOVL4 mutations and/or a reduced presence of n3 VLC-PUFA in retinal cells and tissues, are associated with degenerative, neurodegenerative, and retinal degenerative diseases, which are linked to excessive and persistent inflammatory environment. Thus, the structures, properties, and effects of n3 VLC-PUFA in cells and tissues of the retina, where they are known to play dominant roles were evaluated.

Experiments were done using human retinal pigment epithelial (RPE) cells that are neuroectoderm-derived postmitotic cells of the retina, an integral part of the central nervous system. These cells are richly endowed with a multitude of mechanisms to protect themselves from injury and to protect other cells, particularly the survival of photoreceptors. They are the most active phagocyte of the human body, critical for the health of photoreceptors and vision, and have the ability to secrete neurotrophins and other beneficial substances.

Figure 6A:
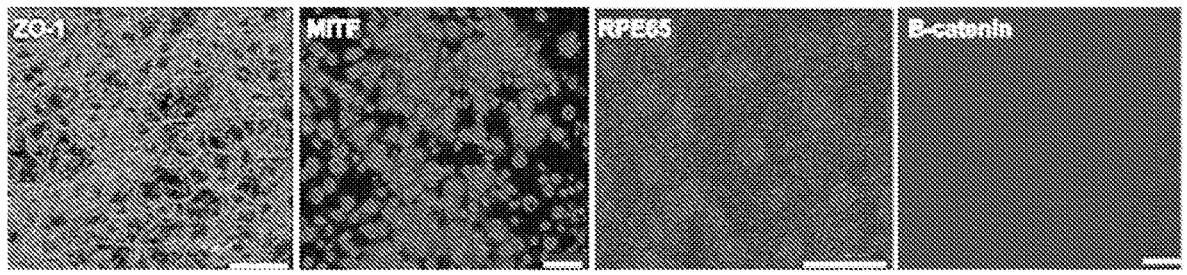
FIG. 6A illustrates confocal images of immunostaining of primary human RPE cells using specific markers ZO-1 (Zona occludens-1), RPE65, MITF (Microphthalmia-associated Transcription Factor), and β-catenin.
Figure 6B:
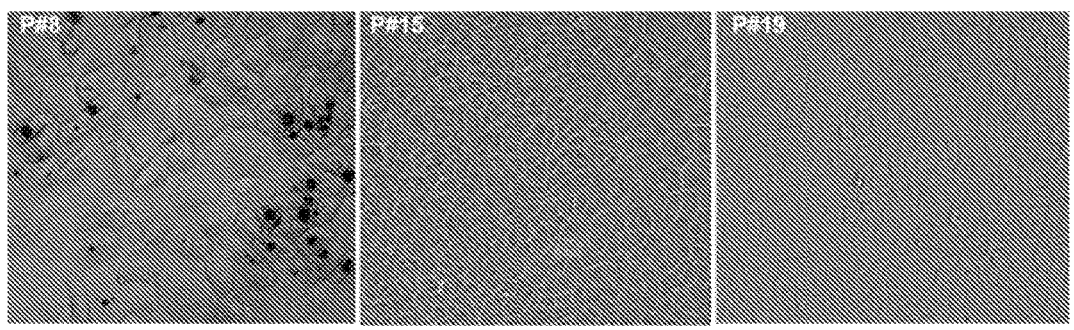
FIG. 6B illustrates light microscopy images depicting primary human RPE cell morphology at different passages in culture. Magnification bars, 50 μm.
Figure 9C:
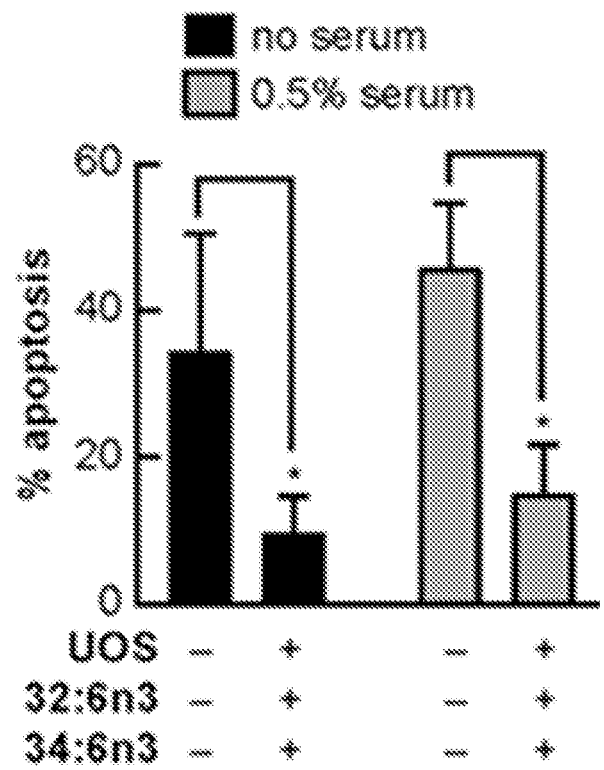

The beneficial roles of n3 VLC-PUFA in retinal degenerative diseases, such as autosomal dominant Stargardt-like macular dystrophy (STGD3), and age-related macular degeneration (AMD) is supported by the following: (a) n3 VLC-PUFA are biosynthesized in the retina and are known to play dominant roles in the retina; (b) Elovanoids ELV-N32 and ELV-N34 were discovered and structurally characterized in primary human retinal pigment epithelial cells (RPE) in culture (FIGS. 1, 6A and 6B); (c) ELOVL4 is a key enzyme involved in the conversion of DHA (C22:6) into n3 VLC-PUFA; (d) Certain mutations in the elongase enzyme ELVOL4 lead to retinal degenerative diseases such as STGD3 and AMD; (e) Genetic ablation of the protein that is necessary to capture DHA into retinal cells containing ELOVL4 products result in drastically decreased levels of VLC-PUFAs with consequent retinal degeneration; (f) Uncompensated oxidative stress (UOS) in RPE cells is associated with the early stages of retinal degenerative diseases; (g) n3 VLC-PUFA C32:6n3 and C34:6n3 provide cytoprotection to human RPE cells exposed to UOS (as shown in FIGS. 7A-8C), which cannot be modified with a lipoxygenase inhibitor (FIGS. 9A-9C); (h) Elovanoids ELV-N32 and ELV-N34 provide cytoprotection to human RPE cells under UOS by upregulating anti-apoptotic proteins (FIGS. 10A-10G) and promoting photoreceptor cell survival (FIGS. 11A-11D); (i) Elovanoids ELV-N32 and ELV-N34 promote photoreceptor cell integrity in Late-Onset Retinal Degeneration (L-ORD) (FIGS. 12A and 12B).

As shown in FIGS. 14A-14C, elovanoids (ELV) counteract Aβ peptide-induced retinal pigment epithelial cell senescence progression. Aβ42, an end product of the amyloidogenic pathway, is a component of drusen in age-related macular degeneration (AMD), and of senile plaques in Alzheimer's disease (AD). To mimic the effect of OAβ in vivo, 6-month-old mice were used and sub-retinally injected with OAβ alone, OAβ+ELVs and ELVs alone. The no injection mice were used as negative control while the PBS injected mice were used as the sham. The injection volume was 2 μl containing of PBS, 10 μM of OAβ, 10 μM of OAβ+200 ng ELV-32, 200 ng ELV-32 alone, 10 μM of OAβ+200 ng ELV-34 or 200 ng ELV-34 alone. At day 3 after injection, mRNA from eyecup was isolated and analyzed the gene expression using q-PCR. Then, at day 7, the mice were subjected to Optical Coherence Tomography (OCT) analysis and then the eyes were enucleated and processed for histology, whole mount RPE staining, and western blotting (WB). OCT and histology uncovers that in OAβ induced retinal degeneration, the thickness of retina was thinner in OAβ injected group when compared to the controls as well as ELVs treatment groups. The whole-mount staining with ZO-1 revealed that the tight junction was disrupted by OAβ also. Interestingly, the co-injection of ELVs and OAβ showed that ELVs were able to restore the morphology and homeostasis of RPE layer. Furthermore, in the WB analysis, the protein level of p16INK4a, a senescence marker, was up-regulated in OAβ group but was suppressed in ELVs co-treatment and control groups. Finally, the gene expression analysis showed that ELVs reduced the level of both senescent and AMD markers, which were triggered by OAβ injection, while it induced the expression of RPE functional genes, which were down-regulated in OAβ-injected group. This data demonstrated that ELV-32 and ELV-34 protect RPE and retina from OAβ induced senescence by down-regulating senescence, AMD, and inflammation-associated gene expression, and by preserving the expression of RPE-functional genes, resulting in restored retinal structure and sustained homeostasis.

Elovanoid (ELV) compounds: 1. ELV C32:6-acetylenic methyl ester; 2. ELV C32:6-NPD1-like sodium salt; 3. ELV C34:6-acetylenic methyl ester; 4. ELV C32:6-NPD1-like methyl ester; 5. ELV C34:6-NPD1-like methyl ester.

There are more than 100 genes involved in the autophagic process. The following genes are elevated in AMD disease:

ATG3 (Autophagy Related 3) This gene encodes a ubiquitin-like-conjugating enzyme and is a component of ubiquitination-like systems involved in autophagy, the process of degradation, turnover and recycling of cytoplasmic constituents in eukaryotic cells. This protein is known to play a role in regulation of autophagy during cell death.

ATG5 (Autophagy Related 5) The protein encoded by this gene, in combination with autophagy protein 12, functions as an E1-like activating enzyme in a ubiquitin-like conjugating system. The encoded protein is involved in several cellular processes, including autophagic vesicle formation, mitochondrial quality control after oxidative damage, negative regulation of the innate antiviral immune response, lymphocyte development and proliferation, MHC II antigen presentation, adipocyte differentiation, and apoptosis.

ATG7 (Autophagy Related 7) This gene encodes an E1-like activating enzyme that is essential for autophagy and cytoplasmic to vacuole transport. The encoded protein is also thought to modulate p53-dependent cell cycle pathways during prolonged metabolic stress. It has been associated with multiple functions, including axon membrane trafficking, axonal homeostasis, mitophagy, adipose differentiation, and hematopoietic stem cell maintenance.

BECN1 (Beclin 1) This gene encodes a protein that regulates autophagy, a catabolic process of degradation induced by starvation. The encoded protein is a component of the phosphatidylinositol-3-kinase (PI3K) complex which mediates vesicle-trafficking processes. This protein is thought to play a role in multiple cellular processes, including tumorigenesis, neurodegeneration and apoptosis.

Senescent cells have several distinguishing characteristics, such as increased cell size, induced enzymatic activity of the lysosomal hydrolase senescence-associated β-galactosidase (SA-β-GAL). (2). Besides these features, there are also the activation of the senescence signaling pathways, including p16INK4a, p21CIP1, p27KIP and p53. (3)

p16INK4a (also known as cyclin-dependent kinase inhibitor 2A, Cyclin-Dependent Kinase 4 Inhibitor A or several other synonyms), is a tumor suppressor protein. This protein is encoded by the CDKN2A gene. p16 plays an important role in cell cycle regulation by decelerating cells progression from G1 phase to S phase.

p21Cip1 (also known as p21Waf1, cyclin-dependent kinase inhibitor 1 or CDK-interacting protein 1) is a cyclin-dependent kinase inhibitor (CKI) that is capable of inhibiting all cyclin/CDK complexes. This protein is encoded by the CDKN1A gene. p21 represents a major target of p53 activity and thus is associated with linking DNA damage to cell cycle arrest.

p27Kip1 (also known as cyclin-dependent kinase inhibitor 1B) is an enzyme inhibitor. This protein is encoded by the CDKN1B gene. It encodes a protein which belongs to the Cip/Kip family of cyclin dependent kinase (Cdk) inhibitor proteins. The encoded protein binds to and prevents the activation of cyclin E-CDK2 or cyclin D-CDK4 complexes, and thus controls the cell cycle progression at Cl. It is often referred to as a cell cycle inhibitor protein because its major function is to stop or slow down the cell division cycle.

p53 (also known as Tumor protein p53, tumor suppressor p53) is also a cell cycle inhibitor. This protein is encoded by the TP53 (humans) and Trp53 (mice). Multiple stressors can activate directly or indirectly p53 through the kinases. The consequence is the inhibition of all cyclin and cause the cell arrest.

The data provide support for the therapeutic or preventive use of n3 VLC-PUFA, or their elovanoids (e.g. ELV-N32, ELV-N34), in the eye, including the treatment of retinal degenerative diseases and other ophthalmic diseases and conditions, including glaucoma, cataracts, diabetic retinopathy, Stargardt-like macular dystrophy (STGD3), and age-related macular degeneration (AMD).

Beneficial Use of n3 VLC-PUFA and Elovanoids in Brain Diseases and Conditions:

The VLC-PUFA and elovanoid pathways are active in the central nervous system (CNS), including the brain, and neuronal cells.

ELV-N32 (Na or Me forms) or ELV-N34 (Na or Me forms), when applied to cerebral-cortical mixed neuronal cells or hippocampal cells in culture, are able to overcome the damaging effects of uncompensated oxidative stress, NMDA-induced neuronal excitotoxicity or OGD. The majority of strokes are ischemic in nature and deprivation of oxygen and glucose leads to a cascade of events involving mitochondrial damage, which ultimately leads to neuronal death. Therefore, the in vitro OGD model provides an opportunity for teasing out the cellular events and putative underlying neuroprotective signaling pathways in which ELVs participate. Both ELV-N32 and ELV-N34 elicit neuroprotection and overcome neuronal cytotoxicity. The 32-carbon omega-3 VLC-PUFA (C32:6n3) precursor of ELVs, when applied at a dose of 250 nM after 2 h of re-oxygenation phase following a 90 mins of OGD insult, was able to provide neuroprotection to cerebral cortical neurons. In conclusion, the endogenously-generated elovanoids (ELV-N32 or ELV-N34) ameliorated neuronal injury induced by several stressors like NMDA, uncompensated oxidative stress or OGD in cerebral cortical and hippocampal neurons in culture. These novel bioactive lipids belong to a new class of lipid mediators, termed elovanoids (ELV), which are derived from phospholipid molecular species having two PUFAs at positions C1 and C2.

All ELV treatments, delivered at 1 h after 2 h of experimental ischemic stroke, improved neurological recovery throughout the 7-day survival period. The rapid induction of brain edema following focal ischemia is a leading cause of morbidity and death after stroke. Maximum protection was detected in the cortex (the penumbral area) and also in the subcortical area. Histopathology revealed smaller infarcts in cortical and subcortical areas with less pancellular damage, denser areas of eosinophilic, and shrunken neurons along the infarct margin, all of which were detected in elovanoid-treated rats.

Cerebral ischemia initiates a complex cascade of cellular, molecular and metabolic events that lead to irreversible brain damage. Dead neurons and injured tissue are scavenged by activated resident microglia and/or macrophages that invade the injured tissue from the blood stream. Surviving astrocytes and activated microglia in the penumbra may facilitate restoration of neuronal integrity by producing growth factors, cytokines, and extracellular matrix molecules involved in repair mechanisms. The results demonstrate that ELV treatment increased the number of NeuN-positive neurons, GFAP-positive reactive astrocytes, and SMI-71-positive blood vessel density in the cortex. Blood vessel integrity facilitates neurogenesis and synaptogenesis, which in turn contributes to improved functional recovery.

After cerebral ischemia, the integrity of the BBB is compromised, allowing uncontrolled entry of molecules into the brain parenchyma that worsens damage caused by ischemia. In patients, a loss of BBB integrity is associated with worse stroke outcome. Ischemic disruption of the BBB by infiltration of endogenous IgG into the brain parenchyma was measured. Treatment with ELV-N34-Na and ELV-N34-Me attenuated BBB disruption induced by focal cerebral ischemia.

The newly-identified ELVs protected neurons undergoing oxygen glucose deprivation or NMDA receptor-mediated excitotoxicity. Moreover, ELVs attenuated infarct volumes, rescued the ischemic core and penumbra, diminished BBB damage, and promoted cell survival accompanied with neurological/behavioral recovery. Thus, without wishing to be bound by theory novel ELVs therapy can be used for treating focal ischemic stroke and other conditions that engage inflammatory/homeostatic disruptions.

The beneficial roles of ELOVL4 and n3 VLC-PUFA in the CNS is provided herein: (a) ELOVL4 is expressed in the CNS, including neuronal cells, and is involved in the conversion of DHA (C22:6) into n3 VLC-PUFA; (b) In an in vitro model of Oxygen-Glucose Deprivation (OGD) in primary cortical neurons, n3 VLC-PUFA are released by primary cortical neurons in response to OGD and are enzymatically converted to mono-hydroxy elovanoids 27(S)-hydroxy-32:6n3 (FIG. 13B) and 29(S)-hydroxy-34:6n3 (FIG. 13C). However, in control media, where the neurons are not exposed to OGD, the levels of n3 VLC-PUFA (e.g.

C32:6n3 and C34:6n3) and mono-hydroxy elovanoids are negligible (FIGS. 13B and 13C).

As shown in FIGS. 13A-13D, n3 VLC-PUFA (e.g. C32: 6n3 and C34:6n3) are endogenously released by primary cortical neurons from SD rat embryos in response to oxygen-glucose deprivation (OGD); and are enzymatically converted to elovanoids, including 29(S)-hydroxy-34:6n3 and 27(S)-hydroxy-32:6n3. In control media where the neurons are not exposed to OGD the levels of VLC-PUFA (e.g. C32:6n3 and C34:6n3) and elovanoids are negligible. An in vitro OGD model was established and primary mixed cortical neurons were cultured from SD rat embryos. On DIV 12, cells were washed with phosphate-buffered saline (PBS) and incubated with glucose-free Neurobasal medium (Gibco) for 30 min. After that, the cells were placed in a modular incubator chamber (Billups-Rothenberg Inc.) and incubated in an anaerobic chamber (95% N2 and 5% $CO_2$) for OGD for 90 min at 37° C. After 90 min of OGD exposure, cells were returned to the original medium [Neurobasal medium (Gibco) containing 2% B27 (Gibco) and 2% N-2 (Gibco) supplements, along with 0.5 mM glutamine and Pen Strep (50 U/ml) (Gibco)] and maintained in a normoxic chamber (37° C., 5% $CO_2$) for 12 h. For the normoxic (control) conditions, neurons were washed with PBS but maintained in a regular medium [Neurobasal medium (Gibco) containing 2% B27 (Gibco) and 2% N-2 (Gibco) supplements, along with 0.5 mM glutamine and Pen Strep (50 U/ml) (Gibco)] during the course of 120 min when the other cells were subjected to OGD stress. Following this, the control cells were subjected to subsequent regular medium change to match the timings of the cells that were OGD-stressed.

After 12 h, both control and OGD plates were washed with ice-cold phosphate-buffered saline (PBS), and the cells were scraped and collected in methanol for LC-MS/MS analysis. Fatty acids were extracted using a liquid-liquid lipid extraction method from the collected cell culture medium. Extracts were loaded onto a liquid chromatography tandem mass spectrometer for analysis. We analyzed fatty acids, monohydroxy fatty acid derivatives (27-S-hydroxy 32:6 and 29-S-hydroxy 34:6), ELV-N32 (20,27-dihydroxy-fatty acid 32:6n3), and ELV-N34 (22,29-dihydroxy-fatty acid 34:6n3). The samples were normalized to internal standard (AA-d8) for comparison.

Presumably, OGD triggers the release of mono-hydroxy elovanoids, and to a lesser degree of ELV-N32 and ELV-N34, that would protect primary cortical neurons. These data suggest a neuroprotective role for n3 VLC-PUFA and elovanoids.

Elovanoids ELV-N32 and ELV-N34 elicit protection of: (a) cerebral cortical neurons exposed to OGD (FIGS. 18A-18I) or NMDA toxicity (FIGS. 15A-15L and FIG. 19A-19H); (b) cerebral cortical mixed and hippocampal neuronal cultures exposed to uncompensated oxidative stress (UOS), oxygen glucose deprivation (OGD) or NMDA excitotoxicity (FIGS. 16A-16I), where cell survival was assessed (FIG. 17).

Elovanoids ELV-N32 and ELV-N34 improve neurological/behavioral score, protect the penumbra and reduce MRI lesion volumes after ischemic stroke (FIGS. 20A-2D).

Elovanoids ELV-N32 and ELV-N34 attenuate experimental ischemic stroke-induced neuronal and astrocyte cellular damage (FIG. 21A-21C).

Elovanoids ELV-N32 and ELV-N34 diminish the disruption of the neurovascular unit (NVU) and reduce brain infarction after ischemic stroke (FIG. 22A-22D).

Elovanoids ELV-N32 and ELV-N34 provide neuroprotection and improve neurological deficit following traumatic brain injury (TBI) (FIGS. 23A-23C).

Together the data validate therapeutic or preventive uses of n3 VLC-PUFA and the elovanoids (e.g. ELV-N32, ELV-N34) in the brain, including the treatment of brain-related inflammatory, degenerative or neurodegenerative diseases and conditions, such as Alzheimer's disease, Parkinson's disease, multiple sclerosis, ischemic stroke, traumatic brain injury, epilepsy, and amyotrophic lateral sclerosis.

Use of n3 VLC-PUFA and Elovanoids in Systemic and/or Age-Related Diseases and Conditions:

Systemic diseases arising from inflammatory, autoimmune, degenerative, neurodegenerative, stress-related, age-related, or traumatic conditions can affect vital organs such as the heart, muscles, stomach, intestines, liver, kidneys and lungs, and can lead to age-related chronic inflammatory diseases such as rheumatoid arthritis, cardiovascular disease, cerebrovascular disease, atherosclerosis, lupus, and other aging-related diseases and conditions. Given their unique beneficial roles in protecting the function of key cells and organs that prevent chronic diseases and conditions, the provided n3 VLC-PUFA and/or elovanoid compounds are expected to be effective for the treatment of a wide range of these chronic diseases and conditions.

Beneficial Roles of n3 VLC-PUFA and Elovanoids in Skin Diseases and Conditions: Skin inflammatory or degenerative diseases and conditions often result from skin damage from sun exposure or other factors, including skin inflammation (dermatitis or eczema), atopic dermatitis (atopic eczema), skin dehydration, or from abnormal cell proliferation of the skin that results in excess flaking. Skin damage from sun exposure or other factors is associated with numerous diseases and conditions, such as eczema, psoriasis, atopic dermatitis or neurodermatitis, and can result by exposure to ultraviolet light and other types of contact dermatitis. Additionally, pruritus resulting from certain systemic diseases and conditions, provokes skin itching from various inflammatory and other types of stimuli, and causes the need to scratch, which can lead to further skin damage or altered skin appearance.

Considering the overall importance of skin health, skin function, and skin appearance, numerous efforts have been dedicated to the development of methods for skin protection and overall skin health. Most current treatments involve the dermal delivery of corticosteroids, or the use of oils and lotions containing vitamins, minerals, or herbal ingredients, which often are not able to effectively prevent or treat many types of skin damage, and also have side-effects such as skin thinning and muscle loss. While such preparations can offer some protection, there is an unmet need to develop compounds, compositions and methods that effectively protect damaged skin, prevent skin damage, restore skin health, improve skin appearance, and delay skin aging.

Although the provided compounds have profound protective, neuroprotective, restorative, and other beneficial effects to the skin and other tissues, they are biosynthesized locally in limited quantities. Over time, and as a consequence of skin damage and skin aging, the local supply of the provided compounds would be inadequate for providing the required protection to the damaged tissues.

Therefore, by providing a composition of the provided compounds in a manner that can be directly and locally absorbed to the skin, the provided compounds and compositions would provide significant benefits to the skin affected by damage or aging, resulting in the restoration of skin health, the cosmetic improvement of skin appearance, and the delay of skin aging.

By suppressing aging-related skin tissue damage, and by preventing neuronal damage and restoring neuronal function, the provided compounds, compositions and methods are able to protect the skin from being damaged, improve skin health and skin appearance, and delay skin aging. Given their unique beneficial roles in protecting the function of key cells and organs, including skin, the provided n3 VLC-PUFA and/or elovanoid compounds are expected to be effective for the treatment of a wide range of skin diseases and conditions, including skin-related inflammatory, autoimmune, degenerative or neurodegenerative skin diseases and conditions.

Taken together, the above data and analysis, provide the basis for the present disclosure that the provided compounds, dermatological or cosmetic compositions, and methods of use of the provided compounds to skin tissues, are able to provide protection, prevention and treatment of skin that is damaged by inflammation, dehydration, aging, or other causes.

Beneficial Roles of n3 VLC-PUFA as Therapeutics:

The concepts and data described herein, validate the beneficial use of the provided n3 VLC-PUFA and/or elovanoid compounds, as therapeutics for the prevention and treatment of retinal degenerative diseases, as well as diseases related to the brain, the CNS, and other unmet therapeutic needs related to inflammatory or degenerative diseases and conditions.

Origin of the Compounds of the Disclosure:

The provided compounds were not isolated from tissues naturally occurring in nature, but from the result of an artificial experiment combining a human cell and a chemically synthesized n3-VLC-PUFA. The general structures of our synthetic elovanoid compounds were matched using HPLC and mass spectrometry with compounds biosynthesized in human retinal pigment epithelial cells or detected in neuronal cell cultures. However, the natural occurrence of the provided mono- and di-hydroxylated elovanoids with specifically defined stereochemistry is not known at this time. Moreover, the provided compounds are not obtained from natural sources, but they are prepared by adapting stereocontrolled synthetic methods known in the art, starting with commercially available materials. The provided preparation methods were designed to be suitable to the unique hydrophobic properties of n3 VLC-PUFA, which differ significantly from compounds that have a total number of carbons of 22 carbons or less.

The present disclosure encompasses compounds that have stereochemically pure structures and are chemically synthesized and modified to have additional structural features and properties that enable them to exert pharmacological activity. The provided compounds are chemically modified pharmaceutically acceptable derivatives in the form of carboxylic esters or salts that enhance their chemical and biological stability and enable their use in therapeutic applications involving various forms of drug delivery.

The disclosure also provides pharmacologically effective compositions of the provided compounds that enhance their ability to be delivered to a subject in a manner that can reach the targeted cells and tissues.

Overall Beneficial Use of n3 VLC-PUFA and Elovanoids:

The present disclosure provides compounds and compositions for the prevention and treatment of a wide range of systemic inflammatory, degenerative, and neurodegenerative diseases, including skin diseases, ophthalmic diseases, brain diseases, including neurotrauma.

The compounds and compositions provided by this disclosure are able to restore homeostasis and induce cell survival signaling in certain cells undergoing uncompensated oxidative stress or other homeostatic disruptions.

The disclosure also provides methods of use of the provided compounds and compositions containing a hydroxylated derivative of omega-3 very long chain polyunsaturated fatty acids, as the free carboxylic acids or their pharmaceutically acceptable salts, or as their corresponding esters or other prodrug derivatives. The provided compounds can be readily prepared by adapting methods known in the art, starting with commercially available materials.

Administration of a pharmaceutical composition containing a provided compound and a pharmaceutically acceptable carrier restores the homeostatic balance and promotes the survival of certain cells that are essential for maintaining normal function. The provided compounds, compositions, and methods can be used for the preventive and therapeutic treatment of inflammatory, degenerative, and neurodegenerative diseases.

This disclosure targets critical steps of the initiation and early progression of these conditions by mimicking the specific biology of intrinsic cellular/organs responses to attain potency, selectivity, devoid of side effects and sustained bioactivity.

Compounds

Described herein are compounds based on omega-3 very long chain polyunsaturated fatty acids and their hydroxylated derivatives, termed "elovanoids".

The omega-3 very long chain polyunsaturated fatty acids have the structures of A or B, or derivatives thereof:

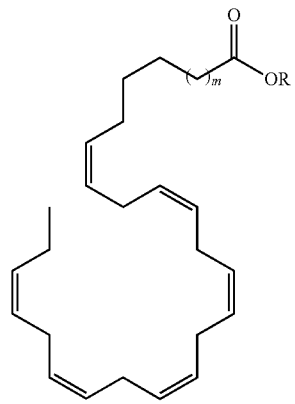

A

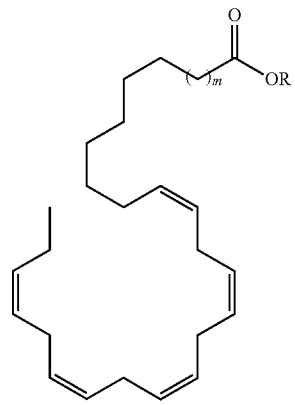

B wherein: A contains a total from 23 to 42 carbon atoms in the carbon chain, and with 6 alternating cis carbon-carbon double bonds starting at positions n-3, n-6, n-9, n-12, n-15 and n-18, and wherein B contains a total from 23 to 42 carbon atoms in the carbon chain, and with 5 alternating cis carbon-carbon double bonds starting at positions n-3, n-6, n-9, n-12 and n-15. R can be hydrogen, methyl, ethyl, alkyl, or a cation such as an ammonium cation, an iminium cation, or a metal cation including, but not limited to, sodium, potassium, magnesium, zinc, or calcium cation, and wherein m is a number from 0 to 19.

The omega-3 very long chain polyunsaturated fatty acids of the disclosure can have a terminal carboxyl group "—COOR" wherein "R" is intended to designate a group covalently bonded to the carboxyl such as an alkyl group. In the alternative, the carboxyl group is further intended to have a negative charge as "—COO⁻" and R is a cation including a metal cation, an ammonium cation and the like.

In some omega-3 very long chain polyunsaturated fatty acids, m is a number selected from a group consisting of 0 to 15. Thus, m may be a number selected from 1, 3, 5, 7, 9, 11, 13, or 15 where the fatty acid component contains a total of 24, 26, 28, 30, 32, 34, 36 or 38 carbon atoms in its carbon chain. In other omega-3 very long chain polyunsaturated fatty acids, m is a number selected from a group consisting of 0, 2, 4, 6, 8, 10, 12 or 14, where the fatty acid component contains a total of 23, 25, 27, 19, 31, 33, 35 or 37 carbon atoms in its carbon chain. In some omega-3 very long chain polyunsaturated fatty acids, m is a number selected from a group consisting of 5 to 15, where the fatty acid component contains a total of 28, 29, 30, 31, 32, 33, 34, 35, 36, 37 or 38 carbon atoms in its carbon chain. In some omega-3 very long chain polyunsaturated fatty acids, m is a number selected from a group consisting of 9 to 11, where the fatty acid component contains a total of 32 or 34 carbon atoms in its carbon chain.

In some embodiments the omega-3 very long chain polyunsaturated fatty acids is a carboxylic acid, i.e. R is hydrogen. In other embodiments the omega-3 very long chain polyunsaturated fatty acids is a carboxylic ester, wherein R is methyl, ethyl or alkyl. When the omega-3 very long chain polyunsaturated fatty acid is a carboxylic ester, R can be, but is not limited to, methyl or ethyl. In some embodiments the omega-3 very long chain polyunsaturated fatty acid is a carboxylic ester, wherein R is methyl.

In some embodiments the omega-3 very long chain polyunsaturated fatty acid can be a carboxylate salt, wherein R is an ammonium cation, iminium cation, or a metal cation selected from a group consisting of sodium, potassium, magnesium, zinc, or calcium cation. In some advantageous embodiments, R is ammonium cation or iminium cation. R can be a sodium cation or a potassium cation. In some embodiments, R is a sodium cation.

The omega-3 very long chain polyunsaturated fatty acid or derivative of the disclosure can have 32- or 34 carbons in its carbon chain and 6 alternating cis double bonds starting at the n-3 position, and have the formula A1 (14Z,17Z,20Z,23Z,26Z,29Z)-dotriaconta-14,17,20,23,26,29-hexaenoic acid) or formula A2 (16Z,19Z,22Z,25Z,28Z,31Z)-tetratriaconta-16,19,22,25,28,31-hexaenoic acid):

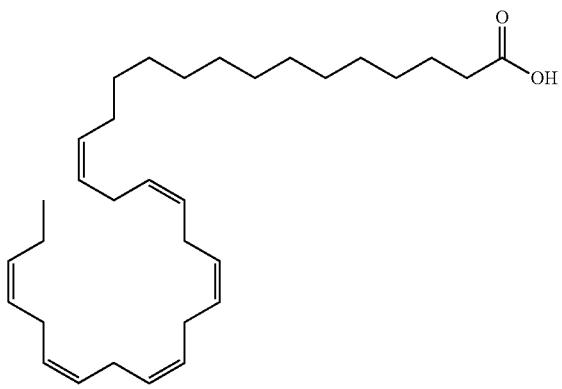

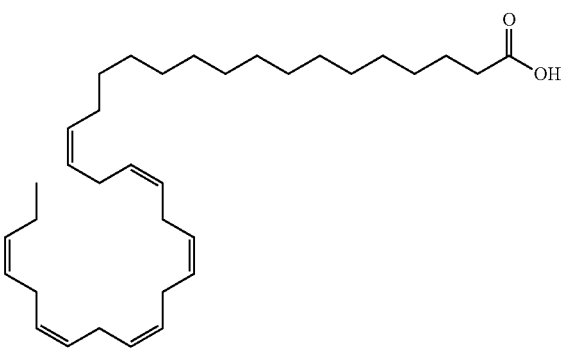

In some embodiments of the omega-3 very long chain polyunsaturated fatty acids, the carboxyl derivative is part of a glycerol-derived phospholipid, which can be readily prepared starting with the carboxylic acid form of the n3 VLC-PUFA of structure A or B, by utilizing methods known in the art, and represented by structures C, D, E, or F:

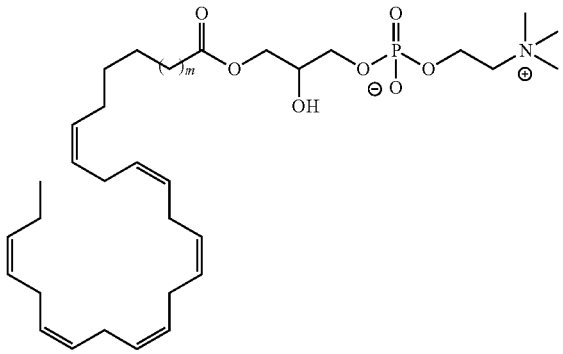

D
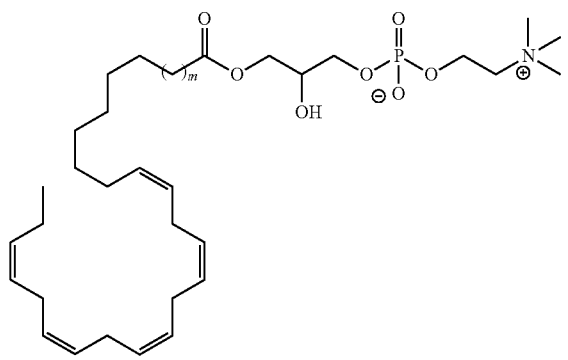

E
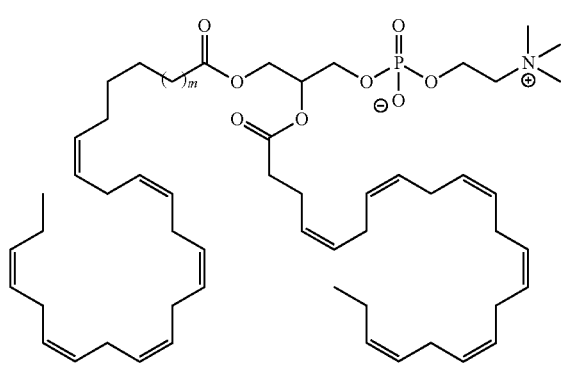

F
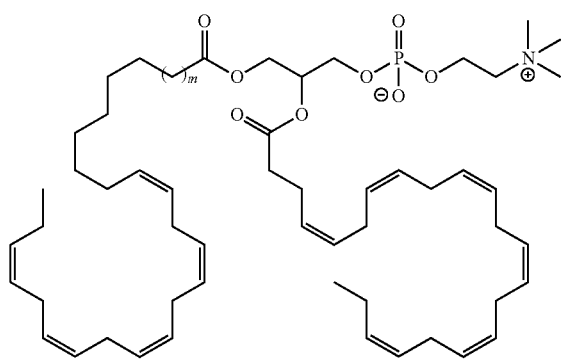

wherein C or E contains a total from 23 to 42 carbon atoms in the carbon chain, and with 6 alternating cis carbon-carbon double bonds starting at positions n-3, n-6, n-9, n-12, n-15 and n-18, and wherein D or E contains a total from 23 to 42 carbon atoms in the carbon chain, and with 5 alternating cis carbon-carbon double bonds starting at positions n-3, n-6, n-9, n-12 and n-15. In advantageous embodiments, m is a number selected from a group consisting of 0 to 15. In other embodiments, m is a number selected from 1, 3, 5, 7, 9, 11, 13, or 15 where the fatty acid component contains a total of 24, 26, 28, 30, 32, 34, 36 or 38 carbon atoms in its carbon chain. In additional advantageous embodiments, m is a number selected from a group consisting of 0, 2, 4, 6, 8, 10, 12 or 14, where the fatty acid component contains a total of 23, 25, 27, 19, 31, 33, 35 or 37 carbon atoms in its carbon chain.

In some embodiments, m is a number selected from a group consisting of 5 to 15, where the fatty acid component contains a total of 28, 29, 30, 31, 32, 33, 34, 35, 36, 37 or 38 carbon atoms in its carbon chain. In some embodiments, m is a number selected from a group consisting of 5, 7, 9, 11, 13, or 15, where the fatty acid component contains a total of 28, 30, 32, 34, 36 or 38 carbon atoms in its carbon chain. In other embodiments, m is a number selected from a group consisting of 4, 6, 8, 10, 12 or 14, where the fatty acid component contains a total of 27, 29, 31, 33, 35 or 37 carbon atoms in its carbon chain. In advantageous embodiments, m is a number selected from a group consisting of 9 to 11, where the fatty acid component contains a total of 32 or 34 carbon atoms in its carbon chain.

The mono-hydroxylated elovanoids of the disclosure can have the structures of G, H, I or J:

G
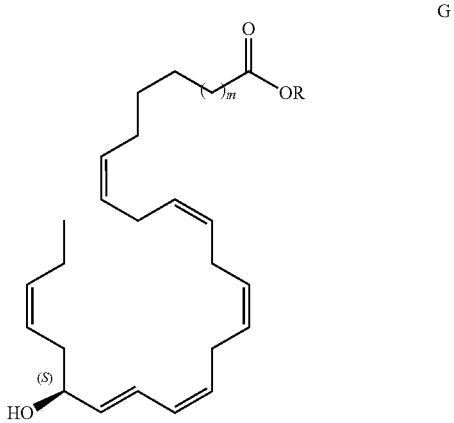

H
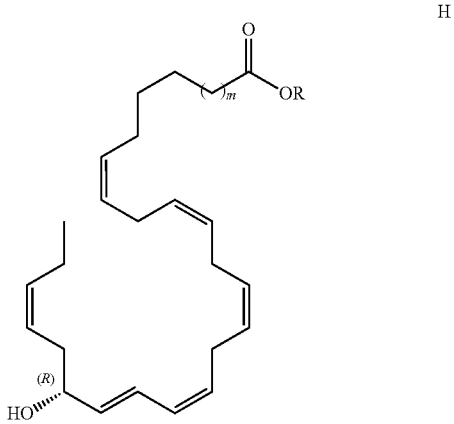

I
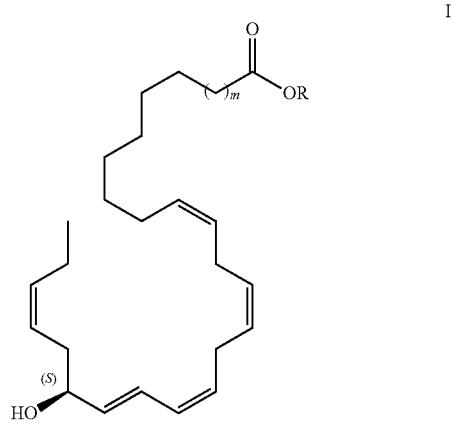

J

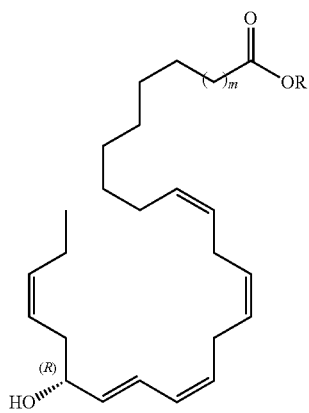

wherein compounds G and H have a total from 23 to 42 carbon atoms in the carbon chain, with 5 cis carbon-carbon double bonds starting at positions n-3, n-9, n-12, n-15 and n-18 and a trans carbon-carbon double bond starting at positions n-7; and wherein compounds I and J have a total from 23 to 42 carbon atoms in the carbon chain, and with 4 cis carbon-carbon double bonds starting at positions n-3, n-9, n-12 and n-15, and a trans carbon-carbon double bond starting at positions n-7; wherein R is hydrogen, methyl, ethyl, alkyl, or a cation selected from a group consisting of: ammonium cation, iminium cation, or a metal cation selected from a group consisting of sodium, potassium, magnesium, zinc, or calcium cation, and wherein m is a number selected from a group consisting of 0 to 19; wherein compounds G and H can exist as an equimolar mixture; wherein compounds I and J can exist as an equimolar mixture; wherein, the provided compounds G and H are predominately one enantiomer with a defined (S) or (R) chirality at the carbon bearing the hydroxyl group; and wherein, the compounds G and H are predominately one enantiomer with a defined (S) or (R) chirality at the carbon bearing the hydroxyl group.

As used herein and in other structures of the present disclosure, the compounds of the disclosure are shown having a terminal carboxyl group "—COOR" the "R" is intended to designate a group covalently bonded to the carboxyl such as an alkyl group. In the alternative, the carboxyl group is further intended to have a negative charge as "—COO⁻" and R is a cation including a metal cation, an ammonium cation and the like.

In some embodiments of the mono-hydroxylated elovanoids of the disclosure, m is a number selected from a group consisting of 0 to 15. In other advantageous embodiments, m is a number selected from 1, 3, 5, 7, 9, 11, 13, or 15 where the fatty acid component contains a total of 24, 26, 28, 30, 32, 34, 36 or 38 carbon atoms in its carbon chain. In other embodiments, m is a number selected from a group consisting of 0, 2, 4, 6, 8, 10, 12 or 14, where the fatty acid component contains a total of 23, 25, 27, 19, 31, 33, 35 or 37 carbon atoms in its carbon chain.

In some embodiments, m is a number selected from a group consisting of 5 to 15, where the fatty acid component contains a total of 28, 29, 30, 31, 32, 33, 34, 35, 36, 37 or 38 carbon atoms in its carbon chain. In some embodiments, m is a number selected from a group consisting of 5, 7, 9, 11, 13, or 15, where the fatty acid component contains a total of 28, 30, 32, 34, 36 or 38 carbon atoms in its carbon chain. In other embodiments, m is a number selected from a group consisting of 4, 6, 8, 10, 12 or 14, where the fatty acid component contains a total of 27, 29, 31, 33, 35 or 37 carbon atoms in its carbon chain. In advantageous embodiments, m is a number selected from a group consisting of 9 to 11, where the fatty acid component contains a total of 32 or 34 carbon atoms in its carbon chain.

In some embodiments the mono-hydroxylated elovanoids of the disclosure are a carboxylic acid, i.e. R is hydrogen. In other embodiments the compound is a carboxylic ester, wherein R is methyl, ethyl or alkyl. In advantageous embodiments the compound is a carboxylic ester, wherein R is methyl or ethyl. In advantageous embodiments the compound is a carboxylic ester, wherein R is methyl. In other advantageous embodiments the compound is a carboxylate salt, wherein R is an ammonium cation, iminium cation, or a metal cation selected from a group consisting of sodium, potassium, magnesium, zinc, or calcium cation. In some advantageous embodiments, R is ammonium cation or iminium cation. In other advantageous embodiments, R is a sodium cation or a potassium cation. In advantageous embodiments, R is a sodium cation.

The di-hydroxylated elovanoids of the disclosure can have the structures K, L, M, or N

K

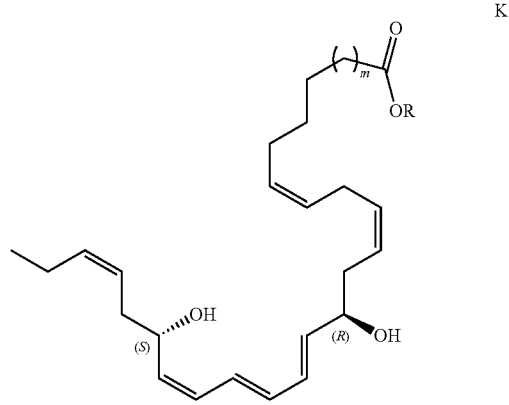

L

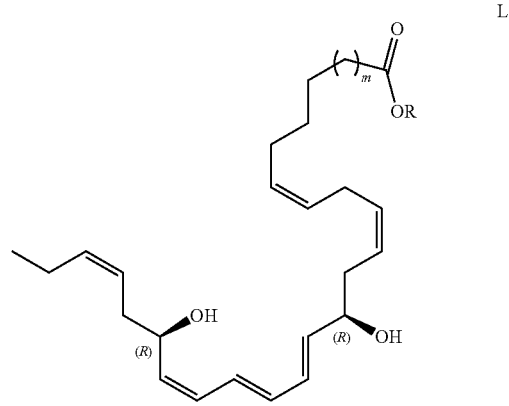

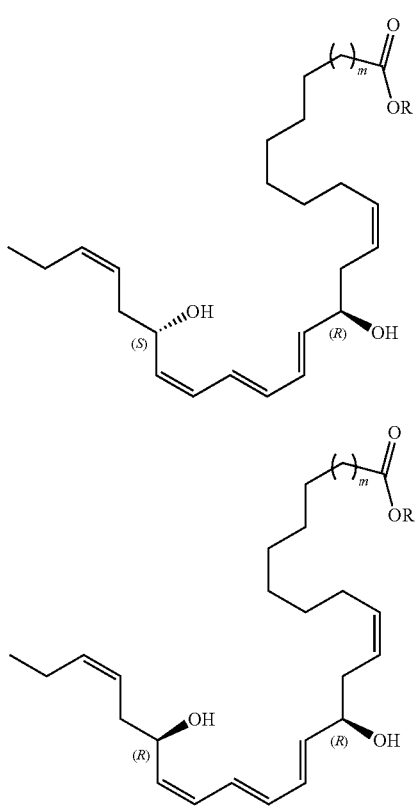

wherein compounds K and L have a total from 23 to 42 carbon atoms in the carbon chain, with 4 cis carbon-carbon double bonds starting at positions n-3, n-7, n-15 and n-18, and 2 trans carbon-carbon bonds starting at positions n-9, n-11; and wherein compounds M and N have a total from 23 to 42 carbon atoms in the carbon chain, with 3 cis carbon-carbon double bonds starting at positions n-3, n-7, n-12 and n-15, and 2 trans carbon-carbon bonds starting at positions n-9, n-11, wherein R is hydrogen, methyl, ethyl, alkyl, or a cation selected from a group consisting of: ammonium cation, iminium cation, or a metal cation selected from a group consisting of sodium, potassium, magnesium, zinc, or calcium cation, and wherein m is a number selected from a group consisting of 0 to 19; wherein compounds K and L can exist as an equimolar mixture; wherein compounds M and N can exist as an equimolar mixture, wherein the compounds K and L are predominately one enantiomer with a defined (S) or (R) chirality at the carbon bearing the hydroxyl group; and wherein, the provided compounds M and N are predominately one enantiomer with a defined (S) or (R) chirality at the carbon bearing the hydroxyl group.

As used herein and in other structures of the present disclosure, the compounds of the disclosure are shown having a terminal carboxyl group "—COOR" the "R" is intended to designate a group covalently bonded to the carboxyl such as an alkyl group. In the alternative, the carboxyl group is further intended to have a negative charge as "—COO⁻" and R is a cation including a metal cation, an ammonium cation and the like.

In some embodiments of the di-hydroxylated elovanoids of the disclosure, m is a number selected from a group consisting of 5 to 15, where the fatty acid component contains a total of 28, 29, 30, 31, 32, 33, 34, 35, 36, 37 or 38 carbon atoms in its carbon chain. In advantageous embodiments, m is a number selected from a group consisting of 5, 7, 9, 11, 13, or 15, where the fatty acid component contains a total of 28, 30, 32, 34, 36 or 38 carbon atoms in its carbon chain. In other embodiments, m is a number selected from a group consisting of 4, 6, 8, 10, 12 or 14, where the fatty acid component contains a total of 27, 29, 31, 33, 35 or 37 carbon atoms in its carbon chain. In advantageous embodiments, m is a number selected from a group consisting of 9 to 11, where the fatty acid component contains a total of 32 or 34 carbon atoms in its carbon chain.

Some di-hydroxylated elovanoids of the disclosure are carboxylic acid, i.e. R is hydrogen. In other embodiments the di-hydroxylated elovanoid of the disclosure is a carboxylic ester, wherein R is methyl, ethyl or alkyl. In advantageous embodiments the compound is a carboxylic ester, wherein R is methyl or ethyl. In advantageous embodiments the compound is a carboxylic ester, wherein R is methyl.

In other embodiments the di-hydroxylated elovanoid of the disclosure is a carboxylate salt, wherein R is an ammonium cation, iminium cation, or a metal cation selected from a group consisting of sodium, potassium, magnesium, zinc, or calcium cation. In some advantageous embodiments, R is ammonium cation or iminium cation. In other advantageous embodiments, R is a sodium cation or a potassium cation. In advantageous embodiments, R is a sodium cation.

The alkynyl mono-hydroxylated elovanoids of the disclosure can have the structures of O, P, Q or R:

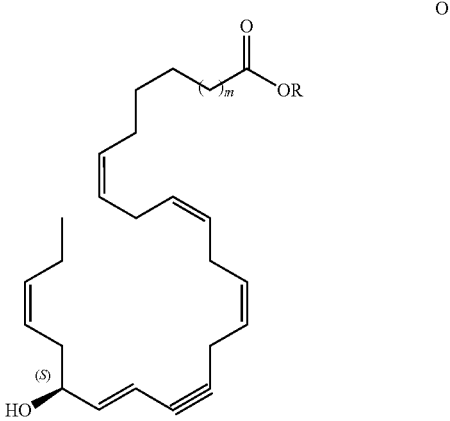

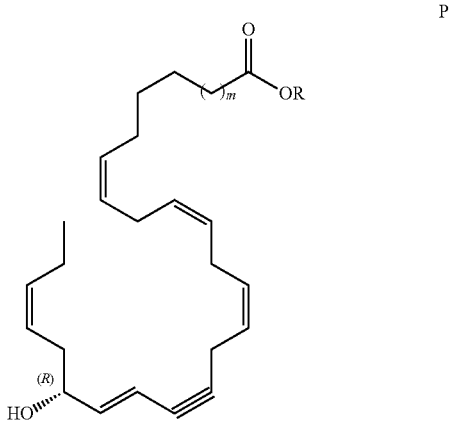

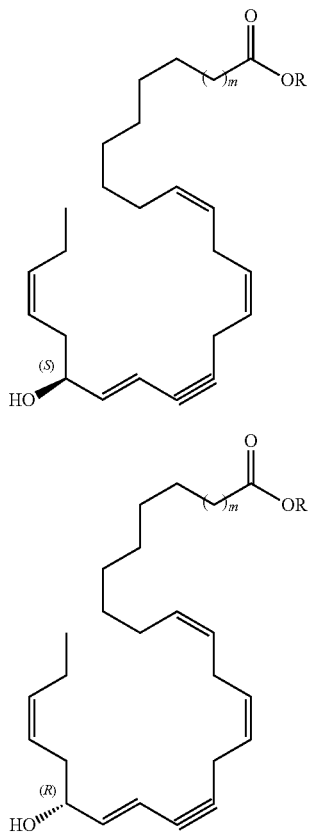

wherein compounds O and P have a total from 23 to 42 carbon atoms in the carbon chain, with 4 cis carbon-carbon double bonds starting at positions n-3, n-12, n-15 and n-18, a trans carbon-carbon bond starting at position n-7, and a carbon-carbon triple bond starting at position n-9; and wherein compounds I and J have a total from 23 to 42 carbon atoms in the carbon chain, with 3 cis carbon-carbon double bonds starting at positions n-3, n-12 and n-15, a trans carbon-carbon bond starting at position n-7, and a carbon-carbon triple bond starting at position n-9; wherein R is hydrogen, methyl, ethyl, alkyl, or a cation selected from a group consisting of: ammonium cation, iminium cation, or a metal cation selected from a group consisting of sodium, potassium, magnesium, zinc, or calcium cation, and wherein m is a number selected from a group consisting of 0 to 19; wherein compounds O and P can exist as an equimolar mixture; wherein compounds Q and R can exist as an equimolar mixture; wherein, the provided compounds O and P are predominately one enantiomer with a defined (S) or (R) chirality at the carbon bearing the hydroxyl group; and wherein, the provided compounds O and P are predominately one enantiomer with a defined (S) or (R) chirality at the carbon bearing the hydroxyl group.

As used herein and in other structures of the present invention, the alkynyl mono-hydroxylated elovanoids of the disclosure are shown having a terminal carboxyl group "—COOK" the "R" is intended to designate a group covalently bonded to the carboxyl such as an alkyl group. In the alternative, the carboxyl group is further intended to have a negative charge as "—COO⁻" and R is a cation including a metal cation, an ammonium cation and the like.

In some embodiments, m is a number selected from a group consisting of 0 to 15. In other embodiments, m is a number selected from 1, 3, 5, 7, 9, 11, 13, or 15 where the fatty acid component contains a total of 24, 26, 28, 30, 32, 34, 36 or 38 carbon atoms in its carbon chain.

In additional embodiments, m is a number selected from a group consisting of 0, 2, 4, 6, 8, 10, 12 or 14, where the fatty acid component contains a total of 23, 25, 27, 19, 31, 33, 35 or 37 carbon atoms in its carbon chain. In some embodiments, m is a number selected from a group consisting of 5 to 15, where the fatty acid component contains a total of 28, 29, 30, 31, 32, 33, 34, 35, 36, 37 or 38 carbon atoms in its carbon chain. In embodiments, m is a number selected from a group consisting of 5, 7, 9, 11, 13, or 15, where the fatty acid component contains a total of 28, 30, 32, 34, 36 or 38 carbon atoms in its carbon chain. In other embodiments, m is a number selected from a group consisting of 4, 6, 8, 10, 12 or 14, where the fatty acid component contains a total of 27, 29, 31, 33, 35 or 37 carbon atoms in its carbon chain. In some embodiments, m is a number selected from a group consisting of 9 to 11, where the fatty acid component contains a total of 32 or 34 carbon atoms in its carbon chain.

In some embodiments the alkynyl mono-hydroxylated elovanoids of the disclosure are carboxylic acids, i.e. R is hydrogen. In other embodiments the alkynyl mono-hydroxylated elovanoids of the disclosure are carboxylic esters, wherein R is methyl, ethyl or alkyl. In embodiments the alkynyl mono-hydroxylated elovanoids of the disclosure are carboxylic esters, wherein R is methyl or ethyl.

In some embodiments R is methyl. In other embodiments, alkynyl mono-hydroxylated elovanoids of the disclosure can be a carboxylate salt, wherein R is an ammonium cation, iminium cation, or a metal cation selected from a group consisting of sodium, potassium, magnesium, zinc, or calcium cation. In some embodiments, R is ammonium cation or iminium cation. In other embodiments, R is a sodium cation or a potassium cation. In embodiments, R is a sodium cation.

The alkynyl di-hydroxylated elovanoids can have the structures of S, T, U or V:

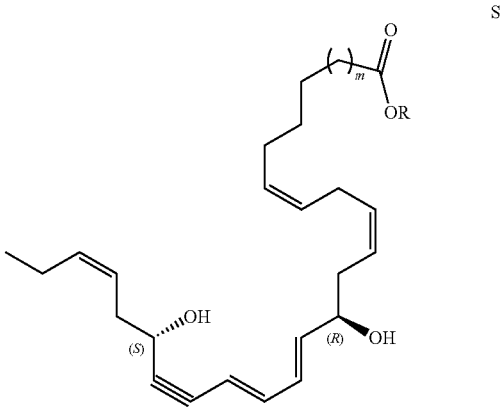

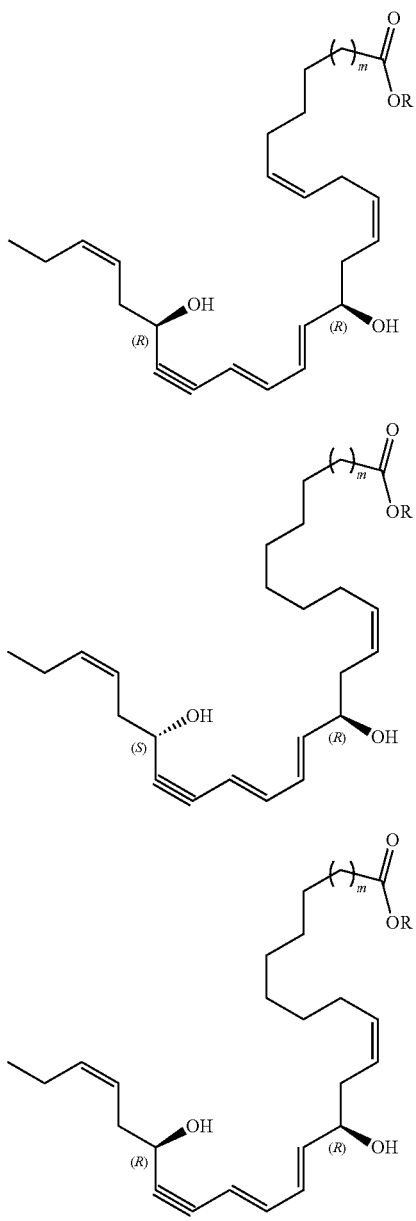

wherein compounds S and T have a total from 23 to 42 carbon atoms in the carbon chain, with 3 cis carbon-carbon double bonds starting at positions n-3, n-12, n-15 and n-18, with 2 trans carbon-carbon double bonds starting at positions n-9 and n-11, and a carbon-carbon triple bond starting at position n-7; and wherein compounds U and V have a total from 23 to 42 carbon atoms in the carbon chain, and with 2 cis carbon-carbon double bonds starting at positions n-3 and n-15, with 2 trans carbon-carbon double bonds starting at positions n-9 and n-11, and a carbon-carbon triple bond starting at position n-7; wherein R is hydrogen, methyl, ethyl, alkyl, or a cation selected from a group consisting of: ammonium cation, iminium cation, or a metal cation selected from a group consisting of sodium, potassium, magnesium, zinc, or calcium cation, and wherein m is a number selected from a group consisting of 0 to 19; wherein compounds S and T can exist as an equimolar mixture; wherein compounds U and V can exist as an equimolar mixture.

In some embodiments, the provided compounds S and T are predominately one enantiomer with a defined (S) or (R) chirality at the carbon bearing the hydroxyl group; and wherein, the provided compounds U and V are predominately one enantiomer with a defined (S) or (R) chirality at the carbon bearing the hydroxyl group.

As used herein and in other structures of the present invention, the compounds of the invention are shown having a terminal carboxyl group "—COOR" the "R" is intended to designate a group covalently bonded to the carboxyl such as an alkyl group. In the alternative, the carboxyl group is further intended to have a negative charge as "—COO$^-$" and R is a cation including a metal cation, an ammonium cation and the like.

In some embodiments, m is a number selected from a group consisting of 5 to 15, where the fatty acid component contains a total of 28, 29, 30, 31, 32, 33, 34, 35, 36, 37 or 38 carbon atoms in its carbon chain. In embodiments, m is a number selected from a group consisting of 5, 7, 9, 11, 13, or 15, where the fatty acid component contains a total of 28, 30, 32, 34, 36 or 38 carbon atoms in its carbon chain. In other embodiments, m is a number selected from a group consisting of 4, 6, 8, 10, 12 or 14, where the fatty acid component contains a total of 27, 29, 31, 33, 35 or 37 carbon atoms in its carbon chain. In embodiments, m is a number selected from a group consisting of 9 to 11, where the fatty acid component contains a total of 32 or 34 carbon atoms in its carbon chain.

In some embodiments the provided compound is a carboxylic acid, i.e. R is hydrogen.

In other embodiments the provided compound is a carboxylic ester, wherein R is methyl, ethyl or alkyl. In embodiments the provided compound is a carboxylic ester, wherein R is methyl or ethyl. In embodiments the provided compound is a carboxylic ester, wherein R is methyl. In other embodiments the provided compound is a carboxylate salt, wherein R is an ammonium cation, iminium cation, or a metal cation selected from a group consisting of sodium, potassium, magnesium, zinc, or calcium cation. In some embodiments, R is ammonium cation or iminium cation. In other embodiments, R is a sodium cation or a potassium cation. In embodiments, R is a sodium cation.

In advantageous embodiments, the present disclosure provides a mono-hydroxylated 32-carbon methyl ester of formula G1, having the name: methyl (S,14Z,17Z,20Z,23Z,25E,29Z)-27-hydroxytriaconta-14,17,20,23,25,29-hexaenoate; a mono-hydroxylated 32-carbon sodium salt of formula G2, having the name: sodium (S,14Z,17Z,20Z,23Z,25E,29Z)-27-hydroxytriaconta-14,17,20,23,25,29-hexaenoate; a mono-hydroxylated 34-carbon methyl ester of formula G3, having the name: methyl (S,16Z,19Z,22Z,25Z,27E,31Z)-29-hydroxytetratriaconta-16,19,22,25,27,31-hexaenoate; or a mono-hydroxylated 34-carbon sodium salt of formula G4, having the name sodium (S,16Z,19Z,22Z,25Z,27E,31Z)-29-hydroxytetratriaconta-16,19,22,25,27,31-hexaenoate:

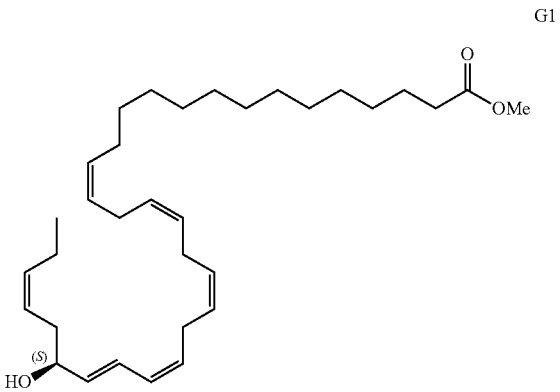

G1

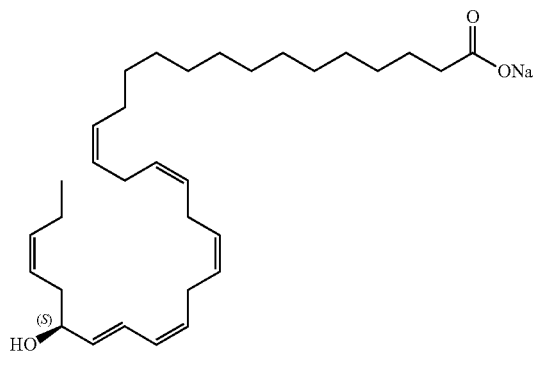

G2

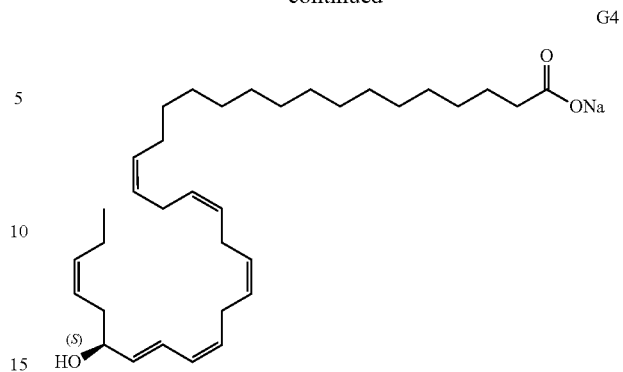

G4

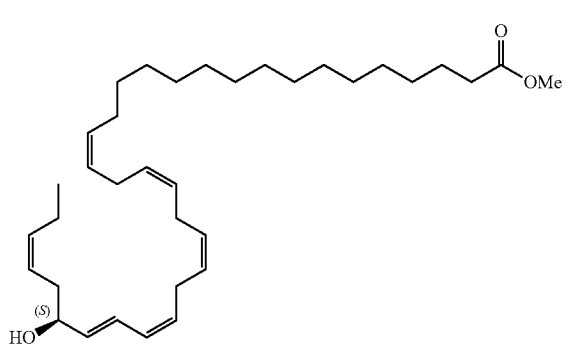

G3

In other advantageous embodiments, the present disclosure provides a di-hydroxylated 32-carbon methyl ester of formula K1, having the name: methyl (14Z,17Z,20R,21E,23E,25Z,27S,29Z)-20,27-dihydroxydotriaconta-14,17,21,23,25,29-hexaenoate; a di-hydroxylated 32-carbon sodium salt of formula K2, having the name: sodium (14Z,17Z,20R,21E,23E,25Z,27S,29Z)-20,27-dihydroxydotriaconta-14,17,21,23,25,29-hexaenoate; or a di-hydroxylated 34-carbon methyl ester of formula K3, having the name: methyl (16Z,19Z,22R,23E,25E,27Z,29S,31Z)-22,29-dihydroxytetratriaconta-16,19,23,25,27,31-hexaenoate; or a di-hydroxylated 34-carbon sodium salt of formula K4, having the name: sodium (16Z,19Z,22R,23E,25E,27Z,29S,31Z)-22,29-dihydroxytetratriaconta-16,19,23,25,27,31-hexaenoate:

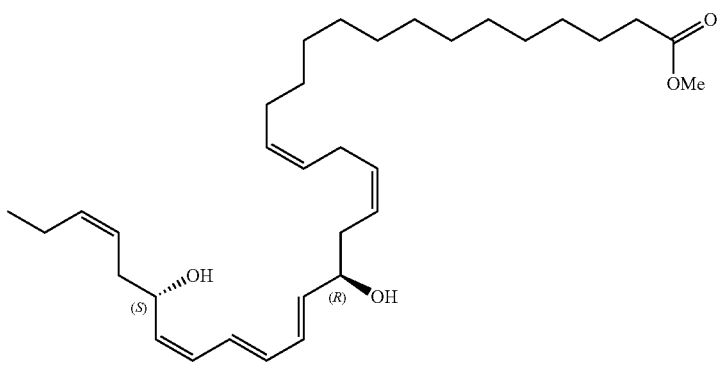

K1

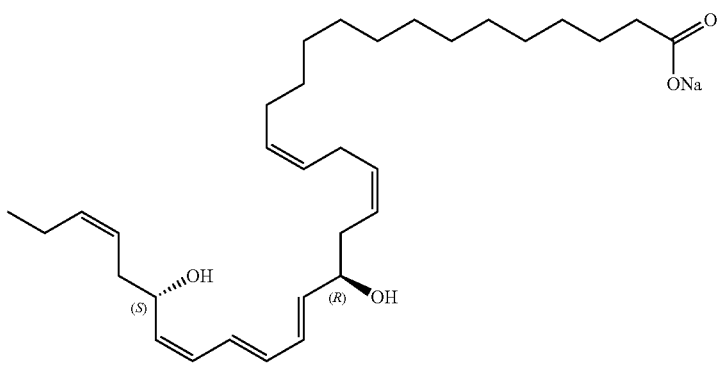

K2

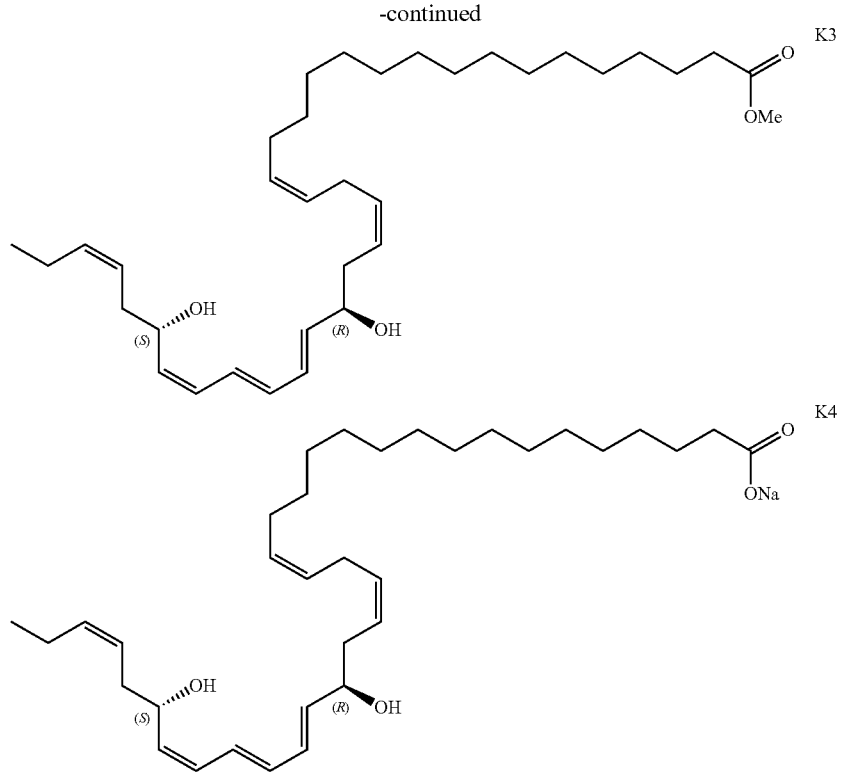

In other embodiments, the present invention provides an alkynyl mono-hydroxylated 32-carbon methyl ester of formula O1, having the name: methyl (S,14Z,17Z,20Z,25E,29Z)-27-hydroxydotriaconta-14,17,20,25,29-pentaen-23-ynoate; an alkynyl mono-hydroxylated 32-carbon sodium salt of formula O2, having the name: sodium (S,17Z,20Z,25E,29Z)-27-hydroxydotriaconta-17,20,25,29-tetraen-23-ynoate; an alkynyl mono-hydroxylated 34-carbon methyl ester of formula O3, having the name: methyl (S,16Z,19Z,22Z,27E,31Z)-29-hydroxytetratriaconta-16,19,22,27,31-pentaen-25-ynoate; an alkynyl mono-hydroxylated 34-carbon sodium salt of formula O4, having the name: sodium (S,16Z,19Z,22Z,27E,31Z)-29-hydroxytetratriaconta-16,19,22,27,31-pentaen-25-ynoate:

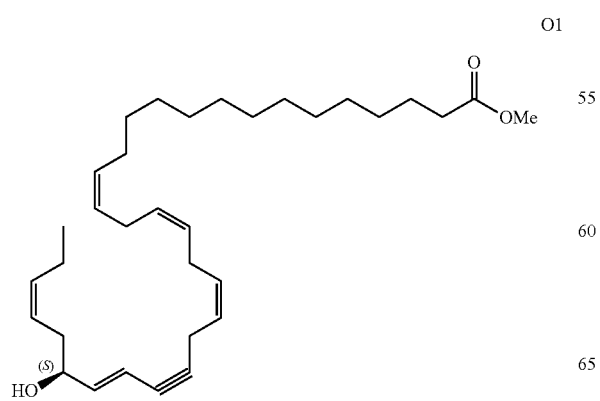

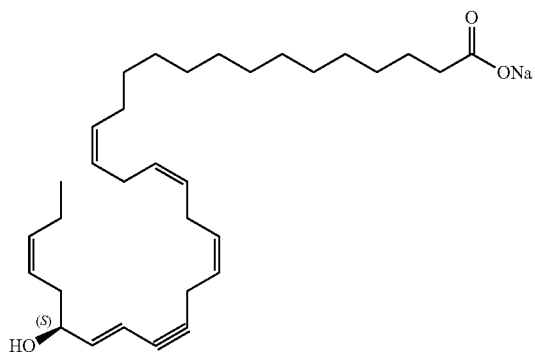

-continued

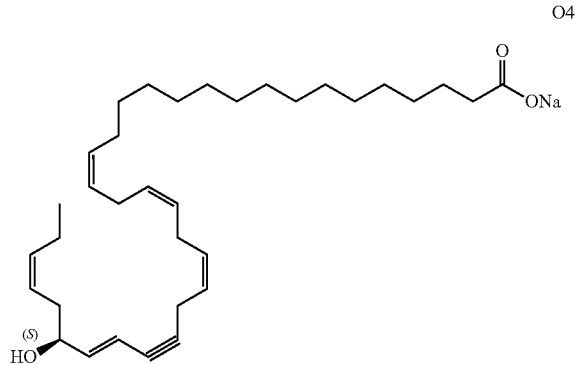

O4

In other advantageous embodiments, the present invention provides an alkynyl di-hydroxylated 32-carbon methyl ester of formula S1, having the name: methyl (14Z,17Z,20R,21E,23E,27S,29Z)-20,27-dihydroxydotriaconta-14,17,21,23,29-pentaen-25-ynoate; an alkynyl di-hydroxylated 32-carbon sodium salt of formula S2, having the name: sodium (14Z,17Z,20R,21E,23E,27S,29Z)-20,27-dihydroxydotriaconta-14,17,21,23,29-pentaen-25-ynoate; or an alkynyl di-hydroxylated 34-carbon methyl ester of formula S3, having the name: methyl (16Z,19Z,22R,23E,25E,29S,31Z)-22,29-dihydroxytetratriaconta-16,19,23,25,31-pentaen-27-ynoate; or an alkynyl di-hydroxylated 34-carbon sodium salt of formula S4, having the name: sodium (16Z,19Z,22R,23E,25E,29S,31Z)-22,29-dihydroxytetratriaconta-16,19,23,25,31-pentaen-27-ynoate.

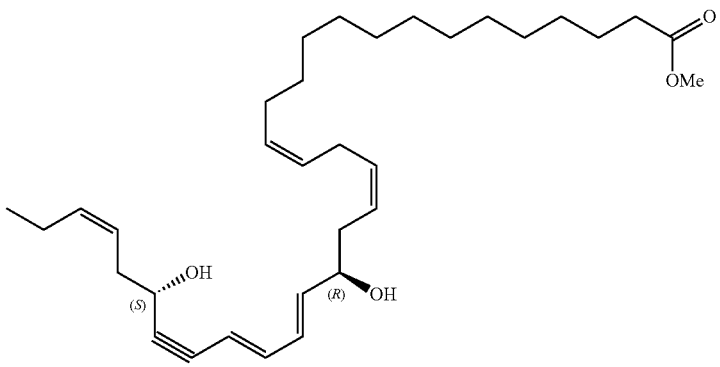

S1

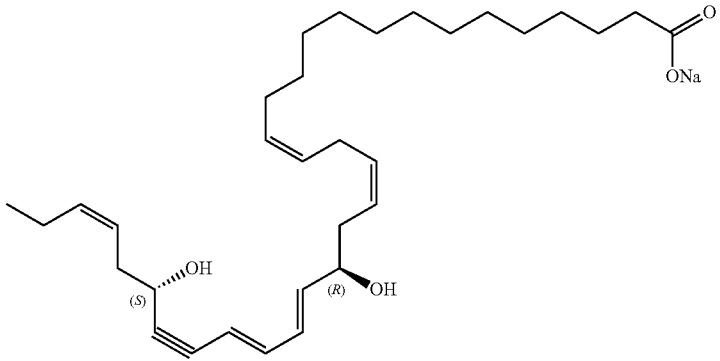

S2

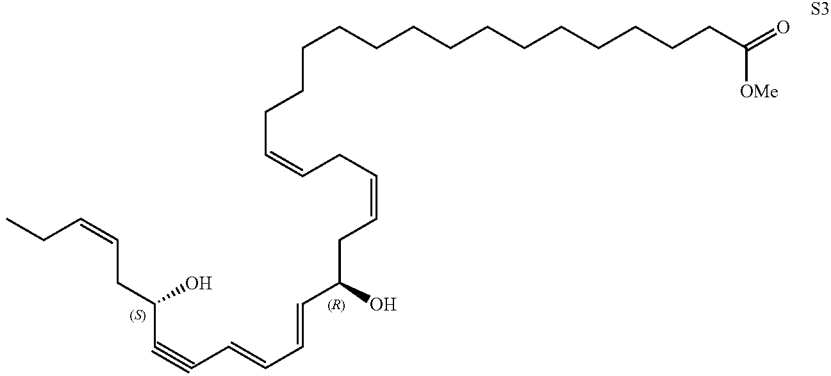

S3

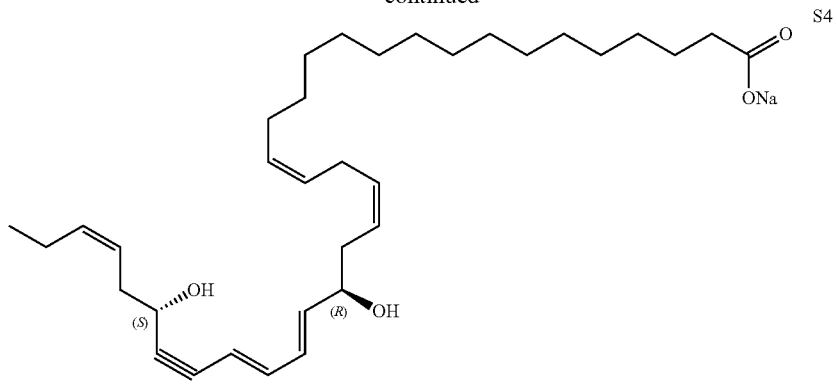

Methods of Preparation and Manufacturing of Provided Compounds:

The provided compounds of the disclosure can be readily prepared by adapting methods known in the art, starting with commercially available materials as summarized in Schemes 1-5 as shown in FIGS. 24-28.

Scheme 1 (FIG. 24) shows the detailed approach for the stereocontrolled total synthesis of compounds of type O, wherein n is 9, and the fatty acid chain contains a total of 32 carbon atoms, and the R group is methyl or sodium cation. In particular, Scheme 1 shows the synthesis of compounds ELV-N32-Me and ELV-N32-Na, starting with methyl pentadec-14-ynoate (S1). By starting with heptadec-16-ynoate (T1), this process affords compounds ELV-N34-Me and ELV-N34-Na. The alkynyl precursors of ELV-N32-Me and ELV-N32-Na, namely 13a, 13b, 15a, and 15b are also among the provided compounds X and Z in this disclosure. Scheme 1 provides the reagents and conditions for the preparations of the provided compounds, by employing reaction conditions that are typical for this type of reactions.

Scheme 2 (FIG. 25) describes the total synthesis of the di-hydroxylated elovanoids K and L and their alkyne precursors S and T, by starting with intermediates 2, 5, and 7 that were also used in Scheme 1. The conversion of the protected (R) epoxide 4 to intermediate 15, and the coupling of 7 and 15 followed by conversion into intermediate 17 can be done according to literature procedures (Tetrahedron Lett. 2012; 53(14):1695-8).

Catalytic cross-coupling between intermediates 2 or 17 or between intermediates 5 or 17, followed by deprotection, leads to the formation of alkynyl compounds S and T, which are then selectively reduced to form di-hydroxylated elovanoids K and L. Hydrolysis and acidification affords the corresponding carboxylic acids, which can be converted into carboxylate salts with the addition of equivalent amounts of the corresponding base. Di-hydroxylated elovanoids of types K, L, S and T with at least 23 carbons and up to 42 carbons in their carbon chain, can be similarly prepared by varying the number of carbons in the alkyne starting material 7.

Scheme 3 (FIG. 26) describes the total synthesis of di-hydroxylated elovanoids with five unsaturated double bonds of types M and N, as well as their alkyne precursors U and V, by utilizing the same alkynyl intermediates 2 and 5, which were also used in Scheme 1. (Tetrahedron Lett. 2012; 53(14):1695-8).

The synthesis of the common intermediate 22 begins with the carboxylic acid 18, which is converted into orthoester 19, using known methodologies (Tetrahedron Lett. 1983, 24 (50), 5571-4). Reaction of the lithiated alkyne with epoxide 1 affords intermediate 21, which is converted into the iodide intermediate 22, similarly to the conversion of 16 to 17. Catalytic cross-coupling between intermediates 2 or 5 with 22, followed by deprotection, leads to the formation of alkynyl di-hydroxy elovanoids U and V, which are then selectively reduced to form di-hydroxylated elovanoids M and N.

Hydrolysis and acidification affords the corresponding carboxylic acids, which can be converted into carboxylate salts with the addition of equivalent amounts of the corresponding base. Di-hydroxylated elovanoids of types M, N, U and V with at least 23 carbons and up to 42 carbons in their carbon chain, can be similarly prepared by varying the number of carbons in the alkyne carboxylic acid 18.

Scheme 4 (FIG. 27) shows the stereocontrolled total synthesis of 32-carbon dihydroxylated elovanoids, starting with alkyne methyl ester 23, intermediate 15, and alkyne intermediate 2. In particular, this scheme shows the total synthesis of the 32-carbon alkynyl elovanoid compound ELV-N32-Me-Acetylenic, and its conversion to elovanoid methyl ester ELV-N32-Me, the elovanoid carboxylic acid ELV-N32-H, and the elovanoid sodium salt ELV-N32-Na.

Scheme 5 (FIG. 28) shows the stereocontrolled total synthesis of 34-carbon dihydroxylated elovanoids, starting with alkyne methyl ester 30, and by employing the same sequence of reactions as in Scheme 4.

In particular, this scheme shows the total synthesis of the 34-carbon alkynyl elovanoid compound ELV-N34-Me-Acetylenic, and its conversion to elovanoid methyl ester ELV-N34-Me, the elovanoid carboxylic acid ELV-N34-H, and the elovanoid sodium salt ELV-N34-Na.

The chemistry presented in Schemes 1-5 (FIGS. 24-28) can be also readily adapted for the total synthesis of additional mono-hydroxylated and di-hydroxylated elovanoids, having at least 23 carbons and up to 42 carbons in their carbon chain.

Pharmaceutical Compositions for the Treatment of Diseases:

In other embodiments, the present disclosure provides formulations of pharmaceutical compositions containing therapeutically effective amounts of one or more of compounds provided herein or their salts thereof in a pharmaceutically acceptable carrier.

The provided compositions contain one or more compounds provided herein or their salts thereof, and a pharmaceutically acceptable excipient, diluent, carrier and/or adjuvant. The compounds are preferably formulated into suitable pharmaceutical preparations such as solutions, suspensions, tablets, dispersible tablets, pills, capsules, powders, sustained release formulations or elixirs, for oral, buccal, intranasal, vaginal, rectal, ocular administration, sustained release from intravitreal implanted reservoirs or nano-devices or dendrimers, embedded in collagen or other materials on the eye surface, or in sterile solutions or suspensions for parenteral administration, dermal patches as well as transdermal patch preparation and dry powder inhalers. The provided formulations may be in the form of a drop, such as an eye drop, and the pharmaceutical formulation may further contain antioxidants and/or known agents for the treatment of eye diseases. Typically, the compounds described above are formulated into pharmaceutical compositions using techniques and procedures well known in the art (see, e.g., Ansel Introduction to Pharmaceutical Dosage Forms, Fourth Edition 1985, 126).

Advantageous embodiments of the disclosure provide pharmaceutical compositions containing various forms of the provided compounds, as the free carboxylic acids or their pharmaceutically acceptable salts, or as their corresponding esters or their phospholipid derivatives. In other advantageous embodiments, the disclosure provides pharmaceutical compositions containing one or more elovanoid that contains one or two hydroxyl groups at positions located between n-3 to n-18 of the very long chain polyunsaturated fatty acids, as the free carboxylic acids or their pharmaceutically acceptable salts, or as their corresponding esters.

In a further advantageous embodiment, the disclosure provides a pharmaceutical composition for preservation and protection of the skin at all ages and for the treatment of a skin disease or disorder. In some embodiments, the skin disease or disorder involves skin inflammation, skin hyperproliferation, or skin dehydration.

In embodiments, the disclosure provides a composition for the treatment of skin diseases or disorders selected from a group consisting of: dermatitis, eczema, atopic dermatitis, neurodermatitis, photocontact dermatitis, xerotic eczema, seborrheic eczema, dyshidrosis, discoid eczema, venous eczema, dermatitis herpetiformis, neurodermatitis and autoeczematisation, radiation-induced skin inflammation, or psoriasis.

In the provided compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of a disease, disorder or condition.

As described herein, the compositions can be readily prepared by adapting methods known in the art. The compositions can be a component of a pharmaceutical formulation. The pharmaceutical formulation may further contain known agents for the treatment of inflammatory or degenerative diseases, including neurodegenerative diseases. The provided compositions can serve as pro-drug precursors of the fatty acids and can be converted to the free fatty acids upon localization to the site of the disease.

The present disclosure also provides packaged composition(s) or pharmaceutical composition(s) for prevention, restoration, or use in treating the disease or condition. Other packaged compositions or pharmaceutical compositions provided by the present disclosure further include indicia including at least one of: instructions for using the composition to treat the disease or condition. The kit can further include appropriate buffers and reagents known in the art for administering various combinations of the components listed above to the host.

Pharmaceutical Formulations:

Embodiments of the present disclosure include a composition or pharmaceutical composition as identified herein and can be formulated with one or more pharmaceutically acceptable excipients, diluents, carriers, naturally occurring or synthetic antioxidants, and/or adjuvants. In addition, embodiments of the present disclosure include a composition or pharmaceutical composition formulated with one or more pharmaceutically acceptable auxiliary substances. In particular the composition or pharmaceutical composition can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the composition or pharmaceutical composition can be administered to the subject using any means capable of resulting in the desired effect. Thus, the composition or pharmaceutical composition can be incorporated into a variety of formulations for therapeutic administration. For example, the composition or pharmaceutical composition can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles for the composition or pharmaceutical composition are, for example, water, saline, dextrose, glycerol, ethanol, or the like, and combinations thereof. In addition, if desired, the vehicle may contain minor amounts of auxiliary substances such as wetting or emulsifying agents, antioxidants or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the composition or pharmaceutical composition adequate to achieve the desired state in the subject being treated.

Compositions of the present disclosure can include those that comprise a sustained release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. In another embodiment, the pharmaceutical composition of the present disclosure (as well as combination compositions) can be delivered in a controlled release system. For example, the composition or pharmaceutical composition may be administered using intravenous infusion, an implantable osmotic pump, a transdermal patch, liposomes, or other modes of administration. In one embodiment, a pump may be used (Sefton (1987). CRC Crit. Ref. Biomed. Eng. 14:201; Buchwald et al. (1980). Surgery 88:507; Saudek et al. (1989). N. Engl. J. Med. 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). Science 249:1527-1533.

In another embodiment, the compositions of the present disclosure (as well as combination compositions separately or together) include those formed by impregnation of the composition or pharmaceutical composition described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

In another embodiment, the compositions or pharmaceutical compositions of the present disclosure (as well as combination compositions separately or together) can be part of a delayed-release formulation. Delayed-release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Embodiments of the composition or pharmaceutical composition can be administered to a subject in one or more doses. Those of skill will readily appreciate that dose levels can vary as a function of the specific the composition or pharmaceutical composition administered, the severity of the symptoms and the susceptibility of the subject to side effects. Advantageous dosages for a given compound are readily determinable by those of skill in the art by a variety of means.

In an embodiment, multiple doses of the composition or pharmaceutical composition are administered. The frequency of administration of the composition or pharmaceutical composition can vary depending on any of a variety of factors, e.g., severity of the symptoms, and the like. For example, in an embodiment, the composition or pharmaceutical composition can be administered once per month, twice per month, three times per month, every other week (qow), once per week (qw), twice per week (biw), three times per week (tiw), four times per week, five times per week, six times per week, every other day (qod), daily (qd), twice a day (qid), three times a day (tid), or four times a day. As discussed above, in an embodiment, the composition or pharmaceutical composition is administered 1 to 4 times a day over a 1 to 10-day time period.

The duration of administration of the composition or pharmaceutical composition analogue, e.g., the period of time over which the composition or pharmaceutical composition is administered, can vary, depending on any of a variety of factors, e.g., patient response, etc. For example, the composition or pharmaceutical composition in combination or separately, can be administered over a period of time of about one day to one week, about one day to two weeks.

The amount of the compositions and pharmaceutical compositions of the present disclosure that can be effective in treating the condition or disease can be determined by standard clinical techniques. In addition, in vitro or in vivo assays can optionally be employed to help identify optimal dosage ranges. The precise dose to be employed can also depend on the route of administration, and can be decided according to the judgment of the practitioner and each patient's circumstances.

Routes of Administration:

Embodiments of the present disclosure provide methods and compositions for the administration of the active agent(s) to a subject (e.g., a human) using any available method and route suitable for drug delivery, including in vivo and ex vivo methods, as well as systemic and localized routes of administration. Routes of administration include intranasal, intramuscular, intratracheal, subcutaneous, intradermal, intravitreal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

The n-3 VLC-PUFA and their biogenic derivatives are formed in cells and are not a component of human diet. Advantageous routes of administration of the novel compounds provided herein will include oral and parenteral administration, including on the ocular surface, intravitreal and subretinal injection into the eye to bypass intestinal absorption, the gut-liver, and the blood-ocular barrier. The provided formulations may be delivered in the form of a drop, such as an eye drop, or any other customary method for the treatment of eye diseases.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to affect systemic or local delivery of the composition. Where systemic delivery is desired, administration typically involves invasive or systemically absorbed topical or mucosal administration of pharmaceutical preparations. In an embodiment, the composition or pharmaceutical composition can also be delivered to the subject by enteral administration. Enteral routes of administration include, but are not limited to, oral and rectal (e.g., using a suppository) delivery.

Methods of administration of the composition or pharmaceutical composition through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

The compounds and compositions provided by this disclosure are able to restore homeostasis and induce survival signaling in certain cells undergoing oxidative stress or other homeostatic disruptions. The disclosure also provides methods of use of the provided compounds and compositions containing a hydroxylated derivative of very long chain polyunsaturated fatty acids, as the free carboxylic acids or their pharmaceutically acceptable salts, or as their corresponding esters or other prodrug derivatives. The provided compounds can be readily prepared by adapting methods known in the art, starting with commercially available materials.

The bioactivity of the provided compounds, as exemplified by the elovanoid derivatives ELV-N32-Me, ELV-N32-Na, ELV-N34-Me and ELV-N34-Na, is attributed to their ability to reach the targeted human cells and exert their biological actions either by entering into the cell or/and by acting at a membrane bound receptor. Alternatively, the provided compounds can act via intracellular receptors (e.g. nuclear membrane), and thus they would work specifically by affecting key signaling events. Administration of a pharmaceutical composition, containing a provided compound and a pharmaceutically acceptable carrier, restores the homeostatic balance and promotes the survival of certain cells that are essential for maintaining normal function. The provided compounds, compositions, and methods can be used for the preventive and therapeutic treatment of inflammatory, degenerative, and neurodegenerative diseases. This disclosure targets critical steps of the initiation and early progression of these conditions by mimicking the specific biology of intrinsic cellular/organs responses to attain potency, selectivity, devoid of side effects and sustained bioactivity.

Accordingly, one aspect of the disclosure encompasses embodiments of a composition comprising at least one very long chain polyunsaturated fatty acid having at least 23 carbon atoms in its carbon chain.

In some embodiments of this aspect of the disclosure, the composition can further comprise a pharmaceutically-acceptable carrier and formulated for delivery of an amount of the at least one very long chain polyunsaturated fatty acid effective in reducing a pathological condition of a tissue of a recipient subject or the onset of a pathological condition of a tissue of a recipient subject.

In some embodiments of this aspect of the disclosure, the pathological condition can be aging or inflammation of a tissue of the recipient subject.

In some embodiments of this aspect of the disclosure, the composition can be formulated for topical delivery of the at least one very long chain polyunsaturated fatty acid tissue to the skin of a recipient subject.

In some embodiments of this aspect of the disclosure, the pathological condition can be of a neurological tissue of the recipient subject.

In some embodiments of this aspect of the disclosure, the composition can further comprise at least one nutritional component, and the composition can be formulated for the oral or parenteral delivery of the at least one very long chain polyunsaturated fatty acid to a recipient subject.

In some embodiments of this aspect of the disclosure, the at least one very long chain polyunsaturated fatty acid can have from about 26 to about 42 carbon atoms in its carbon chain.

In some embodiments of this aspect of the disclosure, the at least one very long chain polyunsaturated fatty acid can have 32 or 34 carbon atoms in its carbon chain.

In some embodiments of this aspect of the disclosure, the very long chain polyunsaturated fatty acid can have in its carbon chain five or six double bonds with cis geometry.

In some embodiments of this aspect of the disclosure, the very long chain polyunsaturated fatty acid is 14Z,17Z,20Z,23Z,26Z,29Z)-dotriaconta-14,17,20,23,26,29-hexaenoic acid or (16Z,19Z,22Z,25Z,28Z,31Z)-tetratriaconta-16,19,22,25,28,31-hexaenoic acid.

Another aspect of the disclosure encompasses embodiments of a composition comprising at least one elovanoid having at least 23 carbon atoms in its carbon chain.

In some embodiments of this aspect of the disclosure, the composition can further comprise a pharmaceutically-acceptable carrier and can be formulated for delivery of an amount of the at least one elovanoid effective in reducing a pathological condition of a tissue of a recipient subject or delaying at least one effect of aging in a tissue of a recipient subject.

In some embodiments of this aspect of the disclosure, the pathological condition can be aging or inflammation of a tissue of the recipient subject.

In some embodiments of this aspect of the disclosure, the composition can be formulated for topical delivery of the at least one elovanoid to the skin of a recipient subject.

In some embodiments of this aspect of the disclosure, the pathological condition can be of a neurological tissue of the recipient subject.

In some embodiments of this aspect of the disclosure, the composition can further comprise at least one nutritional component, and the composition can be formulated for the oral or parenteral delivery of the at least one elovanoid to a recipient subject.

In some embodiments of this aspect of the disclosure, the at least one elovanoid can be selected from the group consisting of: a mono-hydroxylated elovanoid, a di-hydroxylated elovanoid, an alkynyl mono-hydroxylated elovanoid, and an alkynyl di-hydroxylated elovanoid, or any combination thereof.

In some embodiments of this aspect of the disclosure, the at least one elovanoid can be a combination of elovanoids, wherein the combination is selected from the group consisting of: a mono-hydroxylated elovanoid and a di-hydroxylated elovanoid; a mono-hydroxylated elovanoid and an alkynyl mono-hydroxylated elovanoid; a mono-hydroxylated elovanoid and an alkynyl di-hydroxylated elovanoid; a di-hydroxylated elovanoid and an alkynyl mono-hydroxylated elovanoid; a di-hydroxylated elovanoid and an alkynyl di-hydroxylated elovanoid; a mono-hydroxylated elovanoid, a di-hydroxylated elovanoid, and an alkynyl mono-hydroxylated elovanoid; a mono-hydroxylated elovanoid, a di-hydroxylated elovanoid, and an alkynyl di-hydroxylated elovanoid; and a mono-hydroxylated elovanoid, a di-hydroxylated elovanoid, and an alkynyl mono-hydroxylated elovanoid an alkynyl di-hydroxylated elovanoid, wherein each elovanoid is independently a racemic mixture, an isolated enantiomer, or a combination of enantiomers wherein the amount of one enantiomer greater than the amount of another enantiomer; and wherein each di-hydroxylated elovanoid is independently a diastereomeric mixture, an isolated diastereomer, or a combination of diastereomers wherein the amount of one diastereomer is greater than the amount of another diastereomer.

In some embodiments of this aspect of the disclosure, the composition can further comprise at least one very long-chain polyunsaturated fatty acid having at least 23 carbon atoms in its carbon chain.

In some embodiments of this aspect of the disclosure, the at least one very long chain polyunsaturated fatty acid can have from about 26 to about 42 carbon atoms in its carbon chain.

In some embodiments of this aspect of the disclosure, the at least one very long chain polyunsaturated fatty acid can have in its carbon chain five or six double bonds with cis geometry.

In some embodiments of this aspect of the disclosure, the at least one very long chain polyunsaturated fatty acid can be 14Z,17Z,20Z,23Z,26Z,29Z)-dotriaconta-14,17,20,23,26,29-hexaenoic acid or (16Z,19Z,22Z,25Z,28Z,31Z)-tetratriaconta-16,19,22,25,28,31-hexaenoic acid.

In some embodiments of this aspect of the disclosure, the mono-hydroxylated elovanoid can be selected from the group consisting of the formulas G, H, I or J:

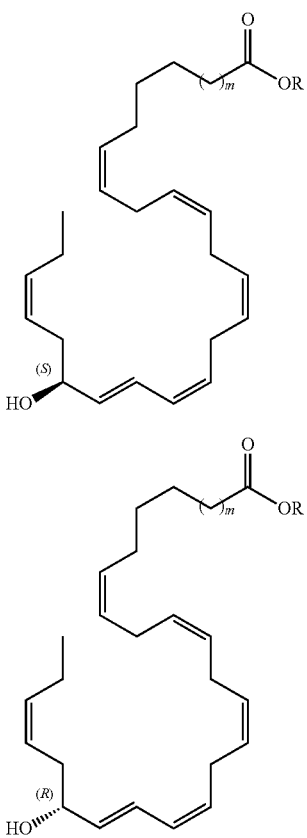

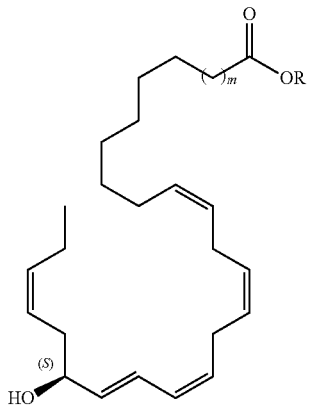

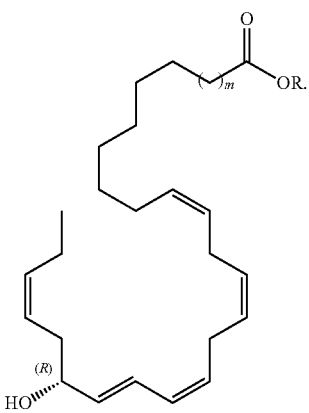

wherein: n can be 0 to 19 and —CO—OR can be a carboxylic acid group, or a salt or an ester thereof, and wherein: if —CO—OR can be a carboxylic acid group and the compound G, H, I or J can be a salt thereof, the cation of the salt can be a pharmaceutically acceptable cation, and if —CO—OR can be an ester, then R can be an alkyl group.

In some embodiments of this aspect of the disclosure, the pharmaceutically acceptable cation can be an ammonium cation, an iminium cation, or a metal cation.

In some embodiments of this aspect of the disclosure, the metal cation can be a sodium, potassium, magnesium, zinc, or calcium cation.

In some embodiments of this aspect of the disclosure, the composition can comprise equimolar amounts of the enantiomers G and H wherein the enantiomers have (S) or (R) chirality at the carbon bearing the hydroxyl group.

In some embodiments of this aspect of the disclosure, the composition can comprise amounts of the enantiomers I and J wherein the enantiomers have (S) or (R) chirality at the carbon bearing the hydroxyl group.

In some embodiments of this aspect of the disclosure, the composition can comprise one of the enantiomers of G or H in an amount exceeding the amount of the other enantiomer of G or H.

In some embodiments of this aspect of the disclosure, the composition can comprise one of the enantiomers of I or J in an amount exceeding the amount of the other enantiomer of I or J.

In some embodiments of this aspect of the disclosure, the mono-hydroxylated elovanoid can be selected from a group consisting of: methyl (S,14Z,17Z,20Z,23Z,25E,29Z)-27-hydroxydotriaconta-14,17,20,23,25,29-hexaenoate (G1), sodium (S,14Z,17Z,20Z,23Z,25E,29Z)-27-hydroxydotriaconta-14,17,20,23,25,29-hexaenoate (G2), methyl (S,16Z,19Z,22Z,25Z,27E,31Z)-29-hydroxytetratriaconta-16,19,22,25,27,31-hexaenoate (G3); and sodium (S,16Z,19Z,22Z,25Z,27E,31Z)-29-hydroxytetratriaconta-16,19,22,25,27,31-hexaenoate (G4) having the formulas, respectively:
G1
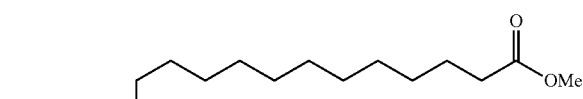
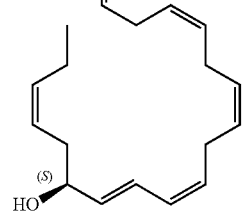
G2
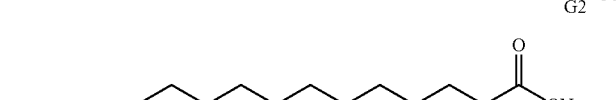
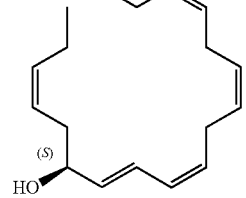
G3
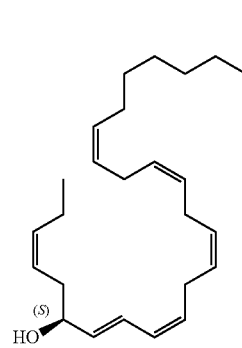
G4
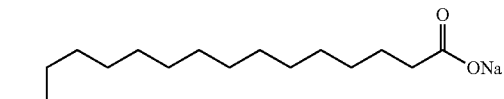
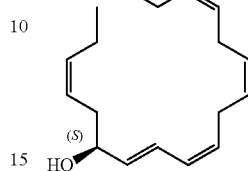
In some embodiments of this aspect of the disclosure, the di-hydroxylated elovanoid can be selected from the group consisting of the formulas K, L, M, and N:
K
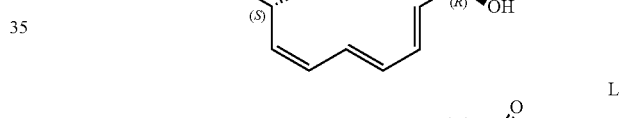
L
M

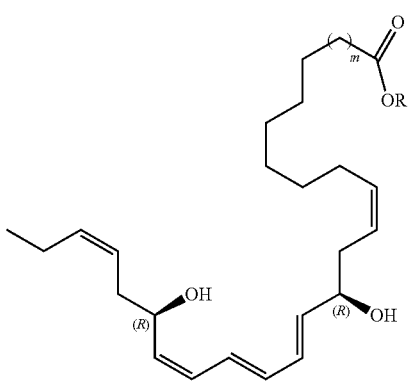

wherein: m can be 0 to 19 and —CO—OR can be a carboxylic acid group, or a salt or an ester thereof,
and wherein: if —CO—OR can be a carboxylic acid group and the compound K, L, M, or N can be a salt thereof, the cation of the salt can be a pharmaceutically acceptable cation, and if —CO—OR can be an ester, then R can be an alkyl group.

In some embodiments of this aspect of the disclosure, the pharmaceutically acceptable cation can be an ammonium cation, an iminium cation, or a metal cation.

In some embodiments of this aspect of the disclosure, the metal cation can be a sodium, potassium, magnesium, zinc, or calcium cation.

In some embodiments of this aspect of the disclosure, the composition can comprise equimolar amounts of the diastereomers K and L wherein the diastereomers have either (S) or (R) chirality at position n-6, and (R) chirality at position n-13.

In some embodiments of this aspect of the disclosure, the composition can comprise equimolar amounts of the diastereomers M and N wherein the diastereomers have either (S) or (R) chirality at position n-6, and (R) chirality at position n-13.

In some embodiments of this aspect of the disclosure, the composition can comprise one of the diastereomers of K or L in an amount exceeding the amount of the other diastereomer of K or L.

In some embodiments of this aspect of the disclosure, the composition can comprise one of the diastereomers of M or N in an amount exceeding the amount of the other diastereomer of M or N.

In some embodiments of this aspect of the disclosure, the di-hydroxylated elovanoid can be selected from the group consisting of: methyl (14Z,17Z,20R,21E,23E,25Z,27S,29Z)-20,27-dihydroxydotriaconta-14,17,21,23,25,29-hexaenoate (K1), sodium (14Z,17Z,20R,21E,23E,25Z,27S,29Z)-20,27-dihydroxydotriaconta-14,17,21,23,25,29-hexaenoate (K2), methyl (16Z,19Z,22R,23E,25E,27Z,29S,31Z)-22,29-dihydroxytetratriaconta-16,19,23,25,27,31-hexaenoate (K3), and sodium (16Z,19Z,22R,23E,25E,27Z,29S,31Z)-22,29-dihydroxytetratriaconta-16,19,23,25,27,31-hexaenoate (K4) having the formulas, respectively:

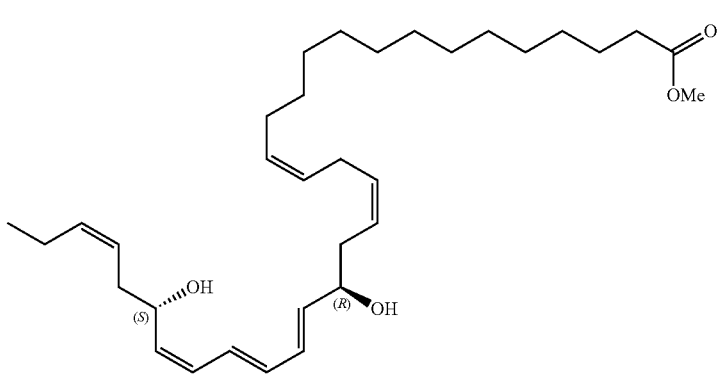

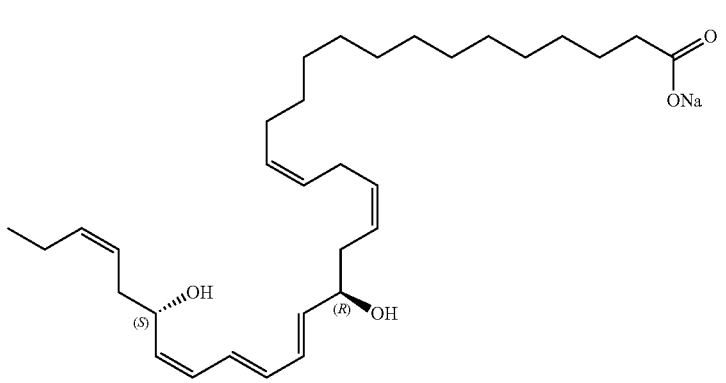

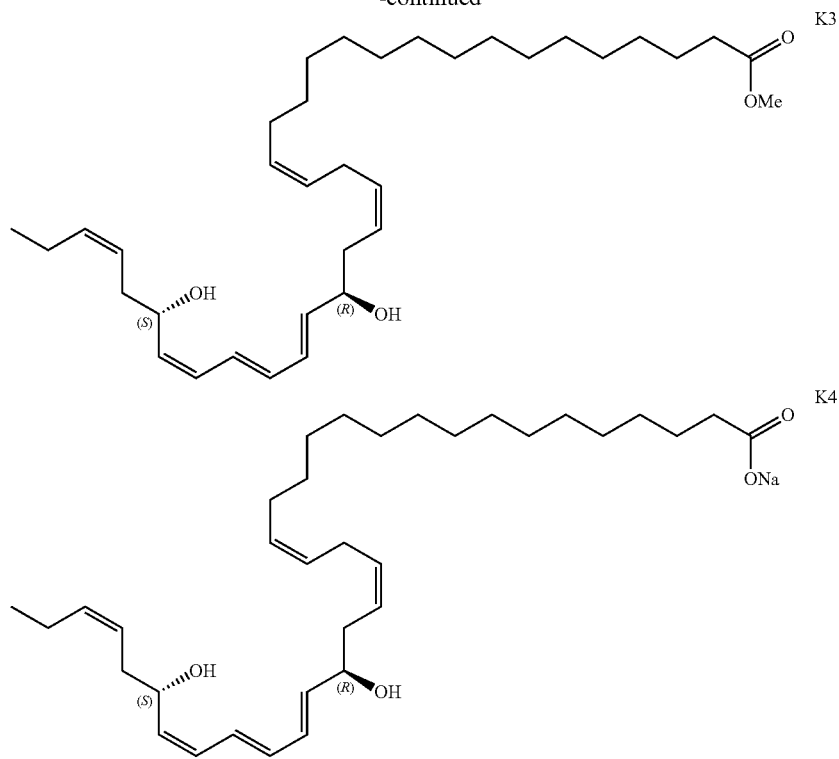
In some embodiments of this aspect of the disclosure, the alkynyl mono-hydroxylated elovanoid can be selected from the group consisting of the formulas O, P, Q or R:
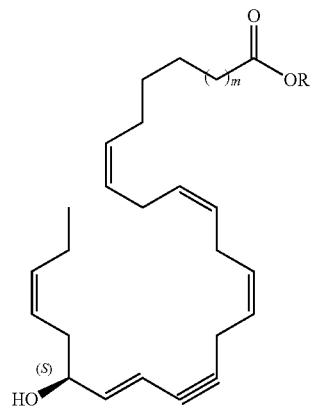
O
-continued
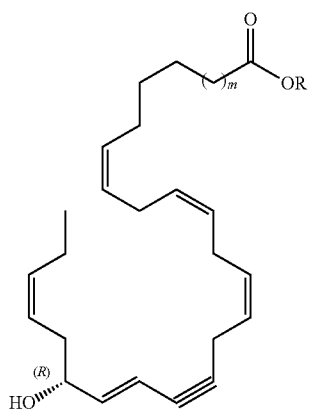
P
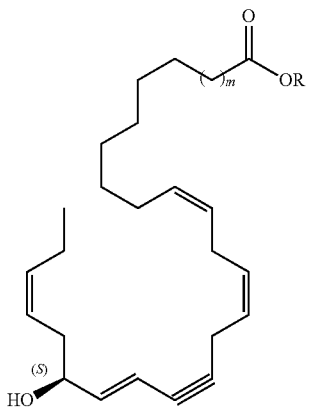
Q

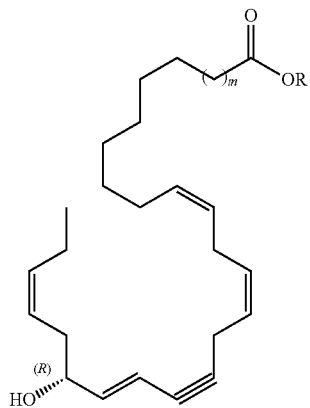

wherein: m can be 0 to 19 and —CO—OR can be a carboxylic acid group, or a salt or an ester thereof, and wherein: if —CO—OR can be a carboxylic acid group and the compound O, P, Q or R can be a salt thereof, the cation of the salt can be a pharmaceutically acceptable cation, and if —CO—OR can be an ester, then R can be an alkyl group, and wherein: compounds O and P each have a total from 23 to 42 carbon atoms in the carbon chain, with 4 cis carbon-carbon double bonds located at positions starting at n-3, n-12, n-15 and n-18; with a trans carbon-carbon double bond at position starting at n-7, and a carbon-carbon triple bond starting at position n-9; and compounds Q and R each have a total from 23 to 42 carbon atoms in the carbon chain, with 3 cis carbon-carbon double bond starting at positions n-3, n-12 and n-15, with a trans carbon-carbon double bond at position starting at n-7, and a carbon-carbon triple bond starting at position n-9.

In some embodiments of this aspect of the disclosure, the alkynyl mono-hydroxylated elovanoid can be selected from the group consisting of: methyl (S,14Z,17Z,20Z,25E,29Z)-27-hydroxydotriaconta-14,17,20,25,29-pentaen-23-ynoate (O1); sodium (S,17Z,20Z,25E,29Z)-27-hydroxydotriaconta-17,20,25,29-tetraen-23-ynoate (O2); methyl (S,16Z,19Z,22Z,27E,31Z)-29-hydroxytetratriaconta-16,19,22,27,31-pentaen-25-ynoate (O3); and sodium (S,16Z,19Z,22Z,27E,31Z)-29-hydroxytetratriaconta-16,19,22,27,31-pentaen-25-ynoate (O4) and having the formulas, respectively:

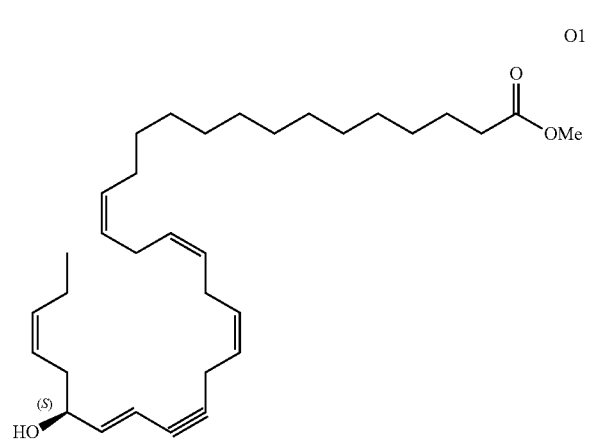

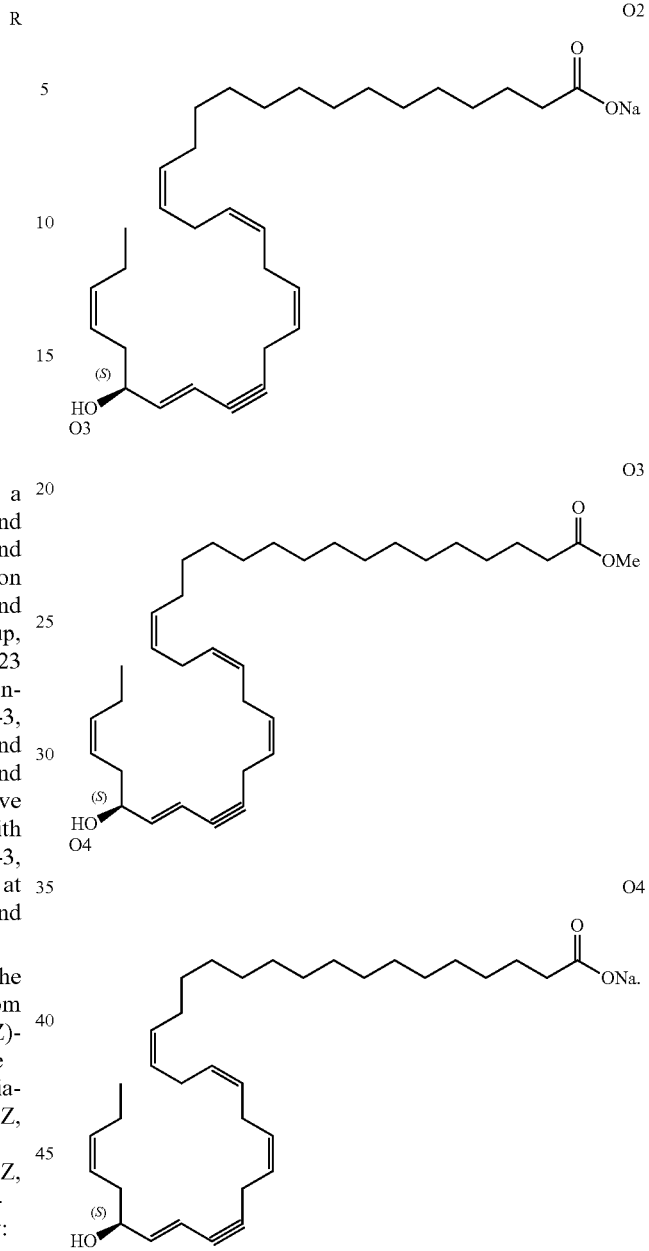

In some embodiments of this aspect of the disclosure, the pharmaceutically acceptable cation can be an ammonium cation, an iminium cation, or a metal cation.

In some embodiments of this aspect of the disclosure, the metal cation can be a sodium, potassium, magnesium, zinc, or calcium cation.

In some embodiments of this aspect of the disclosure, the composition can comprise equimolar amounts of the enantiomers O and P wherein the enantiomers have (S) or (R) chirality at the carbon bearing the hydroxyl group.

In some embodiments of this aspect of the disclosure, the composition can comprise equimolar amounts of the enantiomers Q and R wherein the enantiomers have (S) or (R) chirality at the carbon bearing the hydroxyl group.

In some embodiments of this aspect of the disclosure, the composition can comprise one of the enantiomers of O or P in an amount exceeding the amount of the other enantiomer of O or P.

In some embodiments of this aspect of the disclosure, the composition can comprise one of the enantiomers of Q or R in an amount exceeding the amount of the other enantiomer of Q or R.

In some embodiments of this aspect of the disclosure, the elovanoid can be an alkynyl di-hydroxylated elovanoid selected from the group consisting of the formulas S, T, U or V:

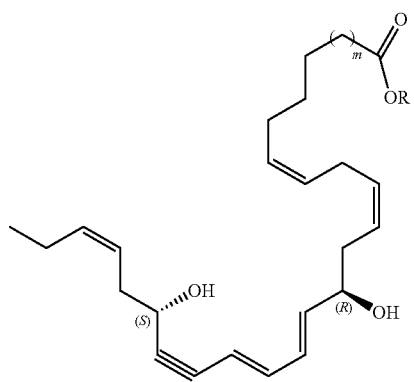

S

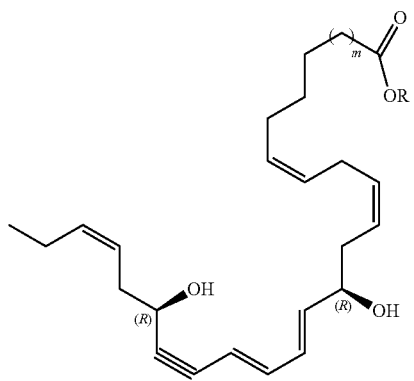

T

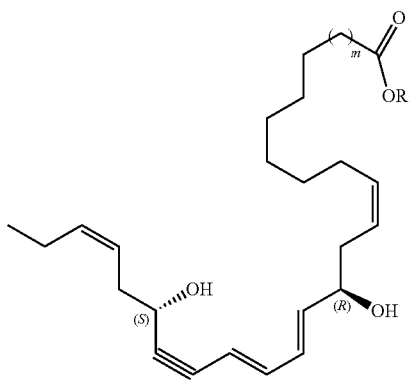

U

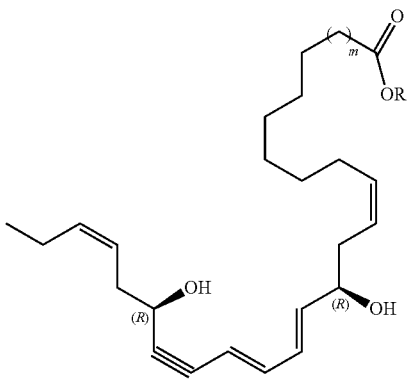

V wherein: m can be 0 to 19 and —CO—OR can be a carboxylic acid group, or a salt or an ester thereof, and wherein: if —CO—OR can be a carboxylic acid group and the compound S, T, U or V can be a salt thereof, the cation of the salt can be a pharmaceutically acceptable cation, and if —CO—OR can be an ester, then R can be an alkyl group, and wherein: compounds S and T each have a total from 23 to 42 carbon atoms in the carbon chain, with 3 cis carbon-carbon double bonds starting at positions n-3, n-15 and n-18; 2 trans carbon-carbon double bonds starting at positions n-9, n-11; and a carbon-carbon triple bond starting at position n-7; and compounds U and V each have a total from 23 to 42 carbon atoms in the carbon chain, with 2 cis carbon-carbon double bond starting at positions n-3, and n-15; 2 trans carbon-carbon double bonds starting at positions n-9 and n-11; and a carbon-carbon triple bond starting at position n-7.

In some embodiments of this aspect of the disclosure, the pharmaceutically acceptable cation is an ammonium cation, an iminium cation, or a metal cation.

In some embodiments of this aspect of the disclosure, the metal cation is a sodium, potassium, magnesium, zinc, or calcium cation.

In some embodiments of this aspect of the disclosure, the alkynyl mono-hydroxylated elovanoid can be selected from the group consisting of: methyl (14Z,17Z,20R,21E,23E,27S,29Z)-20,27-dihydroxydotriaconta-14,17,21,23,29-pentaen-25-ynoate (S1); sodium (14Z,17Z,20R,21E,23E,27S,29Z)-20,27-dihydroxydotriaconta-14,17,21,23,29-pentaen-25-ynoate (S2); methyl (16Z,19Z,22R,23E,25E,29S,31Z)-22,29-dihydroxytetratriaconta-16,19,23,25,31-pentaen-27-ynoate (S3); and sodium (16Z,19Z,22R,23E,25E,29S,31Z)-22,29-dihydroxytetratriaconta-16,19,23,25,31-pentaen-27-ynoate (S4), and having the formula, respectively:

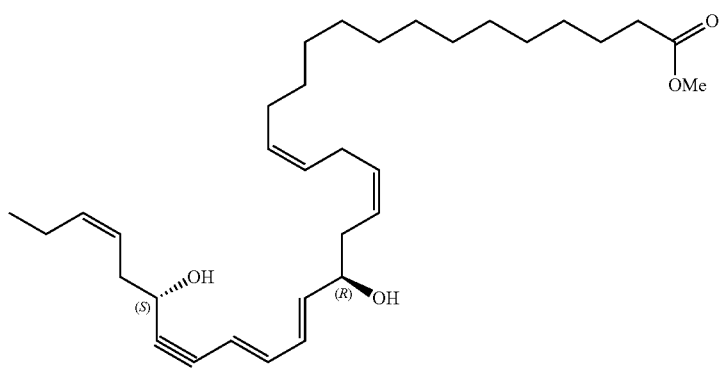
S1
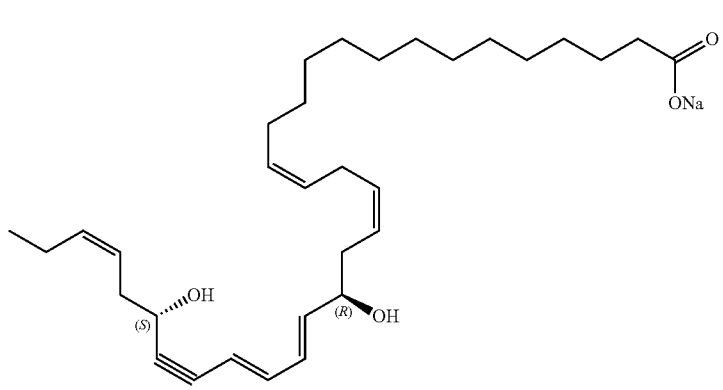
S2
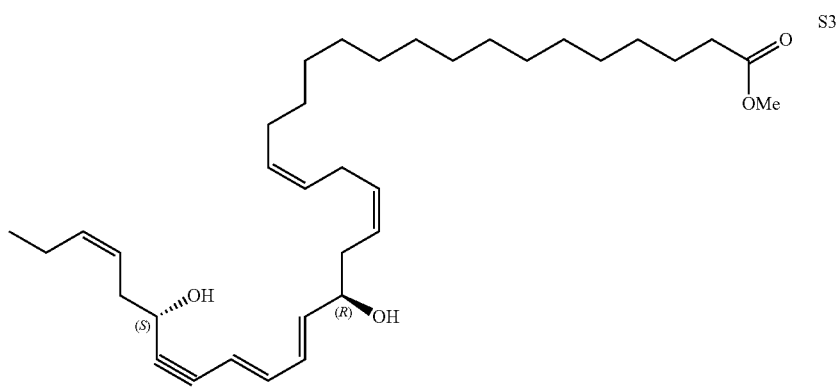
S3
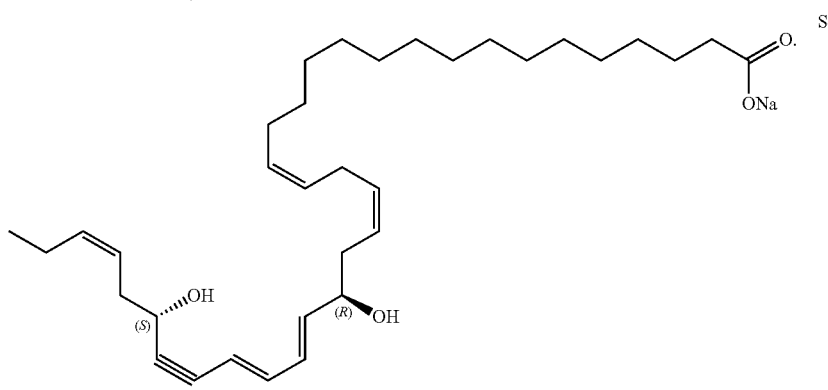
S4

In some embodiments of this aspect of the disclosure, the composition can comprise equimolar amounts of the diastereomers S and T wherein the diastereomers have (S) or (R) chirality at the carbons bearing the hydroxyl groups.

In some embodiments of this aspect of the disclosure, the composition can comprise equimolar amounts of the diastereomers U and V wherein the diastereomers have either (S) or (R) chirality at position n-6, and (R) chirality at position n-13.

In some embodiments of this aspect of the disclosure, the composition can comprises one of the diastereomers of S or T in an amount exceeding the amount of the other diastereomer of S or T.

In some embodiments of this aspect of the disclosure, the composition can comprise one of the diastereomers of U or V in an amount exceeding the amount of the other diastereomer of U or V.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

EXAMPLES

Example 1

Primary Cultures of Cortical Neurons:

Primary cultures of cortical and hippocampal neurons were harvested from 18-day-old embryos (E18) taken from timed-pregnant, two-month-old Sprague-Dawley (SD) rats (Charles River Lab., Wilmington, Mass.). Briefly, timed-pregnant SD rats were euthanized and embryos were collected in sterile conditions. Embryonic brains were dissected out by forceps on ice and placed in a petri dish containing ice-cold Hank's Balanced Salt Solution (HBSS) (GIBCO). Meninges were removed under a dissecting microscope and cortical tissues were chopped into small pieces with microspring scissors. These tissues were transferred to 15 ml tubes containing trypsin-EDTA (0.025% in HBSS) and DNase I. The tubes were incubated in 37° C. chamber for 15 mins and were agitated every 5 mins. After stopping the trypsinization with 5 ml 10% FBS, these tissues were triturated 15 times with a fire polished Pasteur pipet. Cell clumps were left to settle for 2 mins and the supernatant was transferred to a 15 ml Eppendorf tube. The supernatant was filtered through a 70 μm pore-sized filter (Corning cell strainer) and centrifuged for 5 mins at 1000 rpm. The cells were then resuspended in Neurobasal medium (GIBCO) containing 2% B27 (GIBCO) and 2% N2 (GIBCO) supplements, along with 0.5 mM glutamine, 50 U/ml penicillin/streptomycin.

Cells were counted using a Neubauer hemocytometer. $1\times10^6$ cells were seeded on poly-D-lysine-coated 12 well cell culture dish (CORNING) and cultured in incubator (37° C., 5% $CO_2$). Culture medium was first replaced after 24 h, then half of the medium was replaced with fresh medium every three days. As a result, approximately, 90% purity of neurons was obtained as determined by class-III-β tubulin, GFAP and Hoechst 33258 staining. Cells were maintained in culture for about 2 weeks until they were exposed to uncompensated oxidative stress, OGD, or NMDA excitotoxicity.

Example 2

Antibodies:

The following antibodies were used: β-catenin (catalog #sc-7963, lot #K0812) Santa Cruz Biotechnology: (concentration used 1:50); ZO-1 (catalog #187430, lot #1633993A) Life Technologies: (concentration used 1:100); MITF (catalog #ab59232, lot #GR52475-3) ABCAM: (concentration used 1:250); RPE65 (catalog #ab78036, lot 3GR254004-1), ABCAM: (concentration used 1:250).

Example 3

Human RPE Cell Cultures:

Primary human retinal pigment epithelia (RPE) cells, prepared from donor eyes without eye pathology, were plated and transformed after passage eight. Cells were cultured in T75 flasks in MEM medium containing 10% FBS, 5% NCS, MEM-NEAA (ThermoFisher Scientific, Waltham, Mass.), 1× penicillin/streptomycin and 10 ng/ml FGF at 37° C. 5% $CO_2$, 99% relative humidity for 24-48 h followed by a 24-h incubation with 10 μM free 32:6 and 34:6 fatty acid mixture.

FIGS. 6A and 6B depicts immunostaining of primary human RPE cells using specific markers ZO-1 (Zona occludens-1), RPE65, MITF (Micro-ophtalmia-associated Transcription Factor) and β-catenin, as well as light microscopy depicting primary human RPE cell morphology at different passages in culture. ARPE-19 cells were grown and maintained in T-75 mM flasks in DMEM F-12 medium containing 10% FBS and incubated at 37° C. with a constant supply of 5% $CO_2$. Cells at 75-80% confluence (72 h growth in DMEM/F12+10% FBS) in 6-well plates were serum-starved for 8 h before exposure.

Example 4

Exposure of RPE Cells to UOS and VLC-PUFA:

For cell viability assay experiments hRPE cells were treated concomitantly with NPD1 (200 nM), 32-6, 34-6 (3 μM each) fatty acids or both 32-6 and 34-6 simultaneously. The hRPE medium was supplemented with 3 μM of 32-6 and 34-6 for the entire duration of the experiment. 15 lox-1 inhibitor (10 μM) was added to the cells 1 hour prior the OS induction and kept throughout the experiment. Cells were fixed with 4% PFA and stained with Hoescht.

ARPE19 cells at 75-80% confluence (72 h growth in DMEM/F12+10% FBS) in 6-well plates were serum-starved for 8 h before exposure. The serum-starved cells were treated with TNF-α (Sigma-Aldrich, St. Louis, Mo.) (10 ng/ml) and $H_2O_2$ (600 μM) to induce oxidative stress and challenged with increasing concentrations (50-500 nM) of VLC-PUFA (C32:6n3 and C34:6n3) simultaneously with oxidative stress for 16 h (apoptosis) and 6 h (Western-blot) before detection of apoptosis and harvesting for protein analysis. In some experiments, DHA at a concentration of 100 nM and 15-LOX-1 inhibitor PD146176 at a concentration of 1 μM was added to treat the RPE cells under stress. Cell extracts were made and protein concentrations adjusted by Bio-Rad (Hercules, Calif.) protein reagent and used for Western blot analysis.

Example 5

Analysis of Proteins:

Bcl-2 family proteins, SIRT1 and Proinhibitin (type-1), and Iduna proteins were analyze by Western blot analysis. In brief, 20-25 μg equivalents of each cell extracts were subject to electrophoresis on a 4-12% gel (Promega) at 125 V for 2 h. The proteins were transferred to nitrocellulose membrane by I-blot transfer apparatus. The membranes were subjected to treatment with primary antibodies specific for Bcl-2, Bcl-xL, Bax, Bid, Bim, SIRT1 and Prohibitin (type-1) (Santa Cruz Biotechnology) and Iduna antibody (NeuroMab Lab, UCLA, Los Angeles, Calif.) overnight at 4° C. and probed for 45 mins with secondary antibody, goat anti-mouse Ig:horseradish peroxidase, and horseradish peroxidase-conjugated anti-biotin antibody, and then proteins were evaluated by using an ECL kit (Amersham).

Example 6

Immunocytochemistry and Cell Apoptosis Assessment:
Immunocytochemistry assays were performed in 8-well slide chambers. Briefly, cells were fixed in 4% paraformaldehyde (FA) for 20 mins, permeabilized with 0.1% Triton X-100 in PBS. Non-specific epitopes were blocked in 10% Bovine serum albumin (BSA) in 1×PBS for 1 h at room temperature. Immunostaining was by incubating primary antibody overnight at 4° C. Samples were stained for 2 h at room temperature with Alexa Fluor 555-conjugated secondary antibodies diluted 1 in 250 (MeridianLife Science Inc., Memphis, Tenn., USA), and nuclei were stained with Hoechst (2 μM Hoechst 33258). Pictures were taken with a Zeiss LSM 510 confocal microscope and a Zeiss Axioplan-2 deconvolution microscope.

To assess cell death, hRPE and ARPE-19 cells were fixed with methanol for 15 mins, washed with 1×PBS then loaded with 2 μM Hoechst dissolved in a Locke's solution (Promega) and incubated for another 15 mins before imaging. Cells were then viewed by using a Zeiss LSM 510 confocal microscope under UV fluorescence. Images were recorded and cell apoptosis was assessed by using an automated unbiased method.

Example 7

LC-MS/MS of Elovanoids ELV-N32 and ELV-N34 in RPE Cells:
Human RPE cells (ABC cells p #19) were cultured in T75 flasks for 24-48 h followed by a 24 hr incubation with 10 μM free 32:6 and 34:6 fatty acid mixture. Cells were incubated with 1 mM $H_2O_2$ for 24 h promptly after a 24-h serum deprivation. Fatty acids were extracted using liquid-liquid lipid extraction method from the collected cell culture medium followed by Mass Spectrometry analysis. Extracts were loaded onto a liquid chromatography tandem mass spectrometer (LC-MS/MS) for analysis. Fatty acids, monohydroxy fatty acid derivatives (27-hydroxy-fatty acid C32: 6n3 and 29-hydroxyl-fatty acid 34:6n3), and ELV-N32 (20, 27-dihydroxy-fatty acid C32:6n3) and ELV-N34 (22,29-dihydroxy-fatty acid C34:6n3) were analyzed). ELV-N32 and ELV-N34 and their deuterium-labeled derivatives ELV-N32-d2 and ELV-N34-d2 were prepared by stereo-controlled chemical synthesis and used for matching with cell-generated derivatives.

Example 8

Photo-Oxidative Stress:
C57/Bl6 wild-type and AdipoR1 knock-out mice were housed in a temperature-controlled room at 21-23° C. with a 12 h:12 h light-dark cycle. For light-induced oxidative stress, mice were exposed for 1 h of bright light (an 8-light array of 10-inch circular fluorescent 22 W bulbs; Cool White, FTC8T9/CW; Electric, Fairfield, Conn.; 18 klux; 270 μE m-2 s). After light exposure, animals were sacrificed by cervical dislocation and eyes were enucleated. The cornea, iris and lens were discarded and the retina was separated from the rest of the eyecup. These tissues were then flash-frozen. Retinas from animals of the same genotype were pooled together. Samples were processed for lipid extraction and LC-MS/MS-based lipidomic analysis.

Example 9

Oxygen Glucose Deprivation (OGD), NMDA Excitotoxicity or Uncompensated Oxidative Stress (UOS) Exposure:
An in vitro oxygen glucose deprivation (OGD) model was established. Primary cortical neurons were cultured from SD rat embryos. On day in vitro (DIV) 12, cells were washed with phosphate-buffered saline and incubated in glucose-free Neurobasal medium (GIBCO) for 30 mins. The cells were then placed in a modular incubator chamber and incubated in an anaerobic chamber (95% N2, 5% $CO_2$) at 37° C. for 90 mins for OGD.

After 90 mins of OGD exposure, cells were returned to the original medium (Neurobasal medium (GIBCO) containing 2% B27 (GIBCO) and 2% N2 (GIBCO) supplements, along with 0.5 mM glutamine, 50 U/ml penicillin/streptomycin) and placed in a normoxic chamber (37° C., 5% $CO_2$) for 2 h. Then the medium was changed with medium containing either ELV-N32 or ELV-N34 [500 nM] and maintained in a normoxic chamber (37° C., 5% $CO_2$) for 12 h, after which cells were sampled and assayed for cell viability using different methods as previously described (25-28). Cerebral cortical mixed neuronal cells or hippocampal cells in culture were exposed to either NMDA or uncompensated oxidative stress (UOS) for 12 h by addition of either NMDA (25 μM, 50 μM, or 100 μM) concentration or by the addition of TNFα (10 ng/mL) and $H_2O_2$ (50 μM, 100 μM, or 200 μM). Cell viability and neuroprotection in the presence of ELV-N32, ELV-N34, 32:6, or 34:6 were assayed after 12 h.

Example 10

Hoechst Staining and Unbiased Image Analysis:
Cells were washed with 1× Dulbecco's Phosphate Buffered Saline (DPBS) containing no calcium or magnesium (GIBCO) and fixed for 10 mins using ice-cold 4% paraformaldehyde (PFA) followed by 15 mins incubation in 100% methanol. Cells were washed with 1× Phosphate Buffered Saline (PBS) pH 7.4 (GIBCO) and incubated in PBS containing 20 μM Hoechst 33258 (Molecular Probes) for 20 mins. Cells were then washed 3 times with 1×PBS and stored in 1×PBS at 4° C. until they were imaged for microscopy.

One 4×4 tile mosaic was acquired from the center of each well using a Zeiss 510 Meta laser confocal microscope and LSM 510 Meta software. Images were imported into image analysis software ImageJ (National Institutes of Health, Bethesda, Md.) and batch processed using custom macros. An Otsu auto threshold was applied to each image of Hoechst-stained nuclei, and the area of each detected object was recorded. Objects with areas <10 μm$^2$ were excluded from analysis. To estimate percentage non-pyknotic nuclei, a size cutoff value was chosen above which objects were assumed to be non-pyknotic. The size cutoff for pyknosis was chosen based on the shapes of nuclear size distributions from various populations of cells. The results were exported into Microsoft Excel and analyzed.

Example 11

Calcein AM-Propidium Iodide Live/Dead Assay and MTT 3-(4, 5-dimethylthiazol-2-yl)-2,5-Diphenyltetrazolium Bromide Assay:

A 10 mL solution was prepared combining both the components of the live/dead cytotoxicity kit (Invitrogen) using 20 µL of component A (Calcein-AM) and 20 µL of component B (Propidium Iodide). On each well of a 12-well cell culture plate, 50 µL of this solution was added and the cells were incubated in a normoxic chamber (37° C., 5% $CO_2$) for 1-2 h. Then the cells were imaged using an Olympus Fluoview laser confocal microscope. Images were imported into NIH image analysis software ImageJ and green and red channels were separated. Using the cell counter, the images were counted to determine the number of live cells (green) and dead nuclei (red). The results were exported into Microsoft Excel and analyzed.

The MTT assay is based on the cleavage of the yellow tetrazolium salt MTT to purple formazan crystals by metabolically-active cells. The assay was performed to measure the viability of primary cortical neurons in each treatment group. Briefly, methylthiazolyldiphenyl-tetrazolium bromide (MTT) (Sigma-Aldrich) (5 mg/ml and 100 µL per well) was added to the cells in 12-well plates and incubated in a normoxic chamber (37° C., 5% $CO_2$) for 2 h. Then, the generated blue formazan reduction product, due to the action of succinate dehydrogenase in living cells on the dye, was dissolved in 1 mL isopropyl alcohol, transferred to triplicate wells in a 96-well plate, and its absorbance was read at 490 nm using a Molecular Probes Spectramax microplate reader. The results were expressed as percentage of cell survival.

Example 12

Middle Cerebral Artery Occlusion and Cannula Implantation into the Right Lateral Ventricle:

Male Sprague-Dawley rats (Charles River Lab., Wilmington, Mass.) weighing 280-340 g were fasted overnight but allowed free access to water. Atropine sulfate (0.5 mg/kg, i.p.) was injected 10 mins before anesthesia. Anesthesia was induced with 3% isoflurane in a mixture of 70% nitrous oxide and 30% oxygen. All rats were orally intubated and mechanically ventilated. During ventilation, the animals were paralyzed with pancuronium bromide (0.6 mg/kg, i.p.). The catheters were implanted into the right femoral artery and vein for the blood sampling and infusion of drug. Serial analyses of arterial blood gases, plasma glucose, arterial blood pressure and heart beating rate were conducted before and during surgical procedure. Rectal (CMA/150 Temperature Controller, CMA/Microdialysis AB, Stockholm, Sweden) and cranial (temporalis muscle; Omega Engineering, Stamford, Conn.) temperatures were closely monitored before, during and after MCAo. Rectal temperature and body weight were monitored daily until sacrifice.

Rats underwent 2 h of right middle cerebral artery occlusion (MCAo) by an intraluminal-filament. In brief, the right common carotid artery (CCA) bifurcation was exposed through a midline neck incision and the occipital artery branches of the external carotid artery were isolated, ligated and dissected. After careful isolation of the internal carotid artery (ICA), a 3-0 monofilament coated with poly-L-lysine was advanced through the ICA to the MCA until mild resistance was felt. The neck incision was closed with a silk suture and the animals were then allowed to recover. After 2 h of MCAo, rats were re-anesthetized with the same anesthetic combination. Temperature probes were re-inserted, and intraluminal sutures were carefully removed. The animals given free access to food and water for 7 days.

Thirty minutes after suture removal, a brain infusion cannula was implanted into the right lateral ventricle for treatment administration in each rat. Rats were anesthetized with 3% isoflurane and were secured to a stereotaxic apparatus with skull leveled between bregma and lambda. A sterile stainless steel cannula (5-mm long) was implanted into the lateral ventricle using the stereotaxic coordinates (0.2 mm caudal to bregma, 2 mm lateral to midline, and 5 mm below the dura). Cannulas were removed after treatment was completed.

Example 13

Treatment:

Elovanoids (ELV) as sodium salts (Na) or methyl esters (Me) were dissolved in artificial cerebral spinal fluid (CSF) and administered into right lateral ventricle 1 hour after 2 h of MCAo. The following ELVs were used: ELV-N32-Na, ELV-N32-Me, ELV-N34-Na and ELV-N34-Me (5 µg/50p1) or CSF (50 µl). All treatments were administered by a researcher blinded to the treatment groups.

Example 14

Neurological/Behavioral Tests:

Behavioral tests were performed by an observer blinded to the treatment groups at 60 mins (during MCAo) and then on days 1, 2, 3 and 7 after MCAo. The battery consisted of two tests that have been used previously to evaluate various aspects of neurologic function: (1) the postural reflex test, to examine upper body posture while the animal is suspended by the tail; and (2) the forelimb placing test, to examine sensorimotor integration in forelimb placing responses to visual, tactile and proprioceptive stimuli. Neurological function was graded on a scale of 0-12 (normal score=0, maximal score=12). Rats that did not demonstrate high-grade contralateral deficit (score, 10-11) at 60 mins during MCAo were excluded from further study.

Example 15

Magnetic Resonance Imaging (MRI) Acquisition and Analysis of Total Lesion, Core and Penumbra Volumes:

High resolution ex vivo MRI was performed on 4% paraformaldehyde-fixed brains on day 7 using an 11.7T Bruker Advance 8.9 cm horizontal bore instrument equipped with an 89 mm (ID) receiver coil (Bruker Biospin, Billerica, Mass.). T2 weighted images (T2WI), diffusion weighted images (DWI), 3D volumes, and apparent diffusion coefficient (ADC) maps were collected. T2 and ADC maps were computed from T2WI and DWI, respectively. Hierarchical Region Splitting (HRS) was used to automatically identify core and penumbra volumes (total lesion=core+penumbra) from T2 relaxation and water mobility (ADC). The penumbral tissue determination by HRS was confirmed by use of PWI/DWI subtractions at each brain level. The penumbra is be defined as the difference between the PWI and abnormal ADC (diffusion-perfusion mismatch) (2 STD elevation or reduction compared to normal tissues).

Example 16

Histopathology and Immunohistochemistry:

After 7 days after MCAo, rats were re-anesthetized with 3% isoflurane, 70% nitrous oxide and a balance of oxygen, and transcardially perfused with 0.9% saline followed by 4% paraformaldehyde. Brains were removed and embedded in a gelatin matrix using MultiBrain® Technology (Neuro-Science Associates, Knoxville, Tenn.). To quantitate infarct volume, histological sections were digitized (MCID core imaging software; InterFocus Imaging Ltd., Cambridge, England) at nine standardized coronal levels (bregma levels: +5.2, +2.7, +1.2, −0.3, −1.3, −1.8, −3.8, −5.0 and −7.3 mm) using a CCD camera (QICAM Fast 1394, QIMAGING, British Columbia, Canada) (30). Brain sections were imaged on a motorized microscope BX61VS (Olympus, Japan) at 10× objective. An investigator blinded to the experimental groups outlined the zone of the cortical and subcortical infarct as well as the left and right hemispheres of each section. Infarct volume was calculated as the integrated product of the cross-sectional area and inter-sectional distance, and corrected for brain swelling.

Brain edema was measured by the differences of ipsi- and contra-lateral hemispheres. Immunohistochemical procedures were performed on the adjacent sections to identify specific vascular and neuronal elements in the ischemic core and penumbra. The following antibodies were used: rat blood-brain barrier (SMI-71, BioLegend, San Diego, Calif.) as a vascular marker; glial fibrillary acid protein (GFAP, Agilent Tech. Santa Clara, Calif.) to label reactive astrocytes; and neuron-specific nuclear protein (NeuN, Chemicon/Millipore, Billerica, Mass.) and biotinylated anti-rat immunoglobulin (IgG) antibody (BioLegend, San Diego, Calif.) to detect BBB breakdown. The number of positive cells and immunopositive vessels were counted in the cortex and striatum at the level of the central lesion (bregma level −0.3 mm). Data were expressed as numbers of positive cells and vessels per high-power microscopic field (magnification ×40).

The images of sections were obtained using confocal laser microscope (LSM510, Carl Zeiss MicroImaging, Irvine, Calif.) following specific experimental protocols. The images were acquired with dimension 212.3 μm×212.3 μm using Zen software (Carl Zeiss MicroImaging). Image analysis was conducted using ImageJ software. Analyses were conducted by an investigator blinded to experimental conditions. IgG staining intensity was calculated and averaged at the same levels as assessed for ischemic damage as previously described (23, 31). To calculate the intensity of IgG staining, the images were converted to gray scale, and the mean gray values were recorded and compared. ImageJ software assigns black pixels for the numerical value of "0" and white pixels for the numerical value of "1". Gradations of gray are assigned the numerical values in between, increasing with pixel lightness and decreasing with pixel darkness. As such, IgG intensity values were expressed as the reciprocal of mean gray for graphical clarity. All sections were imaged at the same time with the same settings and with no adjustment to brightness or contrast. IgG stain intensity was measured in the entire contralateral and ipsilateral hemispheres, as well as the cortex and striatum.

Statistical Analysis:

For cell cultures: All results were expressed as means±SEM. Data from all experiments were evaluated using one-way ANOVA (analysis of variance) followed by Sidak's multiple comparisons post hoc test. Statistical analyses were performed using Graphpad Prism software Version 7.02. A value of p<0.05 was considered to be statistically significant.

For ischemic stroke: Values are presented as means±SD. Repeated measures ANOVA, followed by Bonferroni procedures to correct for multiple comparisons, were used for intergroup comparisons of neurobehavioral scores over time and infarct areas across coronal levels. Two-tailed Student's t tests were used for two-group comparisons. Differences at p<0.05 were considered statistically significant.

Example 17

Structure and Stereochemistry of ELV-N32 and ELV-N34 in Mixed Neuronal Cultures:

The complete structures and stereochemistry of the novel elovanoids ELV-N32 and ELV-N34 were established through a direct comparison with compounds prepared via stereocontrolled total organic synthesis by adapting our previously reported methodologies for the total synthesis of NPD1. Further validation of these structural assignments was established by synthesizing deuterium-labelled derivatives for liquid chromatography tandem mass spectrometry (LC-MS/MS) analysis.

Figure 4A:
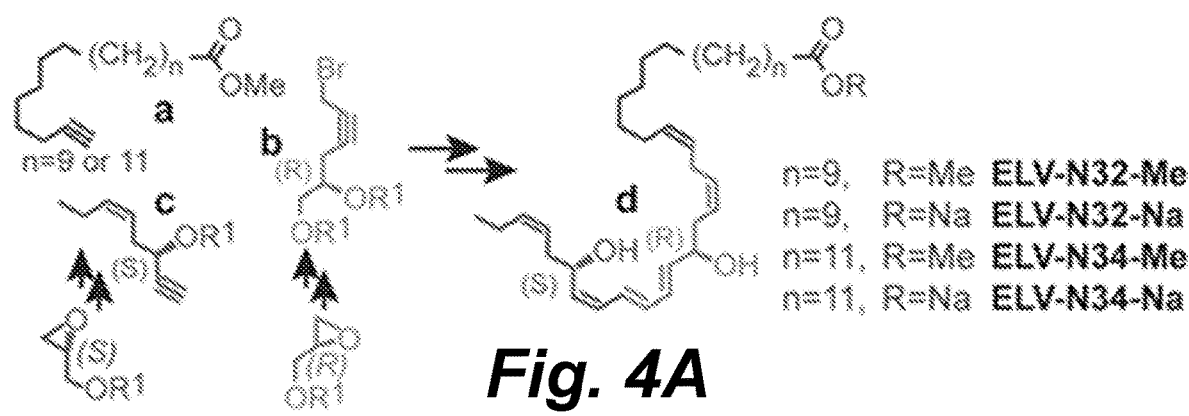
FIGS. 4A-4K illustrate the structural characterization of elovanoids ELV-N32 and ELV-N34 from neuronal cell cultures. Cerebral cortical mixed neuronal cells were incubated with 32:6n3 and 34:6n3 10 μM each under OGD conditions.

ELV-N32 and ELV-N34 were prepared by stereocontrolled total chemical synthesis (FIG. 4A). The availability of these synthetic ELVs with fully-defined structures and stereochemistry allowed us to determine the complete R/S configuration as well as the Z/E geometry of the double bonds in these mixed neuronal cell culture-derived ELVs. Also generated were synthetic stereochemically-pure deuterium-labeled ELVs, and by matching them with endogenously-produced molecules by LC-MS/MS, confirming their structure and stereochemistry.

Figure 4B:
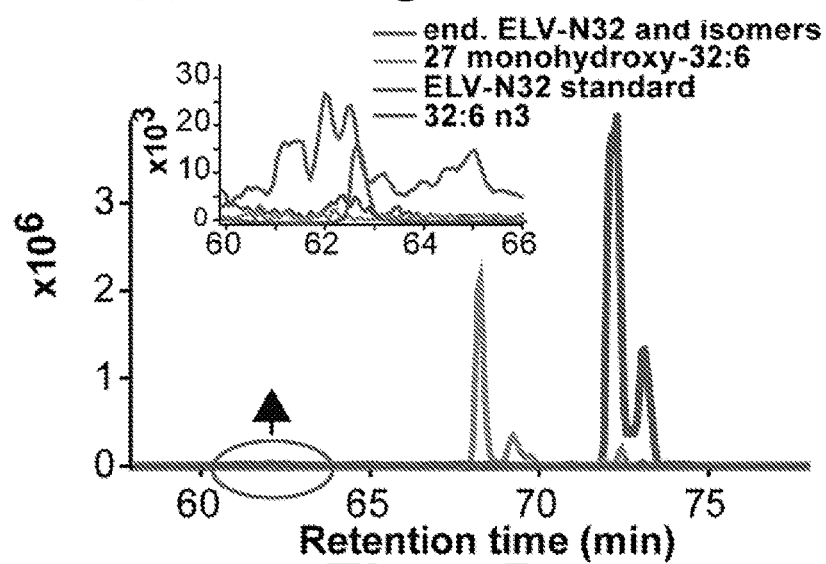
Figure 4C:
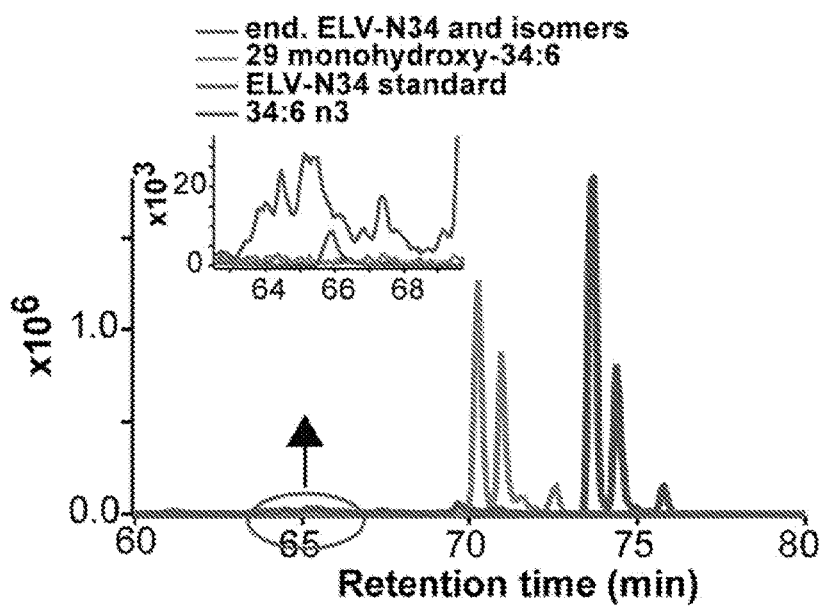
Figure 4D:
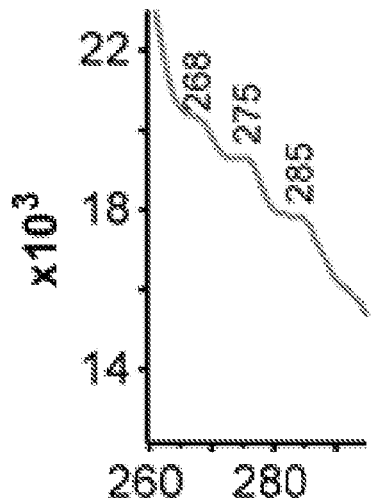
Figure 4E:
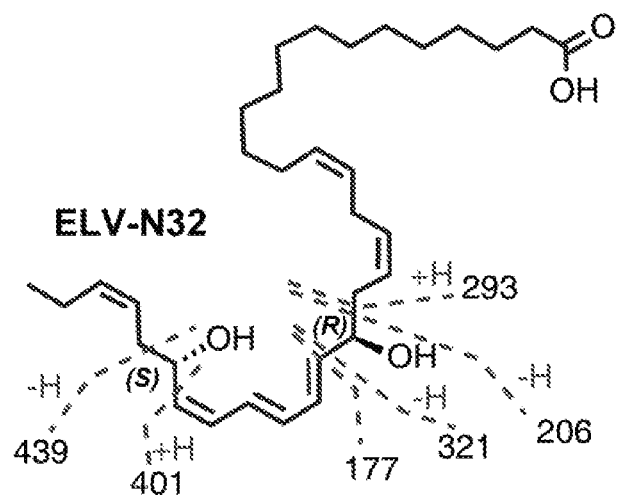
Figure 4F:
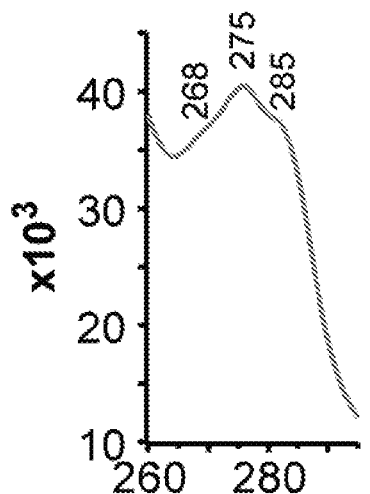

Both ELVs and their precursors were detected in cells under OGD stress. (FIGS. 4B-4K) m/z 499→93 and 499→401 MRM transitions were used for ELV-N32 detection (FIG. 4B), and m/z 527→93 and 527→429 transitions for ELV-N34 detection (FIG. 4C). For their corresponding mono-hydroxy precursors, m/z 483→385 for 27-hydroxy-C32:6n3 were used (FIG. 4B), and m/z 511→413 for 29-hydroxyl-C34:6n3 (FIG. 4C). For further identification, full fragmentation was performed on ELVs and found good matches to the synthetically-produced standards. Both ELVs had UV maxima at 275 nm that are consistent with a conjugated triene structure (FIGS. 4D and 4F).

Figure 4G:
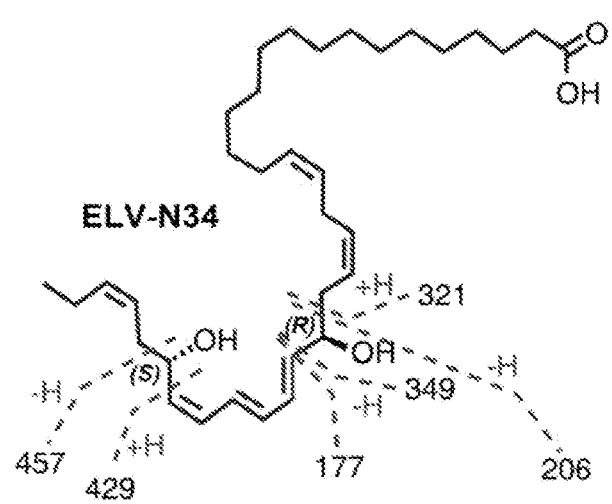
Figure 4H:
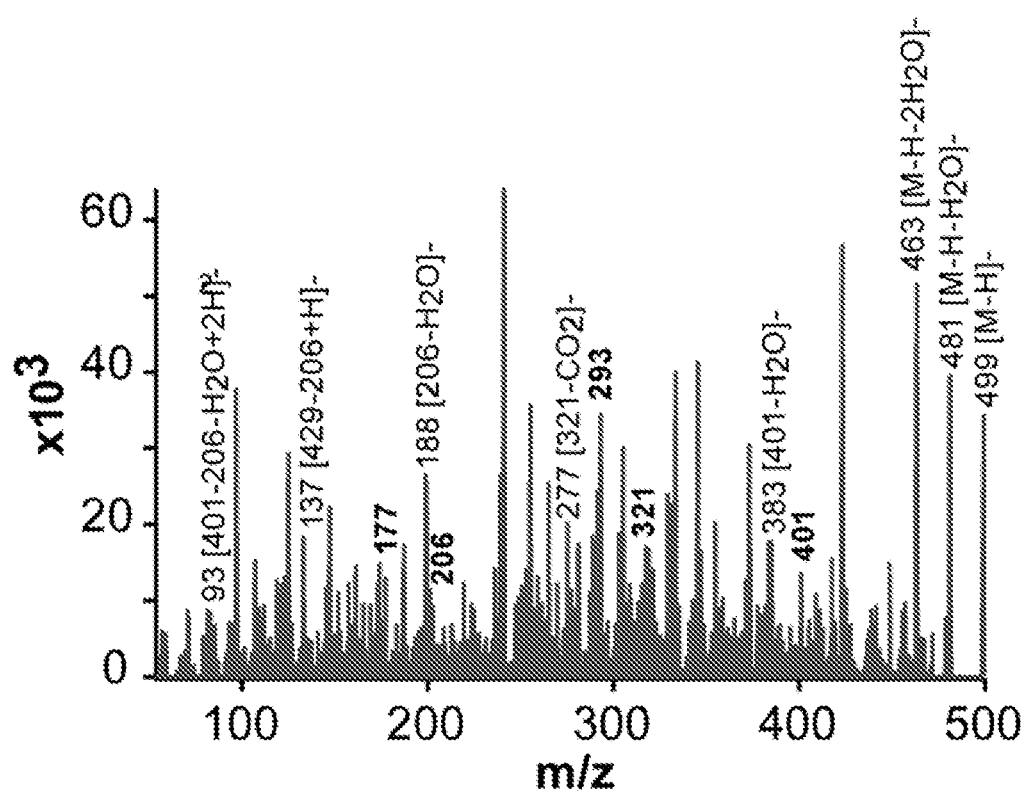
Figure 4I:
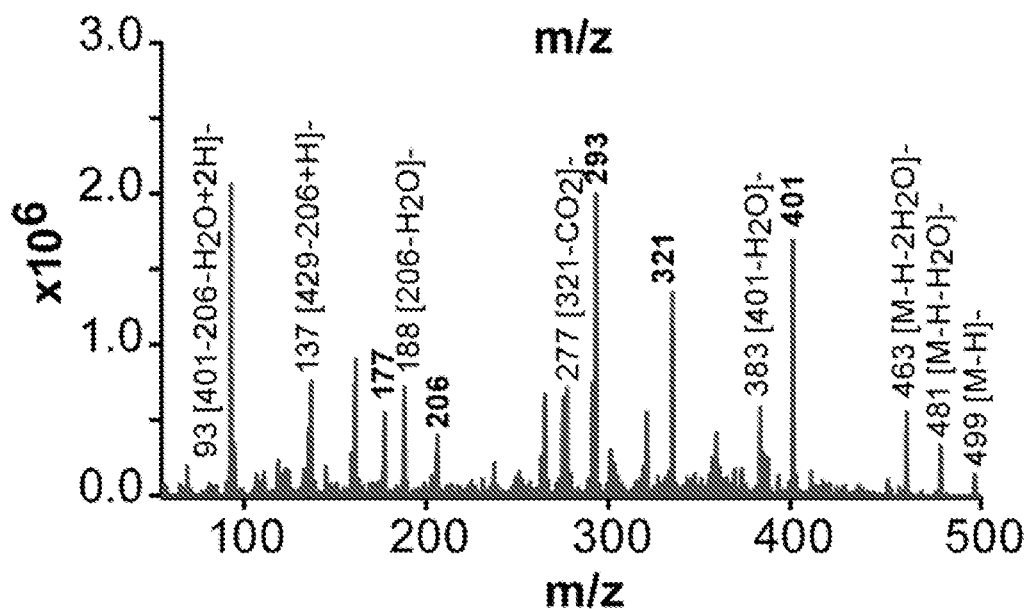
Figure 4J:
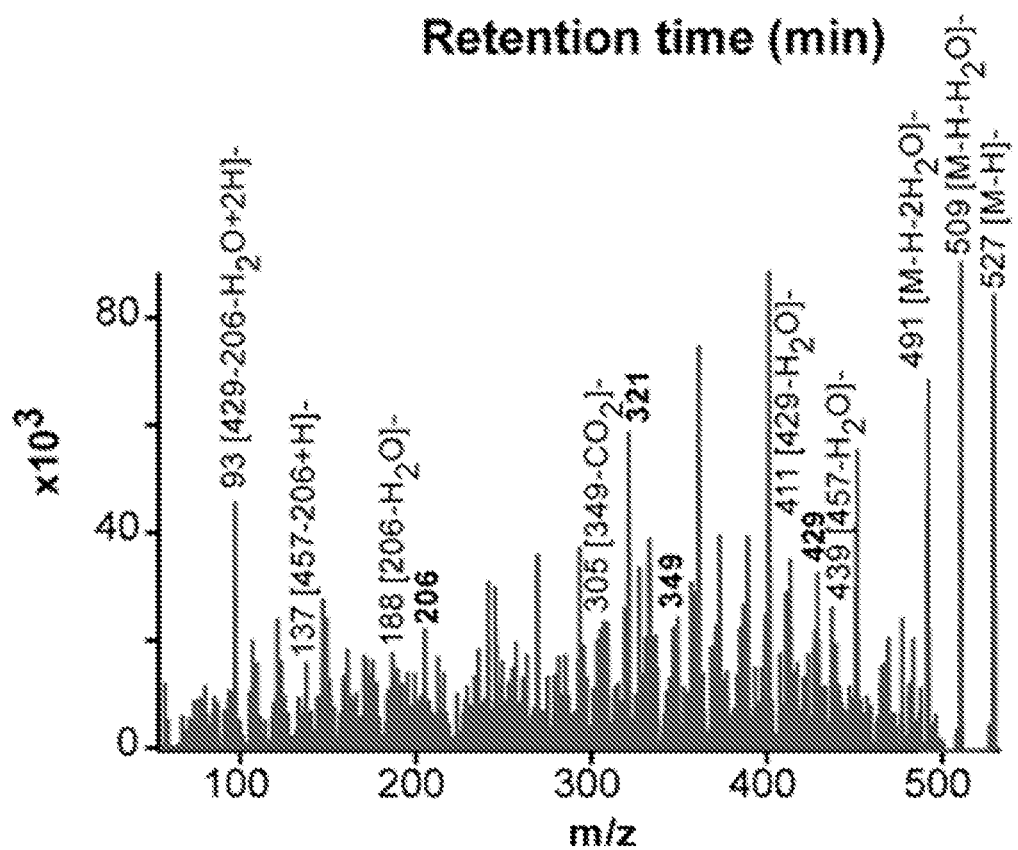
Figure 4K:
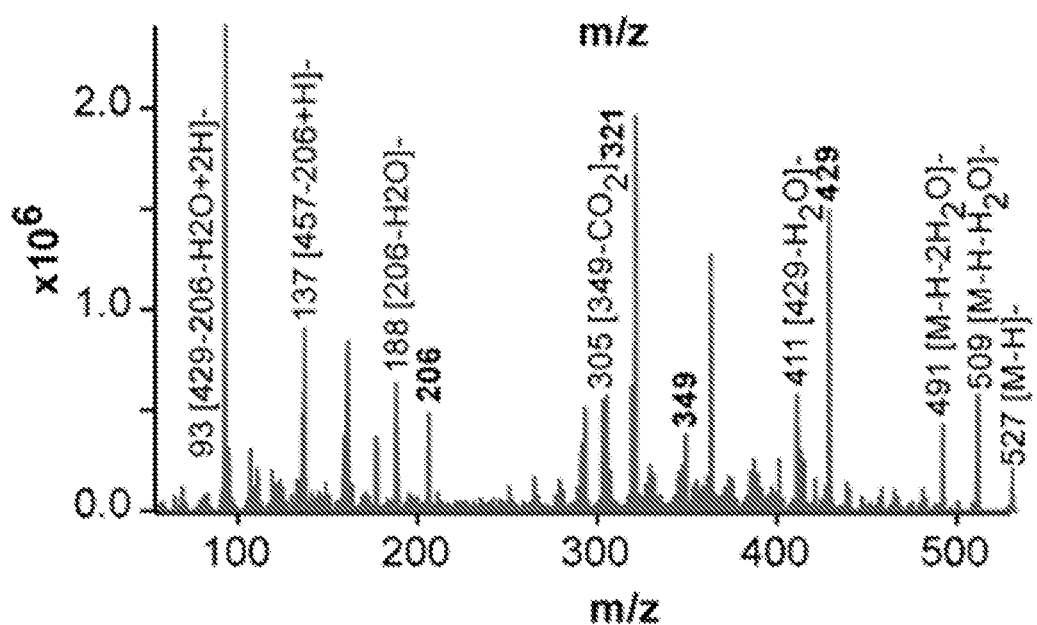

Following matching of synthetic ELVs with biogenic ELVs derived from mixed neuronal cells in culture, the complete structure and stereochemistry of ELV-N32 and ELV-N34 were established. The structures of ELV-N32 (elovanoid neuroprotectin-like, derived from a 32-carbon omega-3 polyunsaturated fatty acid) and ELV-N34 (elovanoid neuroprotectin-like, derived from a 34-carbon omega-3 polyunsaturated fatty acid) were determined to be: ELV-N32: (14Z,17Z,20R,21E,23E,25Z,27S,29Z)-20,27-dihydroxydo-triaconta-14,17,21,23,25,29-hexaenoic acid (FIG. 1E); ELV-N34: (16Z,19Z,22R,23E,25E,27Z,29S,31Z)-22,29-dihydroxytetra-triaconta-16,19,23,25,27,31-hexaenoic acid (FIG. 4G).

Example 18

Neuro Protection by ELVs in Uncompensated Oxidative Stress, Oxygen/Glucose Deprivation or NMDA-Induced Excitotoxicity:

At 200 nM concentration, the sodium salt ELV-N32-Na or the methyl ester ELV-N32-Me evoked neuroprotection to cerebral-cortical mixed neuronal cells in culture exposed for 12 h to uncompensated oxidative stress, which was induced by addition of tumor necrosis factor alpha (TNFα) at 10 ng/mL and $H_2O_2$ (50 µM, 100 µM or 200 µM). There was a dose-dependent increase of apoptotic nuclei that was counteracted by ELV-N32-Na or ELV-N32-Me (FIG. 16B).

To determine the neuroprotective bioactivity of ELV-N32 or ELV-N34 against OGD-induced neuronal cell death, cerebral cortical mixed neuronal cells in culture or hippocampal neurons in culture were exposed to OGD for 90 mins. After 2 h of reoxygenation, ELV-N32 or ELV-N34 were added at either 200 nM, 500 nM or 1 µM concentration, and then cell viability was assessed either by Hoechst-positive nuclei counting, or calcein-positive cell counting, or MTT assays. Under all different conditions and concentrations, it was found that ELV-N32-Na, ELV-N32-Me, ELV-N34-Na or ELV-N34-Me elicited neuroprotection when compared to cells exposed to OGD alone (FIGS. 15F-15H, 15K, and 15L; FIGS. 16D-16G, and 16I). Moreover, the results also showed that the precursor 34:6 could elicit neuroprotection at a concentration as low as 250 nM when added after OGD exposure (Supplemental FIG. 1H).

Furthermore, NMDA exposure at 25 µM, 50 µM or 100 µM concentration for 12 h induced neuronal death in cerebral-cortical mixed neuronal cells and hippocampal neuronsin culture (FIGS. 15C-15E, and 15-15, J; FIGS. 16A, 16C, and 16H), which was compensated for by adding either ELV-N32 (Na or Me) or ELV-N34 (Na or Me) at either 200 nM or 500 nM concentration, when added simultaneously along with NMDA. There was a dose-dependent increase of apoptotic nuclei when cells were exposed to NMDA at either 25 µM, 50 µM or 100 µM concentration, which was compensated for in the presence of ELV-N32-Na or ELV-N32-Me. For one experiment, whether there was synergy by the addition of ELV-N32 (Na or Me) at 200 nM along with NPD1 at 100 nM concentration was tested. ELV-N32-Na and ELV-N32-Me both showed synergy in neuroprotection against NMDA excitotoxicity at 100 µM for 12 h (FIG. 16A). But ELV-N32-Me in addition to NPD1 was more potent than ELV-N32-Na and NPD1 together. We also found that the NMDA excitotoxicity can be overcome by addition of non-competitive NMDA receptor antagonist MK801 maleate (dizocilpine, 10 µM). The addition of MK801 and NPD1 together to either ELV-N32-Na or ELV-N32-Me improved the neuroprotection elicited by ELV-N32-Na or ELV-N32-Me alone. In addition, the precursor 34:6 at a concentration of 500 nM attenuates NMDA receptor-mediated excitotoxicity (FIG. 16H).

Example 19

ELV-Induced a Sustained Neurological Improvement and Protection after Ischemic Stroke:

Focal ischemic stroke leads to impaired sensorimotor and cognitive functions with 70-80% of patients displaying hemiparesis immediately after stroke. ELVs were administered the through stereotaxically-implanted infusion cannulas into the right lateral ventricle 1 h after 2 h of middle cerebral artery occlusion (MCAo). Functional deficits in rodents following MCAo resemble sensorimotor deficits, and since the ultimate goal of any stroke therapy is the restoration of neurological/behavioral functions, two tests of the sensorimotor battery were used to detect neurological deficits following experimental ischemic stroke.

All ELV-treated animals greatly improved neurologic scores in a sustained fashion up to the 7-day survival period compared to the cerebral spinal fluid (CSF) group (FIG. 20A). CSF-treated rats continued to exhibit severe impairments through this period. T2-weighted imaging (T2WI) revealed large lesions, and T2 hyperintensities were observed in the ischemic core and penumbra of CSF-treated rats, consistent with edema formation (FIGS. 20B and 20C). In contrast, ischemic core and penumbra volumes (computed from T2WI) were significantly reduced by all ELV treatments (FIG. 4B). Total lesion volumes were significantly reduced by ELV-N32-Na, ELV-N32-Me, ELV-N34-Na and ELV-N34-Me compared to CSF-treated group (by 60%, 56%, 99% and 91%, respectively) (FIG. 20B). Three-dimensional (3D) lesion volumes were computed from T2WI on day 7 after MCAo (FIG. 20D). Lesion volume was dramatically reduced with elovanoid treatment and was mostly localized only in the subcortical areas of the brain (FIG. 20D).

Example 20

ELV-Attenuated Cellular Damage, Blood Vessel Integrity and BBB Disruption:

Neurons, astrocytes and blood vessels implicated in cerebral infarction were examined using immunohistochemistry on day 7. CSF-treated rats exhibited large lesions involving cortical and subcortical regions, characterized by loss of neuronal, glial, and vascular elements (FIGS. 21A and 21B).

In contrast, ELV-treated rats showed less infarction with an increased number of NeuN-, GFAP-positive cells and SMI-71-positive vessels in the cortex compared to the CSF-treated group. Cellular counts for NeuN, SMI-71 and GFAP (regions delineated in the diagram in FIG. 21C) demonstrated that all ELV treatments increased NeuN-positive neurons and GFAP-positive reactive astrocytes, and protected blood vessel integrity (FIG. 21C). As a result of almost all ELV treatments (except for ELV-N32-Na), blood vessel density (SMI-71) was increased within the penumbral tissues, with parallel formation of denser GFAP-rich scar tissue. Thus, enhancement of blood vessel density likely facilitates neurogenesis and synaptogenesis, which in turn contributes to improved repair and, ultimately, improved functional recovery.

Ischemic disruption of the blood-brain barrier (BBB) was measured initially by infiltration of endogenous IgG into the brain parenchyma (FIGS. 22A and 22B). IgG-staining intensity was observed in the ipsilateral hemisphere after MCAo (FIG. 22A). Staining intensity at 7 days was similar among the CSF-, ELV-N32-Na- and ELV-N32-Me-treated groups. In contrast, treatment with ELV-N34-Na and ELV-N34-Me showed significantly less IgG staining in the cortex; staining was mostly localized in the core of infarction (subcortex). In addition, IgG immunoreactivity from the whole hemisphere (total) was reduced (FIG. 22B) (all animals survived uneventfully). Brains from CSF-treated rats exhibited a pannecrotic lesion involving both cortical and subcortical regions of the right hemisphere (FIG. 22C). By contrast, infarct size in the rats treated with the ELV compounds showed less extensive damage, mostly in the subcortical area. ELV-mediated protection was extensive in the frontal-parietal cortex (tissue was salvaged by 57-96%) and sub-cortex (73-75%) compared to the CSF-treated group (FIG.

22D). Total infarct volume, corrected for brain swelling, was dramatically reduced in all ELV-treated groups by 55-91% (FIG. 22D).

Example 21

Figure 3A:
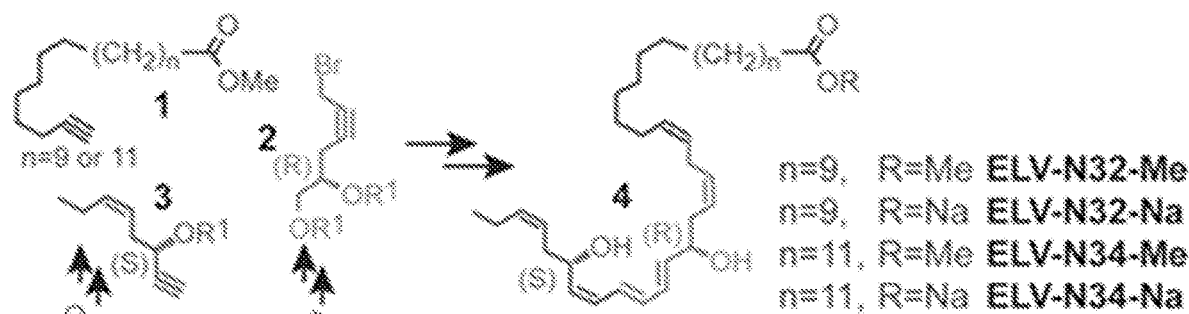
FIGS. 3A-3K illustrate the generation and structural characterization of elovanoids ELV-N32 and ELV-N34 from cultured primary human retinal pigment epithelial cells (RPE).
Figure 3B:
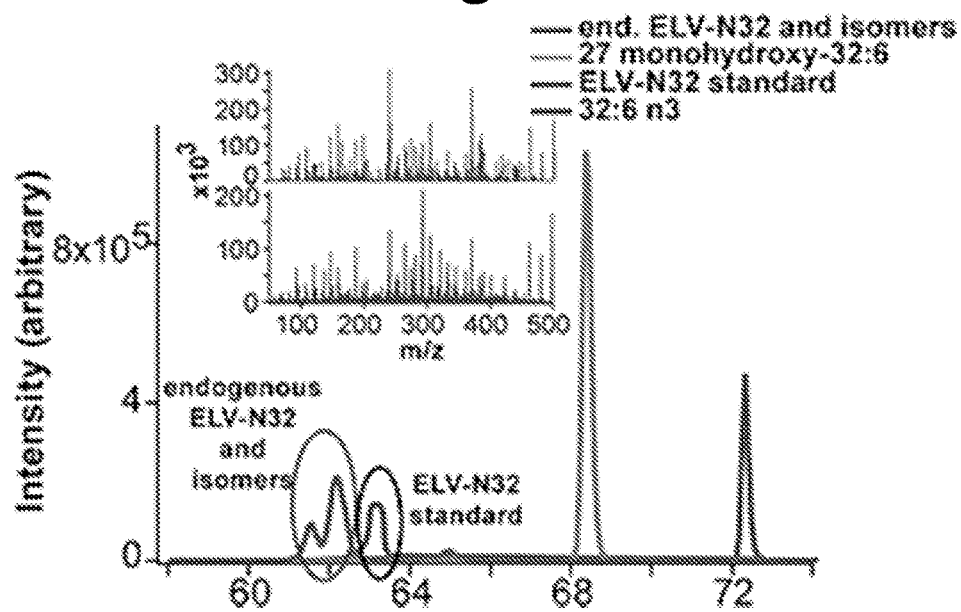
Figure 3C:
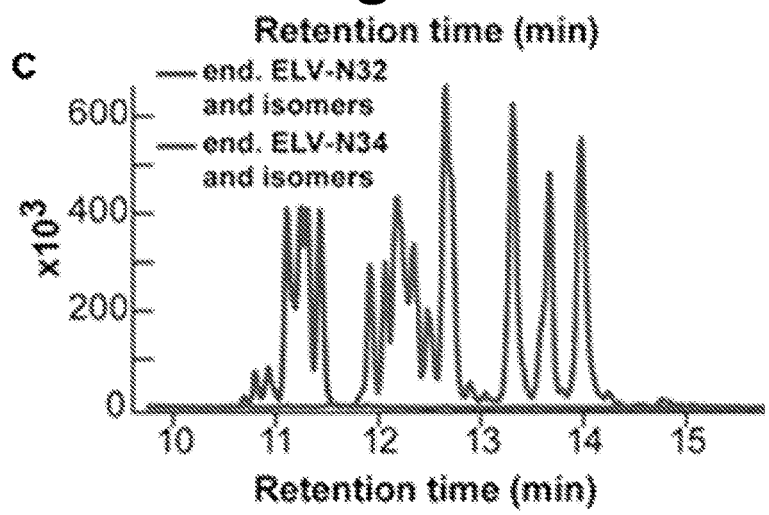
Figure 3D:
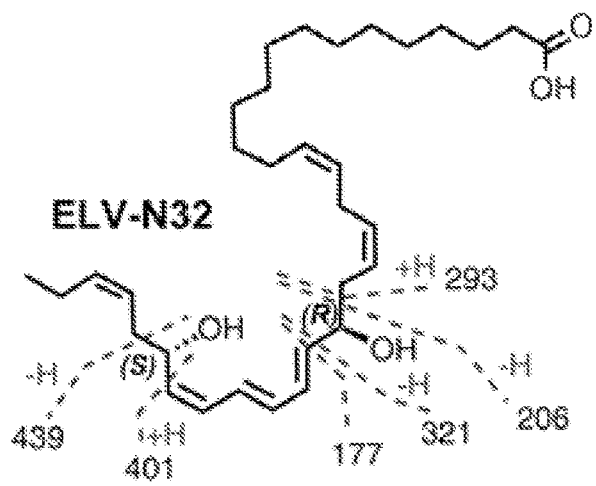
Figure 3E:
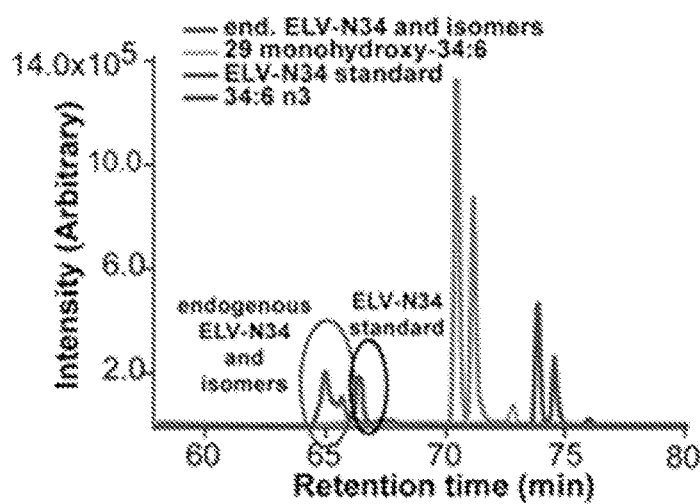
Figure 3F:
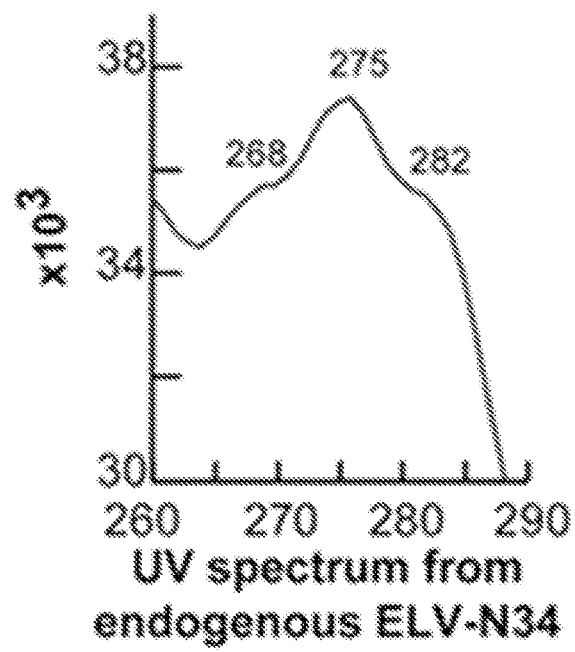
Figure 3G:
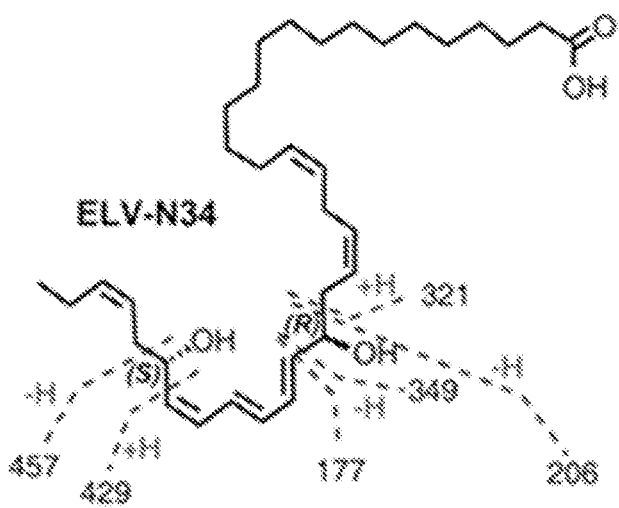
Figure 3H:
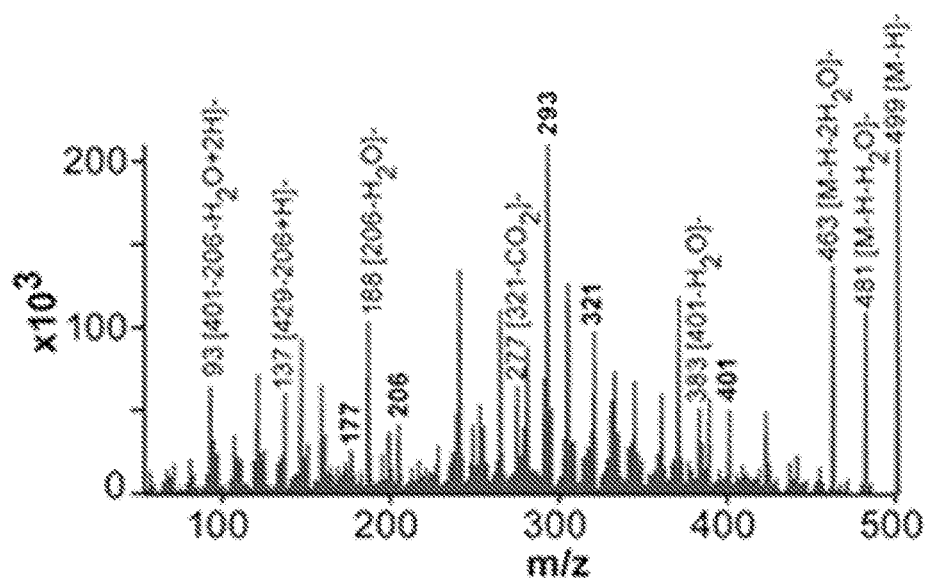
Figure 3I:
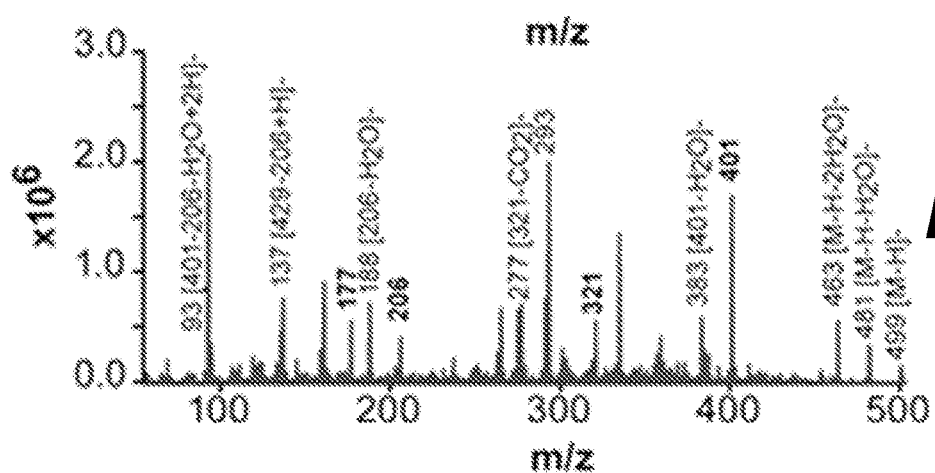
Figure 3J:
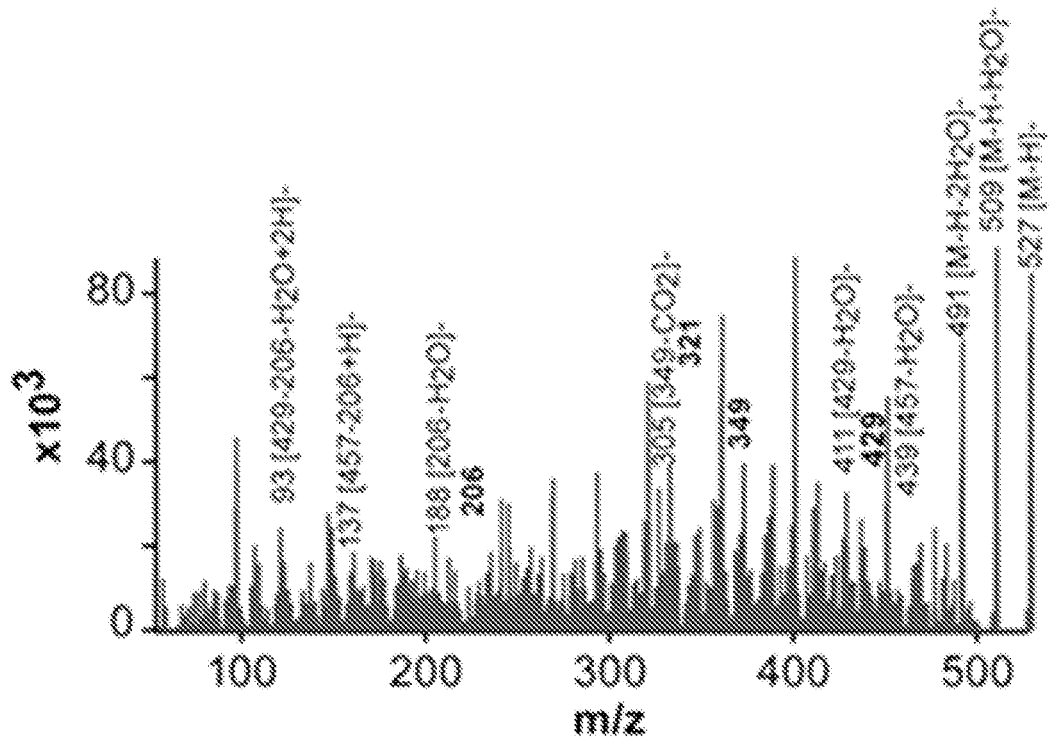
Figure 3K:
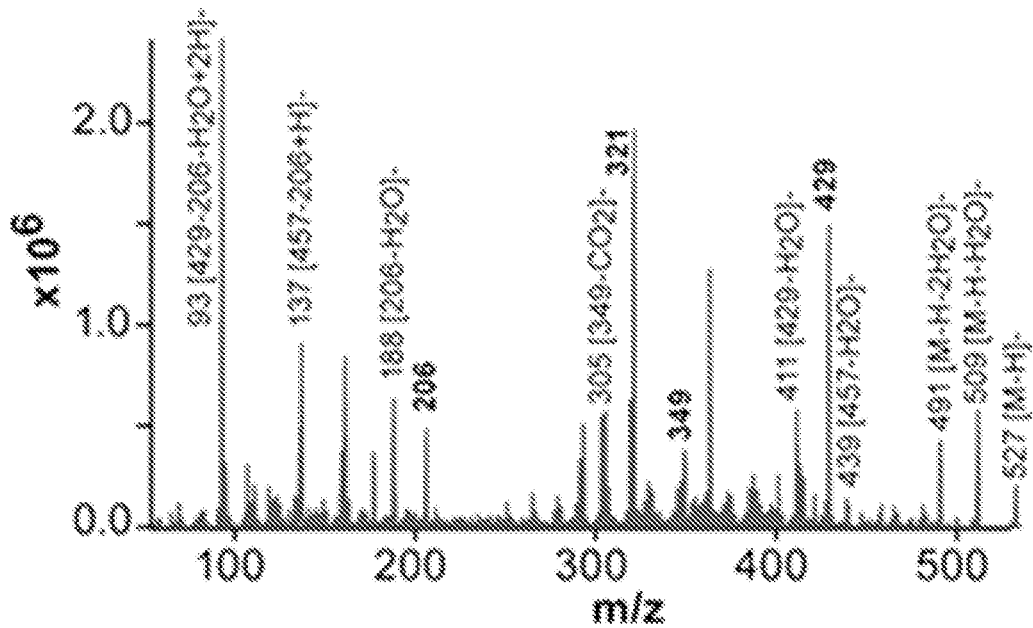

RPE Cells, ELV Structure and Stereochemistry:

The complete structures and stereochemistry of the novel 32- and 34-carbon elovanoids ELV-N32 and ELV-N34 were established through a direct comparison with compounds prepared via stereo-controlled total organic synthesis by adapting previously reported methodologies for the total synthesis of the DHA-derived lipid mediator neuroprotectin D1 (NPD1; 10R,17S)-dihydroxydocosa-(4Z,7Z,11E,13E,15Z,19Z)-hexaenoic acid). Further validation of these structural assignments was established by synthesizing deuterium-labelled derivatives (ELV-N32-d2 and ELV-N34-d2) for liquid chromatography tandem mass spectrometry (LC-MS/MS) analysis. ELV-N32 and ELV-N34 were prepared by stereo-controlled total chemical synthesis (FIG. 3A). The availability of synthetic materials with fully defined structures and stereochemistry allowed us to determine the complete R/S configuration as well as the Z/E geometry of the double bonds in these human primary RPE cell-derived ELVs. Confocal images of immunostaining of primary human RPE cells using specific markers ZO-1 (Zona occludens-1), RPE65, MITF (Micro-opthalmia-associated Transcription Factor) and β-catenin are depicted in FIGS. 6A and 6B, as well as light microscopy morphology at different passages in culture.

In brief, these cells were cultured for 24-48 h followed by a 24 h incubation with 10 μM free 32:6,n6 plus 34:6,n6. Then cells were incubated with 1 mM $H_2O_2$ for 24 h after a 24 h serum deprivation. The incubation media were collected, and lipids were extracted and loaded onto a liquid chromatography tandem mass spectrometer (LC-MS/MS) for analysis. Synthetic stereochemically-pure deuterium-labeled ELVs were also generated, and by matching them with endogenously-produced molecules by LC-MS/MS, confirming their structure and stereochemistry. Following matching with human primary RPE cell culture media-derived elovanoids, the complete structures of ELV-N32 (from a 32C omega-3 polyunsaturated fatty acid) and ELV-N34 (from a 34C omega-3 polyunsaturated fatty acid) were confirmed to be as follows: ELV-N32: (14Z,17Z,20R,21E,23E,25Z,27S,29Z)-20,27-dihydroxydo-triaconta-14,17,21,23,25,29-hexaenoic acid; ELV-N34: (16Z,19Z,22R,23E,25E,27Z,29S,31Z)-22,29-dihydroxytetra-triaconta-16,19,23,25,27,31-hexaenoic acid.

Both ELVs and their pre-cursor VLC-PUFAs were detected in RPE cells under UOS (FIGS. 3B-3K). m/z 499→93 and 499→401 MRM transitions were used for ELV-N32, and m/z 527→93 and 527→429 transitions for ELV-N34 for detection. For corresponding precursors, m/z 483→385 were used for 27-hydroxy-32:6n3, and m/z 511→413 for 29-hydroxyl-34:6n3. For further identification, full fragmentation was performed on ELVs and found good matches to the standards.

Example 22

ELVs N32 and N34 Elicit Potent Cytoprotection:

It is shown that free 32:6n3 or 34:6n3 elicit protection against UOS in ARPE-19 cells (FIGS. 7A and 7B), and that a lipoxygenase inhibitor blocks this effect (FIG. 10C). To test the efficacy of 32:6n3 and 34:6n3 VLC-PUFAs to modulate human RPE cell homeostasis and survival rates, human RPE cells undergoing UOS were incubated with both VLC-PUFAs (3 μM each) and NPD1 (200 nM) 16 h. The addition of $H_2O_2$ (800 μM) induced apoptosis (50% cell death). Both 32:6n3 and 34:6n3 successfully prevented cell death (4% and 18%, respectively); NPD1 reduced apoptosis to 11% (FIGS. 7K and 7L).

Oxidative stress stimulation initiates the enzymatic oxygenation of DHA through the activation of 15-lipoxygenase-1 (15-LOX-1), leading to the biosynthesis of NPD1[11]. NPD1 is a stress-response lipid mediator derived from DHA, and it enhances survival signaling in RPE cells confronted with oxidative stress by promoting modulation of the activity and content of proteins directly involved in deciding cell fate.

hRPE cells, formerly serum deprived for 12 h, were incubated with the 15 lipoxygenase 1 (15-LOX-1) inhibitor (PD146176) (10 μM for 1 h), then bathed with 600 μM $H_2O_2$/TNF-α in conjunction with a mixture of 32:6n3 and 34:6n3 (3 μM each) for 16 h. The 15-LOX-1 inhibitor sensitizes cells; therefore, a lower concentration of $H_2O_2$ than in the cytoprotection experiment was used. Addition of $H_2O_2$/TNF-α induced RPE cell apoptosis, and treatment with a mixture of 32:6n3 and 34:6n3, successfully prevented cell death (FIG. 7I), indicating that 15-LOX-1 is not involved in this free fatty acid cell protection mechanism using primary human RPE cells.

Example 23

Figure 7A:
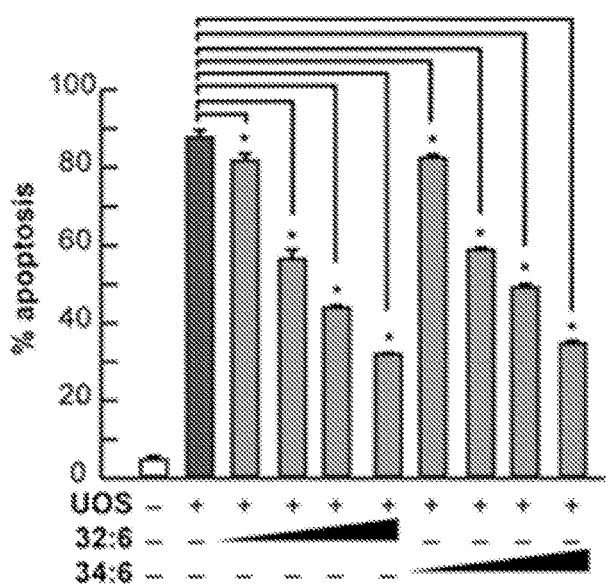
FIGS. 7A-7L illustrate cytoprotection by 32:6n3 and 34:6n3 in human RPE cells under UOS.
Figure 7B:
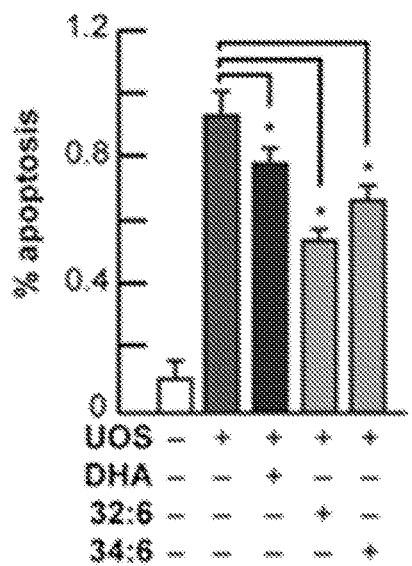
Figure 7C:
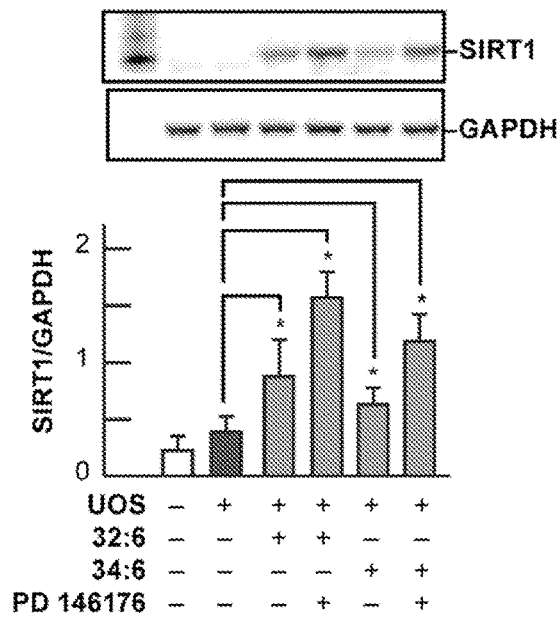
Figure 7E:
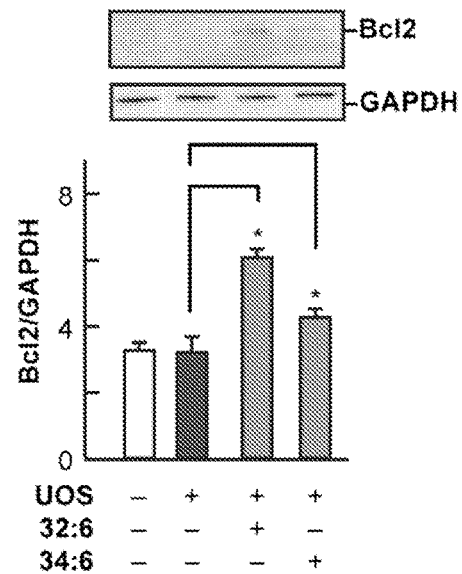
Figure 7D:
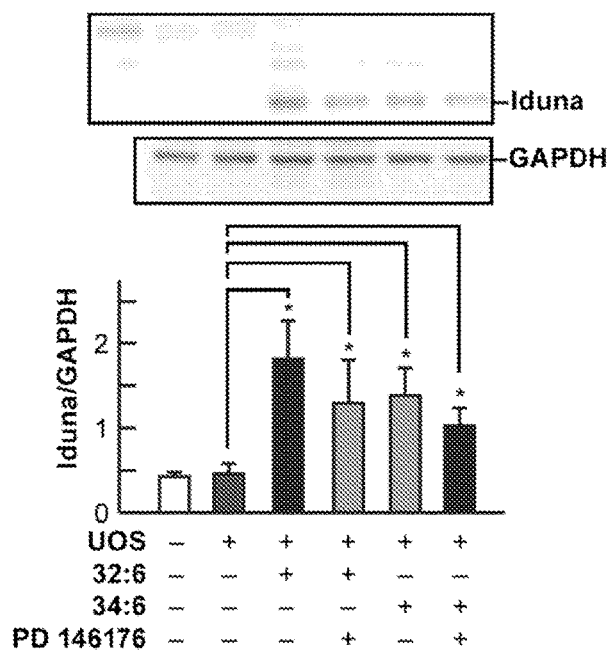
Figure 7F:
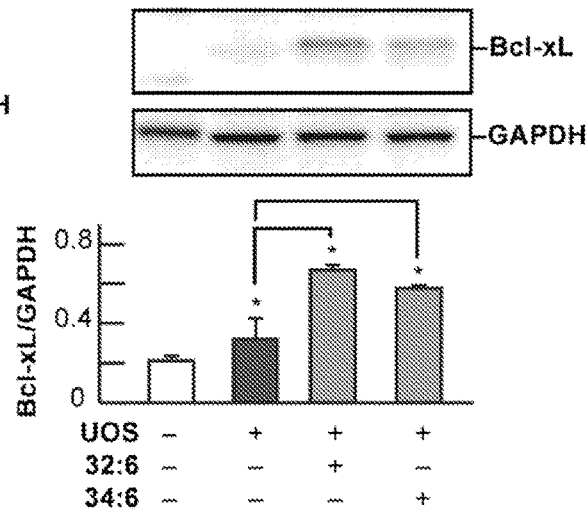
Figure 7G:
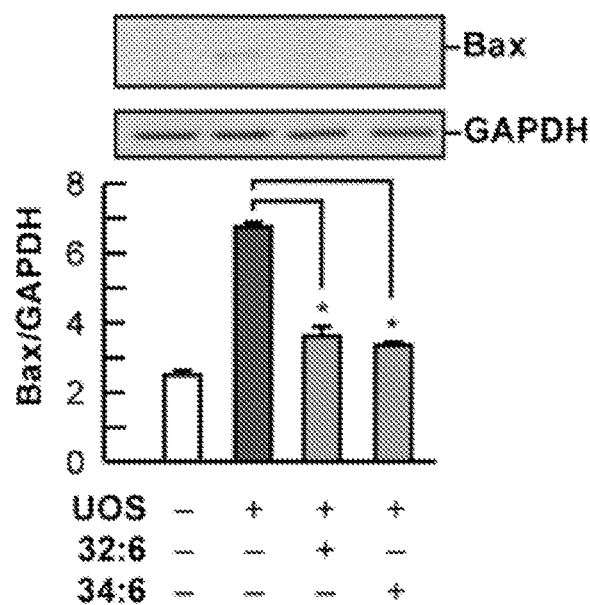
Figure 7H:
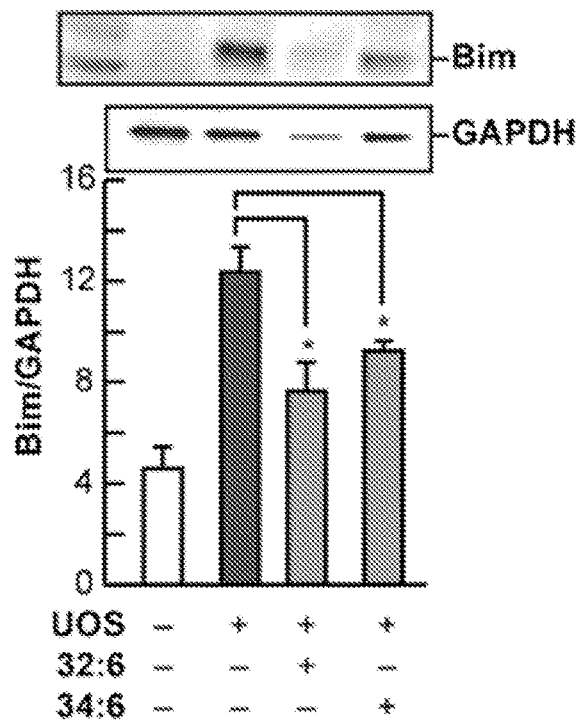
Figure 7I:
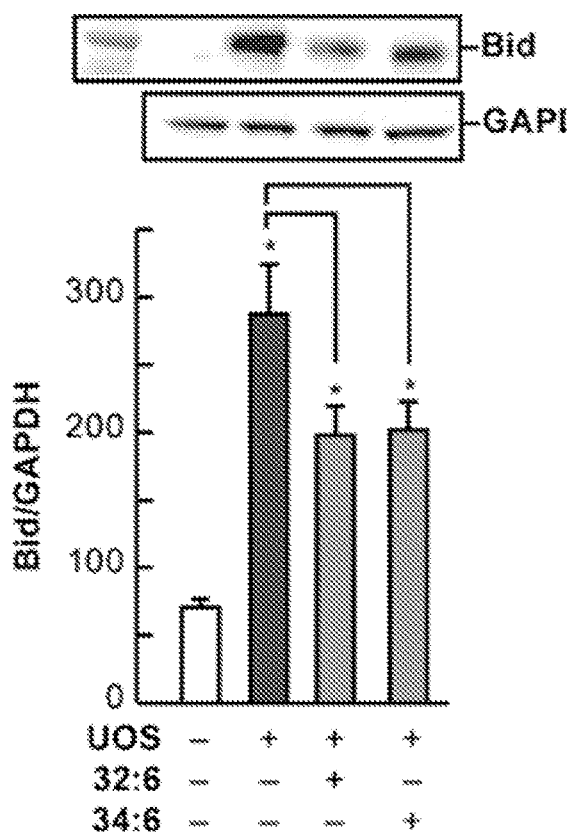
Figure 7J:
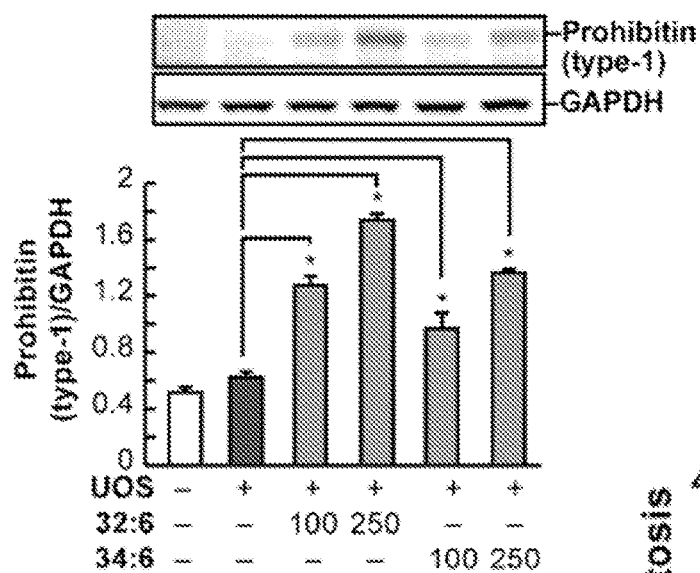
Figure 7K:
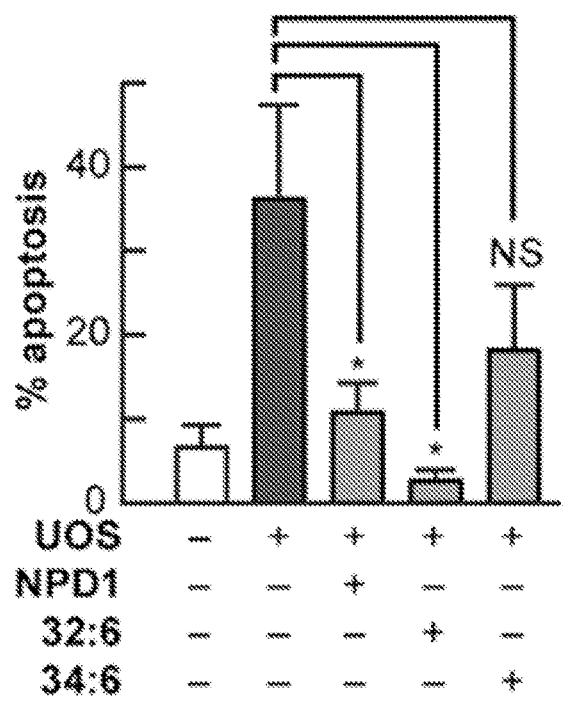
Figure 7L:
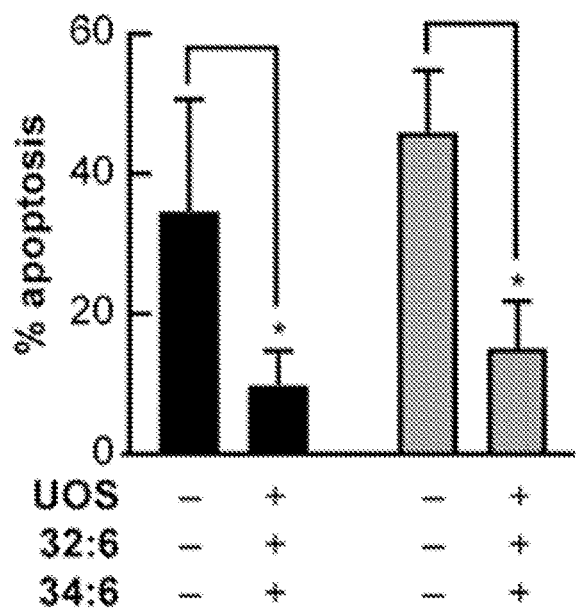
Figure 8A:
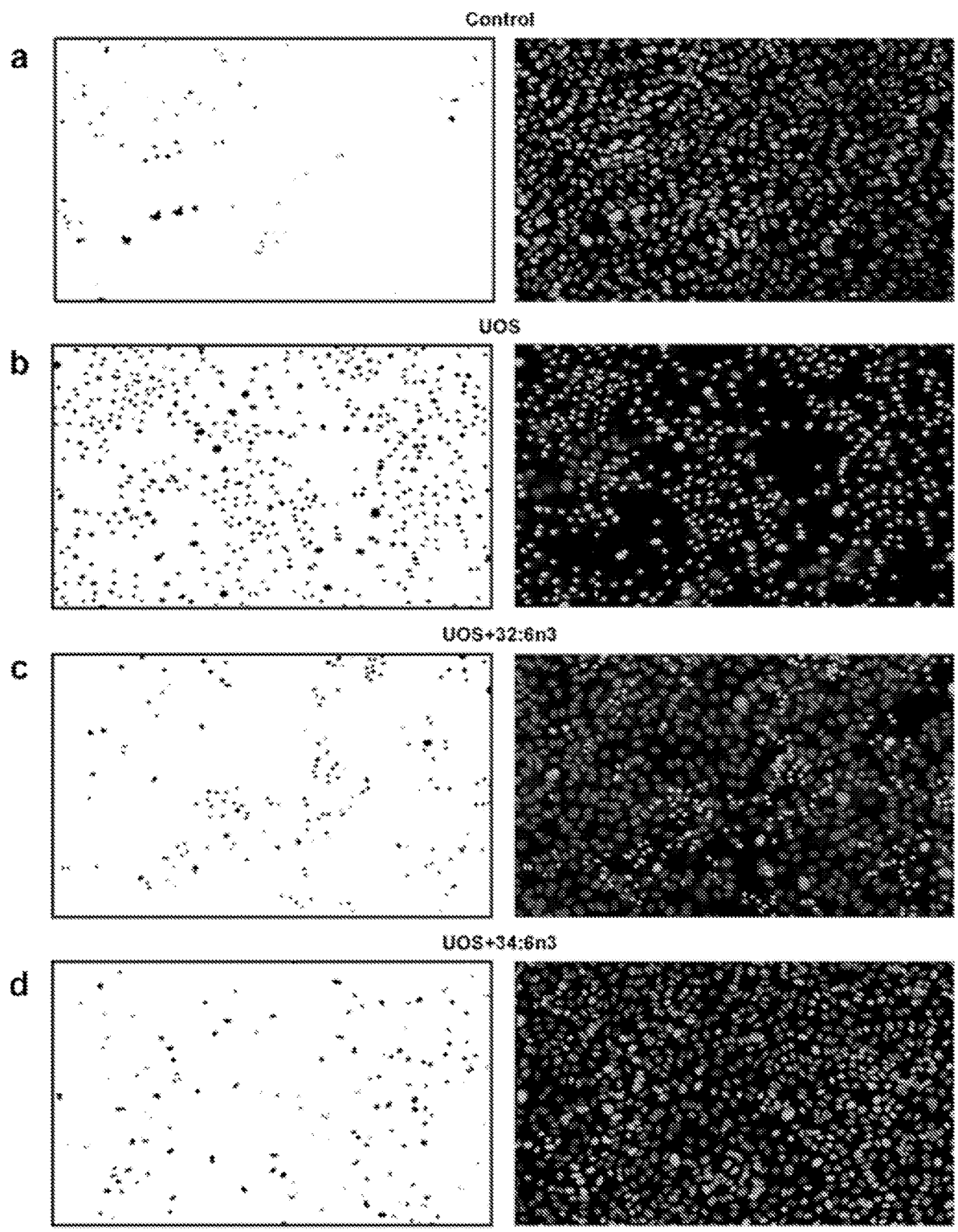
FIG. 8A (Panels a-d) illustrate that VLC-PUFA 32:6n3 and 34:6n3 ameliorate uncompensated oxidative stress (UOS)-induced primary human RPE cell death. Panel a: untreated (control) RPE cells; Panel b: RPE cells with UOS for 16 h; Panel c: RPE cells with UOS for 16 h+32:6n3; Panel d: RPE cells with UOS for 16 h+34:6n3. When 32:6n3 or 34:6n3 were added, cell death was prevented (Panels c and d). Typical fields of cell cultures are represented in the right image in each panel. Nuclei are labeled with Hoechst staining, and the dead cells are highlighted. These were separated using an intensity threshold algorithm and counted using an Image J macro (left column).
Figure 8B:
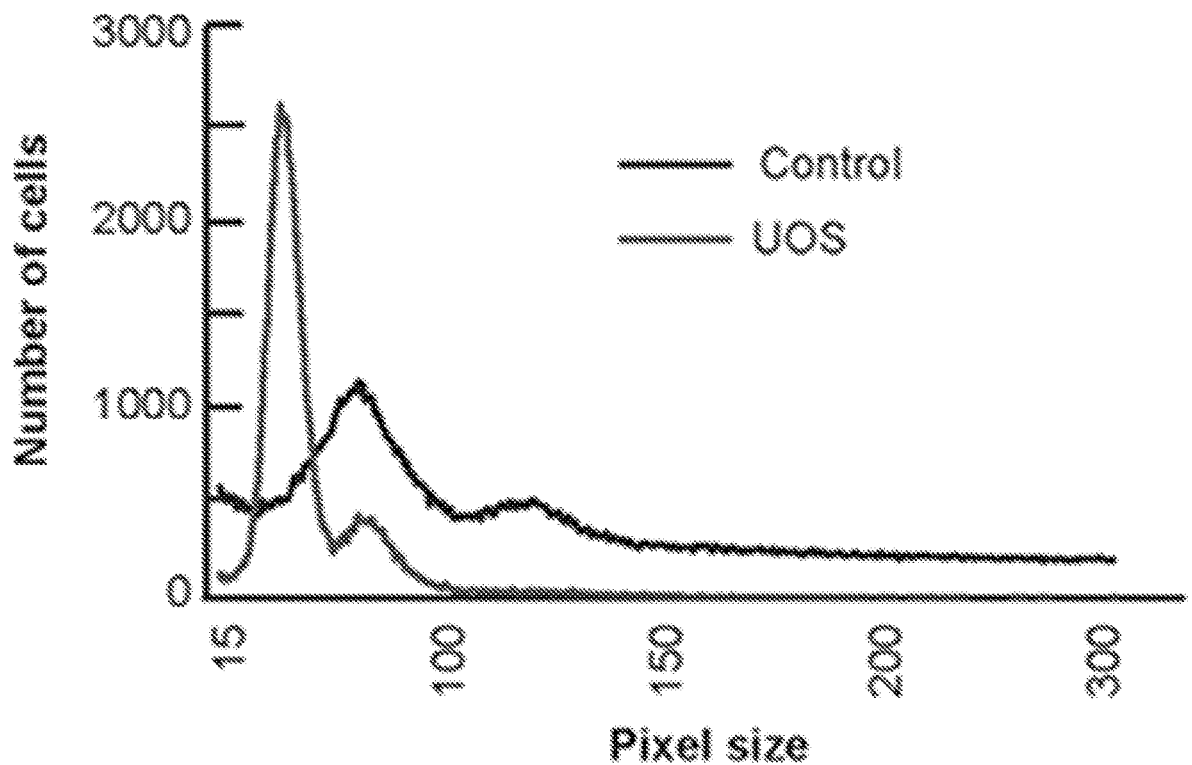
FIG. 8B illustrates the quantification of live (control cells) and dead (UOS cells) cells was based on nuclear size. Error bars, SEM; *p<0.05.
Figure 8C:
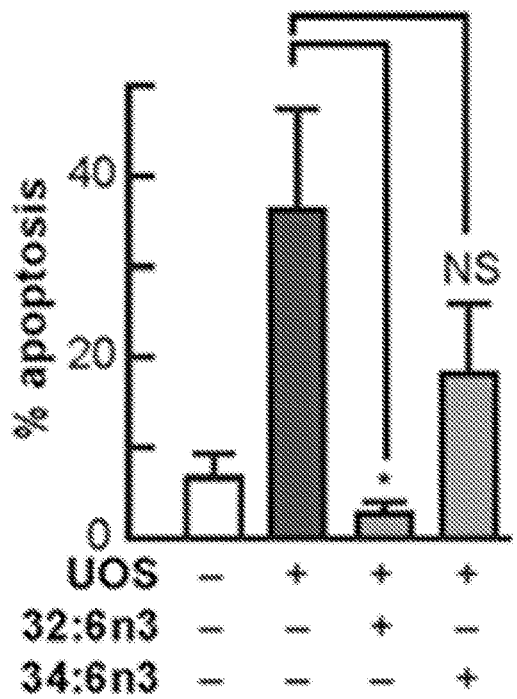
FIG. 8C illustrates that when 32:6n3 or 34:6n3 were added, cell death was prevented.

32:6n3 and 34:6n3 VLC-PUFAs Enhance Anti-Apoptotic and Pro-Survival Protein Expression:

In FIGS. 7A-7K, 32:6n3 and 34:6n3 upregulate the expression of pro-survival BcL2 and BcL-$x_L$ (FIGS. 7E and 7F) and down regulated the pro-apoptotic proteins Bax, Bim, and Bid (FIGS. 7G-7I). Moreover, the pro-homeostatic effects of 32:6n3 and 34:6n3 s is concentration dependent (FIG. 7J). The expression of Sirtuin-1 (SIRT1) was augmented in the presence of 15-LOX-1 inhibitor (FIG. 7C), while the effect of the inhibitor on Iduna expression was unaffected (FIG. 7D).

Example 24

ELVs N32 and N34 Attenuate Apoptosis in RPE:

It was tested whether ELVs are capable of inhibiting UOS-induced apoptosis in RPE cells. As shown in FIG. 10C, ELV-N32-Na and ELV-N34-Na mimic the UOS-mediated attenuation of apoptosis in RPE cells at a concentration of 200 nM. Interestingly, two different 15-LOX-1 inhibitors (15-LOX-1 inhibitor or PD146176) at concentrations of 1 μM were able to compensate for ELV-mediated inhibition of apoptosis in RPE cells undergoing UOS (FIG. 10C). UOS-induced apoptotic cell death was attenuated by ELV-N32-Na or ELV-N34-Me in RPE cells in a concentration-dependent manner (50-500 nM); the highest inhibition was at 500 nM (for both sodium salt and methyl ester forms) and the lowest was at 50 nM (FIG. 10G).

Example 25

ELVs Upregulate Pro-Homeostatic and Anti-Apoptotic Proteins:

It was explored whether ELVs, enhance the expression of pro-survival and pro-homeostatic proteins in RPE cells undergoing UOS. FIG. 10Aa shows that ELV-N32-Na and ELV-N34-Na upregulate Sirtuin1 (SIRT1) in UOS RPE cells in a dose-dependent manner (100-200 nM) and that ELV- N32-Na is more potent than ELV-N34-Na in upregulating SIRT1. ELV-N32-Na and ELV-N34-Na enhanced Iduna expression in RPE cells under UOS at concentrations of 200 nM (FIG. 10B). PD-146176, an inhibitor of 15-LOX-1, blocked these effects at 1 µM concentration in ARPE-19 cells undergoing UOS. Prohibitin (type-1), a cell-survival protein, was upregulated by both ELV-N32 and ELV-N34 (sodium salts and methyl ester forms) in a concentration-dependent manner (100-200 nM) in RPE cells undergoing UOS (FIG. 10H). In FIG. 10D it is shown that ELV-N32-Na or ELV-N34-Na enhanced the abundance of anti-apoptotic proteins Bcl-2 and Bcl-xL. On the other hand, pro-apoptotic Bax, Bim, and Bid are decreased by ELV-N32 or ELV-N34 (sodium salts or methyl esters) (FIGS. 10D-10F). It is interesting to note that while Bcl-2 and Bcl-xL are upregulated (FIG. 10D), Bax, Bim, and Bid are downregulated by either the sodium salts or methyl esters (FIGS. 10D-10F).

Example 26

AdipoR1 Regulates DHA Uptake and ELV Formation:

RPE cells sustain PRC functional integrity, and their demise is involved in the onset of several forms of retinal degenerations (FIG. 11D). One of the functions of the RPE cell is to retrieve DHA during PRC renewal and return it through the interphotoreceptor matrix to the PRC inner segment for new outer segment disc membrane biogenesis[37]. Recently, adiponectin receptor 1 (AdipoR1) was found to be necessary for DHA availability to photoreceptor cells[28] and that a single amino acid mutation is causative of autosomal dominant retinitis pigmentosa[38]. Genetic ablation of this receptor leads to PRC degeneration and to shutting-off VLC-PUFA synthesis in the retina. Pool size of free C32:6n3 and of 34:6n3 in retinas of AdipoR1 knockout (KO) mice (red) is drastically decreased as compared with that in WT (blue). Moreover, ELV-N32 and ELV-N34 in KO (red) were undetectable. Mono-hydroxy 32:6n3 and C34: 6n3, the stable derivatives of the hydroperoxy precursors of ELV-N32 and of ELV-N34 respectively, lack a detectable signal in the KO (red), unlike the wild type (blue) (FIGS. 11B and 11C).

Example 27

ELVs Protect RPE Cells, which Sustain PRC Integrity:

DHA elongation in the inner segment of photoreceptors by ELOVL4 leads to the biosynthesis of VLC-PUFAs and their insertion at the C1 position of phosphatidylcholine within PRC disk membranes. However, under conditions of stress, these VLC-PUFAs are cleaved by PLA1 for the synthesis of mono- and di-hydroxy VLC-PUFAs (ELVs) (FIG. 11A). Light-induced oxidative stress in mouse retinas triggers the production of free VLC-PUFAs, 32:6n3 and 34:6n3, and their mono- and di-hydroxy derivatives (FIG. 11A). In AdipoR1 KO mice, no detectable amounts of these molecules are found (FIG. 5b, c, red curves). Therefore, the lack of the VLC-PUFA precursor DHA results in retinal degeneration (FIG. 11D), preceded by a remarkable downregulation of the free VLC-PUFA omega-3 molecular species and ELV biosynthesis.

Example 28

Use of Elovanoids and their Precursors (27- and 29-Molecules) for Neuroprotection by Intravenous, Intra-Nasal or Sub-Lingual Delivery Acutely after the Initial Diagnosis of an Ischemic Stroke:

Intracranial thrombectomy rates are currently low In the United States (U.S.), reaching 9.3% In the largest metro areas (source: Definitive HealthCare based on US Medicare data, 2017). This is likely due to various factors, including lack of local expertise in neurovascular rescue and mechanical thrombectomy. However, stroke telenetworks are increasing In number across the U.S. As such, the role of telemedicine for diagnosis and to initiate treatment, such as intravenous (Iv) thrombolysis (tissue plasminogen activator, tPA), can be successful. However, this is only the case in a relatively small number of patients.

Under one embodiment, once the diagnosis of ischemic stroke is made in an urgent care or hospital emergency room with telemedicine capacity and the standard of care stroke treatment started, the patient with an ischemic stroke will benefit from delivery of elovanoids by either an intravenous infusion, intra-nasal or sublingual route(s) so that neuroprotection can ensue. Elovanoids are potent neuroprotection molecules that have the capacity to cross the blood-brain barrier with much greater ease than traditional small molecules thru their potent and multiple-acting modes of neuroprotection. Thus elovanoid administration can minimize the burden of the ischemic stroke. Through this delivery of this technology, the penumbra will be preserved and the size of the core Infarct minimized.

As the diagnosis of an ischemic stroke is made, under one embodiment, the patient receives iv-infusion of tPA, if he or she is deemed to be a candidate, and the elovanoids are administered. The patient can then be transferred for thrombectomy and neurorescue at a tertiary referral or center with that expertise, if deemed appropriate, where elovanoids may also be delivered after mechanical thrombectomy to further preserve the penumbra by minimizing neuronal cell death, attenuating the deleterious effects of ischemic reperfusion and diminishing inflammation and edema formation.

Example 29

Unique Therapeutic Features of Elovanoids:
   Biomimetic therapeutic approach
      Use of synthetically-produced materials of endogenously generated lipid mediators with protective and restorative activities.
      Neuroprotection & Neurorestoration
   Restoration of homeostasis
   Unique therapeutic benefits to the brain
      Traumatic brain injury (TBI)
      Stroke systemic application
   Unique therapeutic benefits to the eye
      Retinal injury restoration
ELOVANOIDS (EL Vs)—Newly-Discovered Lipid Mediators with Neuroprotective & Restorative Properties:
   Endogenously biosynthesized
   Unique bioactivity
   Protection of neurons, cells & tissues
   Protection of the brain & eye
   Restoration of homeostasis
   Synthetically produced Elovanoids
   Unique biomimetic therapeutics Example 30

TBI can refer to traumatically induced structural injury and/or physiological disruption of brain function as a result of an external force that is indicated by new onset or worsening of at least one of the following clinical signs, immediately following the event.

Non-limiting examples of external forces comprise
the head being struck by an object,
the head striking an object,
the brain undergoing an acceleration/deceleration movement without direct external trauma to the head,
a foreign body penetrating the brain,
forces generated from events such as a blast or explosion, or
other forces.

| Stratifying TBI Severity | | | |
|---|---|---|---|
| Criteria | Mild | Moderate | Severe |
| Structural imaging | Normal | Normal or abnormal | Normal or abnormal |
| Loss of Consciousness (LOC) | 0-30 min | >30 min and <24 hrs | >24 hrs |
| Alteration of consciousness/mental state (AOC)* | a moment up to 24 hrs | >24 hours. Severity is based on other criteria | |
| Post-traumatic amnesia (PTA) | 0-1 day | >1 and <7 days | >7 days |
| Glascow Coma Scale (best available score in first 24 hours) | 13-15 | 9-12 | <9 |

*Alteration of mental status must be immediately related to the trauma to the head. Typical symptoms would be: looking and feeling dazed and uncertain of what is happening, confusion, difficulty thinking clearly or responding appropriately to mental status questions, and being unable to describe events immediately before or after the trauma event.

Example 31

We provide here strong data validating that nasal application of a mixture of Elovanoids (ELVs) and produces and sustains neurological recovery after an experimental mild form of Traumatic Brian Injury (TBI) in rats. Side by side experiments demonstrate that also intravenous application of ELVs protects TBI consequences. The MRI data enclosed demonstrates this protection on similar cortex and collosum. TBI is a frequent injury in service members in military training or in combat. Most TBI injuries are mild, but even those can result in serious long-term neurological perturbations. There is a lack of an effective therapy for TBI currently, treatment is only symptomatic. While the role of neuroinflammation in TBI is established, the clinical use of conventional anti-inflammatory agents has failed; the same is true for other targets. Thus, there is an urgent need to develop therapy for TBI because even mild forms often transition to CTE (Chronic traumatic encephalopathy), a form of neurodegenerative disease, that includes dementia. While the role of neuroinflammation in TBI is established, the clinical use of conventional anti-inflammatory agents has failed; the same is true for other targets. Thus, there is an urgent need to develop therapy for TBI because even mild forms often transition to CTE (Chronic traumatic encephalopathy), a form of neurodegenerative disease, that includes dementia.

Brain penetrant synthetic ELVs, based on endogenously neuroprotective mediators (devoid of side effects), would counteract disruptions of homeostasis after TBI and provide recovery, slow down and/or block initiation and progression to CTE. Our drug candidates are based on ELVs, which are dihydroxylated fatty acids biosynthesized from precursors made by the neuronal specific ELOVL4 (Sherry D, et al., Front. Neuroanat. 2017; 11. PMID: 28507511). In addition to the discovery and structural characterization of ELV, we have developed the chemistry for their synthesis, and demonstrated their potent actions in brain and retina. Without wishing to be bound by theory and given the properties of ELV, we identify a drug candidate for TBI. We have developed chemical synthetic strategies for stereo controlled total synthesis of ELV-N32, ELV-N34, with fully defined structures and stereochemistry, complete R/S configuration and Z/E geometry of the double bonds. Our discovery included defining ELVs neuroprotective bioactivities in neuronal cultures and in vivo in brain damage (Bhattacharjee S, et al. Sci Adv. 2017; 3. PMID: '28959727). After completion of the studies, we will proceed with development, formulation and upscale manufacturing; IND-enabling pharmacology, toxicology and safety studies; and submission of an IND to the FDA to conduct First in Human (FIH) clinical trials. We will build a strategy to develop an ELVs IND and clinical trials for TBI.

The discovery of protective neurorestorative Elovanoids (ELVs) offers a new therapeutic avenue for TBI. Docosahexaenoic acid (DHA, 22:6n-3), through ELOVL4, generates 32:6n-3, 34n-3, and they, in turn, lead to the synthesis of the mediators ELV-N32 or ELV-N34, respectively. These mediators target key mechanisms that include blocking excitotoxicity, upregulate the expression of protective proteins, downregulate expression of damaging proteins and modulate neuroinflammation (Bhattacharjee S, et al. Sci Adv. 2017; 3. PMID: 28959727; Bazan N G, Mo/Aspects Med. 2018; 64. PMID: 30244005). Our preliminary data shows ELV-34:6 is protective in TBI (FIG. 41, mild fluid percussion injury) in rats. The ELV bioactivity represents a totally new mechanism from elongated precursors of DHA. For example previously was reported that DHA inhibits ER stress in TBI when given by intra peritoneal injection and no specific mediators where identified (Begun G, et al. J. Neurosc. 2014. PMID: 24599472.)

Without being bound by theory, ELVs will attenuate and delay initiation and progression of brain injury; improve behavioral outcome; diminish blood-brain barrier damage and enhance cell survival. The ELV protection on CC has important implications on interhemispheric cortical plasticity and reorganization (Petrus E, et al. PNAS. 2019,pii: 201810132. PMID:30846552) and its significance in neurological TBI-mediated impairments.

REFERENCES CITED IN THESE EXAMPLES

1. Mukherjee, P. K., Marcheselli, V. L., Serhan, C. N. & Bazan, N. G. Neuroprotectin D1: a docosahexaenoic acid-derived docosatriene protects human retinal pigment epithelial cells from oxidative stress. *Proc. Natl. Acad. Sci. U.S.A.* 101, 8491-8496 (2004)

2. Bazan, N. G. Homeostatic regulation of photoreceptor cell integrity: significance of the potent mediator neuroprotectin D1 biosynthesized from docosahexaenoic acid: The Proctor Lecture. Invest. Opthalmol. Vis. Sci. 48, 4866-4881 (2007)
3. Bazan N. G. (2009). Cellular and molecular events mediated by docosahexaenoic acid-derived neuroprotectin D1 signaling in photoreceptor cell survival and brain protection. Prostaglandins Leukot. Essent. Fatty Acids. 81, 205-211.
4. Bazan, N. G. Neuroprotectin D1-mediated anti-inflammatory and survival signaling in stroke, retinal degenerations, and Alzheimer's disease. J. Lipid Res. 50 Suppl., S400-S405 (2009)
5. Bazan N G, Eady T N, Khoutorova L, Atkins K D, Hong S, Lu Y, Zhang C, Jun B, Obenaus A, Fredman G, Zhu M, Winkler J W, Petasis N A, Serhan C N, Belayev L. Novel aspirin-triggered neuroprotectin D1 attenuates cerebral ischemic injury after experimental stroke. Exp Neurol. 2012; 236(1):122-30
6. Serhan, C. N. & Petasis, N. A. Resolvins and protectins in inflammation resolution. Chem. Rev. 111, 5922-5943, (2011).
7. Lagali, et. al. et al. Evolutionarily conserved ELOVL4 gene expression in the vertebrate retina. Invest. Opthalmol. Vis. Sci. 44, 2841-50 (2003)
8. Agabaga, M. P. et al. Role of Stargardt-3 macular dystrophy protein (ELOVL4) in the biosynthesis of very long chain fatty acids. Proc. Nat. Acad. Sci. USA 105, 12843-12848 (2008)
9. Agabaga, M. P. et al. Retinal very long-chain PUFAs: new insights from studies on ELOVL4 protein. J. Lipid Res. 51, 1624-1642 (2010)
10. Monroig, O. et al. Expression and role of Elovl4 elongases in biosynthesis of very long-chain fatty acids during zebrafish Danio rerio early development. Biochemica et Biophysica Acta. 1801, 1145-1154 (2010)
11. Cameron, D. J. et al. Essential role of Elovl4 in very long chain fatty acid synthesis, skin permeability barrier function, and neonatal survival. Int. J. Biol. Sci. 3, 111-119 (2007)
12. Agbaga, M. P. Different mutations in ELOVL4 affect very long chain fatty acid biosynthesis to cause variable neurological disorders in humans. Adv. Exp. Med. Biol. 854, 129-135 (2016)
13. Aldahmesh, M. A. et al. Recessive mutations in ELOVL4 cause ichthyosis, intellectual disability, and spastic quadriplegia. Am. J. Hum. Genet. 89, 745-750 (2011)
14. Aveldano M I. Phospholipid species containing long and very long polyenoic fatty acids remain with rhodopsin after hexane extraction of photoreceptor membranes. Biochemistry. 27, 1229-1239 (1988).
15. Rice, D. et al. Adiponectin receptor 1 conserves docosahexaenoic acid and promotes photoreceptor cell survival. Nat. Commun. 6, 6228 (2015)
16. Serhan C N, Gotlinger K, Hong S, Lu Y, Siegelman J, Baer T, Yang R, Colgan S P, Petasis N A. Anti-inflammatory actions of neuroprotectin D1/protectin D1 and its natural stereoisomers: Assignments of dihydroxy-containing docosatrienes. J Immunol. 176(3):1848-5 (2006).
17. Petasis N A, Yang R, Winkler J W, Zhu M, Uddin J, Bazan N G, Serhan C N. Stereocontrolled total synthesis of Neuroprotectin D1/Protectin D1 and its aspirin-triggered stereoisomer. Tetrahedron Lett 53(14):1695-8, (2012).
18. Calandria, J. M. et al. Selective survival rescue in 15-lipoxygenase-1-deficient retinal pigment epithelial cells by the novel docosahexaenoic acid-derived mediator, neuroprotectin D1. J. Biol. Chem. 284, 17877-17882 (2009)
19. Bazan, N. G. The docosanoid neuroprotectin D1 induces homeostatic regulation of neuroinflammation. Prostaglandins Leukot. Essent. Fatty Acids, 88, 127-129 (2013)
20. Bazan, N. G. Cell survival matters: docosahexaenoic acid signaling, neuroprotection and photoreceptors. Trends Neurosci. 29, 263-271 (2006)
21. Bazan, N. G., Calandria, J. M. & Serhan, C. N. Rescue and repair during photoreceptor cell renewal mediated by docosahexaenoic acid-derived neuroprotectin D1. J. Lipid Res. 51, 2018-2031 (2010)
22. Mukherjee, P. K., Chawla, A., Loayza, M. S., Bazan, N. G. Docosanoids are multifunctional regulators of neural cell integrity and fate: significance in aging and disease. Prostaglandins Leukot. Essent. Fatty Acids. 77, 233-238 (2007)
23. Mukherjee, P. K., Chawla, A., Loayza, M. S., Bazan, N. G. Docosanoids are multifunctional regulators of neural cell integrity and fate: significance in aging and disease. Prostaglandins Leukot. Essent. Fatty Acids. 77, 233-238 (2007
24. Li, L. et al. Prohibitin gene delivery promotes functional recovery in rats with spinal cord injury, Neuroscience. 286, 27-36 (2015)
25. Sripathi, S. R. et al. Prohibitin as the molecular binding switch in the retinal pigment epithelium. Protein J. 35, 1-16 (2016)
26. Sripathi, S. R. et al. Altered cytoskeleton as a mitochondrial decay signature in the retinal pigment epithelium. Protein J. 35, 179-192 (2016)
27. Nijtmans, L. G. et al. Prohibitins act as a membrane-bound chaperone for the stabilization of mitochondrial proteins. EMBO J. 19, 2444-2451 (2000)
28. Roberts, S. B. & Rosenberg, I. Nutrition and aging: changes in the regulation of energy metabolism with aging. Physiol. Rev. 86, 651-667 (2006)
29. Balaban, R. S., Nemoto, S. & Finkel, T. Mitochondria, oxidants, and aging. Cell 120, 483-495 (2005)
30. Back, J. W. et al. A structure for the yeast prohibitin complex: structure prediction and evidence from chemical crosslinking and mass spectrometry. Protein Sci. 11, 2471-2478 (2002)
31. Bligh, E. G. & Dyer, W. J. A rapid method of total lipid extraction and purification. Can. J. Biocjem. Physiol. 37, 911-917 (1959)
32. D. T. Stark, N. G. Bazan. Synaptic and extrasynaptic NMDA receptors differentially modulate neuronal cyclooxygenase-2 function, lipid peroxidation, and neuroprotection. J. Neurosci. 31, 13710-13721 (2011)
33. Harkewicz R, Du H, Tong Z, Alkuraya H, Bedell M, Sun W, Wang X, Hsu Y-H, Esteve-Rudd J, Hughes G, Su Z, Zhang M, Lopes V S, Molday R S, Williams D S, Dennis E A, Zhang K. Essential Role of ELOVL4 Protein in Very Long Chain Fatty Acid Synthesis and Retinal Function. J Biol Chem. 2012; 287(14):11469-80.
34. Corey E J, Raju N. A new synthetic route to bridged carboxylic ortho esters. Tetrahedron Lett. 1983; 24(50): 5571-4.
35. Durand S, Parrain J-L, Santelli M. Construction of (Z,Z) skipped 1,4-dienes. Application to the synthesis of polyunsaturated fatty acids and derivatives. Journal of the Chemical Society, Perkin Transactions 1. 2000(3):253-73.

36. E. H. Lo, T. Dalkara, M. A. Moskowitz, Mechanisms, challenges and opportunities in stroke. *Nat. Rev. Neurosci.* 4, 399-415 (2003). pmid: 12728267; doi: 10.1038/nrn1106
37. K. Eltzschig, T. Eckle, Ischemia and reperfusion—from mechanism to translation. *Nat Med.* 17, 1391-1401 (2011). pmid: 22064429; doi: 10.1038/nm.2507
38. L. Belayev, O. F. Alonso, R. Busto, W. Zhao, M. D. Ginsberg, Middle cerebral artery occlusion in the rat by intraluminal suture. Neurological and pathological evaluation of an improved model. *Stroke.* 27, 1616-1622 (1996). pmid: 8784138
39. S. H. Shi, Z. F. Qi, Y. M. Luo, X. M. Ji, K. J. Liu, Normobaric oxygen treatment in acute ischemic stroke: a clinical perspective. *Med. Gas. Res.* 6, 147-153 (2016). pmid: 27867482; doi: 10.4103/2045-9912.191360
40. Jun B, Mukherjee P K, Asatryan A, Kautzmann M-A, Heap J, Gordon W C, Bhattacharjee S, Yang R, Petasis N A, Bazan N G. Elovanoids are novel cell-specific lipid mediators necessary for neuroprotective signaling for photoreceptor cell integrity. Scientific Reports. 2017; 7(5279):1-14
41. Bhattacharjee S, Jun B, Belayev L, Heap J, Kautzmann M-A, Obenaus A, Menghani H, Marcell S J, Khoutorova L, Yang R, Petasis N A, Bazan N G. Elovanoids are a novel class of homeostatic lipid mediators that protect neural cell integrity upon injury. Science Advances. 2017; 3(9):1-13

We claim:

1. A method for improving skin appearance, wherein the method comprises administering a composition comprising at least one elovanoid having at least 23 carbon atoms in its carbon chain.

2. The method of claim 1, wherein the composition further comprises a pharmaceutically-acceptable carrier.

3. The method of claim 1, wherein the composition is formulated for topical delivery of the at least one elovanoid to the skin of a recipient subject.

4. The method of claim 1, wherein the at least one elovanoid is selected from the group consisting of: a mono-hydroxylated elovanoid, a di-hydroxylated elovanoid, an alkynyl mono-hydroxylated elovanoid, and an alkynyl di-hydroxylated elovanoid, or any combination thereof.

5. The method of claim 1, wherein the at least one elovanoid is a combination of elovanoids wherein the combination is selected from the group consisting of: a mono-hydroxylated elovanoid and a di-hydroxylated elovanoid; a mono-hydroxylated elovanoid and an alkynyl mono-hydroxylated elovanoid; a mono-hydroxylated elovanoid and an alkynyl di-hydroxylated elovanoid; a di-hydroxylated elovanoid and an alkynyl mono-hydroxylated elovanoid; a di-hydroxylated elovanoid and an alkynyl di-hydroxylated elovanoid; a mono-hydroxylated elovanoid, a di-hydroxylated elovanoid, and an alkynyl mono-hydroxylated elovanoid; a mono-hydroxylated elovanoid, a di-hydroxylated elovanoid, and an alkynyl di-hydroxylated elovanoid; and a mono-hydroxylated elovanoid, a di-hydroxylated elovanoid, and an alkynyl mono-hydroxylated elovanoid an alkynyl di-hydroxylated elovanoid, wherein each elovanoid is independently a racemic mixture or a diastereomeric mixture, an isolated enantiomer, or a combination of enantiomers wherein the amount of one enantiomer greater than the amount of another enantiomer.

6. The method of claim 1, wherein the composition further comprises at least one omega-3 very long-chain polyunsaturated fatty acid having at least 23 carbon atoms in its carbon chain.

7. The method of claim 6, wherein the at least one omega-3 very long chain polyunsaturated fatty acid has from about 26 to about 42 carbon atoms in its carbon chain.

8. The method of claim 6, wherein the at least one omega-3 very long chain polyunsaturated fatty acid has in its carbon chain five or six double bonds with cis geometry.

9. The method of claim 6, wherein the at least one very long chain polyunsaturated fatty acid is 14Z,17Z,20Z,23Z,26Z,29Z)-dotriaconta-14,17,20,23,26,29-hexaenoic acid or (16Z,19Z,22Z,25Z,28Z,31Z)-tetratriaconta-16,19,22,25,28,31-hexaenoic acid.

10. The method of claim 4, wherein the mono-hydroxylated elovanoid is selected from the group consisting of the formulas G, H, I or J:

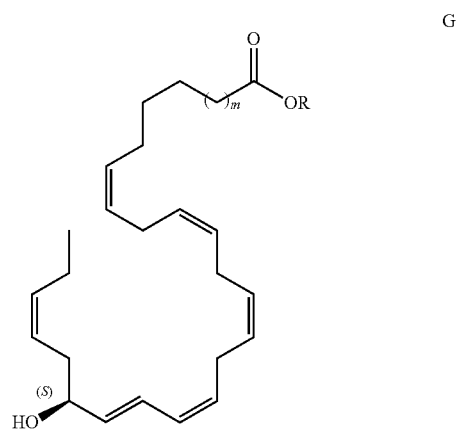

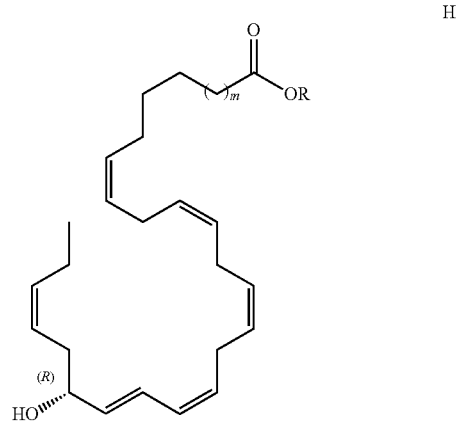

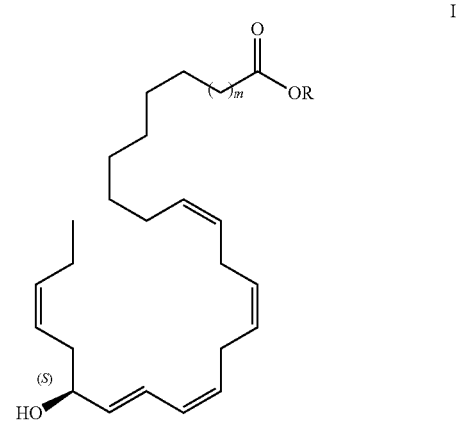

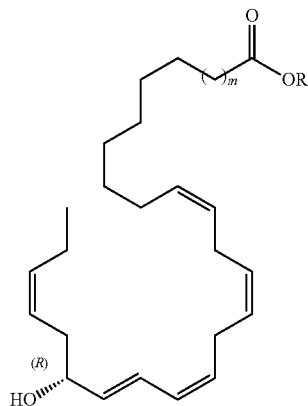

J

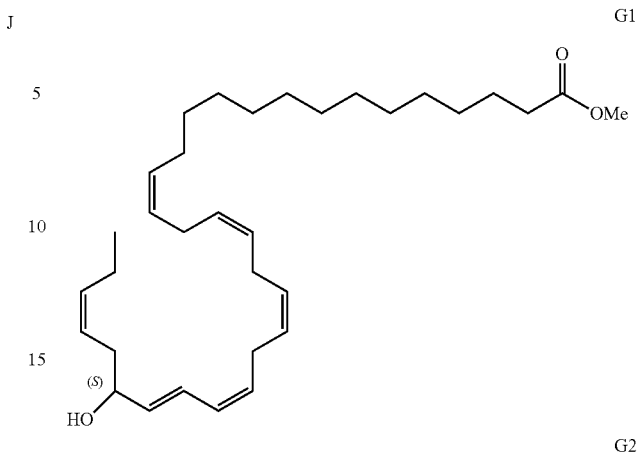

G1

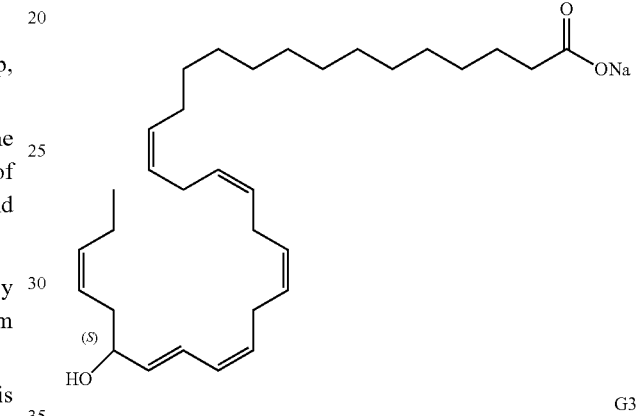

G2

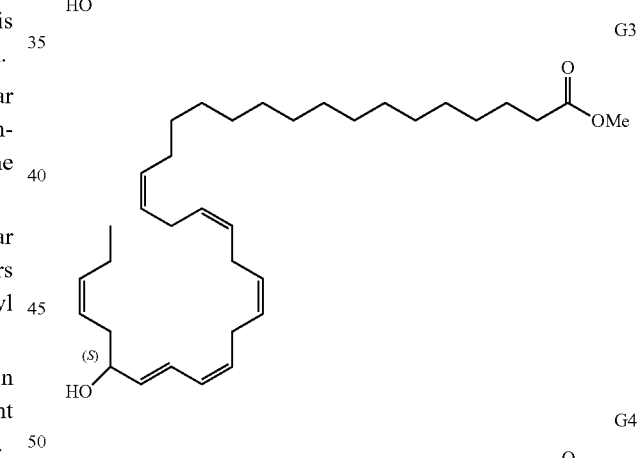

G3

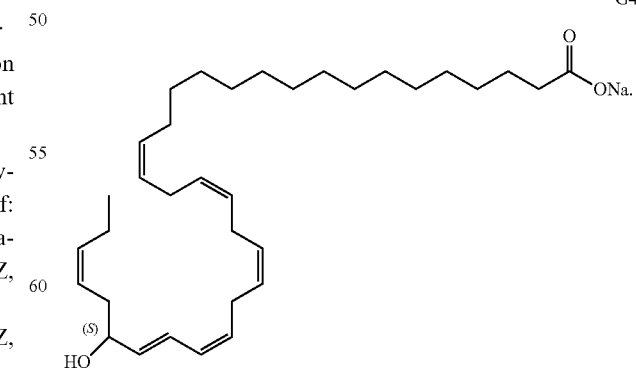

G4 wherein:

m is 0 to 19 and —CO—OR is a carboxylic acid group, or a salt or an ester thereof, and wherein:

if —CO—OR is a carboxylic acid group and the compound G, H, I or J is a salt thereof, the cation of the salt is a pharmaceutically acceptable cation, and if —CO—OR is an ester, then R is an alkyl group.

11. The method of claim 10, wherein the pharmaceutically acceptable cation is an ammonium cation, an iminium cation, or a metal cation.

12. The method of claim 11, wherein the metal cation is a sodium, potassium, magnesium, zinc, or calcium cation.

13. The method of claim 10, comprising equimolar amounts of the enantiomers G and H wherein the enantiomers have (S) or (R) chirality at the carbon bearing the hydroxyl group.

14. The method of claim 10, comprising equimolar amounts of the enantiomers I and J wherein the enantiomers have (S) or (R) chirality at the carbon bearing the hydroxyl group.

15. The method of claim 10, wherein the composition comprises one of the enantiomers of G or H in an amount exceeding the amount of the other enantiomer of G or H.

16. The method of claim 10, wherein the composition comprises one of the enantiomers of I or J in an amount exceeding the amount of the other enantiomer of I or J.

17. The method of claim 10, wherein the mono-hydroxylated elovanoid is selected from a group consisting of: methyl (S,14Z,17Z,20Z,23Z,25E,29Z)-27-hydroxydotriaconta-14,17,20,23,25,29-hexaenoate (G1), sodium (S,14Z,17Z,20Z,23Z,25E,29Z)-27-hydroxydotriaconta-14,17,20,23,25,29-hexaenoate (G2), methyl (S,16Z,19Z,22Z,25Z,27E,31Z)-29-hydroxytetratriaconta-16,19,22,25,27,31-hexaenoate (G3); and sodium (S,16Z,19Z,22Z,25Z,27E,31Z)-29-hydroxytetratriaconta-16,19,22,25,27,31-hexaenoate (G4) having the formulas, respectively:

18. The method of claim 4, wherein the di-hydroxylated elovanoid is selected from the group consisting of the formulas K, L, M, and N:

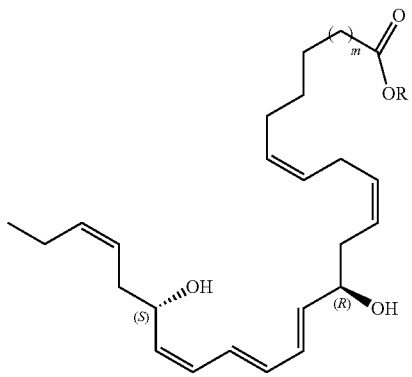

K

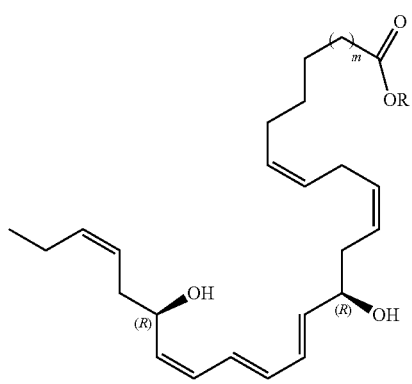

L

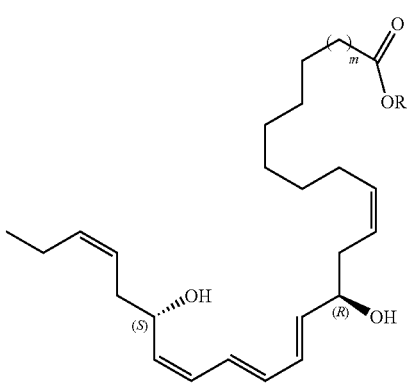

M

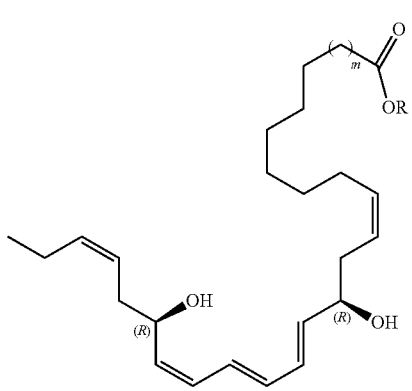

N wherein:

m is 0 to 19 and —CO—OR is a carboxylic acid group, or a salt or an ester thereof, and wherein:

if —CO—OR is a carboxylic acid group and the compound K, L, M, or N is a salt thereof, the cation of the salt is a pharmaceutically acceptable cation, and if —CO—OR is an ester, then R is an alkyl group.

19. The method of claim 18, wherein the pharmaceutically acceptable cation is an ammonium cation, an iminium cation, or a metal cation.

20. The method of claim 19, wherein the metal cation is a sodium, potassium, magnesium, zinc, or calcium cation.

21. The method of claim 18, comprising equimolar amounts of the diastereomers K and L wherein the diastereomers have (S) or (R) chirality at the n-6 carbon bearing the hydroxyl group.

22. The method of claim 18, comprising equimolar amounts of the diastereomers M and N wherein the diastereomers have (S) or (R) chirality at the n-6 carbon bearing the hydroxyl group.

23. The method of claim 18, wherein the composition comprises one of the diastereomers of K or L in an amount exceeding the amount of the other diastereomer of K or L.

24. The method of claim 18, wherein the composition comprises one of the diastereomers of M or N in an amount exceeding the amount of the other diastereomer of M or N.

25. The method of claim 18, wherein the di-hydroxylated elovanoid is selected from the group consisting of: methyl (14Z,17Z,20R,21E,23E,25Z,27S,29Z)-20,27-dihydroxydotriaconta-14,17,21,23,25,29-hexaenoate (K), sodium (14Z,17Z,20R,21E,23E,25Z,27S,29Z)-20,27-dihydroxydotriaconta-14,17,21,23,25,29-hexaenoate (K2), methyl (16Z,19Z,22R,23E,25E,27Z,29S,31Z)-22,29-dihydroxytetratriaconta-16,19,23,25,27,31-hexaenoate (K3), and sodium (16Z,19Z,22R,23E,25E,27Z,29S,31Z)-22,29-dihydroxytetratriaconta-16,19,23,25,27,31-hexaenoate (K4) having the formulas, respectively:

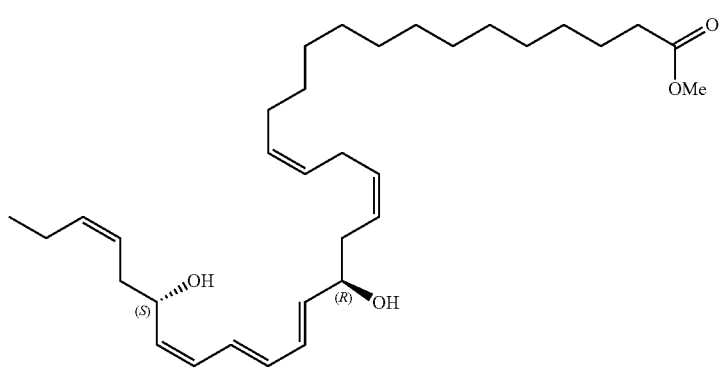
K1
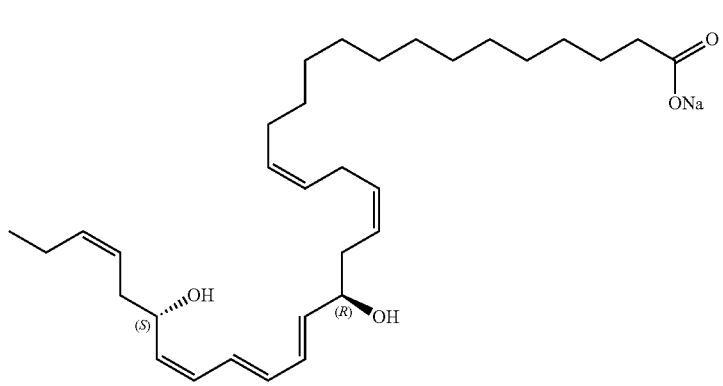
K2
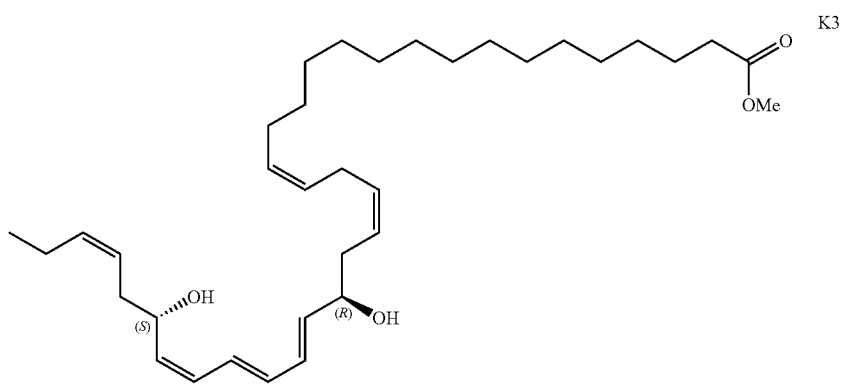
K3
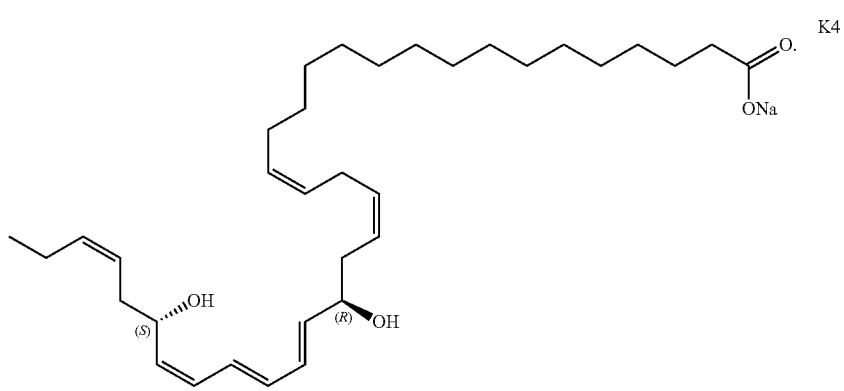
K4

26. The method of claim 4, wherein the alkynyl monohydroxylated elovanoid is selected from the group consisting of the formulas O, P, Q or R:

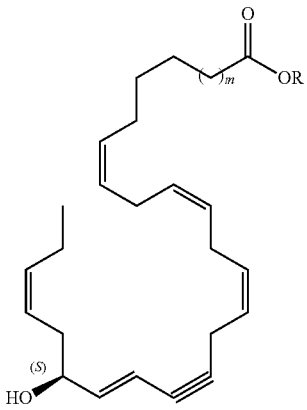

O

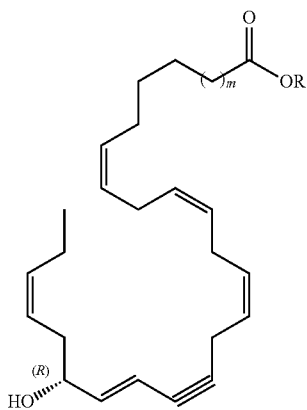

P

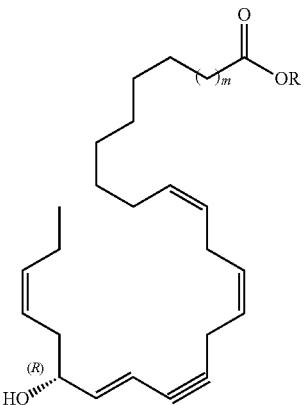

Q

R

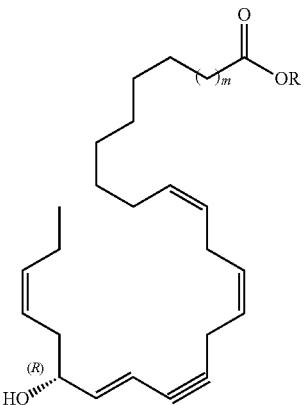

wherein:
m is 0 to 19 and —CO—OR is a carboxylic acid group, or a salt or an ester thereof,
and wherein:
if —CO—OR is a carboxylic acid group and the compound O, P, Q or R is a salt thereof, the cation of the salt is a pharmaceutically acceptable cation, and
if —CO—OR is an ester, then R is an alkyl group,
and wherein:
compounds O and P each have a total from 23 to 42 carbon atoms in the carbon chain, with 4 cis carbon-carbon double bonds starting at positions n-3, n-12, n-15 and n-18, a trans carbon-carbon bond starting at position n-7, and a carbon-carbon triple bond starting at position n-9; and
compounds Q and R each have a total from 23 to 42 carbon atoms in the carbon chain, with 3 cis carbon-carbon double bonds starting at positions n-3, n-12 and n-15, a trans carbon-carbon bond starting at position n-7, and a carbon-carbon triple bond starting at position n-9.

27. The method of claim 26, wherein the alkynyl monohydroxylated elovanoid is selected from the group consisting of: methyl (S,14Z,17Z,20Z,25E,29Z)-27-hydroxydotriaconta-14,17,20,25,29-pentaen-23-ynoate (O1); sodium (S,17Z,20Z,25E,29Z)-27-hydroxydotriaconta-17,20,25,29-tetraen-23-ynoate (O2); methyl (S,16Z,19Z,22Z,27E,31Z)-29-hydroxytetratriaconta-16,19,22,27,31-pentaen-25-ynoate (O3); and sodium (S,16Z,19Z,22Z,27E,31Z)-29-hydroxytetratriaconta-16,19,22,27,31-pentaen-25-ynoate (O4) and having the formulas, respectively:

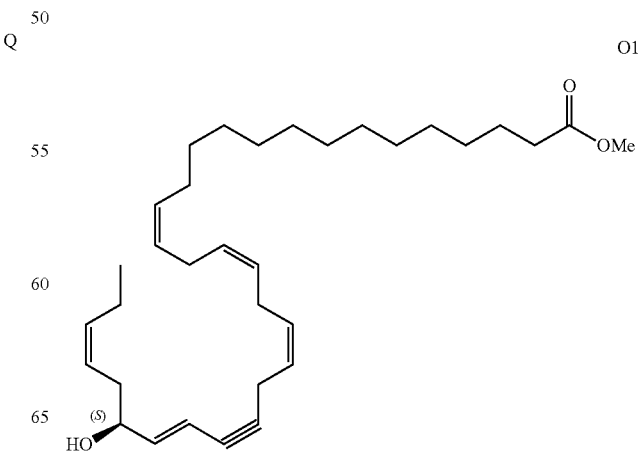

O1

-continued

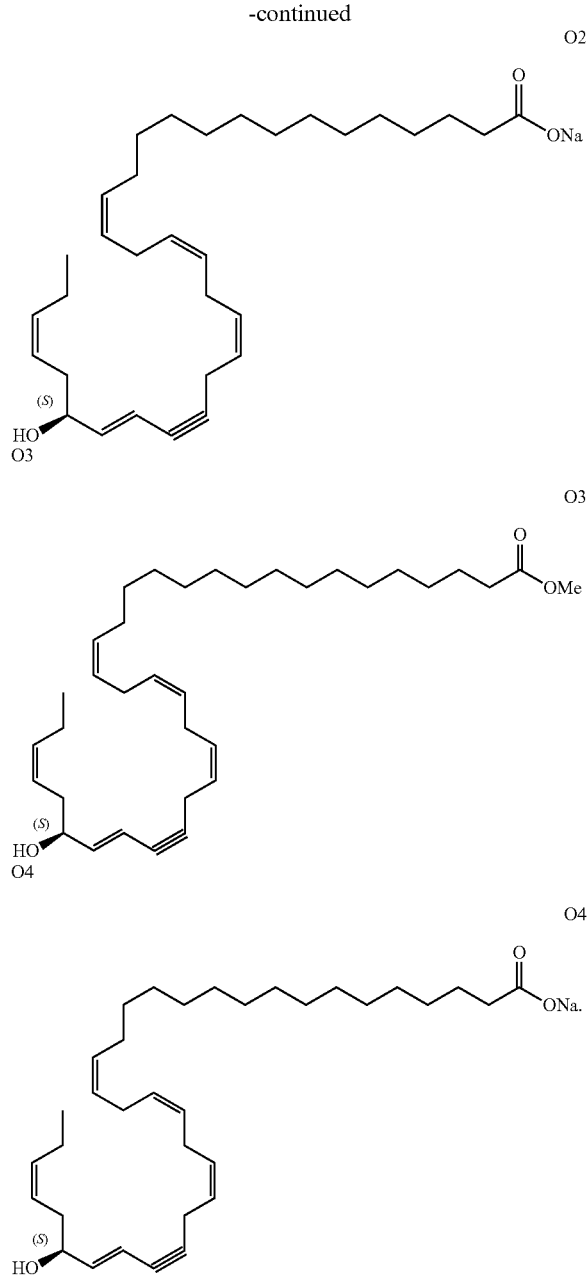

O2

O3

O3

O4

O4

28. The method of claim 26, wherein the pharmaceutically acceptable cation is an ammonium cation, an iminium cation, or a metal cation.

29. The method of claim 28, wherein the metal cation is a sodium, potassium, magnesium, zinc, or calcium cation.

30. The method of claim 26, comprising equimolar amounts of the enantiomers O and P wherein the enantiomers have (S) or (R) chirality at the carbon bearing the hydroxyl group.

31. The method of claim 26, comprising equimolar amounts of the enantiomers Q and R wherein the enantiomers have (S) or (R) chirality at the carbon bearing the hydroxyl group.

32. The method of claim 26, wherein the composition comprises one of the enantiomers of O or P in an amount exceeding the amount of the other enantiomer of O or P.

33. The method of claim 26, wherein the composition comprises one of the enantiomers of Q or R in an amount exceeding the amount of the other enantiomer of Q or R.

34. The method of claim 4, wherein the elovanoid is an alkynyl di-hydroxylated elovanoid selected from the group consisting of the formulas S, T, U or V:

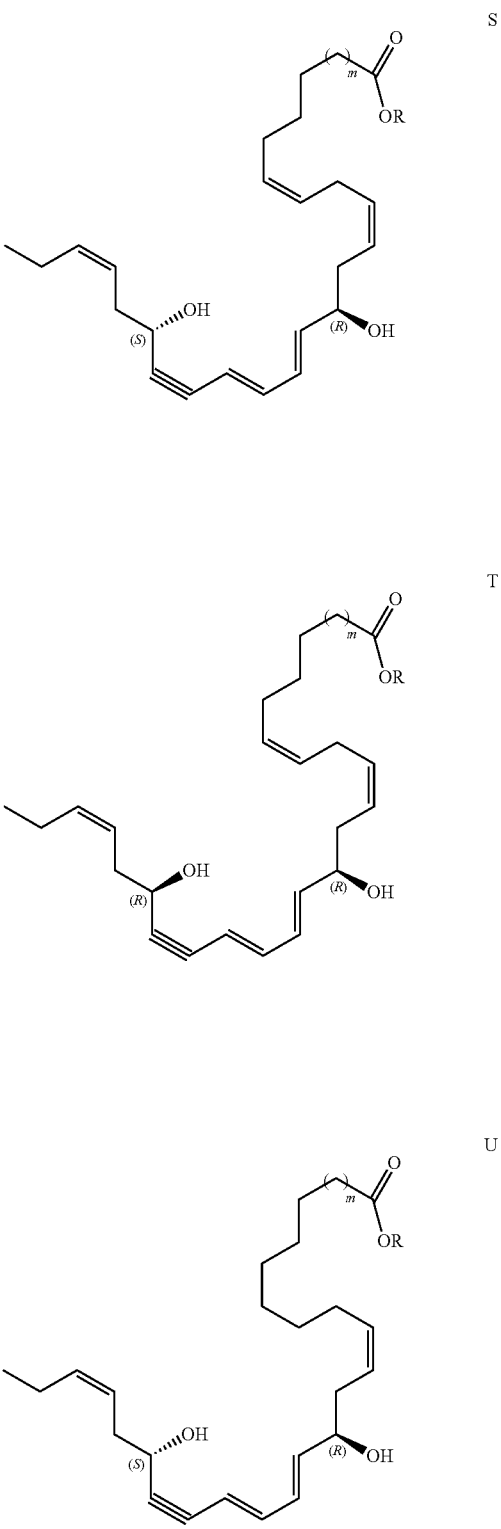

S

T

U

-continued

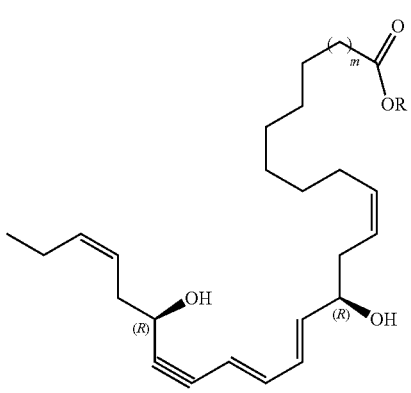

V wherein:
m is 0 to 19 and —CO—OR is a carboxylic acid group, or a salt or an ester thereof,
and wherein:
if —CO—OR is a carboxylic acid group and the compound S, T, U or V is a salt thereof, the cation of the salt is a pharmaceutically acceptable cation, and
if —CO—OR is an ester, then R is an alkyl group,
and wherein:
compounds S and T each have a total from 23 to 42 carbon atoms in the carbon chain, with 3 cis carbon-carbon double bonds starting at positions n-3, n-15 and n-18, with 2 trans carbon-carbon double bonds located at positions starting at n-9 and n-11, and a carbon-carbon triple bond starting at position n-7; and
compounds U and V each have a total from 23 to 42 carbon atoms in the carbon chain, with 3 cis carbon-carbon double bonds starting at positions n-3 and n-15, with 2 trans carbon-carbon double bonds located at positions starting at n-9, n-11, and a carbon-carbon triple bond starting at position n-7.

35. The method of claim 34, wherein the pharmaceutically acceptable cation is an ammonium cation, an iminium cation, or a metal cation.

36. The method of claim 35, wherein the metal cation is a sodium, potassium, magnesium, zinc, or calcium cation.

37. The method of claim 34, wherein the alkynyl dihydroxylated elovanoid is selected from the group consisting of: methyl (14Z,17Z,20R,21E,23E,27S,29Z)-20,27-dihydroxydotriaconta-14,17,21,23,29-pentaen-25-ynoate (S1); sodium (14Z,17Z,20R,21E,23E,27S,29Z)-20,27-dihydroxydotriaconta-14,17,21,23,29-pentaen-25-ynoate (S2); methyl (16Z,19Z,22R,23E,25E,29S,31Z)-22,29-dihydroxytetratriaconta-16,19,23,25,31-pentaen-27-ynoate (S3); and sodium (16Z,19Z,22R,23E,25E,29S,31Z)-22,29-dihydroxytetratriaconta-16,19,23,25,31-pentaen-27-ynoate (S4), and having the formula, respectively:

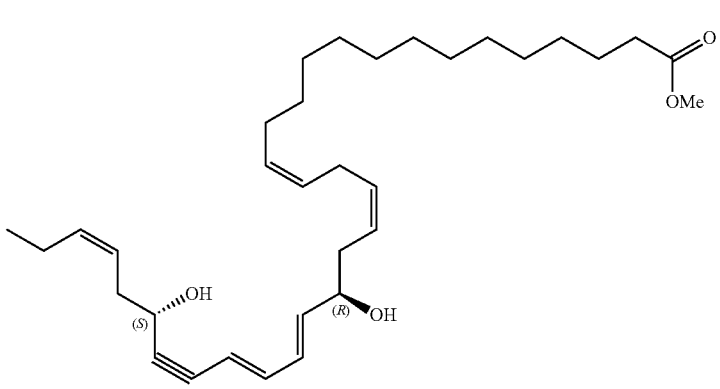

S1

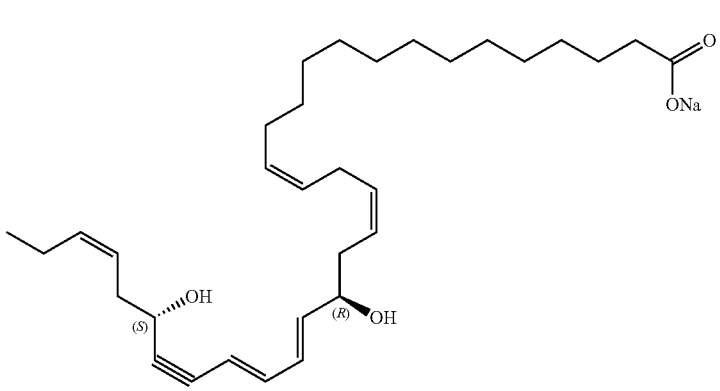

S2

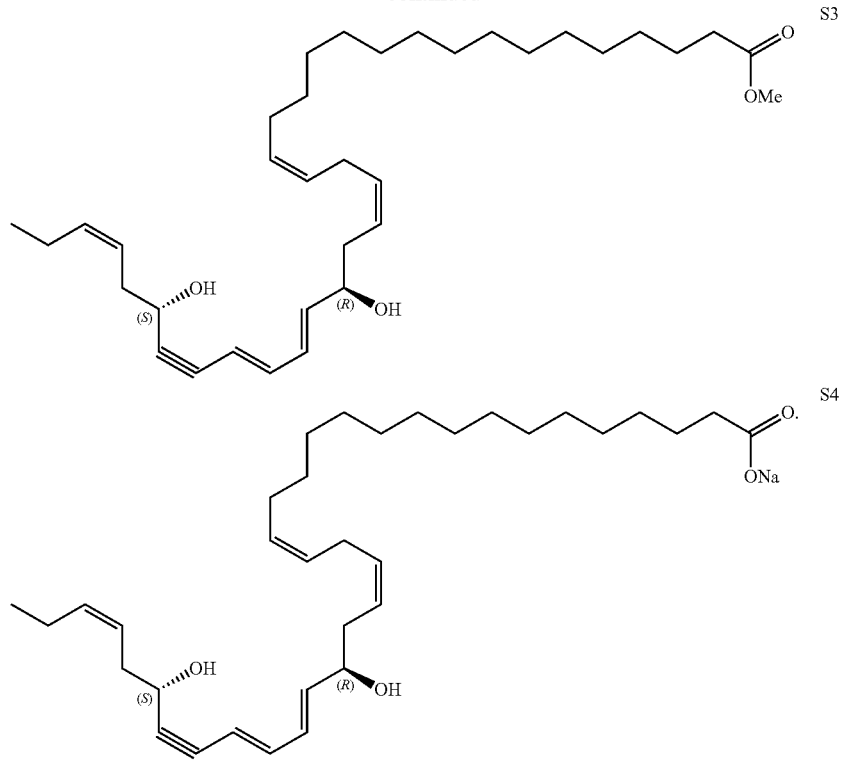

38. The method of claim 34, comprising equimolar amounts of the diastereomers S and T wherein the diastereomers have either (S) or (R) chirality at position n-6, and (R) chirality at position n-13.

39. The method of claim 34, comprising equimolar amounts of the diastereomers U and V wherein the diastereomers have either (S) or (R) chirality at position n-6, and (R) chirality at position n-13.

40. The of claim 34, wherein the composition comprises one of the diastereomers of S or T in an amount exceeding the amount of the other diastereomer of S or T.

41. The method of claim 34, wherein the composition comprises one of the diastereomers of U or V in an amount exceeding the amount of the other diastereomer of U or V.

* * * * *